US011635815B2

(12) United States Patent
Hewage et al.

(10) Patent No.: US 11,635,815 B2
(45) Date of Patent: Apr. 25, 2023

(54) NEURAL INTERFACE

(71) Applicant: BIOS HEALTH LTD, Cambridgeshire (GB)

(72) Inventors: Emil Hewage, Aberdeenshire (GB); Oliver Armitage, London (GB); Tristan Edwards, Oxfordshire (GB)

(73) Assignee: BIOS HEALTH LTD, Cambridgeshire (GB)

( * ) Notice: Subject to any disclaimer, the term of this patent is extended or adjusted under 35 U.S.C. 154(b) by 130 days.

(21) Appl. No.: 16/763,964

(22) PCT Filed: Nov. 13, 2018

(86) PCT No.: PCT/GB2018/053284
§ 371 (c)(1),
(2) Date: May 13, 2020

(87) PCT Pub. No.: WO2019/092456
PCT Pub. Date: May 16, 2019

(65) Prior Publication Data
US 2021/0365114 A1    Nov. 25, 2021

(30) Foreign Application Priority Data

Nov. 13, 2017  (GB) ..................................... 1718756
Jul. 25, 2018  (GB) ..................................... 1812130

(51) Int. Cl.
*G05B 13/02*   (2006.01)
*G06F 3/01*    (2006.01)
*A61F 2/72*    (2006.01)

(52) U.S. Cl.
CPC ........... *G06F 3/015* (2013.01); *G05B 13/027* (2013.01); *A61F 2/72* (2013.01)

(58) Field of Classification Search
CPC .......... G06F 3/015; G05B 13/027; A61F 2/72
See application file for complete search history.

(56) References Cited

U.S. PATENT DOCUMENTS

2008/0208781 A1*  8/2008  Snyder ................... G16H 40/63
                                                    706/20
2010/0280579 A1* 11/2010  Denison ............... G06K 9/6268
                                                    607/62

FOREIGN PATENT DOCUMENTS

JP     2016-538980 A    12/2016
JP     2017-529209 A    10/2017
               (Continued)

OTHER PUBLICATIONS

International Search Report and Written Opinion corresponding to PCT/GB2018/053284 dated Feb. 13, 2019.
(Continued)

*Primary Examiner* — Gary Collins
(74) *Attorney, Agent, or Firm* — ArentFox Schiff LLP

(57) ABSTRACT

Method(s) and apparatus are provided for interfacing with a nervous system of a subject. In response to receiving a plurality of neurological signals associated with the neural activity of the first portion of nervous system: processing neural sample data representative of the received plurality of neurological signals using a first one or more machine learning (ML) technique(s) trained for generating estimates of neural data representative of the neural activity of the first portion of nervous system; and transmitting data representative of the neural data estimates to a first device associated with the first portion of nervous system; and in response to receiving device data from a second device associated with a second portion of the nervous system: generating one or more neurological stimulus signal(s) by inputting the received device data to a second one or more ML technique(s) trained for estimating one or more neurological stimulus signal(s) associated with the device data for input to the second portion of nervous system; and transmitting
(Continued)

the one or more estimated neurological stimulus signal(s) towards the second portion of nervous system of the subject.

11 Claims, 41 Drawing Sheets

(56) References Cited

FOREIGN PATENT DOCUMENTS

| WO | 2008/137346 A3 | 11/2008 |
|---|---|---|
| WO | 2016/154298 A1 | 9/2016 |
| WO | 2017094267 A1 | 6/2017 |

OTHER PUBLICATIONS

Sebelius F C P et al, "Refined Myoelectric Control in Below-Elbow Amputees Using Artificial Neural Networks and a Data Glove", The Journal of Hand Sur, W.B. Saunders, Amsterdam, NL, vol. 30, No. 4, Jul. 1, 2005 (Jul. 1, 2005), p. 780-789.

Examination Report issued in corresponding European Patent Application No. 18808465.1, dated Sep. 23, 2022.

Gaetan Hadjeres et al: "GLSR-VAE: Geodesic Latent Space Regularization for Variational AutoEncoder Architectures", arxiv.org, Cornell University Library, 201 Olin Librar Ornell University Ithaca, NY 14853, XP080776843, DOI: 10.1109/SSCI.2017. 8280895, Jul. 14, 2017 (Jul. 14, 2017).

Office Action in Japanese Patent Application No. 2020-526409, dated Nov. 22, 2022.

Second Office Action in Japanese Patent Application No. 2020-526409, dated Jan. 10, 2023, 5 pages.

Irina Higgins, Nicholas Sonnerat, Loic Matthey, Christopher P. Burgess, Matthew Botvinik, Demis Hassabis, Alexander Lerchner, "SCAN: Learning Abstract Hierarchical Compositional Visual Concepts", DeepMind 2017, 12 pages, Yetrieved online at: https://github.com/miyosuda/scan.

Ryosuke Tachibana, Takashi Matsubara, Kuniaki Uebara, "Label Estimation and Semi-Supervised Learning Using Adversarial Networks in Deep Learning", Department of Computer Science and Systems Engineering, Graduate School of System Informatics, Kobe University, the 30th Annual Conference of the Japanese Society for Artificial Intelligence, 5 pages, 2016, retrieved online: tachibana@gai.cs.kube-u.ac.jp.

Examination Report issued in European Patent Application No. 18822112.1, dated Oct. 26, 2022, 5 pages.

Sebelius F C Pet Al: "Refined Myoelectric Control in Below-Elbow Amputees Using Artificial Neural Networks and a Data Glove", The Journal of Hand Sur, W.B. Saunders, Amsterdam, NL, vol. 30, No. 4, Jul. 1, 2005 (Jul. 1, 2005), pp. 780-789, XP004986588, ISSN: 0363-5023, DOI: 10.1016/J.JHSA.2005.01.002.

\* cited by examiner

NEURAL INTERFACE

The present application relates to a system, apparatus and method(s) for operating a neural interface.

BACKGROUND

Human Computer Interaction (HCI) systems or Human Machine Interaction (HMI) systems are an important part of modern life for anyone that uses a computer or controls a computing device, apparatus or vehicle. Conventional HCI systems have included use of the voice, keyboard, mouse, joystick, touch screen, gestures or movement and/or other devices for interacting with a computing device of some form or another. However, these systems are generally designed with fully able persons or subjects in mind. Recently, there has been an interest in HCI and/or HMI systems exploiting a subject's nervous system by using biomedical signals such as Electro-Encephalogram (EEG), Electrooculogram (EOG), and Electromyogram (EMG) for operating various devices, apparatus and/or systems.

Although such systems may improve the quality of life for less able subjects, these biomedical signals only provide a low level of granularity. Such signals are not sufficient for use in more advanced HCI or HMI systems requiring a finer control for the subject. For example, more advanced HCI or HMI systems such as, by way of example only but not limited to, devices, apparatus and systems for controlling, monitoring and/or operating parts or bodily functions of the subject may include: prosthetic limbs, organ stimulators and/or neuromodulation devices such as, by way of example only but not limited to, heart pacemakers, eye and/or ear implants, or pancreas controllers, or any other device or apparatus for controlling, monitoring and/or operating any other bodily function, body part/portion or organ/tissue of the subject. Such advanced HCI and HMI systems and/or device(s) would benefit from direct access to the subject's nervous system.

The nervous system of mammals is generally made up of nerves comprising a plurality of neurons and consists of two main parts: the central nervous system (CNS) and the peripheral nervous system (PNS). In most animals and humans, herein referred to as a subject, the CNS includes the brain and the spinal cord, which are made up of special nerves. The PNS includes the somatic nervous system (SoNS) and the autonomic nervous system (ANS), which are made up of many different types of nerves such as, by way of example only but not limited to, afferent nerves (e.g. sensory nerves), efferent nerves (e.g. motor nerves), and/or mixed nerves. The SoNS may carry, by way of example only but is not limited to, conscious motor control for motion and sensation. The ANS may carry, by way of example only but is not limited to, unconscious organ control or unconscious control of bodily functions of the subject.

The SoNS is associated with voluntary control of body movements (e.g. control of skeletal muscles). For example, in the SoNS, afferent nerves include sensory neurons and are responsible for relaying sensation from the body to the CNS and efferent nerves include non-sensory neurons and are responsible for sending out neural information, commands, intent, which may also be referred to as bodily variables as described below, from the CNS to the body (e.g. stimulating muscle contraction). The ANS includes, by way of example only but is not limited to, the sympathetic nervous system (SNS), the parasympathetic nervous system (PSNS) and the enteric nervous system (ENS).

The PNS is essentially a set of nerves that connect the CNS to every other bodily function/body part/portion (e.g. muscles, organs, cells) of the subject. Nerves serve as a conduit for transmission of neural impulses or signals to/from the CNS. For example, SoNS nerves that transmit neural impulses, signals or information from the CNS are called efferent nerves (e.g. motor nerves), while other SoNS nerves that transmit neural impulses, signals or information from one or more parts/portions of the body of the subject to the CNS are called afferent nerves (e.g. sensory nerves). Some nerves in the SoNS may have both efferent and afferent functionality and may be called mixed nerves.

In essence, the nervous system is made up of a set of nerves in which each nerve is made up of a plurality of neurons or a bundle of neurons that receive or transmit such as neural impulses or signals. A neuron has a special cellular structure that allows a nerve to send and propagate neural information rapidly and precisely to other cells, bodily functions or body parts/portions in the body of the subject. For example, the neurons in a nerve include long structures called axons that allow them to send neural impulses or signals in the form of an electrochemical gradient, also known as neural activity. A neuronal population may comprise or represent one or more neurons clustered in a location or a target site on one or more nerves of a subject.

Essentially, neural activity may comprise or represent any electrical, mechanical, chemical and or temporal activity present in the one or more neurons (or the neuronal population), which often make up one or more nerves or section(s) of neural tissue. Neural activity may convey information associated with, by way of example only but not limited to, the body of a subject and/or information about the environment affecting the body of a subject. The information conveyed by neural activity may include data representative of neural data, neural information, neural intent, end effect, tissue state, body state, neural state or state of the body, and/or or any other data, variable or information representative of the information carried or contained in neural activity and interpreted and/or passed by neurons or neuronal populations to the body of the subject. For example, neural data may include any data that is representative of the information or data that is contained or conveyed by neural activity of one or more neurons or a neuronal population. The neural data may include, by way of example only but is not limited to, data representative of estimates of one or more bodily variable(s) associated with the corresponding neural activity, or any other data, variable or information representative of the information carried or contained or conveyed by neural activity.

This information may be represented in an information theoretic point of view as one or more variables associated with the body, which are referred to herein as bodily variable(s). A bodily variable comprises or represents an end effect or tissue state describing a state of some portion of the body. The bodily variable may itself be classified as a state, sensory, control or other variable based on the role or function of this information and the use of it by the body. Bodily variables can be transmitted to or from the CNS via neural activity in portions of the nervous system. One or more instances of neural activity at one or more neural locations can be said to be an encoding of one or more bodily variables, portions thereof and/or combinations thereof. For example, neural activity of one or more neurons of nerve(s) may be generated or modulated by part of the body to encode one or more bodily variables for reception by other parts of the body, which decode the neural activity to gain access to the bodily variable, portions thereof and/or combinations thereof. Both encoding and decoding of bodily variables can be performed by the CNS and/or bodily tissues therefore facilitating transmission of information around the body of a subject. Bodily variables can be afferent signals transmitted towards the CNS for provision of information regarding the state of bodily variables or efferent signals transmitted away from the CNS for modifying a bodily variable at an end effector organ or tissue.

Examples of bodily variables in the organ systems of the body, and often encoded in the ANS, could include parameters such as, by way of example only but is not limited to, current blood glucose concentration, temperature of a portion, part or whole of the body of a subject, concentration of a protein or other key agent, current fullness state of the bladder or bowel, current heart rate or blood pressure, current breathing rate, current blood oxygenation, instructions regarding insulin/glucagon production, instructions regarding heart pacing, instructions regarding blood vessel dilation or constriction for changing blood pressure, instructions regarding changing breathing rate, instructions regarding modifying alveoli dilation to modify oxygen concentration, instructions regarding modifying gastric activity, instructions regarding modifying liver activity, instructions regarding opening/closing of sphincters for voiding/retaining of the bladder or bowel. It is appreciated that bodily variables could be either the raw encodings or combinations of these, for instance bodily variables could include current activity of a whole organ or organ construct or measurements of whole bodily functions or actions such as sweating, defecating, hard breathing, walking, exercising, running etc; each of which it is appreciated could be described as a combination of multiple more fine grained bodily variables. In the ANS, each instance of a bodily variable may be associated with a modified organ function, modifying an organ function, or modifying a bodily function (e.g. one or more bodily variable(s) or the state of an organ or tissue). In other examples, a bodily variable may be associated with any activity in the ANS such as, by way of example only but is not limited to, organ measurement and/or modification of activity.

In another example, in the SoNS, one or more bodily variable(s) generated by the CNS may be transmitted via the PNS as efferent neural activity that is associated with one or more instances of motion (e.g. each bodily variable may be associated with a different motion or movement of a limb, contraction/extension of a single muscle fibre/fibre group/ whole muscle/group of muscles, instructions to modify speed/strength length of a muscle contraction, and the like etc.) The CNS may also receive an afferent neural activity encoding a bodily variable corresponding to sensory neural information (e.g. a sensory bodily variable), where in this case the sensory bodily variable represents an encoding of sensory information such as, by way of example only but is not limited to, temperature or pressure on a section or portion of skin, the state of a limb or other muscle group including, angle or position of a joint, position of a whole limb or section of the body, an abstract parameter of activity of the whole body or sub-part of the body, transmitted by one or more neuron(s) or one or more neuronal population(s) associated with the limb or other moving bodily part and the like. The CNS receives the afferent neural activity and then deciphers or decodes this neural activity to understand the sensory bodily variable(s) and responds accordingly.

Although several examples of bodily variables have been described, this is for simplicity and by way of example only, it is to be appreciated by the skilled person that the present disclosure is not so limited and that there are a plurality of bodily variables that may be generated by the body of a subject and which may be sent between parts of the body or around the body as neural activity. Although neural activity may encode one or more bodily variables, portions thereof and/or combinations thereof, it is to be appreciated by the skilled person that one or more bodily variables of a subject may be measurable, derivable, and/or calculated based on sensor data from sensors capable of detecting and/or making measurements associated with such bodily variables of the subject. It is also to be appreciated by the skilled person that a bodily variable is a direct measurement of any one parameter and could be represented as a generalised parameter of activity or function in an area. This would include bodily variables such as mental states which can not be easily related to low level function such as, experiencing depression, having an epileptic fit, experiencing anxiety, having a migraine.

Although the term bodily variable is described and used herein, this is by way of example only and the present disclosure is not so limited, it is to be appreciated by the skilled person that other equivalent terms from one or more other fields (e.g. medical fields, pharmaceutical fields, biomedical fields, clinicians, biomarker fields, genomics fields, medical engineering fields) may be used in place of the term bodily variable, or used interchangeably or even in conjunction with the term bodily variable, including, by way of example only but is not limited to, one or more of the following terms or fields: vital sign(s), which is often used by clinicians to describe parameters they use for patient monitoring, such as by way of example only but is not limited to, ECG, heart rate, pulse, blood pressure, body temperature, respiratory rate, pain, menstrual cycle, heart rate variation, pulse oximetry, blood glucose, gait speed, etc.; biomarker, which may be used by biologists to describe, by way of example only but is not limited to, protein levels, or measurable indicator of some biological state or condition etc., this term has been further adopted by the Deep Brain Stimulation & Spinal Cord Stimulation clinical fields to refer to recordings of brain wave state or other neural events as well as measurement of environmental conditions including, but not limited to, motion; physiological variable/ physiological data, which may often be used by scientists to describe things like ECG, heart rate, blood glucose, and/or blood pressure and the like, this term is also used by Data Sciences International who make implants for recording physiological variables such as ECG, heart-rate, blood pressure, blood glucose, etc.; one or more biosignals, which is often used by medical engineers to describe a signal recording coming from a biological system such as ECoG, ECG, EKG; any information, parameter metric about a subject in, by way of example only but not limited to, the genetic fields including, by way of example only but not limited to, genomic information, epigenetics, phenotype, genotype, other "omics" which can include, by way of example only but is not limited to, transcriptomics, proteomics and metabolomics, microbiomics, and/or other omics related fields and the like; and/or any other term describing a number, metric, state, variable or information associated with the whole body of a subject, any part and/or subpart of the body of the subject and the like.

Although examples of bodily variables are given herein, this is by way of example only and the description is not so limited, it is to be appreciated by the skilled person that the list of bodily variables is extremely large because a bodily variable may be, by way of example only but is not limited to, any number, parameter, metric, variable or information describing some state of the whole body of a subject, any portion, part and/or subpart of the body of the subject and that a bodily variable may be based on, or derived from, one or more combinations of one or more bodily variables or other bodily variables and the like. For example it is appreciated that bodily variables measured at a neurological level, biomarker level, cellular level, and/or tissue level, could combine to form bodily variables observed at a whole system state level such as regarding the vital signs of a subject; physiological meta data of a subject; sensor data representative of one or more bodily variables describing something about the body, parts of the body, or whole body of the subject; state, motion, or output of the body, part of subpart of the body of a subject and the like; modifications thereof, and/or combinations thereof and/or as herein described. Hence it is appreciated that, one or more bodily variables described at one or more higher levels of granularity may be based on a combination of one or more bodily variables described at one or more lower levels of granularity.

Although it is possible to tap into the one or more neuronal population(s) thereby effecting a direct linkage to the nervous system of a subject, there have been problems in capturing and interpreting bodily variable(s) from the neural activity generated by the neuronal population(s) and/or providing or applying neural stimulus signal(s) in order to evoke targeted responses in the form of neural activity in neuronal populations which is equivalent to or directly representing a bodily variable from device(s) to the nervous system of the subject. The bodily variable(s) may be naturally represented by neural activity associated with extremely short electrical pulses from multiple neurons. The neural activity may be received by one or more neural receivers adjacent one or more neurons or neuronal population(s) as neurological signals. These neurological signals may be sampled in which the neurological signal sampling typically provides an information rich dataset that is inordinately large, unwieldy to process, and is usually subject/experiment specific. This has led to attempts at understanding neurological signal(s) by extracting several key features thought to be representative of its information content such as bodily variable(s) encoded as neural activity.

For example, one example of neurological signal sampling is energy signal classification, which uses spike sorting to distinguish spikes in the neurological signal(s) received from different neurons. This is considered too computationally expensive in live analysis or real-time situations. Another method may be to look at the neural activity as an electrical signal and reduce this electrical signal to a basic/reduced set of features such as, by way of example only but not limited to: mean weighted power, power over certain frequency bands, max-mean amplitude of the signal; and so on. Once the neural activity has been reduced to several simple features or measurements, a decision may be made based on the state of these features. However, this results in a loss of information associated with the one or more bodily variable(s) encoded in the neural activity. Such systems or techniques are not sufficient for use in most advanced applications such as, by way of example only but not limited to, closed/open loop control via a device or apparatus of one or more body parts/portions (e.g. muscles, organs and/or cells) of the body of a subject.

There is a desire for an efficient mechanism capable of capturing and/or interpreting bodily variable(s) encoded as neural activity and for providing an accurate estimate of one or more bodily variable(s) to any device performing advanced open or closed loop control, monitoring and/or any other operation associated with one or more bodily functions, one or more body parts and/or portions of the body of a subject. There is a further desire for an efficient mechanism capable of capturing and/or interpreting bodily variable signal(s) produced by any device performing advanced open or closed loop control, monitoring and/or any other operations associated with one or more body parts or portions of the body of a subject and for providing a corresponding stimulus to the nervous system of the subject associated with the bodily variable signal(s).

The embodiments described below are not limited to implementations which solve any or all of the disadvantages of the known approaches described above.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter; variants and alternative features which facilitate the working of the invention and/or serve to achieve a substantially similar technical effect should be considered as falling into the scope of the invention disclosed herein.

The present disclosure provides methods and apparatus for a neural interface that receives one or more neurological signals representative of neural activity of part of the nervous system of a subject. The neural interface processes the neurological signals using one or more of a combination of machine learning (ML) technique(s) trained to determine an output data representation of an estimate of the bodily variable(s) associated with the neural activity represented by the neurological signals. The output data representation of the bodily variable estimate(s) is a reflection of the desired end effect or state that was transmitted, by way of example only but not limited to, by the CNS as neural activity encoding one or more bodily variables. The ML technique(s) enable the neural interface to decipher and/or understand the one or more bodily variable(s) and, where necessary, use or send a data representation of bodily variable estimate(s) in an efficient fashion to a device. The device may be for, by way of example only but is not limited to, controlling or operating a prosthetic or bionic limb or prosthetic device, or controlling, operating or modifying organ function or a bodily function of the subject or any other suitable device etc.

The present disclosure provides method(s) and apparatus for inserting ML technique(s) in-between a device delivering some care or assistance to the body of a subject (e.g. apparatus providing motion, controlling, operating and/or monitoring body parts/portions or organs of the subject) and the nervous system of the body of a subject. The methods and apparatus receive neurological signals associated with neural activity, the neural activity encoding a bodily variable, from one or more neuronal populations or clusters of neurons, and apply ML technique(s) trained on determining and/or estimating a rich informational and/or efficient data representation of the bodily variable based on the received neurological signals. The estimated bodily variable may be labelled or classified. A data representation of the bodily variable estimate and/or its classification/labelling may be sent to one or more device(s) or apparatus delivering some care or assistance to the body of the subject.

In addition, the present disclosure provides methods and apparatus for operating on bodily variable signal(s) generated by one or more device(s) or apparatus. The bodily variable signal(s) may be received from the one or more device(s) or apparatus in which one or more ML technique(s) trained or configured to determine a suitable neural stimulus signal based on the received bodily variable signal(s) that is transmitted to one or more neural transmitter(s). The neural transmitter(s) may apply the neural stimulus signal to a cluster of neurons or a neuronal population to generate neural activity associated the bodily variable signal(s).

The methods, apparatus and systems of the present disclosure provide an efficient mechanism capable of capturing and/or interpreting neurological signals associated with neural activity of one or more neurons, in which the neural activity encodes one or more bodily variable, and for providing, using one or more ML technique(s), an accurate estimate or data representation of the bodily variable(s) to any device or apparatus performing advanced open or closed loop control, monitoring and/or operations associated with one or more bodily functions, one or more body parts or portions of a subject. Furthermore, methods, apparatus and systems of the present disclosure further provide an efficient mechanism capable of capturing and/or interpreting bodily variable signal(s) generated from any device or apparatus performing advanced open or closed loop control, monitoring and/or operations associated with one or more bodily functions, one or more body parts or portions of a subject and, using one or more ML techniques, for determining a neural stimulus signal or neural stimulus associated with the bodily variable signal(s) for application to the nervous system of the subject. The present disclosure enables closed loop control of a bodily function, a body part/portion of the subject and/or control and operation of devices and apparatus associated with a bodily function, a body part/portion of the subject.

In a first aspect, the present disclosure provides a computer implemented method for interfacing with a nervous system of a subject, the method comprising: in response to receiving a plurality of neurological signals associated with the neural activity of the first portion of nervous system, performing the steps of: processing neural sample data representative of the received plurality of neurological signals using a first one or more machine learning (ML) technique(s) trained for generating estimates of neural data representative of the neural activity of the first portion of nervous system; and transmitting data representative of the neural data estimates to a first device associated with the first portion of nervous system; and in response to receiving device data from a second device associated with a second portion of the nervous system, performing the steps of: generating one or more neurological stimulus signal(s) by inputting the received device data to a second one or more ML technique(s) trained for estimating one or more neurological stimulus signal(s) associated with the device data for input to the second portion of nervous system; and transmitting the one or more estimated neurological stimulus signal(s) towards the second portion of nervous system of the subject.

Preferably, the estimates of neural data representative of neural activity as generated or calculated by at least one of the ML techniques are associated with one or more bodily variables.

Preferably, the computer implemented method further comprising: receiving at least one set of performance data associated with the first one or more ML technique(s) or the second one or more ML technique(s); evaluating the set of performance data to determine whether to retrain the first one or more ML technique(s) or the second one or more ML technique(s); and retraining the first one or more ML technique(s) in response to determining to retrain the first one or more ML technique(s) or the second one or more ML.

Preferably, the computer implemented method further comprising: transmitting data representative of the neural data estimates to a first device associated with the first portion of nervous system; or transmitting the one or more estimated neurological stimulus signal(s) towards the second portion of nervous system of the subject.

Preferably, the computer implemented method wherein the first portion of the nervous system comprises a first plurality of neurons of the subject clustered around multiple neural receivers, each neural receiver configured for outputting neurological signals associated with neural activity on one or more of the plurality of neurons, the method comprising: receiving one or more neurological signals from the neural receivers associated with the plurality of neurons of the subject; and classifying the one or more neurological signals into one or more categories of neural data using at least one of the first one or more ML technique(s).

Preferably, the computer implemented method further comprising generating neural sample data representative of the neurological signals by capturing samples of the neurological signals when neural activity is detected; and processing the neural sample data using at least one of the first one or more ML technique(s) to generate neural data representative of neural information associated with the neural activity.

Preferably, the computer implemented method further comprising generating a training set of neural sample data by: storing captured neural sample data received from the plurality of neurological signals, wherein the neural sample data is timestamped; capturing and storing sensor data from one or more sensors trained on the subject, wherein the sensor data is timestamped; synchronising the neural sample data with the sensor data; and identifying portions of the neural sample data associated with neural activity; determining neural data labels for each identified portion of neural sample data by analysing portions of the sensor data corresponding to the identified portion of neural sample data; labelling the identified portions of neural sample data based on the determined neural data labels; and storing the labelled identified portions of neural sample data as the training set of neural sample data.

Preferably, the computer implemented method further comprising analysing the detected portions of neural sample data using at least one of the first one or more ML technique(s) to generate a set of classification vectors associated with neural data contained within detected portions of neural sample data; and labelling the classification vectors with neural data labels determined from corresponding portions of the neural sample data and sensor data.

Preferably, the computer implemented method further comprising training at least one of the first one or more ML technique(s) based on a training set of neural sample data, wherein each neural sample data in the training set is labelled associated with a neural data label identifying the neural data contained therein.

Preferably, the computer implemented method wherein at least one of the first one or more ML technique(s) comprise at least one or more ML technique(s) or combinations thereof from the group of: neural networks; Hidden Markov Models; Gaussian process dynamics models; autoencoder/decoder networks; adversarial/discriminator networks; convolutional neural networks; long short term memory neural networks; and any other ML or classifier/classification technique or combinations thereof suitable for operating on said received neurological signal(s).

Preferably, the computer implemented method wherein at least one of the first one or more ML technique(s) is based on a neural network autoencoder structure, the neural network autoencoder structure comprising an encoding network and a decoding network, the encoding network comprising one or more hidden layer(s) and the decoding network comprising one or more hidden layer(s), wherein the neural network autoencoder is trained to output a neural data label vector that is capable of classifying each portion of neural sample data from a training set of neural sample data into one or more neural data labels, the method comprising: inputting neural sample data to the autoencoder for real-time classification of neurological signals.

Preferably, the computer implemented method further comprising training the neural network autoencoder for outputting a neural data label vector that is capable of classifying each portion of neural sample data from a training set of neural sample data into one or more neural data labels; and using the trained weights of the hidden layer(s) of the autoencoder for real-time classification of neurological signals.

Preferably, the computer implemented method wherein the neural network autoencoding structure further comprises: a latent representation layer for outputting a label vector, y, for classifying each portion of neural sample data from the training set of neural sample data, wherein the number of elements of the label vector, y, corresponds to a number of neural data categories to be labelled; and an adversarial network coupled to the latent representation layer of the neural network autoencoder, the adversarial network comprising an input layer, one or more hidden layer(s), and an output layer, the method further comprising: training the adversarial network to distinguish between label vectors, y, generated by the latent representation layer and samples from a categorical distribution of a set of one hot vectors of the same dimension as the label vector, y.

Preferably, the computer implemented method wherein the training set of neural sample data comprises a training set of neurological sample vector sequences $\{(x_i)^k\}_{k=1}^T$, where $1 \leq i \leq L_k$ and $1 \leq k \leq T$, in which $L_k$ is the length of the k-th neurological sample vector sequence and T is the number of training neurological sample vector sequences, for each k-th neurological sample vector sequence corresponding to a k-th neural activity that is passed through the autoencoder, the method further comprising: generating a loss or cost function based on the output of the adversarial network, an estimate of k-th neurological sample vector sequence represented as $(\hat{x}_i)^k$ output from the decoding network, the original k-th neurological sample vector sequence $(x_i)^k$, and a latent vector z and label vector y output from the latent representation layer; and updating the weights of the hidden layer(s) using backpropagation through time techniques.

Preferably, the computer implemented method wherein the neural network autoencoding structure further comprises: a latent representation layer for outputting a latent vector, z, representing each input portion of neural sample data in a latent space; and a further adversarial network coupled to the latent representation layer of the neural network autoencoder, the further adversarial network comprising an input layer, one or more hidden layer(s), and an output layer, the method further comprising: training the further adversarial network to distinguish between latent vectors, z, generated by the latent representation layer and sample vectors from a probability distribution (e.g. normal distribution) and of the same dimension as the latent vector, z.

Preferably, the computer implemented method wherein each of the plurality of neurological signals is output from a neural receiver coupled to the neural interface apparatus, and each neural receiver comprises any one or more neural receiver(s) from the group of: an electrode capable of measuring or receiving a neural activity from a neuronal population; an optogenetic sensor; and any apparatus, mechanism, sensor or device capable of detecting and measuring a neural activity from a neuronal population of the nervous system of a subject and outputting a neurological signal representative of the neural activity.

Preferably, the computer-implemented method wherein the neural receiver(s) are located in the vicinity of one or more nerve(s). Additionally, the neural receiver(s) form a neural receiver-nerve construct. Preferably, the neural receiver(s) are located to protect or isolate the neural receiver-nerve construct. Preferably, the computer implemented method wherein the neural receiver(s) may be located adjacent to one or more nerve(s) and may be placed, located, or sheathed in such a way as the neural receiver-nerve construct is protected or isolated from, by way of example only but is not limited to, one or more from the group of: external forces, motion, surrounding signals and/or noise signals and the like.

Preferably, the computer implemented method, wherein the protection or isolation of the neural receiver-nerve construct is achieved by biological tissues, by way of example only but not limited to, at least one from the group of: inside bone, under periosteum, in muscle, or any other part of the subject and the like and/or as the application demands. Additionally or alternatively, as an option, the protection or isolation of the neural receiver-nerve construct is achieved inside engineered materials and/or using engineered materials, by way of example only but not limited to, at least one from the group of: inside, on or under a metal implant, plastic implant and/or any other substructure created for the purpose, and/or as the application demands. Additionally or alternatively, as an option, the engineered materials and/or substructure created may include, by way of example only but is not limited to, solid implant materials or biological or non-biological glues, resins and/or other materials that may be deployed around the neural receiver-nerve construct and/or the like, and/or as the application demands. Additionally or alternatively, as an option, other materials that can be deployed around the neural receiver-nerve construct may include, by way of example only but is not limited to, at least one from the group of: tisseal (or other fibrinogen based glues and sealants), silicon, cyanoacrylate, or otherwise and the like, and/or as the application demands.

Preferably, the computer implemented method further comprising tracking the state of the neural interface over a time interval to determine any variation in the plurality of neurological signals associated with the same one or more neural data or neural data labels at the start of the time interval; and updating the ML technique(s) to take into account any variation in the plurality of neurological signals detected.

Preferably, the computer implemented method further comprising monitoring a first variation in a state of one or more clusters of neurons of the plurality of neurons over time based on capturing short term variability in neural activity associated with the clusters of neurons; monitoring a second variation in a state of one or more clusters of neurons of the plurality of neurons over time based on capturing long term variability in neural activity associated with the clusters of neurons; and sending a notification based on the first or second variations in neural activity.

Preferably, the computer implemented method further comprising employing one or more external computing system(s) for performing one or more from the group of: storing and/or processing neural signal data associated with neurological signals received from the nervous system of the subject; storing and/or processing sensor data associated with one or more sensors trained on the subject; generating one or more training sets of neural sample data based on the neural signal data and/or the sensor data; training one or more ML technique(s) based on the neural sample data, stored neural signal data; and/or transmitting data representative of one or more trained ML techniques for use in processing the neural sample data.

Preferably, the computer implemented method wherein the second portion of the nervous system comprises a second plurality of neurons of the subject clustered around one or more neural transmitters, the one or more neural transmitters for receiving one or more neurological stimulus signals for input to said cluster of neurons, the method further comprising: receiving device data from the second device, the second device for managing the operation of a portion of a body of the subject; generating one or more neurological stimulus signal(s) by inputting the received device data to at least one of the second one or more machine learning (ML) technique(s) trained for estimating one or more neurological stimulus signal(s) for input to the nervous system; and transmitting the one or more estimated neurological stimulus signal(s) to a neural transmitter coupled to the second portion of nervous system associated with the portion of the body.

Preferably, the computer implemented method wherein the neurological stimulus signal comprises one or more from the group of: a) an excitatory signal capable of exciting neural activity of a neuronal population local to a neural transmitter; or b) an inhibitory signal capable of inhibiting neural activity of a neuronal population local to a neural transmitter.

Preferably, the computer implemented method further comprising receiving one or more neurological signals associated with a neural stimulus from one or more neural receivers, wherein one or more neurons clustered around the one or more neural receivers receive the neural stimulus; generating neural stimulus sample data representative of the received neurological signals by capturing samples of the neurological signals when neural activity associated with the neural stimulus is detected; and processing the neural sample data using at least one of the second one or more ML technique(s) to generate a training set of neural stimulus data.

Preferably, the computer implemented method further comprising training at least one of the second one or more ML technique(s) on a training set of neural stimulus sample data, wherein each neural stimulus sample data in the set is labelled based on neural activity associated with a neural stimulus.

Preferably, the computer implemented method further comprising generating a training set of neural stimulus sample data by: storing captured neural stimulus sample data received from the plurality of neurological signals, wherein the neural stimulus sample data is timestamped; capturing and storing sensor data from one or more sensors trained on the subject, wherein the sensor data is timestamped; synchronising the neural stimulus sample data with the sensor data; and identifying portions of the neural stimulus sample data associated with neural activity associated with neural stimuli; determining neural stimulus labels for each identified portion of neural stimulus sample data by analysing portions of the sensor data corresponding to the identified portion of neural stimulus sample data; labelling the identified portions of neural stimulus sample data based on the determined neural stimulus labels; and storing the labelled identified portions of neural stimulus sample data as the training set of neural stimulus sample data.

Preferably, the computer implemented method further comprising analysing the detected portions of neural stimulus sample data using at least one of the second one or more ML technique(s) to generate a set of classification vectors associated with associated with neural stimuli and contained within detected portions of neural stimulus sample data; and labelling the classification vectors with neural stimulus labels determined from corresponding portions of the neural stimulus sample data and sensor data.

Preferably, the computer implemented method wherein at least one of the second one or more ML technique(s) comprise at least one or more ML technique(s) or combinations thereof from the group of: neural networks; Hidden Markov Models; Gaussian process dynamics models; autoencoder/decoder networks; adversarial/discriminator networks; convolutional neural networks; long short term memory neural networks; any other ML or classifier/classification technique or combinations thereof suitable for operating on said received neurological signal(s).

Preferably, the computer implemented method wherein at least one of the second one or more ML technique(s) is based on a neural network autoencoder structure, the neural network autoencoder structure comprising an encoding network and a decoding network, the encoding network comprising one or more hidden layer(s) and the decoding network comprising one or more hidden layer(s), wherein the decoding network of the neural network autoencoder is trained to generate data representative of a neurological stimulus signal based on inputting a neural stimulus label vector to the decoding network, the method comprising: selecting a neural stimulus label vector associated with device data received from the second device; and inputting the selected neural stimulus label vector to the decoding network for generating data representative of a neurological stimulus signal associated with the neural stimulus label vector.

Preferably, the computer implemented method further comprising training the neural network autoencoder for outputting a neural stimulus label vector that is capable of classifying each portion of neural stimulus sample data from a training set of neural stimulus sample data into one or more neural stimulus labels; and using the trained weights of the hidden layer(s) of the decoding network for real-time generation of neurological stimulus signals given input of a device data from the second device.

Preferably, the computer implemented method wherein the neural network autoencoding structure further comprises: a latent representation layer for outputting a label vector, y, for classifying each portion of neural stimulus sample data from the training set of neural stimulus sample data, wherein the number of elements of the label vector, y, corresponds to a number of neural stimulus categories to be labelled; and an adversarial network coupled to the latent representation layer of the neural network autoencoder, the adversarial network comprising an input layer, one or more hidden layer(s), and an output layer, the method further comprising: training the adversarial network to distinguish between label vectors, y, generated by the latent representation layer and samples from a categorical distribution of a set of one hot vectors of the same dimension as the label vector, y.

Preferably, the computer implemented method wherein the training set of neural stimulus sample data comprises a training set of neurological stimulus sample vector sequences $\{(x_i)^k\}_{k=1}^{T}$, where $1 \leq i \leq L_k$ and $1 \leq k \leq T$, in which $L_k$ is the length of the k-th neurological stimulus sample vector sequence and T is the number of training neurological stimulus sample vector sequences, for each k-th neurological stimulus sample vector sequence corresponding to a k-th neural activity associated with a k-th neural stimulus that is passed through the autoencoder, the method further comprising: generating a loss or cost function based on the output of the adversarial network, an estimate of k-th neurological stimulus sample vector sequence represented as $(\hat{x}_i)^k$ output from the decoding network, the original k-th neurological sample vector sequence $(x_i)^k$, and a latent vector z and label vector y output from the latent representation layer; and updating the weights of the hidden layer(s) using backpropagation through time techniques.

Preferably, the computer implemented method wherein the neural network autoencoding structure further comprises: a latent representation layer for outputting a latent vector, z, representing each input portion of neural stimulus sample data in a latent space; and a further adversarial network coupled to the latent representation layer of the neural network autoencoder, the further adversarial network comprising an input layer, one or more hidden layer(s), and an output layer, the method further comprising: training the further adversarial network to distinguish between latent vectors, z, generated by the latent representation layer and sample vectors from a probability distribution (e.g. normal distribution) and of the same dimension as the latent vector, z.

Preferably, the computer implemented method wherein each of the plurality of neurological signals associated with a neural stimulus is output from a neural receiver coupled to the nervous system of a subject, and each neural receiver comprises any one or more neural receiver(s) from the group of: an electrode capable of measuring or receiving neural activity associated with a neural stimulus of a neuronal population; an optogenetic sensor; and any apparatus, mechanism, sensor or device capable of detecting and measuring neural activity associated with a neural stimulus of a neuronal population of the nervous system of a subject and outputting a neurological signal representative of the neural activity.

Preferably, the computer-implemented method wherein the neural receiver(s) are located in the vicinity of one or more nerve(s). Additionally, the neural receiver(s) form a neural receiver-nerve construct. Preferably, the neural receiver(s) are located to protect or isolate the neural receiver-nerve construct. Preferably, the computer implemented method wherein the neural receiver(s) may be located adjacent to one or more nerve(s) and may be placed, located, or sheathed in such a way as the neural receiver-nerve construct is protected or isolated from, by way of example only but is not limited to, one or more from the group of: external forces, motion, surrounding signals and/or noise signals and the like.

Preferably, the computer implemented method, wherein the protection or isolation of the neural receiver-nerve construct is achieved by biological tissues, by way of example only but not limited to, at least one from the group of: inside bone, under periosteum, in muscle, or any other part of the subject and the like and/or as the application demands. Additionally or alternatively, as an option, the protection or isolation of the neural receiver-nerve construct is achieved inside engineered materials and/or using engineered materials, by way of example only but not limited to, at least one from the group of: inside, on or under a metal implant, plastic implant and/or any other substructure created for the purpose, and/or as the application demands. Additionally or alternatively, as an option, the engineered materials and/or substructure created may include, by way of example only but is not limited to, solid implant materials or biological or non-biological glues, resins and/or other materials that may be deployed around the neural receiver-nerve construct and/or the like, and/or as the application demands. Additionally or alternatively, as an option, other materials that can be deployed around the neural receiver-nerve construct may include, by way of example only but is not limited to, at least one from the group of: tisseal (or other fibrinogen based glues and sealants), silicon, cyanoacrylate, or otherwise and the like, and/or as the application demands.

Preferably, the computer implemented method wherein the data representative of a neurological stimulus signal associated with device data received from a second device is transmitted to a neural transmitter coupled to the nervous system of a subject, and each neural transmitter comprises any one or more neural transmitter(s) from the group of: an electrode capable of injecting or transmitting neural activity associated with the data representative of the neurological stimulus signal onto a neuronal population associated with the neurological stimulus signal; an optogenetic sensor; and any apparatus, mechanism, sensor or device capable of coupling neural activity associated with data representative of the neurological stimulus signal to a neuronal population of the nervous system of a subject.

Preferably, the computer implemented method further comprising employing one or more external computing system(s) for performing one or more from the group of: storing and/or processing neural stimulus signal data associated with neurological signals associated with neural stimulus received from the nervous system of the subject; storing and/or processing sensor data associated with one or more sensors trained on the subject; generating one or more training sets of neural stimulus sample data based on the neural stimulus signal data and/or the sensor data; training at least one of the second one or more ML technique(s) based on the neural stimulus sample data; and/or transmitting data representative of one or more trained ML techniques for use in processing the neural stimulus sample data.

Preferably, the computer implemented method wherein the first device or second device may include one or more devices or apparatus from the group of: a prosthetic device or apparatus capable of receiving neural data estimates and operating accordingly and/or capable of transmitting device data for providing corresponding neural stimulus to the subject; a non-prosthetic device or apparatus capable of receiving neural data estimates and operating accordingly and/or capable of transmitting device data for providing corresponding neural stimulus to the subject; a device or apparatus for managing or assisting with the operation or function of any one or more of a number of different organs, tissues, biological sites and/or sub-systems in the body of a subject; a device or apparatus for managing or assisting with the operation or function of any one or more of a number of body parts of the body of a subject; any device or apparatus capable of operating on neural data estimates as the application demands; and any device or apparatus capable of generating and/or transmitting device data for providing corresponding neural stimulus to the subject as the application demands.

Preferably, the computer implemented method wherein the first device is the second device. Preferably, the computer implemented method wherein: at least one of the first one or more ML technique(s) correspond to at least one of the second one or more ML technique(s); or the first one or more ML technique(s) correspond to the second one or more ML technique(s).

Preferably, the computer implemented method wherein device data comprises any one or more from the group of: Data representative of device action; Data representative of device motion; Data representative of device state; Data representative of operations being performed by a device including computation control or motion and used to generate a neural stimulus; Data representative of one or more bodily variable signal(s); and Data representative of any other device data suitable for generating a neural stimulus.

Preferably, the computer implemented method wherein neural activity encodes one or more bodily variables or combinations thereof, and estimates of neural data representative of the neural activity comprises estimates of the one or more bodily variables or combinations thereof associated with the neural activity.

Preferably, the computer implemented method, wherein neural activity encodes one or more bodily variables or combinations thereof.

Preferably, the computer implemented method, wherein a bodily variable comprises data representative of a state of the whole of a subject, a body part of the subject, or a sub-part of the subject.

Preferably, the computer implemented method, wherein a bodily variable includes at least one from the group of: heart rate of the subject; activity of the subject; temperature of the subject; blood glucose of the subject; blood pressure of the subject; any vital sign of the subject.

Preferably, the computer implemented method, wherein a bodily variable includes at least one from the group of, by way of example only but not limited to: any data representative of vital sign(s) of the subject including data representative of at least one from the group of: heart rate of the subject; activity of the subject; temperature of the subject; blood pressure of the subject; blood glucose of the subject; respiratory rate; any other vital sign of the subject; any physiological measurement of the whole of the subject, a body part of the subject, or a sub-part of the subject; any data representative of a state of the whole of a subject, a body part of the subject, or a sub-part of the subject; any data representative of information, values, parameters of the subject associated one or more genomic fields including at least one from the group of: epigenetics; phenotype; genotype; transcriptomics; proteomics; metabolomics; microbiomics; and any other term describing a number, state, metric, variable or information associated with the whole body of a subject, any part and/or subpart of the body of the subject and the like; equivalents thereof, modifications thereof, combinations thereof, as the application demands, any information associated with the body of a subject as the application demands; and/or as herein described.

Preferably, the computer implemented method, wherein one or more sensors comprise at least one sensor from the group of: ECG or heart rate sensor; Activity sensor; Temperature sensor; Blood Glucose sensor; Blood Pressure sensor; any sensor for outputting sensor data associated with one or more vital signs of the subject; any sensor for outputting sensor data associated with physiological measurement of the whole of the subject, a body part of the subject, or a sub-part of the subject; and any sensor for outputting sensor data associated with data representative of a state of the whole of a subject, a body part of the subject, or a sub-part of the subject; any other sensor capable of generating sensor data for deriving, calculating, determining or associated with data representative of one or more bodily variables; any sensor for outputting sensor data associated with data representative one or more number(s), state(s), metric(s), parameter(s), variable(s) and/or information associated with the whole body of a subject, any part and/or subpart of the body of the subject and the like.

Preferably, the computer implemented method, further comprising: generating neural sample data representative of the neurological signals by capturing samples of the neurological signals when neural activity is detected; and capturing sensor data from one or more sensors trained on the subject; synchronising portions of the neural sample data with corresponding portions of the sensor data; analysing and labelling the portions of the sensor data based on a set of bodily variable labels characterising changes in a bodily variable of interest; labelling the portions of the neural sample data based on the labelled portions of the sensor data; and generating a labelled training set of neural sample data associated with the bodily variable of interest based on the labelled portions of neural sample data.

Preferably, the computer implemented method, wherein generating the labelled training set of neural sample data further comprises storing the labelled portions of neural sample data as a labelled training set of neural sample data associated with the bodily variable of interest.

Preferably, the computer implemented method, further comprising: generating neural sample data representative of the neurological signals by capturing samples of the neurological signals when neural activity is detected; capturing sensor data from one or more sensors trained on the subject; synchronising portions of the neural sample data with one or more intermediary low dimensional representative states; synchronising intermediary states with corresponding portions of the sensor data; analysing and labelling the portions of the sensor data based on a set of bodily variable labels characterising changes in a bodily variable of interest; labelling the portions of the neural sample data based on the labelled portions of the sensor data; and generating a labelled training set of neural sample data associated with the bodily variable of interest based on the labelled portions of neural sample data.

Preferably, the computer implemented method, wherein generating the labelled training set of neural sample data further comprises storing the labelled portions of neural sample data as a labelled training set of neural sample data associated with the bodily variable of interest.

Preferably, the computer implemented method, wherein the one or more low dimensional representative states are generated by: training an ML technique to generate an ML model for determining a low dimensional latent space representative of the neurological signals; and generating one or more intermediary low dimensional representative states based on associating the dimensions of the determined low dimensional latent space with one or more bodily variable labels.

The computer implemented method, wherein the one or more low dimensional representative states may be generated by: training an ML technique to generate an ML model for determining a low dimensional latent space representative of the neurological signals using an unsupervised or semi-supervised techniques; and generating one or more intermediary low dimensional representative states based on associating the dimensions of the determined low dimensional latent space with one or more bodily variable labels. Alternatively or additionally, the ML technique to generate the ML model for determining the low dimensional latent space representative of the neurological signals may be based on semi-supervised or supervised techniques that may use a labelled training dataset associated with one or more bodily variables representative of one or more bodily variables; and generating one or more intermediary low dimensional representative states based on associating the dimensions of the determined low dimensional latent space with one or more bodily variable labels.

Preferably, the computer implemented method, further comprising training a ML technique based on the generated labelled training set of neural sample data associated with the bodily variable of interest, wherein the ML technique generates a trained ML model for predicting bodily variable label estimates associated with the bodily variable of interest when neural sample data is input.

Preferably, the computer implemented method, wherein the first portion of the nervous system is the second portion of the nervous system.

Preferably, the computer implemented method wherein the neural transmitter is the neural receiver.

Preferably, the computer implemented method, wherein the Central Nervous System is the site which: a) the plurality of neurological signals is collected from; and/or b) the neural stimulus is applied.

Preferably, the computer implemented method wherein the Peripheral Nervous System is the site which: a) the plurality of neurological signals is collected from; and/or b) the neural stimulus is applied.

In a second aspect, the present disclosure provides a computer implemented method of evaluating performance of a machine learning (ML) technique for interfacing with a nervous system of a subject, the method comprising: in response to receiving a plurality of neurological signals associated with the neural activity of a first portion of nervous system, performing the steps of: selecting a first ML technique from a first one or more ML technique(s) associated with processing neural sample data representative of the plurality of neurological signals for generating estimates of neural data representative of neural activity of the first portion of nervous system; receiving a first set of performance data associated with the first selected ML technique, the first set of performance data including the neural sample data and the generated estimates of neural data; evaluating a first cost function based on the first set of performance data to determine whether to retrain the first selected ML technique; retraining the first selected ML technique in response to determining to retrain the first selected ML technique; in response to receiving device data from a device associated with a second portion of the nervous system, performing the steps of: selecting a second ML technique from a second one or more ML technique(s) associated with processing the received device data for estimating one or more neurological stimulus signal(s) associated with the device data for input to the second portion of the nervous system; receiving a second set of performance data associated with the selected ML technique, the set of performance data including the received device data and the estimated one or more neurological stimulus signal(s); evaluating a second cost function based on the second set of performance data to determine whether to retrain the second selected ML technique; and retraining the second selected ML technique in response to determining to retrain the second selected ML technique.

Preferably, the second aspect of the invention further includes one or more of the features and/or steps associated with the computer implemented method according to the first aspect of the invention as described herein.

In a third aspect, the present disclosure provides a computer implemented method for determining neural activity of a portion of a nervous system of a subject, the method comprising: receiving a plurality of neurological signals associated with the neural activity of the portion of the nervous system; and processing neural sample data representative of the received plurality of neurological signals using one or more machine learning (ML) technique(s) trained for generating estimates of neural activity or combinations thereof associated with the neural activity of the portion of nervous system; and transmitting data representative of the neural activity estimates to a device for performing operations based on the neural activity estimate(s).

Preferably, the computer implemented method further comprising receiving, from an external computing system, one or more data representative of corresponding one or more trained ML technique(s); storing the received data representative of a trained ML technique; selecting and retrieving data representative of a trained ML technique for generating estimates of neural activity or combinations thereof associated with the neural activity of the portion of nervous system.

Preferably, the computer implemented method wherein the neural activity comprises neural activity encoding one or more bodily variable(s) of the portion of the nervous system of the subject, the method further comprising: processing neural sample data representative of the received plurality of neurological signals using one or more machine learning (ML) technique(s) trained for generating estimates of one or more bodily variables or combinations thereof associated with the neural activity of the portion of nervous system; and transmitting data representative of the one or more bodily variable estimates to a device for performing operations based on the bodily variable estimate(s).

Preferably, the computer implemented method wherein the portion of the nervous system comprises a plurality of neurons of the subject clustered around multiple neural receivers, each neural receiver configured for outputting neurological signals associated with neural activity on one or more of the plurality of neurons, the method comprising: receiving one or more neurological signals from the neural receivers associated with the plurality of neurons of the subject; and classifying the one or more neurological signals into one or more categories of bodily variable(s) using the one or more ML technique(s).

Preferably, the computer implemented method further comprising: generating neural sample data representative of the neurological signals by capturing samples of the neurological signals when neural activity encoding one or more bodily variable(s) is detected; and processing the neural sample data using the one or more ML technique(s) to generate data representative of bodily variable estimates.

Preferably, the computer implemented method further comprising generating a training set of neural sample data by: storing captured neural sample data received from the plurality of neurological signals, wherein the neural sample data is timestamped; capturing and storing sensor data from one or more sensors trained on the subject, wherein the sensor data is timestamped; synchronising the neural sample data with the sensor data; and identifying portions of the neural sample data associated with neural activity encoding one or more bodily variable(s); determining bodily variable labels for each identified portion of neural sample data by analysing portions of the sensor data corresponding to the identified portion of neural sample data; labelling the identified portions of neural sample data based on the determined bodily variable labels; and generating a labelled training set of neural sample data associated with the bodily variable of interest based on the labelled identified portions of neural sample data.

Preferably, the computer implemented method, wherein generating the labelled training set of neural sample data further comprises storing the labelled identified portions of neural sample data as the labelled training set of neural sample data.

Preferably, the computer implemented method further comprising analysing the detected portions of neural sample data using one or more ML technique(s) to generate a set of classification vectors associated with one or more bodily variable(s) or combinations thereof contained within detected portions of neural sample data; and labelling the classification vectors with bodily variable labels determined from corresponding portions of the neural sample data and sensor data.

Preferably, the computer implemented method further comprising training one or more ML technique(s) based on a training set of neural sample data, wherein each neural sample data in the training set is labelled associated with a bodily variable label identifying the one or more bodily variables contained therein.

Preferably, the computer implemented method wherein the one or more ML technique(s) comprise at least one or more ML technique(s) from the group of: neural networks; Hidden Markov Models; Gaussian process dynamics models; autoencoder/decoder networks; adversarial/discriminator networks; convolutional neural networks; and long short term memory neural networks; any other ML or classifier/classification technique or combinations thereof suitable for operating on said received neurological signal(s).

Preferably, the computer implemented method, wherein neural activity encodes one or more bodily variables or combinations thereof.

Preferably, the computer implemented method, wherein a bodily variable comprises data representative of a state of the whole of a subject, a body part of the subject, or a sub-part of the subject.

Preferably, the computer implemented method, wherein a bodily variable includes at least one from the group of: heart rate of the subject; activity of the subject; temperature of the subject; blood glucose of the subject; blood pressure of the subject; any vital sign of the subject; any physiological measurement of the whole of the subject, a body part of the subject, or a sub-part of the subject; and any data representative of a state of the whole of a subject, a body part of the subject, or a sub-part of the subject.

Preferably, the computer implemented method, wherein a bodily variable includes at least one from the group of, by way of example only but not limited to: any data representative of vital sign(s) of the subject including data representative of at least one from the group of: heart rate of the subject; activity of the subject; temperature of the subject; blood pressure of the subject; blood glucose of the subject; respiratory rate; any other vital sign of the subject; any physiological measurement of the whole of the subject, a body part of the subject, or a sub-part of the subject; any data representative of a state of the whole of a subject, a body part of the subject, or a sub-part of the subject; any data representative of information, values, parameters of the subject associated one or more genomic fields including at least one from the group of: epigenetics; phenotype; genotype; transcriptomics; proteomics; metabolomics; microbiomics; and any other term describing a number, state, metric, variable or information associated with the whole body of a subject, any part and/or subpart of the body of the subject and the like; equivalents thereof, modifications thereof, combinations thereof, as the application demands, any information associated with the body of a subject as the application demands; and/or as herein described.

Preferably, the computer implemented method, wherein one or more sensors comprise at least one sensor from the group of: ECG or heart rate sensor; Activity sensor; Temperature sensor; Blood Glucose sensor; Blood Pressure sensor; any sensor for outputting sensor data associated with one or more vital signs of the subject; any sensor for outputting sensor data associated with physiological measurement of the whole of the subject, a body part of the subject, or a sub-part of the subject; and any sensor for outputting sensor data associated with data representative of a state of the whole of a subject, a body part of the subject, or a sub-part of the subject; any sensor for outputting sensor data associated with data representative one or more number(s), state(s), metric(s), parameter(s), variable(s) and/or information associated with the whole body of a subject, any part and/or subpart of the body of the subject and the like.

Preferably, the computer implemented method, further comprising: generating neural sample data representative of the neurological signals by capturing samples of the neurological signals when neural activity is detected; and capturing sensor data from one or more sensors trained on the subject; synchronising portions of the neural sample data with corresponding portions of the sensor data; analysing and labelling the portions of the sensor data based on a set of bodily variable labels characterising changes in a bodily variable of interest; labelling the portions of the neural sample data based on the labelled portions of the sensor data; and generating a labelled training set of neural sample data associated with the bodily variable of interest based on the labelled portions of neural sample data.

Preferably, the computer implemented method, wherein generating the labelled training set of neural sample data further comprises storing the labelled portions of neural sample data as a labelled training set of neural sample data associated with the bodily variable of interest.

Preferably, the computer implemented method, further comprising: generating neural sample data representative of the neurological signals by capturing samples of the neurological signals when neural activity is detected; capturing sensor data from one or more sensors trained on the subject; synchronising portions of the neural sample data with one or more intermediary low dimensional representative states; synchronising intermediary states with corresponding portions of the sensor data; analysing and labelling the portions of the sensor data based on a set of bodily variable labels characterising changes in a bodily variable of interest; labelling the portions of the neural sample data based on the labelled portions of the sensor data; and generating a labelled training set of neural sample data associated with the bodily variable of interest based on the labelled portions of neural sample data.

Preferably, the computer implemented method, wherein generating the labelled training set of neural sample data further comprises storing the labelled portions of neural sample data as a labelled training set of neural sample data associated with the bodily variable of interest.

Preferably, the computer implemented method, wherein the one or more low dimensional representative states are generated by: training an ML technique to generate an ML model for determining a low dimensional latent space representative of the neurological signals; and generating one or more intermediary low dimensional representative states based on associating the dimensions of the determined low dimensional latent space with one or more bodily variable labels.

The computer implemented method, wherein the one or more low dimensional representative states may be generated by: training an ML technique to generate an ML model for determining a low dimensional latent space representative of the neurological signals using an unsupervised or semi-supervised techniques; and generating one or more intermediary low dimensional representative states based on associating the dimensions of the determined low dimensional latent space with one or more bodily variable labels. Alternatively or additionally, the ML technique to generate the ML model for determining the low dimensional latent space representative of the neurological signals may be based on semi-supervised or supervised techniques that may use a labelled training dataset associated with one or more bodily variables representative of one or more bodily variables; and generating one or more intermediary low dimensional representative states based on associating the dimensions of the determined low dimensional latent space with one or more bodily variable labels.

Preferably, the computer implemented method, further comprising training a ML technique based on the generated labelled training set of neural sample data associated with the bodily variable of interest, wherein the ML technique generates a trained ML model for predicting bodily variable label estimates associated with the bodily variable of interest when neural sample data is input.

Preferably, the computer implemented method wherein a ML technique is based on a neural network autoencoder structure, the neural network autoencoder structure comprising an encoding network and a decoding network, the encoding network comprising one or more hidden layer(s) and the decoding network comprising one or more hidden layer(s), wherein the neural network autoencoder is trained to output a bodily variable label vector that is capable of classifying each portion of neural sample data from a training set of neural sample data into one or more bodily variable labels, the method comprising: inputting neural sample data to the autoencoder for real-time classification of neurological signals.

Preferably, the computer implemented method further comprising: training the neural network autoencoder for outputting a bodily variable label vector that is capable of classifying each portion of neural sample data from a training set of neural sample data into one or more bodily variable labels; and using the trained weights of the hidden layer(s) of the autoencoder for real-time classification of neurological signals.

Preferably, the computer implemented method wherein the neural network autoencoding structure further comprises: a latent representation layer for outputting a label vector, y, for classifying each portion of neural sample data from the training set of neural sample data, wherein the number of elements of the label vector, y, corresponds to a number of bodily variable categories to be labelled; and an adversarial network coupled to the latent representation layer of the neural network autoencoder, the adversarial network comprising an input layer, one or more hidden layer(s), and an output layer, the method further comprising: training the adversarial network to distinguish between label vectors, y, generated by the latent representation layer and samples from a categorical distribution of a set of one hot vectors of the same dimension as the label vector, y.

Preferably, the computer implemented method wherein the training set of neural sample data comprises a training set of neurological sample vector sequences $\{(x_i)^k\}_{k=1}^{T}$, where $1 \leq i \leq L_k$ and $1 \leq k \leq T$, in which $L_k$ is the length of the k-th neurological sample vector sequence and T is the number of training neurological sample vector sequences, for each k-th neurological sample vector sequence corresponding to a k-th neural activity encoding one or more bodily variables that is passed through the autoencoder, the method further comprising: generating a loss or cost function based on the output of the adversarial network, an estimate of k-th neurological sample vector sequence represented as $(\hat{x}_i)^k$ output from the decoding network, the original k-th neurological sample vector sequence $(x_i)^k$, and a latent vector z and label vector y output from the latent representation layer; and updating the weights of the hidden layer(s) using backpropagation through time techniques.

Preferably, the computer implemented method wherein the neural network autoencoding structure further comprises: a latent representation layer for outputting a latent vector, z, representing each input portion of neural sample data in a latent space; and a further adversarial network coupled to the latent representation layer of the neural network autoencoder, the further adversarial network comprising an input layer, one or more hidden layer(s), and an output layer, the method further comprising: training the further adversarial network to distinguish between latent vectors, z, generated by the latent representation layer and sample vectors from a probability distribution (e.g. normal distribution) and of the same dimension as the latent vector, z.

Preferably, the computer implemented method wherein each of the plurality of neurological signals is output from a neural receiver coupled to the neural interface apparatus, and each neural receiver comprises any one or more neural receiver(s) from the group of: an electrode capable of measuring or receiving a neural activity encoding one or more bodily variables from a neuronal population; an optogenetic sensor; and any apparatus, mechanism, sensor or device capable of detecting and measuring a neural activity encoding one or more bodily variables from a neuronal population of the nervous system of a subject and outputting a neurological signal representative of the neural activity.

Preferably, the computer implemented method further comprising: tracking the state of the neural interface over a time interval to determine any variation in the plurality of neurological signals associated with the same one or more bodily variables at the start of the time interval; and updating the ML technique(s) to take into account any variation in the plurality of neurological signals detected.

Preferably, the computer implemented method further comprising: monitoring a first variation in a state of one or more clusters of neurons of the plurality of neurons over time based on capturing short term variability in neural activity associated with the clusters of neurons; monitoring a second variation in a state of one or more clusters of neurons of the plurality of neurons over time based on capturing long term variability in neural activity associated with the clusters of neurons; and sending a notification based on the first or second variations in neural activity.

Preferably, the computer implemented method further comprising employing one or more external computing system(s) for performing one or more from the group of: storing and/or processing neural signal data associated with neurological signals received from the nervous system of the subject; storing and/or processing sensor data associated with one or more sensors trained on the subject; generating one or more training sets of neural sample data based on the neural signal data and/or the sensor data; training one or more ML technique(s) based on the neural sample data, stored neural signal data; and/or transmitting data representative of one or more trained ML techniques for use in processing the neural sample data.

In a fourth aspect, the present disclosure provides a computer implemented method for stimulating a portion of a nervous system of a subject, the method comprising: receiving device data from a device managing the operation of a portion of a body of the subject; generating one or more neurological stimulus signal(s) by inputting the received device data o a machine learning (ML) technique trained for estimating one or more neurological stimulus signal(s) for input to the nervous system; and transmitting the one or more estimated neurological stimulus signal(s) to a neural transmitter coupled to the nervous system associated with the portion of the body.

Preferably, the computer implemented method wherein the portion of the nervous system comprises a plurality of neurons of the subject clustered around one or more neural transmitters, the one or more neural transmitters for receiving one or more neurological stimulus signals for input to said cluster of neurons.

Preferably, the computer implemented method further comprising receiving, from an external computing system, one or more data representative of corresponding one or more trained ML technique(s); storing the received data representative of a trained ML technique; selecting and retrieving data representative of a trained ML technique for estimating one or more neurological stimulus signal(s) for input to the nervous system.

Preferably, the computer implemented method wherein the neurological stimulus signal comprises one or more from the group of: a) an excitatory signal capable of exciting neural activity of a neuronal population local to a neural transmitter; or b) an inhibitory signal capable of inhibiting neural activity of a neuronal population local to a neural transmitter.

Preferably, the computer implemented method wherein neural activity comprises neural activity encoding one or more bodily variables and the device data comprises data representative of one or more bodily variable signal(s) generated by the device managing the operation of a portion of a body of the subject, the method further comprising: generating one or more neurological stimulus signal(s) by inputting data representative of the received one or more bodily variable signal(s) to a ML technique trained for estimating one or more neurological stimulus signal(s) for input to the nervous system; and transmitting the one or more estimated neurological stimulus signal(s) to a neural transmitter coupled to the nervous system associated with the portion of the body.

Preferably, the computer implemented method, wherein a bodily variable comprises data representative of a state of the whole of a subject, a body part of the subject, or a sub-part of the subject.

Preferably, the computer implemented method, wherein a bodily variable includes at least one from the group of: heart rate of the subject; activity of the subject; temperature of the subject; blood glucose of the subject; blood pressure of the subject; any vital sign of the subject; any physiological measurement of the whole of the subject, a body part of the subject, or a sub-part of the subject; and any data representative of a state of the whole of a subject, a body part of the subject, or a sub-part of the subject.

Preferably, the computer implemented method, wherein a bodily variable includes at least one from the group of, by way of example only but not limited to: any data representative of vital sign(s) of the subject including data representative of at least one from the group of: heart rate of the subject; activity of the subject; temperature of the subject; blood pressure of the subject; blood glucose of the subject; respiratory rate; any other vital sign of the subject; any physiological measurement of the whole of the subject, a body part of the subject, or a sub-part of the subject; any data representative of a state of the whole of a subject, a body part of the subject, or a sub-part of the subject; any data representative of information, values, parameters of the subject associated one or more genomic fields including at least one from the group of: epigenetics; phenotype; genotype; transcriptomics; proteomics; metabolomics; microbiomics; and any other term describing a number, state, metric, variable or information associated with the whole body of a subject, any part and/or subpart of the body of the subject and the like; equivalents thereof, modifications thereof, combinations thereof, as the application demands, any information associated with the body of a subject as the application demands; and/or as herein described.

Preferably, the computer implemented method further comprising: receiving one or more neurological signals associated with a neural stimulus from one or more neural receivers, wherein one or more neurons clustered around the one or more neural receivers receive the neural stimulus; generating neural stimulus sample data representative of the received neurological signals by capturing samples of the neurological signals when neural activity encoding one or more bodily variables associated with the neural stimulus is detected; and processing the neural sample data using the one or more ML technique(s) to generate a training set of neural stimulus data.

Preferably, the computer implemented method further comprising training a ML technique on a training set of neural stimulus sample data, wherein each neural stimulus sample data in the set is labelled based on neural activity encoding one or more bodily variables associated with a neural stimulus.

Preferably, the computer implemented method further comprising generating a training set of neural sample data by: storing captured neural stimulus sample data received from the plurality of neurological signals, wherein the neural stimulus sample data is timestamped; capturing and storing sensor data from one or more sensors trained on the subject, wherein the sensor data is timestamped; synchronising the neural stimulus sample data with the sensor data; and identifying portions of the neural stimulus sample data associated with neural activity encoding one or more bodily variable(s) associated with neural stimuli; determining bodily variable labels for each identified portion of neural stimulus sample data by analysing portions of the sensor data corresponding to the identified portion of neural stimulus sample data; labelling the identified portions of neural stimulus sample data based on the determined bodily variable labels; and generating a labelled training set of neural stimulus sample data associated with the bodily variable of interest based on the labelled identified portions of neural stimulus sample data.

Preferably, the computer implemented method, wherein generating the labelled training set of neural stimulus sample data further comprises storing the labelled identified portions of neural stimulus sample data as the training set of neural stimulus sample data.

Preferably, the computer implemented method further comprising analysing the detected portions of neural stimulus sample data using one or more ML technique(s) to generate a set of classification vectors associated with one or more bodily variable(s) or combinations thereof associated with neural stimuli and contained within detected portions of neural stimulus sample data; and labelling the classification vectors with bodily variable labels determined from corresponding portions of the neural stimulus sample data and sensor data.

Preferably, the computer implemented method wherein the one or more ML technique(s) comprise at least one or more ML technique(s) from the group of: neural networks; Hidden Markov Models; Gaussian process dynamics models; autoencoder/decoder networks; adversarial/discriminator networks; convolutional neural networks; long short term memory neural networks; and/or any other ML or classifier/classification technique or combinations thereof suitable for operating on said received neurological signal(s).

Preferably, the computer implemented method wherein a ML technique is based on a neural network autoencoder structure, the neural network autoencoder structure comprising an encoding network and a decoding network, the encoding network comprising one or more hidden layer(s) and the decoding network comprising one or more hidden layer(s), wherein the decoding network of the neural network autoencoder is trained to generate data representative of a neurological stimulus signal based on inputting a bodily variable label vector to the decoding network, the method comprising: selecting a bodily variable label vector associated with a bodily variable signal received from the device; and inputting the selected bodily variable label vector to the decoding network for generating data representative of a neurological stimulus signal associated with the bodily variable label vector.

Preferably, the computer implemented method further comprising: training the neural network autoencoder for outputting a bodily variable label vector that is capable of classifying each portion of neural stimulus sample data from a training set of neural stimulus sample data into one or more bodily variable labels; and using the trained weights of the hidden layer(s) of the decoding network for real-time generation of neurological stimulus signals given input of a bodily variable signal from the device.

Preferably, the computer implemented method wherein the neural network autoencoding structure further comprises: a latent representation layer for outputting a label vector, y, for classifying each portion of neural stimulus sample data from the training set of neural stimulus sample data, wherein the number of elements of the label vector, y, corresponds to a number of bodily variable categories to be labelled; and an adversarial network coupled to the latent representation layer of the neural network autoencoder, the adversarial network comprising an input layer, one or more hidden layer(s), and an output layer, the method further comprising: training the adversarial network to distinguish between label vectors, y, generated by the latent representation layer and samples from a categorical distribution of a set of one hot vectors of the same dimension as the label vector, y.

Preferably, the computer implemented method wherein the training set of neural stimulus sample data comprises a training set of neurological stimulus sample vector sequences $\{(x_i)^k\}_{k=1}^{T}$, where $1 \leq i \leq L_k$ and $1 \leq k \leq T$, in which $L_k$ is the length of the k-th neurological stimulus sample vector sequence and T is the number of training neurological stimulus sample vector sequences, for each k-th neurological stimulus sample vector sequence corresponding to a k-th neural activity encoding one or more bodily variable associated with a k-th neural stimulus that is passed through the autoencoder, the method further comprising: generating a loss or cost function based on the output of the adversarial network, an estimate of k-th neurological stimulus sample vector sequence represented as $(\hat{x}_i)^k$ output from the decoding network, the original k-th neurological sample vector sequence $(x_i)^k$, and a latent vector z and label vector y output from the latent representation layer; and updating the weights of the hidden layer(s) using backpropagation through time techniques.

Preferably, the computer implemented method wherein the neural network autoencoding structure further comprises: a latent representation layer for outputting a latent vector, z, representing each input portion of neural stimulus sample data in a latent space; and a further adversarial network coupled to the latent representation layer of the neural network autoencoder, the further adversarial network comprising an input layer, one or more hidden layer(s), and an output layer, the method further comprising: training the further adversarial network to distinguish between latent vectors, z, generated by the latent representation layer and sample vectors from a probability distribution (e.g. normal distribution) and of the same dimension as the latent vector, z.

Preferably, the computer implemented method wherein each of the plurality of neurological signals associated with a neural stimulus is output from a neural receiver coupled to the nervous system of a subject, and each neural receiver comprises any one or more neural receiver(s) from the group of: an electrode capable of measuring or receiving neural activity encoding one or more bodily variables associated with a stimulus from a neuronal population; an optogenetic sensor; any apparatus, mechanism, sensor or device capable of detecting and measuring neural activity encoding one or more bodily variables from a neuronal population of the nervous system of a subject and outputting a neurological signal representative of the neural activity; and any apparatus, mechanism, sensor or device capable of detecting and measuring neural activity encoding one or more bodily variables associated with a stimulus of a neuronal population of the nervous system of a subject and outputting a neurological signal representative of the neural activity.

Preferably, the computer implemented method wherein the data representative of a neurological stimulus signal associated with a bodily variable signal received from a device is transmitted to a neural transmitter coupled to the nervous system of a subject, and each neural transmitter comprises any one or more neural transmitter(s) from the group of: an electrode capable of injecting or transmitting neural activity associated with the data representative of the neurological stimulus signal onto a neuronal population associated with the neurological stimulus signal; an optogenetic sensor; and any apparatus, mechanism, sensor or device capable of coupling neural activity associated with data representative of the neurological stimulus signal to a neuronal population of the nervous system of a subject.

Preferably, the computer implemented method further comprising employing one or more external computing system(s) for performing one or more from the group of: storing and/or processing neural stimulus signal data associated with neurological signals associated with neural stimulus received from the nervous system of the subject;

storing and/or processing sensor data associated with one or more sensors trained on the subject; generating one or more training sets of neural stimulus sample data based on the neural stimulus signal data and/or the sensor data; training one or more ML technique(s) based on the neural stimulus sample data; and/or transmitting data representative of one or more trained ML techniques for use in processing the neural stimulus sample data.

Preferably, the computer implemented method wherein the device may include one or more devices or apparatus from the group of: a prosthetic device or apparatus capable of receiving estimates of neural data or bodily variable(s) and operating accordingly and/or capable of transmitting device data or bodily variable signal(s) for providing corresponding neural stimulus to the subject; a non-prosthetic device or apparatus capable of receiving estimates of neural data or bodily variable(s) and operating accordingly and/or capable of transmitting device data or bodily variable signal(s) for providing corresponding neural stimulus to the subject; a device or apparatus for managing or assisting with the operation or function of any one or more of a number of different organs, tissues, biological sites and/or sub-systems in the body of a subject; a device or apparatus for managing or assisting with the operation or function of any one or more of a number of body parts of the body of a subject; any device or apparatus capable of operating on estimates of neural data or bodily variable(s) as the application demands; and any device or apparatus capable of generating and/or transmitting device data or bodily variable signal(s) associated with providing corresponding neural stimulus to the subject as the application demands.

In a fifth aspect, the present disclosure provides an apparatus for interfacing with a nervous system of a subject, the apparatus comprising: a communications interface; a memory unit; and a processor unit, the processor unit connected to the communications interface and the memory unit, wherein: the communications interface is configured to receive a plurality of neurological signals associated with the neural activity of a first portion of nervous system; in response to receiving a plurality of neurological signals associated with the neural activity of the first portion of nervous system, the processor and communication interface are configured to: process neural sample data representative of the received plurality of neurological signals using a first one or more machine learning (ML) technique(s) trained for generating estimates of neural data representative of the neural activity of the first portion of nervous system; and transmit data representative of the neural data estimates to a first device associated with the first portion of nervous system; and the communications interface is further configured to receive device data from a second device associated with a second portion of the nervous system; and in response to receiving device data from the second device associated with the second portion of the nervous system, the processor and communication interface are further configured to: generate one or more neurological stimulus signal(s) by inputting the received device data to a second one or more ML technique(s) trained for estimating one or more neurological stimulus signal(s) associated with the device data for input to the second portion of nervous system; and transmit the one or more estimated neurological stimulus signal(s) towards the second portion of nervous system of the subject.

In a sixth aspect, the present disclosure provides an neural interface apparatus for coupling to a neural receiver connected to a portion of a nervous system of a subject, wherein the neural receiver is configured to receive a plurality of neurological signals associated a neural activity from the portion of the nervous system, the neural interface apparatus comprising: a communications interface; a memory unit; and a processor unit, the processor unit connected to the communications interface and the memory unit, wherein: the communications interface is configured to receive a plurality of neurological signals from the neural receiver; the processor and memory are configured to process neural sample data representative of the received plurality of neurological signals using one or more machine learning (ML) technique(s) trained for generating estimates of neural data associated with the neural activity of the portion of the nervous system; and the communications interface is further configured to transmit data representative of the neural data estimates to a device for performing operations based on the bodily variable estimate(s).

In a seventh aspect, the present disclosure provides neural interface apparatus for coupling to a neural transmitter connected to a portion of a nervous system of a subject, the neural interface apparatus comprising: a communications interface; a memory unit; and a processor unit, the processor unit connected to the communications interface and the memory unit, wherein: the communications interface is configured to receive device data from a device managing the operation of a portion of a body of the subject; and the processor and memory are configured to input the received device data to a machine learning (ML) technique trained for estimating one or more neurological stimulus signal(s) associated with the device data for input to the nervous system; and the communications interface is configured to transmit the one or more estimated neurological stimulus signal(s) to a neural transmitter coupled to the nervous system associated with the portion of the body.

In a eighth aspect, the present disclosure provides an apparatus for communicating with a neural interface, the apparatus comprising: a communications interface; a memory unit; and a processor unit, the processor unit connected to the communications interface and the memory unit, wherein: the communications interface is configured to receive neural sample data representative of a plurality of neurological signals form the neural interface; the processor and memory are configured to process the neural sample data using one or more machine learning (ML) technique(s) trained for generating estimates of one or more bodily variables or combinations thereof associated with neural activity of the portion of the nervous system; and the communications interface is further configured to transmit data representative of the one or more bodily variable estimates to the neural interface for transmission to a device configured for performing operations based on the bodily variable estimate(s).

In a ninth aspect, the present disclosure provides an apparatus for communicating with a neural interface, the apparatus comprising: a communications interface; a memory unit; and a processor unit, the processor unit connected to the communications interface and the memory unit, wherein: the communications interface is configured to receive, via the neural interface, one or more bodily variable signal(s) from a device managing the operation of a portion of a body of the subject; and the processor and memory are configured to input the received one or more bodily variable signal(s) to a machine learning (ML) technique trained for estimating one or more neurological stimulus signal(s) for input to the nervous system; and the communications interface is configured to transmit the one or more estimated neurological stimulus signal(s) to the neural interface for transmission onto the nervous system associated with the portion of the body.

In a tenth aspect, the present disclosure provides an apparatus comprising: a communications interface; a memory unit; and a processor unit, the processor unit connected to the communications interface and the memory unit, wherein the processor unit, storage unit, communications interface are configured to perform or implement the computer implement method of the first aspect of the invention.

Preferably, the tenth aspect of the invention further includes the processor unit, storage unit, communications interface are configured to perform or implement one or more of the further features and/or steps associated with the computer implemented method according to the first aspect of the invention as described herein.

In a eleventh aspect, the present disclosure provides an apparatus comprising: a communications interface; a memory unit; and a processor unit, the processor unit connected to the communications interface and the memory unit, wherein the processor unit, storage unit, communications interface are configured to perform or implement the computer implement method of the second aspect of the invention.

Preferably, the eleventh aspect of the invention further includes the processor unit, storage unit, communications interface are configured to perform or implement one or more of the further features and/or steps associated with the computer implemented method according to the first aspect of the invention as described herein.

In a twelfth aspect, the present disclosure provides an apparatus comprising: a communications interface; a memory unit; and a processor unit, the processor unit connected to the communications interface and the memory unit, wherein the processor unit, storage unit, communications interface are configured to perform or implement the computer implement method of the third aspect of the invention.

Preferably, the twelfth aspect of the invention further includes the processor unit, storage unit, communications interface are configured to perform or implement one or more of the further features and/or steps associated with the computer implemented method according to the third aspect of the invention as described herein.

In a thirteenth aspect, the present disclosure provides an apparatus comprising: a communications interface; a memory unit; and a processor unit, the processor unit connected to the communications interface and the memory unit, wherein the processor unit, storage unit, communications interface are configured to perform or implement the computer implement method of the fourth aspect of the invention.

Preferably, the thirteenth aspect of the invention further includes the processor unit, storage unit, communications interface are configured to perform or implement one or more of the further features and/or steps associated with the computer implemented method according to the fourth aspect of the invention as described herein.

In a fourteenth aspect of the invention, the present disclosure provides a computer readable medium comprising program code stored thereon, which when executed on a processor, causes the processor to perform a method according to any of the first aspect of the invention.

In a fifteenth aspect, the present disclosure provides a computer readable medium comprising program code stored thereon, which when executed on a processor, causes the processor to perform a method according to any of the second aspect of the invention.

In a sixteenth aspect of the invention, the present disclosure provides a computer readable medium comprising program code stored thereon, which when executed on a processor, causes the processor to perform a method according to any of the third aspect of the invention.

In a seventeenth aspect of the invention, the present disclosure provides a computer readable medium comprising program code stored thereon, which when executed on a processor, causes the processor to perform a method according to any of the fourth aspect of the invention.

In an eighteenth aspect of the invention, the present disclosure provides an apparatus of evaluating performance of a machine learning (ML) technique for interfacing with a nervous system of a subject, the apparatus comprising: a communications interface; a memory unit; and a processor unit, the processor unit connected to the communications interface and the memory unit, wherein: in response to receiving a plurality of neurological signals associated with the neural activity of a first portion of nervous system, the processor and communication interface are configured to: select a first ML technique from a first one or more ML technique(s) associated with processing neural sample data representative of the plurality of neurological signals for generating estimates of neural data representative of neural activity of the first portion of nervous system; receive a first set of performance data associated with the first selected ML technique, the first set of performance data including the neural sample data and the generated estimates of neural data; evaluate a first cost function based on the first set of performance data to determine whether to retrain the first selected ML technique; retrain the first selected ML technique in response to determining to retrain the first selected ML technique; and in response to receiving device data from a device associated with a second portion of the nervous system, the processor and/or communication interface are configured to: select a second ML technique from a second one or more ML technique(s) associated with processing the received device data for estimating one or more neurological stimulus signal(s) associated with the device data for input to the second portion of the nervous system; receive a second set of performance data associated with the selected ML technique, the set of performance data including the received device data and the estimated one or more neurological stimulus signal(s); evaluate a second cost function based on the second set of performance data to determine whether to retrain the second selected ML technique; and retrain the second selected ML technique in response to determining to retrain the second selected ML technique.

Preferably, the eighteenth aspect of the invention further includes one or more of the features and/or steps associated with the computer implemented method according to the first aspect of the invention as described herein.

In a nineteenth aspect of the invention, there is provided a computer implemented method for training one or more machine learning (ML) technique(s) based on a training set of neural sample data associated with neural data, the method comprising: retrieving the training set of neural sample data, training one or more machine learning (ML) technique(s); storing data representative of one or more trained ML technique(s); sending at least one data representative of at least one trained ML technique to a neural interface coupled to the nervous system of a subject for use in estimating neural data associated with neural activity of the nervous system.

Preferably, the method wherein each neural sample data in the training set is labelled associated with a bodily variable label identifying the one or more bodily variables contained therein. Preferably, the data representative of at least one trained ML technique comprises trained parameter data (e.g. weights and/or parameters) associated with the at least one trained ML technique.

Preferably, the computer implemented method further comprising generating a training set of neural sample data by: storing captured neural sample data received from the plurality of neurological signals, wherein the neural sample data is timestamped; capturing and storing sensor data from one or more sensors trained on the subject, wherein the sensor data is timestamped; synchronising the neural sample data with the sensor data; and identifying portions of the neural sample data associated with neural activity; determining neural data labels for each identified portion of neural sample data by analysing portions of the sensor data corresponding to the identified portion of neural sample data; labelling the identified portions of neural sample data based on the determined neural data labels; and storing the labelled identified portions of neural sample data as the training set of neural sample data.

Preferably, the method further comprising generating a training set of neural sample data by: storing captured neural sample data received from the plurality of neurological signals, wherein the neural sample data is timestamped; capturing and storing sensor data from one or more sensors trained on the subject, wherein the sensor data is timestamped; synchronising the neural sample data with the sensor data; and identifying portions of the neural sample data associated with neural activity encoding one or more bodily variable(s); determining bodily variable labels for each identified portion of neural sample data by analysing portions of the sensor data corresponding to the identified portion of neural sample data; labelling the identified portions of neural sample data based on the determined bodily variable labels; and storing the labelled identified portions of neural sample data as the training set of neural sample data.

Preferably, the nineteenth aspect of the invention further includes one or more of the features and/or steps associated with the computer implemented method according to one or more of the first to fourth aspects of the invention as described herein.

In a twentieth aspect of the invention, there is provided a computer implemented method for training one or more machine learning (ML) technique(s) based on a training set of neural stimulus sample data associated with neural stimulus, the method comprising: retrieving the training set of neural stimulus sample data and associated device data from a device associated with the neural stimulus, training one or more machine learning (ML) technique(s) to estimate/classify neural stimulus estimates based on device data; storing data representative of one or more trained ML technique(s); sending at least one data representative of at least one trained ML technique to a neural interface coupled to the nervous system of a subject and a device for use in estimating neural stimulus for applying to the nervous system in response to device data from the device.

Preferably, the method wherein each neural stimulus sample data in the training set is labelled associated with a neural stimulus label identifying the one or more bodily variables contained therein. Preferably, the data representative of at least one trained ML technique comprises trained parameter data (e.g. weights and/or parameters) associated with the at least one trained ML technique. Preferably, the method further comprises training at least one of the ML technique(s) on a training set of neural stimulus sample data, wherein each neural stimulus sample data in the set is labelled based on neural activity associated with a neural stimulus.

Preferably, the computer implemented method further comprising generating a training set of neural stimulus sample data by: storing captured neural stimulus sample data received from the plurality of neurological signals, wherein the neural stimulus sample data is timestamped; capturing and storing sensor data from one or more sensors trained on the subject, wherein the sensor data is timestamped; synchronising the neural stimulus sample data with the sensor data; and identifying portions of the neural stimulus sample data associated with neural activity associated with neural stimuli; determining neural stimulus labels for each identified portion of neural stimulus sample data by analysing portions of the sensor data corresponding to the identified portion of neural stimulus sample data; labelling the identified portions of neural stimulus sample data based on the determined neural stimulus labels; and storing the labelled identified portions of neural stimulus sample data as the training set of neural stimulus sample data.

Preferably, the twentieth aspect of the invention further includes one or more of the features and/or steps associated with the computer implemented method according to one or more of the first to fourth aspects of the invention as described herein.

In a twenty first aspect of the invention, there is provided a computer implemented method of generating a machine learning (ML) model for predicting bodily variable label estimates associated with a bodily variable of interest, the method comprising: receiving a labelled training set of neural sample data associated with the bodily variable of interest; training an ML technique based on the labelled training set of neural sample data associated with the bodily variable of interest; comparing the output bodily variable label estimates with those of the labelled training set of neural sample data; updating the ML technique based on the comparison; and repeating the steps of training, comparing and updating until the ML technique outputs a validly trained ML model.

Preferably, the computer implemented method, wherein neural sample data is representative of samples of neurological signals, the neurological signals including neural activity encoding one or more bodily variable(s) of the portion of a nervous system of a subject.

Preferably, the computer implemented method, wherein a bodily variable comprises data representative of a state of the whole of a subject, a body part of the subject, or a sub-part of the subject.

Preferably, the computer implemented method, wherein a bodily variable includes at least one from the group of: heart rate of the subject; activity of the subject; temperature of the subject; blood glucose of the subject; blood pressure of the subject; any vital sign of the subject; any physiological measurement of the whole of the subject, a body part of the subject, or a sub-part of the subject; and any data representative of a state of the whole of a subject, a body part of the subject, or a sub-part of the subject.

Preferably, the computer implemented method, wherein a bodily variable includes at least one from the group of, by way of example only but not limited to: any data representative of vital sign(s) of the subject including data representative of at least one from the group of: heart rate of the subject; activity of the subject; temperature of the subject; blood pressure of the subject; blood glucose of the subject; respiratory rate; any other vital sign of the subject; any physiological measurement of the whole of the subject, a body part of the subject, or a sub-part of the subject; any data representative of a state of the whole of a subject, a body part of the subject, or a sub-part of the subject; any data representative of information, values, parameters of the subject associated one or more genomic fields including at least one from the group of: epigenetics; phenotype; genotype; transcriptomics; proteomics; metabolomics; microbiomics; and any other term describing a number, state, metric, variable or information associated with the whole body of a subject, any part and/or subpart of the body of the subject and the like; equivalents thereof, modifications thereof, combinations thereof, as the application demands, any information associated with the body of a subject as the application demands; and/or as herein described.

Preferably, the computer implemented method, wherein one or more sensors comprise at least one sensor from the group of: ECG or heart rate sensor; Activity sensor; Temperature sensor; Blood Glucose sensor; Blood Pressure sensor; any sensor for outputting sensor data associated with one or more vital signs of the subject; any sensor for outputting sensor data associated with physiological measurement of the whole of the subject, a body part of the subject, or a sub-part of the subject; and any sensor for outputting sensor data associated with data representative of a state of the whole of a subject, a body part of the subject, or a sub-part of the subject; any sensor for outputting sensor data associated with data representative one or more number(s), state(s), metric(s), parameter(s), variable(s) and/or information associated with the whole body of a subject, any part and/or subpart of the body of the subject and the like.

Preferably, the computer implemented method further comprising: generating neural sample data representative of the neurological signals by capturing samples of the neurological signals when neural activity is detected; capturing sensor data from one or more sensors trained on the subject; synchronising portions of the neural sample data with corresponding portions of the sensor data; and analysing and labelling the portions of the sensor data based on a set of bodily variable labels characterising changes in a bodily variable of interest; labelling the portions of the neural sample data based on the labelled portions of the sensor data; and generating a labelled training set of neural sample data associated with the bodily variable of interest based on the labelled portions of neural sample data.

Preferably, the computer implemented method, wherein generating the labelled training set of neural sample data further comprises storing the labelled portions of neural sample data as a labelled training set of neural sample data associated with the bodily variable of interest.

Preferably, the computer implemented method, further comprising: generating neural sample data representative of the neurological signals by capturing samples of the neurological signals when neural activity is detected; capturing sensor data from one or more sensors trained on the subject; synchronising portions of the neural sample data with one or more intermediary low dimensional representative states; synchronising intermediary states with corresponding portions of the sensor data; analysing and labelling the portions of the sensor data based on a set of bodily variable labels characterising changes in a bodily variable of interest; labelling the portions of the neural sample data based on the labelled portions of the sensor data; and generating a labelled training set of neural sample data associated with the bodily variable of interest based on the labelled portions of neural sample data.

Preferably, the computer implemented method, wherein generating the labelled training set of neural sample data further comprises storing the labelled portions of neural sample data as a labelled training set of neural sample data associated with the bodily variable of interest. Additionally or alternatively, the labelled training set of neural sample data is used for generating the ML model for predicting bodily variable label estimates associated with a bodily variable of interest.

Preferably, the computer implemented method, wherein the one or more low dimensional representative states are generated by: training another ML technique to generate another ML model for determining a low dimensional latent space representative of the neurological signals; and generating one or more intermediary low dimensional representative states based on associating the dimensions of the determined low dimensional latent space with one or more bodily variable labels.

Preferably, the computer implemented method, wherein the one or more low dimensional representative states are generated by: training another ML technique to generate another ML model for determining a low dimensional latent space representative of the neurological signals based on a labelled training dataset associated with one or more bodily variable labels representative of one or more bodily variables; and generating one or more intermediary low dimensional representative states based on associating the dimensions of the determined low dimensional latent space with one or more bodily variable labels.

Preferably, the computer implemented method, wherein the one or more low dimensional representative states are generated by: training the ML technique to generate the ML model for determining a low dimensional latent space representative of the neurological signals; and generating one or more intermediary low dimensional representative states based on associating the dimensions of the determined low dimensional latent space with one or more bodily variable labels.

The computer implemented method, wherein the one or more low dimensional representative states may be generated by: training an ML technique to generate an ML model for determining a low dimensional latent space representative of the neurological signals using an unsupervised or semi-supervised techniques; and generating one or more intermediary low dimensional representative states based on associating the dimensions of the determined low dimensional latent space with one or more bodily variable labels. Alternatively or additionally, the ML technique to generate the ML model for determining the low dimensional latent space representative of the neurological signals may be based on semi-supervised or supervised techniques that may use, or be based on, one or more labelled training datasets associated with one or more bodily variables representative of one or more bodily variables; and generating one or more intermediary low dimensional representative states based on associating the dimensions of the determined low dimensional latent space with one or more bodily variable labels.

Preferably, the computer implemented method, wherein capturing samples of neurological signals further comprises: receiving a plurality of neurological signals associated with the neural activity of a portion of a nervous system of a subject; and processing neural sample data representative of the received plurality of neurological signals.

Preferably, the computer implemented method, wherein the portion of the nervous system of the subject comprises a plurality of neurons of the subject clustered around multiple neural receivers, each neural receiver configured for outputting neurological signals associated with neural activity on one or more of the plurality of neurons, the method comprising: receiving one or more neurological signals from the neural receivers associated with the plurality of neurons of the subject.

Preferably, the computer implemented method, further comprising: generating neural sample data representative of the neurological signals by capturing samples of the neurological signals when neural activity encoding one or more bodily variable(s) is detected; and processing the neural sample data using the one or more ML technique(s) to generate data representative of bodily variable estimates.

Preferably, the computer implemented method, wherein one or more ML technique(s) comprises at least one or more ML technique(s) from the group of: neural networks; Hidden Markov Models; Gaussian process dynamics models; auto-encoder/decoder networks; adversarial/discriminator networks; convolutional neural networks; long short term memory neural networks; any other ML technique for generating an ML model based on a time-series labelled training set of neural sample data; any other ML or classifier/classification technique or combinations thereof suitable for operating on said received neurological signal(s); and/or modifications and/or combinations thereof and the like.

In a twenty second aspect of the invention, there if provided a computer implemented method for generating a machine learning (ML) model for predicting bodily variable label estimates associated with a bodily variable of interest, the method comprising: receiving neural sample data representative of neurological signals encoding neural activity associated with one or more bodily variables; training an ML technique to generate an ML model for determining a low dimensional latent space representative of the neurological signals; and generating one or more intermediary low dimensional representative states based on associating the dimensions of the determined low dimensional latent space with one or more bodily variable labels.

Additionally or alternatively, training the ML technique to generate the ML model for determining a low dimensional latent space representative of the neurological signals may be based on unsupervised and/or semi-supervised techniques. Additionally or alternatively, training the ML technique to generate an ML model for determining a low dimensional latent space representative of the neurological signals may be based on semi-supervised and/or supervised techniques and may include or be based on one or more labelled training dataset(s) associated with one or more bodily variable labels representative of one or more bodily variables.

Preferably, the computer implemented method, wherein neural sample data is representative of samples of neurological signals, the neurological signals including neural activity encoding one or more bodily variable(s) of the portion of a nervous system of a subject.

Preferably, the computer implemented method, wherein a bodily variable comprises data representative of a state of the whole of a subject, a body part of the subject, or a sub-part of the subject.

Preferably, the computer implemented method, wherein a bodily variable includes at least one from the group of: heart rate of the subject; activity of the subject; temperature of the subject; blood glucose of the subject; blood pressure of the subject; any vital sign of the subject; any physiological measurement of the whole of a subject, a body part of the subject, or a sub-part of the subject; and any data representative of a state of the whole of a subject, a body part of the subject, or a sub-part of the subject.

Preferably, the computer implemented method, wherein a bodily includes at least one from the group of, by way of example only but not limited to: any data representative of vital sign(s) of the subject including data representative of at least one from the group of: heart rate of the subject; activity of the subject; temperature of the subject; blood pressure of the subject; blood glucose of the subject; respiratory rate; any other vital sign of the subject; any physiological measurement of the whole of the subject, a body part of the subject, or a sub-part of the subject; any data representative of a state of the whole of a subject, a body part of the subject, or a sub-part of the subject; any data representative of information, values, parameters of the subject associated one or more genomic fields including at least one from the group of: epigenetics; phenotype; genotype; transcriptomics; proteomics; metabolomics; microbiomics; and any other term describing a number, state, metric, variable or information associated with the whole body of a subject, any part and/or subpart of the body of the subject and the like; equivalents thereof, modifications thereof, combinations thereof, as the application demands, any information associated with the body of a subject as the application demands; and/or as herein described.

Preferably, the computer implemented method, wherein one or more sensors comprise at least one sensor from the group of: ECG or heart rate sensor; Activity sensor; Temperature sensor; Blood Glucose sensor; Blood Pressure sensor; any sensor for outputting sensor data associated with one or more vital signs of the subject; any sensor for outputting sensor data associated with physiological measurement of the whole of the subject, a body part of the subject, or a sub-part of the subject; and any sensor for outputting sensor data associated with data representative of a state of the whole of a subject, a body part of the subject, or a sub-part of the subject; any sensor for outputting sensor data associated with data representative one or more number(s), state(s), metric(s), parameter(s), variable(s) and/or information associated with the whole body of a subject, any part and/or subpart of the body of the subject and the like.

Preferably, the computer implemented method, further comprising: generating neural sample data representative of the neurological signals by capturing samples of the neurological signals when neural activity is detected; capturing sensor data from one or more sensors trained on the subject; synchronising portions of the neural sample data with one or more intermediary low dimensional representative states; synchronising intermediary states with corresponding portions of the sensor data; analysing and labelling the portions of the sensor data based on a set of bodily variable labels characterising changes in a bodily variable of interest; labelling the portions of the neural sample data based on the labelled portions of the sensor data; and generating a labelled training set of neural sample data associated with the bodily variable of interest based on the labelled portions of neural sample data.

The computer implemented method, wherein generating the labelled training set of neural sample data further comprises storing the labelled portions of neural sample data as a labelled training set of neural sample data associated with the bodily variable of interest.

Preferably, the computer implemented method, further comprising training another ML technique based on the generated labelled training set of neural sample data associated with the bodily variable of interest, wherein the ML technique generates another trained ML model for predicting bodily variable label estimates associated with the bodily variable of interest when neural sample data is input.

Preferably, the computer implemented method, further comprising retraining or updating the ML model by retraining the ML technique based on the generated labelled training set of neural sample data associated with the bodily variable of interest, wherein the ML technique generates an updated ML model for further determining the low dimensional latent space representative of the neurological signals and for predicting bodily variable label estimates associated with the bodily variable of interest when neural sample data is input.

Preferably, the computer implemented method, further including capturing samples of neurological signals based on: receiving a plurality of neurological signals associated with the neural activity of a portion of a nervous system of a subject; and processing neural sample data representative of the received plurality of neurological signals.

Preferably, the computer implemented method, wherein the portion of the nervous system of the subject comprises a plurality of neurons of the subject clustered around multiple neural receivers, each neural receiver configured for outputting neurological signals associated with neural activity on one or more of the plurality of neurons, the method comprising: receiving one or more neurological signals from the neural receivers associated with the plurality of neurons of the subject.

Preferably, the computer implemented method, further comprising: generating neural sample data representative of the neurological signals by capturing samples of the neurological signals when neural activity encoding one or more bodily variable(s) is detected; and processing the neural sample data using the one or more ML technique(s) to generate data representative of bodily variable estimates.

Preferably, the computer implemented method, wherein one or more ML technique(s) comprises at least one or more ML technique(s) from the group of: neural networks; Hidden Markov Models; Gaussian process dynamics models; autoencoder/decoder networks; adversarial/discriminator networks; convolutional neural networks; long short term memory neural networks; any other ML technique for generating an ML model based on a time-series labelled training set of neural sample data; any other ML or classifier/classification technique or combinations thereof suitable for operating on said received neurological signal(s).

In a twenty third aspect of the invention, there is provided a machine learning (ML) model for predicting bodily variable label estimates associated with a bodily variable of interest obtained by the computer implemented method according to any of the features described in relation to the twenty first aspect, the twenty second aspect, and/or modifications thereof, and/or combinations thereof, and/or as herein described.

Preferably, the machine learning (ML) model, further comprising: receiving neural sample data representative of neurological signals based on samples of the neurological signals captured when neural activity encoding one or more bodily variable(s) is detected; processing the received neural sample data; and outputting a bodily variable label estimate based on a set of bodily variable labels associated with the labelled training neural sample data associated with the bodily variable label of interest.

In a twenty fourth aspect of the invention, there is provided an apparatus comprising: a communications interface; a memory unit; and a processor unit, the processor unit connected to the communications interface and the memory unit, wherein the processor unit, memory unit, communications interface are configured to perform the method according to any of the features described in relation to the to the twenty first aspect, the twenty second aspect, and/or modifications thereof, and/or combinations thereof, and/or as herein described.

In a twenty fifth aspect of the invention, there is provided a computer readable medium comprising program code stored thereon, which when executed on a processor, causes the processor to perform a method according any of the features described in relation to the twenty first aspect, the twenty second aspect, and/or modifications thereof, and/or combinations thereof, and/or as herein described.

In a twenty sixth aspect of the invention, there is provided an apparatus comprising: a communications interface; a memory unit; and a processor unit, the processor unit connected to the communications interface and the memory unit, wherein the processor unit, storage unit, communications interface are configured to perform the method according to any of the features described in relation to the twenty first aspect of the invention, and/or modifications thereof, and/or combinations thereof, and/or as herein described.

In a twenty seventh aspect of the invention, there is provided an apparatus comprising: a communications interface; a memory unit; and a processor unit, the processor unit connected to the communications interface and the memory unit, wherein the processor unit, storage unit, communications interface are configured to perform the method according to any of the features described in relation to the twenty second aspect of the invention, and/or modifications thereof, and/or combinations thereof, and/or as herein described.

In a twenty eighth aspect of the invention, there is provided an apparatus comprising: a communications interface; a memory unit; and a processor unit, the processor unit connected to the communications interface and the memory unit, wherein the processor unit, storage unit, communications interface are configured to perform the method according to any of the features described in relation to the twenty third aspect of the invention, and/or modifications thereof, and/or combinations thereof, and/or as herein described.

In a twenty ninth aspect of the invention, there is provided a computer implemented method configured to perform steps to achieve or implement the inventive concept(s), modification(s) thereof, combinations thereof, and/or as described herein.

In a thirtieth aspect of the invention, there is provided a computer implemented method configured to perform steps to achieve or implement the inventive concept(s) according to any of the features of any aspect of the invention, implement the inventive concept(s), modification(s) thereof, combinations thereof, and/or as described herein.

In a thirty first aspect of the invention, there is provided a computer readable medium comprising program code stored thereon, which when executed on a processor, causes the processor to perform a method according to the twenty ninth aspect of the invention, modifications thereof, combinations thereof, and/or as herein described.

In a thirty second aspect of the invention, there is provided an apparatus configured to implement the inventive concept(s) according to any of the features of any aspect of the invention, configured to implement the inventive concept(s), modification(s) thereof, combinations thereof, and/or as described herein.

In a thirty third aspect of the invention, there is provided a neural network apparatus configured to implement the inventive concept(s) according to any of the features of any aspect of the invention, configured to implement the inventive concept(s), modification(s) thereof, combinations thereof, and/or as described herein.

In a thirty third aspect of the invention, there is provided a neural network configured to implement the inventive concept(s) according to any of the features of any aspect of the invention, configured to implement the inventive concept(s), modification(s) thereof, combinations thereof, and/or as described herein.

In a thirty fourth aspect of the invention, there is provided a machine learning technique configured to implement the inventive concept(s) according to any of the features of any aspect of the invention, configured to implement the inventive concept(s), modification(s) thereof, combinations thereof, and/or as described herein.

In a thirty fifth aspect of the invention, there is provided a machine learning model configured to implement the inventive concept(s) according to any of the features of any aspect of the invention, configured to implement the inventive concept(s), modification(s) thereof, combinations thereof, and/or as described herein.

The methods described herein may be performed by software in machine readable form on a tangible storage medium e.g. in the form of a computer program comprising computer program code means adapted to perform all the steps of any of the methods described herein when the program is run on a computer and where the computer program may be embodied on a computer readable medium. Examples of tangible (or non-transitory) storage media include disks, thumb drives, memory cards, cloud computing systems and/or server(s) etc. and do not include propagated signals. The software can be suitable for execution on a parallel processor or a serial processor such that the method steps may be carried out in any suitable order, or simultaneously.

This application acknowledges that firmware and software can be valuable, separately tradable commodities. It is intended to encompass software, which runs on or controls "dumb" or standard hardware, to carry out the desired functions. It is also intended to encompass software which "describes" or defines the configuration of hardware, such as HDL (hardware description language) software, as is used for designing silicon chips, or for configuring universal programmable chips, to carry out desired functions.

The preferred features may be combined as appropriate, as would be apparent to a skilled person, and may be combined with any of the aspects of the invention. Indeed, the order of the embodiments and the ordering and location of the preferable features is indicative only and has no bearing on the features themselves. It is intended for each of the preferable and/or optional features to be interchangeable and/or combinable with not only all of the aspect and embodiments, but also each of preferable features.

BRIEF DESCRIPTION OF THE DRAWINGS

Embodiments of the invention will be described, by way of example, with reference to the following drawings, in which.

Figure 1A:
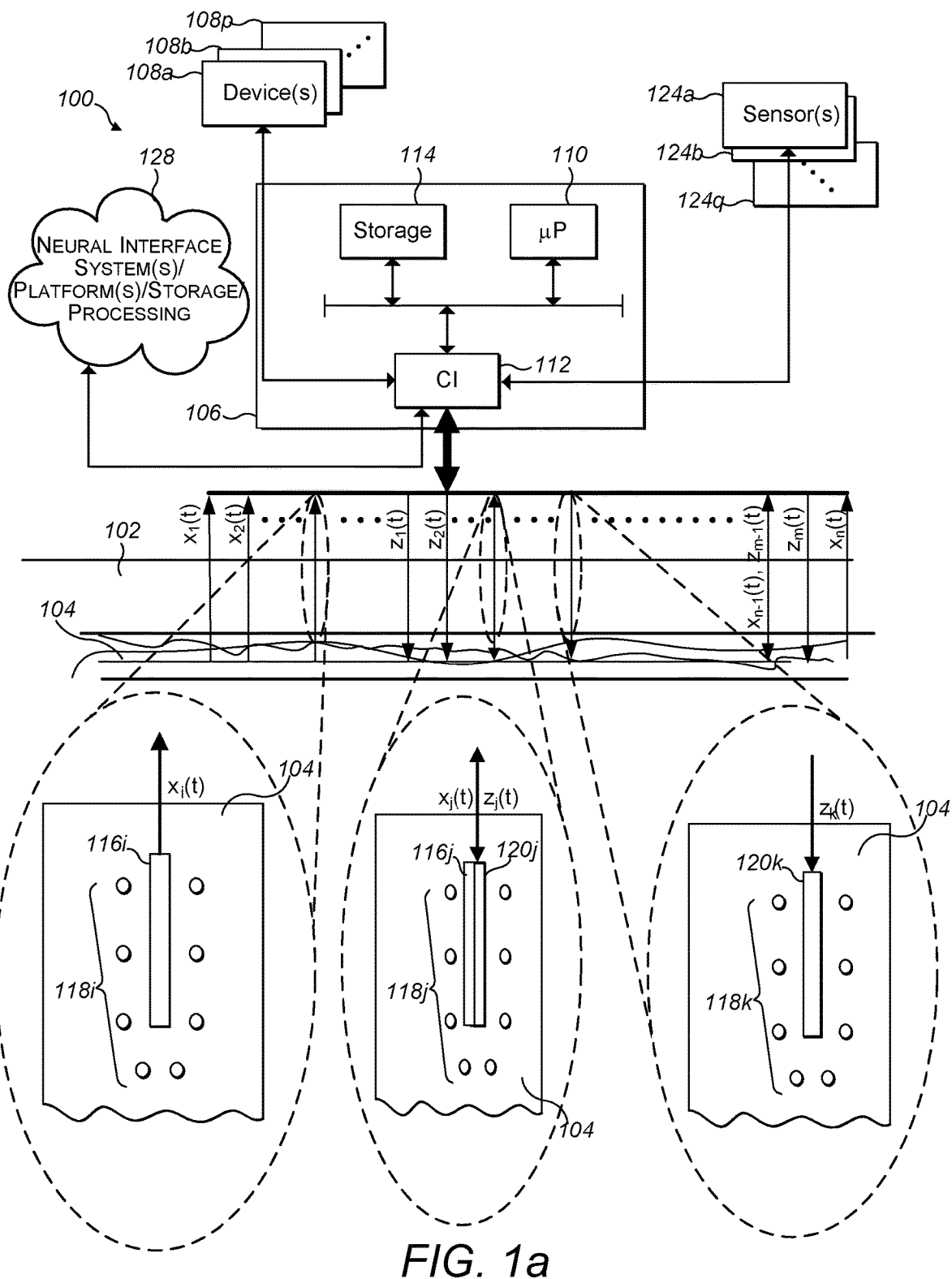
FIG. 1a is a schematic illustration of an example neural interface according to the invention.

Common reference numerals are used throughout the figures to indicate similar features. It should however be noted that even where reference numerals for features used throughout the figures vary, this should not be construed as non-interchangeable or distinct. Indeed, unless specified to the contrary, all features referring to similar components and/or having similar functionalities of all embodiments are interchangeable and/or combinable.

DETAILED DESCRIPTION

Embodiments of the present invention are described below by way of example only. These examples represent the best ways of putting the invention into practice that are currently known to the Applicant although they are not the only ways in which this could be achieved. The description sets forth the functions of the example and the sequence of steps for constructing and operating the example. However, the same or equivalent functions and sequences may be accomplished by different examples. For the avoidance of any doubt, the features described in any embodiment are combinable with the features of any other embodiment and/or any embodiment is combinable with any other embodiment unless express statement to the contrary is provided herein. Simply put, the features described herein are not intended to be distinct or exclusive but rather complementary and/or interchangeable.

The inventors have advantageously found that machine learning technique(s) can be applied in a neural interface that is coupled to the nervous system of a subject allowing neural activity to be captured, intercepted and deciphered at a sufficient level of granularity that enables seamless neural operation of device(s) associated with bodily functions/ organs/body parts/portions of the body of the subject. For example, the neural interface may be configured to be coupled to one or more neural receivers connected to the nervous system of the subject for receiving a neurological signal based on the neural activity sent over one or more nerves (e.g. efferent nerves) to a cluster of neurons or a neuronal population associated with the one or more nerves. The neural interface may be configured to apply machine learning (ML) technique(s) to decipher or interpret the data representative of the neural activity in the received neurological signal(s) and output an information-rich data representation and/or neural data estimate of the corresponding neural activity suitable for delivery to one or more devices. The neural interface may be further configured to be coupled to one or more neural transmitter(s) capable of providing a neural stimulus to the nervous system of the subject. The neural interface is configured to receive a device data generated by one or more devices associated with bodily functions/organs/body parts/portions of the subject and use ML techniques to estimate data representative of a neural stimulus corresponding to the device data for injection or application by the one or more neural transmitter(s) to corresponding one or more neuron(s) or neuronal population(s).

The neural activity may include or represent neural activity encoding one or more bodily variable(s) or combinations thereof. Although neural activity encoding one or more bodily variable(s) or combinations thereof has been described herein, this is by way of example only and is not only limited to this, it is to be appreciated by the skilled person that neural activity may be represented in any other form such as, by way of example only but not limited to, data representative of neural data, neural information, neural intent, end effect, neural state or state of the body, and/or or any other data, variable or information representative of the information carried or contained in neural activity and interpreted by neurons or neuronal populations for performing one or more bodily functions and the like. Neural data may include any data that is representative of the information or data that is contained in neural activity and/or neurological signal(s) associated with neural activity. The neural data may include, by way of example only but is not limited to, data representative of estimates of one or more bodily variable(s) associated with the corresponding neural activity, or any other data, variable or information representative of the information carried or contained in neural activity. Device data may include any data that is representative of the information or data received from a device for use in or intended/generated by the device for use in, by way of example only but not limited to, stimulating one or more neuronal populations or neurons associated with the device data.

The ML technique(s) may include, by way of example only but not limited to, any ML technique that includes one or more, preferably most or all, of the following properties: a) is a model or method that has a representative power to produce, represent or classify time series data with appropriate tolerance to data size and noise; b) is efficient to implement such that it can be evaluated in real-time and is practical given the realities of the size of neurological signal(s) and the required training data associated with neural data (e.g. bodily variable(s)) carried on or by the neurological signals; c) may include the ability to use artificial data or knowledge/theory about a generative model for data to improve training & inference accuracy while also allowing "end to end" type application where model can span a majority or all of the problem between effectively raw neural data storage associated with neural data (e.g. neural information, neural intent, bodily variable(s) and any other data) representative of neural activity and an informational-rich but finite data representation of said neural data(s); d) the model may provide a sufficiently low dimensional representation of the neural data (e.g. bodily variable(s) or other neural information) to be directly or indirectly computed whilst containing an informational-rich data representation of the neural data (e.g. bodily variable(s) or neural information), which may allow the application of ML methods, classification methods, and feature engineering to the neurological signal(s) to be made robust enough in relation to long and short term variability to the reception of neurological signals and/or transmission of neural stimulus data.

Various ML technique(s) and/or method(s) can be leveraged to achieve the above-mentioned properties and may include, by way of example only but are not limited to, one or more ML technique(s), variations and/or combinations thereof from the group of: Hidden Markov Models including, by way of example only but not limited to, with likely derived inference using simplistic Gaussian assumptions for tractability, feature heavy inference such as a random forest method, latent feature/latent variable models (e.g. non-parametric or plain Bayesian); Gaussian process dynamics models, neural networks (NNs)/NN models including, by way of example only but not limited to, convolutional NNs, variational autoencoder NNs, feedforward NNs, recursive NNs (RNNs) with state readout mechanisms, long short term memory NNs, and/or adversarial NNs and the like. Other examples of ML technique(s) include, by way of example only but is not limited to, at least one or more ML technique(s) or combinations thereof from the group of: neural networks; Hidden Markov Models; Gaussian process dynamics models; autoencoder/decoder networks; adversarial/discriminator networks; convolutional neural networks; long short term memory (LSTM) neural networks; and/or any other ML or classifier/classification technique or combinations thereof suitable for operating on said received neurological signal(s).

The neural interface may be coupled with one or more devices associated with operating, controlling, monitoring and/or assisting a subject in relation to one or more body parts/portions and/or organs/tissue and/or cells. A device may comprise or represent any device, apparatus, system or mechanism for operating, controlling, monitoring and/or assisting a subject in relation to one or more biological sites/body parts/portions/sub-systems and/or organs/tissues and cells of the subject based on: a) receiving an information-rich data representation and/or estimate of corresponding neural data (e.g. bodily variable(s) or neural information) associated with the subject output from the ML technique(s) and operates accordingly; and/or b) transmitting suitable device data (e.g. bodily variable signal(s) or other neural data or neural stimulus data) for use by the ML technique(s) of the neural interface for providing neural stimulus to the subject in relation to one or more biological sites/body parts/portions/sub-systems and/or organs/tissues and/or cells.

Examples of devices that may be used in certain embodiments of the described apparatus, methods and systems according to the invention may include, by way of example only but is not limited to, any device or apparatus for managing or assisting with the operation or function of any one or more of a number of different organs, tissues, biological sites and/or sub-systems in the body of a subject; any device or apparatus for managing or assisting with the operation or function of any one or more of a number of body parts of the body of a subject; any device or apparatus capable of operating on neural data estimates as the application demands; and any device or apparatus capable of generating and/or transmitting device data for providing corresponding neural stimulus to the subject as the application demands; any assistance or mobility devices such as prosthetic limb devices capable of receiving estimates of bodily variable(s) and operating accordingly and/or capable of transmitting device data (e.g. bodily variable signal(s)) for providing corresponding neural stimulus to the subject; apparatus, devices, implant or implant devices, sensors, and/or controllers and the like associated with non-prosthetics neural applications for managing or assisting with the operation or function of any one or more of a number of different organs, tissues, biological sites and/or sub-systems in the body of a subject, by way of example only but not limited to (e.g. biological site/targeted disease), bladder nerve/urinary incontinence, abdominal vagus nerve/gastric motility, ovarian plexus/birth control, cardiac innervation/blood pressure, upper vagus/inflammation, spinal cord/chronic pain, abdominal vagus/diabetes, adipose innervation/weight loss, pancreatic nerve/diabetes, subcutaneous cardiac nerve/heart arrhythmia, vagus nerve/chronic migraine; and any other device, apparatus, mechanism or system capable of assisting in the operation of any other biological site/organ or sub-system in the body of a subject based on receiving data representative of a bodily variable from a neuronal population associated with a biological site/organ/tissue or sub-system and/or for providing device data (e.g. bodily variable signal(s)) associated with neural stimulus to a neuronal population associated with the biological site/organ/tissue or sub-system; any device or apparatus capable of operating on neural data estimates as the application demands; and any device or apparatus capable of generating and/or transmitting device data for providing corresponding neural stimulus to the subject as the application demands. It is to be appreciated by the skilled person that, based on the teachings described herein, the skilled person would be able to implement a neural interface, neural interface platform or system according to the invention with any other device as the application demands.

Other examples of device(s) may include, by way of example only but not limited to, any one or more device(s) or apparatus or combinations thereof from the group of: a prosthetic device or apparatus capable of receiving neural data estimates and operating accordingly and/or capable of transmitting device data for providing corresponding neural stimulus to the subject; a non-prosthetic device or apparatus capable of receiving neural data estimates and operating accordingly and/or capable of transmitting device data for providing corresponding neural stimulus to the subject; a device or apparatus for managing or assisting with the operation or function of any one or more of a number of different organs, tissues, biological sites and/or sub-systems in the body of a subject; a device or apparatus for managing or assisting with the operation or function of any one or more of a number of body parts of the body of a subject; any device or apparatus capable of operating on neural data estimates as the application demands and the like; and/or any device or apparatus capable of generating and/or transmitting device data for providing corresponding neural stimulus to the subject as the application demands and the like.

FIG. 1a illustrates a neural interface system 100 in which a body portion of a subject 102 with a nervous system comprising one or more nerve(s) 104 is coupled to a neural interface 106 including, by way of example only but not limited to, a communication interface 112, a processor unit 110 and a storage unit 114, in which the processor unit 110 is connected to the storage unit 114 and communication interface 112. In essence, the neural interface 106 is configured to receive and process a plurality of neurological signals $x_1(t), x_2(t), \ldots, x_i(t), x_j(t), \ldots, x_{n-1}(t), x_n(t)$ output from a corresponding plurality of neural receivers $116i$ or $116j$. The neurological signals $x_1(t), \ldots, x_n(t)$ are processed using one or more ML technique(s) trained for estimating and/or classifying an informational rich data representation of bodily variables encoded as neural activity and communicating data representative of the estimated bodily variable(s) and/or classification thereof to one or more devices 108a-108p for operating on the estimated bodily variable(s).

The data representative of the estimated and/or classified bodily variable(s) may be sent by the communication interface 112 to one or more device(s) 108a-108p. For example, the estimated bodily variable(s) may be interpreted by the one or more device(s) 108a-108p as one or more neural commands for controlling/operating the device 108a-108p. Alternatively, the estimated bodily variable(s) may be operated on by the one or more device(s) 108a-108p, which perform one or more actions that deliver, by way of example only but not limited to, assistance and/or care to part of the body of the subject 102.

Given that the device(s) 108a-108p may operate to deliver assistance or care to parts of the body of the subject 102 based on estimated bodily variable(s) from neural activity, one or more of the device(s) 108a-108p may be configured to alter neural activity to parts of the nervous system of the subject 102. For example, a device 108a may be configured to provide feedback to (e.g. send a touch signal from a prosthetic limb to the subject 102), communicate with and/or operate (e.g. override neural activity already provided by the nervous system to deliver assistance or care to bodily tissues/organs) parts of the nervous system of the subject 102. This may be achieved by the one or more device(s) 108a-108p providing data representative of bodily variable(s) that may be encoded as neural activity in the form of a neural stimulus to corresponding parts of the nervous system (e.g. one or more neurons or neuronal population(s) $118j$ or $118k$) of the subject 102. The data representative of these bodily variable(s) generated by device(s) 108a-108p for encoding as neural activity are herein described as bodily variable signal(s).

The neural interface 106 may be further configured to receive one or more bodily variable signal(s) generated by one or more devices 108a-108p, process the one or more bodily variable signal(s) using one or more ML technique(s) trained for estimating and communicating data representative of one or more neural stimulus signals $z_1(t), z_2(t), z_j(t), \ldots, z_{n-1}(t), z_m(t)$ associated with the one or more bodily variable signal(s). The neural interface 106 communicates the data representative of the one or more estimated neural stimulus signals $z_1(t), \ldots, z_m(t)$ to a corresponding one or more neural transmitter(s) $120j$ or $120k$, which are configured for stimulating the corresponding parts of the nervous system of the subject 102 associated with the neural stimulus signals $z_1(t), \ldots, z_m(t)$ and/or one or more bodily variable signal(s).

A neurological signal, denoted $x_i(t)$ or $x_j(t)$, may comprise or represent a time domain signal associated with the electrical spatial and temporal activity in a neuronal population as detected and/or measured local to one or more neural receivers $116i$ or $116j$ in response to a bodily variable that is generated by the CNS of a subject 102. The CNS of the subject 102 encodes the bodily variable as neural activity, which is communicated along one or more nerves 104 associated with the neuronal population $118i$, $118j$ or $118k$. For example, the neurological signal for the i-th neuronal population (or neuron cluster) $118i$ (or cluster i) may be modelled by, for simplicity and by way of example only but is not limited to, $\sum_{j=1}^{N_i} A_j^i(t)\theta_j^i(t)$, where N is the number of neurons in the i-th neuronal population 118*i* (or cluster i), $\theta_j^i(t)$ is the time varying electrochemical nerve impulse signal from the j-th neuron of the i-th neuronal population 118*i* (or cluster and $A_j^i(t)$ is a non-linear attenuation factor representing a temporally and spatially varying attenuation between the j-th neuron of the i-th neuronal population 118*i* and neural receiver 116*i*. Other components may be added to the modelled neurological signal $x_i(t)$ such as, by way of example only but not limited to, Additive White Gaussian Noise (AWGN), phase error, or other linear or non-linear noise components(s) and the like. A neurological stimulus signal, denoted $z_j(t)$ or $z_k(t)$, may comprise or represent a time domain signal associated with a neural stimulus for use by a neural stimulator/transmitter 120*j* or 120*k* in controlling the electrical spatial and temporal activity (e.g. the neural activity) of a neuronal population 118*j* or 118*k* associated with one or more nerve(s) 104.

A neural receiver 116*i* or 116*j* may comprise or represent any apparatus, mechanism or device capable of detecting and measuring the neural activity of one or more neurons of a neuronal population 118*i* or 118*j* of a subject 102 and outputting a neurological signal $x_i(t)$ or $x_j(t)$ representative of the neural activity. Examples of neural receivers 116*a* or 116*j* that may be used in certain embodiments of the described apparatus, methods and systems may be, by way of example only but is not limited to, any sensor capable of measuring or receiving neural activity from a neuronal population, any electrode capable of measuring or receiving neural activity from a neuronal population such as, by way of example only but not limited to, cuff electrodes, paddle electrodes, helical electrodes, book electrodes, lead wire electrodes, stent electrodes, spike array electrodes, conductive polymer electrodes or any other device capable of measuring or receiving neural activity from a neuronal population such as, by way of example only but not limited to, optogenetic sensors.

The neural receiver(s) 116*i* or 116*j* are capable of detecting and measuring the neural activity of one or more neurons of a neuronal population 118*i* or 118*j*. The neural receiver(s) 116*i* or 116*j* may be located in the vicinity of one or more nerve(s) 104 and form a neural receiver-nerve construct. The neural receiver(s) 116*i* or 116*j* are located to protect or isolate the neural receiver-nerve construct. For example, the neural receiver(s) may be located adjacent to one or more nerve(s) and may be placed, located, and/or sheathed in such a way as the neural receiver-nerve construct is protected or isolated from, by way of example only but is not limited to, one or more from the group of: external forces, motion, surrounding signals and/or noise signals and the like. In some examples protection or isolation is achieved by biological tissues, for instance, by way of example only but not limited to, at least one from the group of: inside bone, under periosteum, in muscle and the like, and/or as the application demands. In other examples, protection or isolation is achieved inside engineered materials or using engineered materials, for instance, by way of example only but not limited to, inside, on or under at least one from the group of: metal implant, plastic implant, or other substructure created for the purpose, which could include solid implant materials or biological or non-biological glues, resins and/or other materials that can be deployed around the neural receiver-nerve construct and the like and/or as the application demands. Other materials that can be deployed around the neural receiver-nerve construct may include, for instance, by way of example only but not limited to, at least one from the group of: tisseal (or other fibrinogen based glues and sealants), silicon, cyanoacrylate, or otherwise and the like.

A neural transmitter 120*j* or 120*k* may comprise or represent any apparatus, mechanism or device capable of receiving a neurological stimulus signal $z_j(t)$ or $z_k(t)$ representative of a neural stimulus and generating a neural activity representative of the neurological stimulus signal $z_j(t)$ or $z_k(t)$ that is applied as a stimulus capable of altering the electrical spatial and temporal activity of one or more neurons of a neuronal population 118*j* or 118*k* corresponding to the neurological stimulus signal $z_j(t)$ or $z_k(t)$. Examples of neural transmitters 120*j* or 120*k* that may be used in certain embodiments of the described apparatus, methods and systems may be, by way of example only but is not limited to, any electrode capable of controlling or injecting a neural stimulus into a neuronal population 118*j* or 118*k*, such electrodes may include, by way of example only but not limited to: cuff electrodes, paddle electrodes, helical electrodes, book electrodes, lead wire electrodes, stent electrodes, spike array electrodes, and/or conductive polymer electrodes; or any other apparatus, device or mechanism capable of controlling and/or injecting or inputting a neural stimulus to a neuronal population 118*j* or 118*k* such as, by way of example only but not limited to, optogenetic sensors.

Although FIG. 1*a* illustrates an example with separate neural receiver(s) and neural transmitter(s) or both, this is by way of example only, it is to be appreciated by the skilled person that a neural receiver may be reconfigured to operate as a neural transmitter and that a neural transmitter may be reconfigured to operate as a neural receiver. For example, an electrode as described above may be configured to be a neural receiver but may also be configured to be a neural transmitter. Electrodes can be reconfigured, and in some cases reconfigured multiple times per second during use, to be either performing a sensing of neural activity encoding bodily variable(s) from a neuronal population or for performing a stimulation function for inputting a neural stimulus signal or neural activity encoding data representative of bodily variable(s) to a neuronal population. For simplicity, the neural interface 106 describes using neural receiver(s) and neural transmitter(s) separately, for simplicity and by way of example only, and it is to be appreciated by the skilled person that a neural receiver may operate on the same or similar neuronal population as a neural transmitter (e.g. a neural receiver may operate as a neural transmitter and vice versa when necessary, i.e. a neural transceiver) and/or that neural receivers can operate on different neuronal populations as the neural transmitters. In the case where neural receivers operate on different neuronal populations as neural transmitters, then further processing may be necessary due to the different non-linear mapping of sensing and stimulation of neuronal population sites.

The neural interface system 100 may further include one or more sensors 124*a*-124*q* that may be trained on or observing the subject 102 and generate sensor data for use in training and/or re-training (or calibrating/re-calibrating) the one or more of the ML technique(s) of the neural interface 106 for estimating and/or classifying bodily variable(s) from received neurological signals $x_1(t), \ldots, x_i(t)$, $x_j(t), \ldots, x_n(t)$ of the subject 102. The one or more sensor(s) 124*a*-124*q* may comprise or represent any sensor or device capable of detecting, sensing, measuring and/or monitoring one or more biological, pathological, chemical, physical processes and/or aspects of the subject 102, generating corresponding sensing data and transmitting or reporting this sensing data. Sensor(s) 124*a*-124*q* may operate outside or be implanted within the body of the subject 102. Examples of sensor(s) 124a-124q that may be used in certain embodiments of the described apparatus, methods and systems may be, by way of example only but not limited to, any sensor capable of measuring and recording one or more pathological, physical or emotional aspects of the subject 102, which may include any sensor such as, by way of example only but not limited to, video camera, audio microphone, inertial measurement unit, motion detection sensors, depth cameras, heart rate sensors or monitors, blood pressure sensors, biomedical sensors, sensors associated with EEG, EOG and/or EMG signals or any other form of heart or brain activity. Some examples of biomedical sensors may include, by way of example only but not limited to, blood constituent monitors for monitoring glucose/hormone levels, insulin levels, oxygen saturation; gastric activity monitors for monitoring oesophageal acidity (e.g. pH), glucose index, temperature; or any other sensor capable of measuring and/or recording one or more biological, pathological or physical aspects of the subject 102.

A set of neurological signals $x_1(t), \ldots, x_i(t), x_j(t), \ldots, x_n(t)$ may be received, sampled and stored (or recorded) during a session or over time to form a training set of neurological data samples whilst at the same time sensor data associated with the subject 102 from one or more sensors 124a-124q trained on the subject 102 may also be stored and/or recorded. The sensor data may be used to identify, classify and/or label the neural activity associated with the neurological signals $x_1(t), \ldots, x_i(t), x_j(t), \ldots, x_n(t)$. Thus, both the neurological signals $x_1(t), \ldots, x_i(t), x_j(t), \ldots, x_n(t)$ and the corresponding sensor data may be used to form a training dataset may be used to train one or more ML technique(s) of the neural interface 106 to transform and recognise/classify the bodily variable(s) encoded as neural activity and received as neurological signals $x_1(t), \ldots, x_i(t), x_j(t), \ldots, x_n(t)$ into a suitable data representation for use by the one or more devices 108a-108p.

For example, the neurological data samples of the received neurological signals $x_1(t), \ldots, x_i(t), x_j(t), \ldots, x_n(t)$ may be labelled based on corresponding sensor data of the subject 102 that is recorded or stored during reception, sampling and recording of the neurological signals $x_1(t), \ldots, x_i(t), x_j(t), \ldots, x_n(t)$ from the subject 102. The neurological data samples and the sensor data from one or more sensors 124a-124q may be timestamped to enable the neurological signals and sensor data 124a-124q to be synchronised. The synchronised neurological sample data and sensor data can be used to identify, classify and/or label any neural activity encoding one or more bodily variable(s) that is present in the neurological signals $x_1(t), \ldots, x_i(t), x_j(t), \ldots, x_n(t)$ based on the response of the subject 102 as measured by the sensor data. This allows the neurological signals and sensor data to be processed into bodily variable training datasets. For example, neural activity that encodes one or more bodily variable(s) may be determined or considered to be present when there is a sudden change or a spike in neurological signals $x_1(t), \ldots, x_i(t), x_j(t), \ldots, x_n(t)$ and hence the neurological sample data.

For example, the neurological sample data associated with the neurological signals $x_1(t), \ldots, x_i(t), x_j(t), \ldots, x_n(t)$ may be timestamped during storage whilst the sensor data is also timestamped during storage to assist in identification of which portions of the sensor data correspond to which portions of the neurological signals or sample data. The sensor data corresponding to a portion of the one or more neurological signal(s) $x_1(t), \ldots, x_i(t), x_j(t), \ldots, x_n(t)$ that is identified to correspond to neural activity encoding one or more bodily variable(s) may be analysed and given a label that identifies the observed activity of the corresponding body portion of the subject 102. This may be used to identify the bodily variable(s) encoded as neural activity. The label(s) given to the portions of sensor data may be used to label/classify or categorise the corresponding portion(s) of the neurological data samples. Once the identified portions of the neurological data samples are labelled and/or classified, they can be used as a set of bodily variable training data for training the one or more ML technique(s) of the neural interface 106.

For example, video camera data representing movement of the subject 102 may be synchronised with neurological signal sample data recorded at the time of movement such that bodily variable(s) or combinations of bodily variable(s) encoded as neural activity associated with the movement can identified in the neurological signal sample data. This identification can be used to generate a bodily variable training dataset such that one or more ML techniques may be trained to identify and classify bodily variable(s) or combinations of bodily variable(s) from a set of received neurological signals $x_1(t), \ldots, x_i(t), x_j(t), \ldots, x_n(t)$ in an informationally rich data representation suitable for sending to and being interpreted/processed by the one or more devices 108a-108p.

Similarly, a neural stimulus training dataset may be generated by recording a set of neurological stimulus signals $z_1(t), \ldots, z_j(t), z_k(t), \ldots, z_m(t)$ that may be generated by one or more neuronal populations 118j or 118k when one or more body parts or portions of the subject 102 is subject to a neural stimulus. For example, the neural stimulus signals $z_1(t), \ldots, z_j(t), z_k(t), \ldots, z_m(t)$ may be the measured neural activity associated with, by way of example only but not limited to, the touch of a finger and/or neural activity associated with the function or operation of a bodily part/organ or tissue. At the same time sensor data from one or more sensor(s) 124a-124q trained or observing the subject 102 may be recorded. Thus, neurological stimulus signals $z_1(t), \ldots, z_j(t), z_k(t), \ldots, z_m(t)$ and corresponding sensor data may be sampled and stored (or recorded) during a session or over time and analysed to form a neural stimulus training dataset. Both the neurological stimulus signals $z_1(t), \ldots, z_j(t), z_k(t), \ldots, z_m(t)$ and the corresponding sensor data may be used to form a neural stimulus training dataset for training one or more ML technique(s) of the neural interface 106 to transform and recognise/classify the bodily variable signal(s) from one or more devices 108 into suitable neural stimulus signal(s) for reception by the one or more neural transmitters 118i or 118k and subsequent application of corresponding neural activity to one or more neurons or neuronal population(s) 118j or 118k.

For example, the neurological stimulus sample data associated with the neurological stimulus signals $z_1(t), \ldots, z_j(t), z_k(t), \ldots, z_m(t)$ generated by the nervous system may be timestamped during storage whilst the sensor data is also timestamped during storage to assist in identification of which portions of the sensor data correspond to which portions of the neurological stimulus signals or sample data. The sensor data corresponding to a portion of the one or more neurological stimulus signals $z_1(t), \ldots, z_j(t), z_k(t), \ldots, z_m(t)$ that is identified to correspond to neural activity encoding one or more bodily variable(s) may be analysed and given a label that identifies the observed activity of the corresponding body portion of the subject 102. This may be used to identify the bodily variable(s) encoded as neural activity in relation to the neural stimulus. The label(s) given to the portions of sensor data may be used to label/classify or categorise the corresponding portion(s)

of the neurological stimulus data samples. Once the identified portions of the neurological stimulus data samples are labelled and/or classified, they can be used as a set of neural stimulus training data for training the one or more ML technique(s) of the neural interface 106 for outputting data representative of suitable neural stimulus signals that correspond to bodily variable signal(s) received from one or more device(s) 108a-108p.

FIG. 1a illustrates a neural interface system 100 in which a body portion of a subject 102 with a nervous system comprising one or more nerve(s) 104 is coupled to a neural interface 106 including, by way of example only but is not limited to, a communication interface 112, a processor unit 110 and a storage unit 114, in which the processor unit 110 is connected to the storage unit 114 and communication interface 112. In essence, the neural interface 106 is configured to receive and process a plurality of neurological signals $x_1(t), x_2(t), \ldots, x_i(t), x_j(t), x_{n-1}(t), x_n(t)$ output from a corresponding plurality of neural receivers 116i or 116j. The neurological signals $x_1(t), \ldots, x_n(t)$ are processed using one or more ML technique(s) trained for estimating and/or classifying an informational-rich data representation of neural data contained in neural activity and communicating data representative of the estimated neural data and/or classification thereof to one or more devices 108a-108p for operating on the estimated neural data.

The data representative of the estimated and/or classified neural data may be sent by the communication interface 112 to one or more device(s) 108a-108p. For example, the estimated neural data may be interpreted by the one or more device(s) 108a-108p as one or more neural commands for controlling/operating the device 108a-108p. Alternatively, the estimated neural data may be operated on or processed by the one or more device(s) 108a-108p, which perform one or more actions that deliver, by way of example only but not limited to, management, control, assistance and/or care to part of the body or functions of one or more body parts/organs/tissue or cells of the subject 102.

Given that the device(s) 108a-108p may operate to deliver assistance or care to parts of the body of the subject 102 and the like based on estimated neural data from neural activity, one or more of the device(s) 108a-108p may be configured to provide neural activity to parts of the nervous system of the subject 102. For example, a device 108a may be configured to provide feedback to (e.g. send a touch signal from a prosthetic limb to the subject 102), communicate with and/or operate (e.g. override neural activity already provided by the nervous system to deliver assistance or care to bodily tissues/organs) parts of the nervous system of the subject 102. This may be achieved by the one or more device(s) 108a-108p providing data representative of device data (e.g. neural stimulus data associated with the neural activity) in the form of, by way of example only but not limited to, a neural stimulus to corresponding parts of the nervous system (e.g. one or more neurons or neuronal population(s) 118j or 118k) of the subject 102. The data representative of this device data generated by device(s) 108a-108p for encoding as neural activity may be herein described as neural stimulus data, or bodily variable signal(s), or any other signal or data representative of data generated by the device 108a-108p for stimulus of the nervous system.

The neural interface 106 may be further configured to receive device data generated by one or more devices 108a-108p, process the device data using one or more ML technique(s) trained for estimating and communicating data representative of one or more neural stimulus signals $z_1(t), z_2(t), \ldots, z_j(t), \ldots, z_{n-1}(t), z_m(t)$ associated with the device data. The neural interface 106 communicates the data representative of the one or more estimated neural stimulus signals $z_1(t), z_m(t)$ to a corresponding one or more neural stimulus transmitter(s) 120j or 120k, which are configured for stimulating the corresponding parts of the nervous system of the subject 102 associated with the neural stimulus signals $z_1(t), \ldots, z_m(t)$ and/or device data.

A neurological signal, denoted $x_i(t)$ or $x_j(t)$, may comprise or represent a time domain signal associated with the electrical spatial and temporal activity in a neuronal population as detected and/or measured local to one or more neural receivers 116i or 116j in response to neural data that is generated by the CNS of a subject 102. The CNS of the subject 102 encodes the neural data as neural activity, which is communicated along one or more nerves 104 associated with the neuronal population 118i, 118j or 118k. For example, the neurological signal for the i-th neuronal population (or neuron cluster) 118i (or cluster i) may be modelled by, for simplicity and by way of example only but is not limited to, $x_i(t) = \sum_{j=1}^{N_i} A_j^i(t) \theta_j^i(t)$, where N is the number of neurons in the i-th neuronal population 118i (or cluster i), Bj (t) is the time varying electrochemical nerve impulse signal from the j-th neuron of the i-th neuronal population 118i (or cluster I), and $A_i(t)$ is a non-linear attenuation factor representing a temporally and spatially varying attenuation between the j-th neuron of the i-th neuronal population 118i and neural receiver 116i. Other components may be added to the modelled neurological signal $x_i(t)$ such as, by way of example only but not limited to, Additive White Gaussian Noise (AWGN), phase error, or other linear or non-linear noise components(s) and the like. A neurological stimulus signal, denoted $z_j(t)$ or $z_k(t)$, may comprise or represent a time domain signal associated with a neural stimulus for use by a neural stimulator/transmitter 120j or 120k in controlling the electrical spatial and temporal activity (e.g. the neural activity) of a neuronal population 118j or 118k associated with one or more nerve(s) 104. The neurological stimulus signal $z_j(t)$ or $z_k(t)$ may include, by way of example only but is not limited to, an excitatory signal associated with a neural stimulus capable of exciting neural activity of a neuronal population local to a neural transmitter, or an inhibitory signal associated with a neural stimulus capable of inhibiting neural activity of a neuronal population local to a neural transmitter.

A neural receiver 116i or 116j may comprise or represent any apparatus, mechanism or device capable of detecting and measuring the neural activity of one or more neurons of a neuronal population 118i or 118j of a subject 102 and outputting a neurological signal $x_i(t)$ or $x_j(t)$ representative of the neural activity. Examples of neural receivers 116a or 116j that may be used in certain embodiments of the described apparatus, methods and systems may be, by way of example only but is not limited to, any sensor capable of measuring or receiving neural activity from a neuronal population, any electrode capable of measuring or receiving neural activity from a neuronal population such as, by way of example only but not limited to, cuff electrodes, paddle electrodes, helical electrodes, book electrodes, lead wire electrodes, stent electrodes, spike array electrodes, conductive polymer electrodes or any other device capable of measuring or receiving neural activity from a neuronal population such as, by way of example only but not limited to, optogenetic sensors.

The neural receiver(s) 116i or 116j are capable of detecting and measuring the neural activity of one or more neurons of a neuronal population 118i or 118j. The neural receiver(s) 116i or 116j may be located in the vicinity of one or more nerve(s) 104 and form a neural receiver-nerve construct. The neural receiver(s) 116i or 116j are located to protect or isolate the neural receiver-nerve construct. For example, the neural receiver(s) may be located adjacent to one or more nerve(s) and may be placed, located, and/or sheathed in such a way as the neural receiver-nerve construct is protected or isolated from, by way of example only but is not limited to, one or more from the group of: external forces, motion, surrounding signals and/or noise signals and the like. In some examples protection or isolation is achieved by biological tissues, for instance, by way of example only but not limited to, at least one from the group of: inside bone, under periosteum, in muscle and the like, and/or as the application demands. In other examples, protection or isolation is achieved inside engineered materials or using engineered materials, for instance, by way of example only but not limited to, inside, on or under at least one from the group of: metal implant, plastic implant, or other substructure created for the purpose, which could include solid implant materials or biological or non-biological glues, resins and/or other materials that can be deployed around the neural receiver-nerve construct and the like and/or as the application demands. Other materials that can be deployed around the neural receiver-nerve construct may include, for instance, by way of example only but is not limited to, at least one from the group of: tisseal (or other fibrinogen based glues and sealants), silicon, cyanoacrylate, or otherwise and the like.

A neural transmitter 120j or 120k may comprise or represent any apparatus, mechanism or device capable of receiving a neurological stimulus signal $z_j(t)$ or $z_k(t)$ representative of a neural stimulus and generating a neural activity representative of the neurological stimulus signal $z_j(t)$ or $z_k(t)$ that is applied as a stimulus capable of altering the electrical spatial and temporal activity of one or more neurons of a neuronal population 118j or 118k corresponding to the neurological stimulus signal $z_j(t)$ or $z_k(t)$. Examples of neural transmitters 118j or 118k that may be used in certain embodiments of the described apparatus, methods and systems may be, by way of example only but is not limited to, any electrode capable of controlling or injecting a neural stimulus into a neuronal population 118j or 118k, such electrodes may include, by way of example only but not limited to: cuff electrodes, paddle electrodes, helical electrodes, book electrodes, lead wire electrodes, stent electrodes, spike array electrodes, and/or conductive polymer electrodes; or any other apparatus, device or mechanism capable of controlling and/or injecting or inputting a neural stimulus to a neuronal population 118j or 118k such as, by way of example only but not limited to, optogenetic sensors.

Although FIG. 1a illustrates an example with separate neural receiver(s) and neural transmitter(s) or both, this is by way of example only, it is to be appreciated by the skilled person that a neural receiver may be reconfigured to operate as a neural transmitter and that a neural transmitter may be reconfigured to operate as a neural receiver. For example, an electrode as described above may be configured to be a neural receiver but may also be configured to be a neural transmitter. Electrodes can be reconfigured, and in some cases reconfigured multiple times per second during use, to be either performing a sensing of neural activity from a neuronal population or for performing a stimulation function for inputting a neural stimulus signal or neural activity to a neuronal population. For simplicity, the neural interface 106 describes using neural receiver(s) and neural transmitter(s) separately, for simplicity and by way of example only, and it is to be appreciated by the skilled person that a neural receiver may operate on the same or similar neuronal population as a neural transmitter (e.g. a neural receiver may operate as a neural transmitter and vice versa when necessary, i.e. a neural transceiver) and/or that neural receivers can operate on different neuronal populations as the neural transmitters. In the case where neural receivers operate on different neuronal populations as neural transmitters, then further processing may be necessary due to the non-symmetric mapping of sensing and stimulation of neuronal population sites.

The neural interface system 100 may further include one or more sensors 124a-124q that may be trained on or observing the subject 102 and generate sensor data for use in training and/or re-training (or calibrating/re-calibrating) the one or more of the ML technique(s) of the neural interface 106 for estimating and/or classifying neural data from received neurological signals $x_1(t), \ldots, x_i(t), x_j(t), \ldots, x_n(t)$ of the subject 102. The one or more sensor(s) 124a-124q may comprise or represent any sensor or device capable of detecting, sensing, measuring and/or monitoring one or more biological, pathological, chemical, physical processes and/or aspects of the subject 102, generating corresponding sensing data and transmitting or reporting this sensing data. Sensor(s) 124a-124q may operate outside or be implanted within the body of the subject 102. Examples of sensor(s) 124a-124q that may be used in certain embodiments of the described apparatus, methods and systems may be, by way of example only but not limited to, any sensor capable of measuring and recording one or more pathological, physical or emotional aspects of the subject 102, which may include any sensor such as, by way of example only but not limited to, video camera, audio microphone, inertial measurement unit, motion detection sensors, depth cameras, heart rate sensors or monitors, blood pressure sensors, biomedical sensors, sensors associated with EEG, EOG and/or EMG signals or any other form of heart or brain activity. Some examples of biomedical sensors may include, by way of example only but not limited to, blood constituent monitors for monitoring glucose/hormone levels, insulin levels, oxygen saturation; gastric activity monitors for monitoring oesophageal acidity (e.g. pH), glucose index, temperature; or any other sensor capable of measuring and/or recording one or more biological, pathological or physical aspects of the subject 102.

A set of neurological signals $x_1(t), \ldots, x_i(t), x_j(t), \ldots, x_n(t)$ may be received, sampled and stored (or recorded) during a session or over time to form a training set of neurological data samples whilst at the same time sensor data associated with the subject 102 from one or more sensors 124a-124q trained on the subject 102 may also be stored and/or recorded. The sensor data may be used to identify, classify and/or label the neural activity associated with the neurological signals $x_1(t), \ldots, x_i(t), x_j(t), \ldots, x_n(t)$. Thus, both the neurological signals $x_1(t), \ldots, x_i(t), x_j(t), \ldots, x_n(t)$ and the corresponding sensor data may be used to form a training dataset may be used to train one or more ML technique(s) of the neural interface 106 to transform and recognise/classify the neural data associated with neural activity and received as neurological signals $x_1(t), \ldots, x_i(t), x_j(t), \ldots, x_n(t)$ into a suitable data representation for use by the one or more devices 108a-108p.

For example, the neurological data samples of the received neurological signals $x_1(t), \ldots, x_i(t), x_j(t), \ldots, x_n(t)$ may be labelled based on corresponding sensor data of the subject 102 that is recorded or stored during reception, sampling and recording of the neurological signals $x_1(t), \ldots, x_i(t), x_j(t), \ldots, x_n(t)$ from the subject 102. The neurological data samples and the sensor data from one or more sensors 124a-124q may be timestamped to enable the neurological signals and sensor data 124a-124q to be synchronised. The synchronised neurological sample data and sensor data can be used to identify, classify and/or label any neural activity including neural data that is present in the neurological signals $x_1(t), \ldots, x_i(t), x_j(t), \ldots, x_n(t)$ based on the response of the subject 102 as measured by the sensor data. This allows the neurological signals and sensor data to be processed into neural data training datasets, training sets of neural data or training sets of neural data samples. For example, neural activity may be determined or considered to be present when there is a sudden change or a spike in neurological signals $x_1(t), \ldots, x_i(t), x_j(t), \ldots, x_n(t)$ and hence the neurological sample data.

For example, the neurological sample data associated with the neurological signals $x_1(t), \ldots, x_i(t), x_j(t), \ldots, x_n(t)$ may be timestamped during storage whilst the sensor data is also timestamped during storage to assist in identification of which portions of the sensor data correspond to which portions of the neurological signals or sample data. The sensor data corresponding to a portion of the one or more neurological signal(s) $x_1(t), \ldots, x_i(t), x_j(t), \ldots, x_n(t)$ that is identified to correspond to neural activity may be analysed and given a label that identifies the observed activity of the corresponding body portion of the subject 102. This may be used to identify the neural data associated with the neural activity. The label(s) given to the portions of sensor data may be used to label/classify or categorise the corresponding portion(s) of the neurological data samples. Once the identified portions of the neurological data samples are labelled and/or classified, they can be used as a set of training data for training the one or more ML technique(s) of the neural interface 106.

Similarly, a neural stimulus training dataset may be generated by recording a set of neurological stimulus signals $z_1(t), \ldots, z_j(t), z_k(t), \ldots, z_m(t)$ that may be generated by one or more neuronal populations 118j or 118k when one or more body parts or portions of the subject 102 is subject to a neural stimulus. For example, the neural stimulus signals $z_1(t), \ldots, z_j(t), z_k(t), \ldots, z_m(t)$ may be the measured neural activity associated with, by way of example only but not limited to, the touch of a finger and/or neural activity associated with the function or operation of a bodily part/organ or tissue. At the same time sensor data from one or more sensor(s) 124a-124q trained or observing the subject 102 may be recorded. Thus, neurological stimulus signals $z_1(t), \ldots, z_j(t), z_k(t), \ldots, z_m(t)$ and corresponding sensor data may be sampled and stored (or recorded) during a session or over time and analysed to form a neural stimulus training dataset. Both the neurological stimulus signals $z_1(t), \ldots, z_j(t), z_k(t), \ldots, z_m(t)$ and the corresponding sensor data may be used to form a neural stimulus training dataset for training one or more ML technique(s) of the neural interface 106 to transform and recognise/classify the device data from one or more devices 108 into suitable neural stimulus signal(s) for reception by the one or more neural transmitters 118i or 118k and subsequent application of corresponding neural activity to one or more neurons or neuronal population(s) 118j or 118k.

For example, the neurological stimulus sample data associated with the neurological stimulus signals $z_1(t), \ldots, z_j(t), z_j(t), \ldots, z_m(t)$ generated by the nervous system may be timestamped during storage whilst the sensor data is also timestamped during storage to assist in identification of which portions of the sensor data correspond to which portions of the neurological stimulus signals or sample data. The sensor data corresponding to a portion of the one or more neurological stimulus signals $z_1(t), \ldots, z_j(t), z_k(t), \ldots, z_m(t)$ that is identified to correspond to neural activity may be analysed and given a label that identifies the observed activity of the corresponding body portion of the subject 102. This may be used to identify the neural data contained in neural activity in relation to the neural stimulus. The label(s) given to the portions of sensor data may be used to label/classify or categorise the corresponding portion(s) of the neurological stimulus data samples. Once the identified portions of the neurological stimulus data samples are labelled and/or classified, they can be used as a set of neural stimulus training data for training the one or more ML technique(s) of the neural interface 106 for outputting data representative of suitable neural stimulus signals that correspond to device data received from one or more device(s) 108a-108p.

As shown in FIG. 1a, the communication interface 112 is coupled to, by way of example only but is not limited to, a plurality of neural receivers 116i or 116j and a plurality of neural transmitters 120j or 120k. It is to be appreciated that the communication interface 112 may be coupled to one or more neural receivers 116a or 116j, one or more neural transmitters 120j or 120k, or both one or more neural receivers 116a or 116j and one or more neural transmitters 120j or 120k. The communication interface 112 may include communication circuitry and the like for: a) receiving a plurality of neurological signal(s) $x_1(t), \ldots, x_i(t), x_j(t), \ldots, x_n(t)$ from one or more neural receiver(s) 116i or 116j; b) transmitting one or more neural stimulus signal(s) $z_1(t), \ldots, z_j(t), z_k(t), \ldots, z_m(t)$ to one or more neural transmitters 120j or 120k; c) transmitting data representative of an estimate of neural data to one or more device(s) 108; d) receiving data representative of a neurological stimulus signal from one or more device(s) 108; and/or e) receiving further sensor data from one or more sensor(s) 124a-124q.

The communication interface 112 may be further configured to process and transmit the received one or more neurological signal(s) $x_1(t), \ldots, x_i(t), x_j(t), \ldots, x_n(t)$ as neurological signal samples or neural data samples and the sensor data to storage unit 114 and/or one or more external computing system(s) 128 that may provide additional one or more storage/processing unit(s) and/or neural interface system(s)/platform(s) (e.g. one or more server(s) and/or cloud storage/processing facilities). Given that the neural interface 106 may be a wearable device fitted to a subject 102, it may have limited computational and storage resources, and may be configured to allow one or more steps of the method(s) and/or process(es) as herein described to make use of additional computational and storage resources of the one or more external computing system(s) 128. For example, the one or more external computing system(s) 128 may be used to, by way of example only but not limited to, generate and store training dataset(s) based on the neurological signal samples and/or corresponding sensor data for training one or more ML technique(s); train one or more ML technique(s) based on the training dataset(s) to estimate neural data from neurological signal samples and transmit data representative of the trained ML technique(s) to neural interface 106 for configuring the ML technique(s) of neural interface 106 accordingly; and/or assist neural interface 106 on further storage and/or processing of neurological signal samples and/or sensor data for, by way of example only but not limited to, calibration and/or retraining of the ML technique(s) of neural interface 106, and/or in estimating neural data associated with neural activity in real-time for neural interface 106. For example, external computing system(s) 128 may train one or more ML technique(s) and transmit data representative of the trained one or more ML technique(s) to the neural interface 106 via the communication interface 112, which may be stored in storage 114 and used to configure the neural interface 106 to operate based on the trained one or more ML technique(s). The communication interface 112 may be configured for wireless and/or wired connection to device(s) 108a-108p, sensors 124a-124q, and/or external computing system(s) 128, wireless and/or wired connection to one or more other components of the neural interface 106, wireless and/or wired transmission and/or wired and/or wireless reception of data and/or signal(s) as described herein.

In this example the neurological signals $x_1(t), \ldots, x_i(t), x_j(t), \ldots, x_n(t)$ are received in parallel by the communication interface 112 as a multi-channel neurological signal. That is, the i-th channel of the multi-channel neurological signal corresponds to the i-th neurological signal $x_i(t)$ received from the i-th neural receiver 116i for $1 \leq i \leq n$. Although a multi-channel signal is described by way of example only, it is to be appreciated by the skilled person that other methods of communicating the neurological signals $x_1(t), \ldots, x_i(t), x_j(t), \ldots, x_n(t)$ from the corresponding neural receivers may be used, by way of example only but not limited to, multiplexing one or more of the neurological signals $x_1(t), \ldots, x_i(t), x_j(t), \ldots, x_n(t)$ onto a single channel or one or more channels at the communication interface 112.

Similarly, the neurological stimulus signals $z_1(t), \ldots, z_j(t), z_k(t), \ldots, z_m(t)$ are transmitted in parallel by the communication interface 112 as a multi-channel neurological stimulus signal. That is, the j-th channel of the multi-channel neurological stimulus signal corresponds to the j-th neurological stimulus signal $z_j(t)$ transmitted to the j-th neural transmitter 116j for $1 \leq j \leq n$. Although a multi-channel neurological stimulus signal is described herein this is by way of example only, and it is to be appreciated by the skilled person that other methods of communicating the neurological stimulus signals $z_1(t), \ldots, z_j(t), z_k(t), \ldots, z_m(t)$ to the corresponding neural transmitters may be used, by way of example only but not limited to, multiplexing one or more of the neurological stimulus $z_1(t), \ldots, z_j(t), z_k(t), \ldots, z_m(t)$ onto a single channel or one or more channels at the communication interface 112.

The neural interface 106 may be configured to use one or more ML technique(s) for estimating an informationally-rich or dense data representation of the neural data associated with neural activity and received as neurological signal(s) $x_1(t), \ldots, x_i(t), x_j(t), \ldots, x_n(t)$. The informationally-rich and/or dense data representation of the neural data may be determined/estimated and represented by a ML technique as a neural data vector of an N-dimensional vector space that can be sent to a device 108a-108p and operated on by the device 108a-108p. In some examples, the ML technique(s) may be applied to transform the neural data associated with the neural activity and received as neurological signal(s) into an N-dimensional vector in a latent space. The ML technique, once trained, may further classify the resulting N-dimensional vector as corresponding to a particular neural data or neural activity. Essentially, the neural interface 106 transforms the neural activity including neural data and received as neurological signal(s) $x_1(t), \ldots, x_i(t), x_j(t), \ldots, x_n(t)$ into a suitable information-rich data representation (e.g. an N-dimensional vector) that can be used and/or operated on by one or more devices 108a-108p for controlling, monitoring or operating mechanisms associated with the one or more body portions/organs/tissues of the subject 102.

Figure 1B:
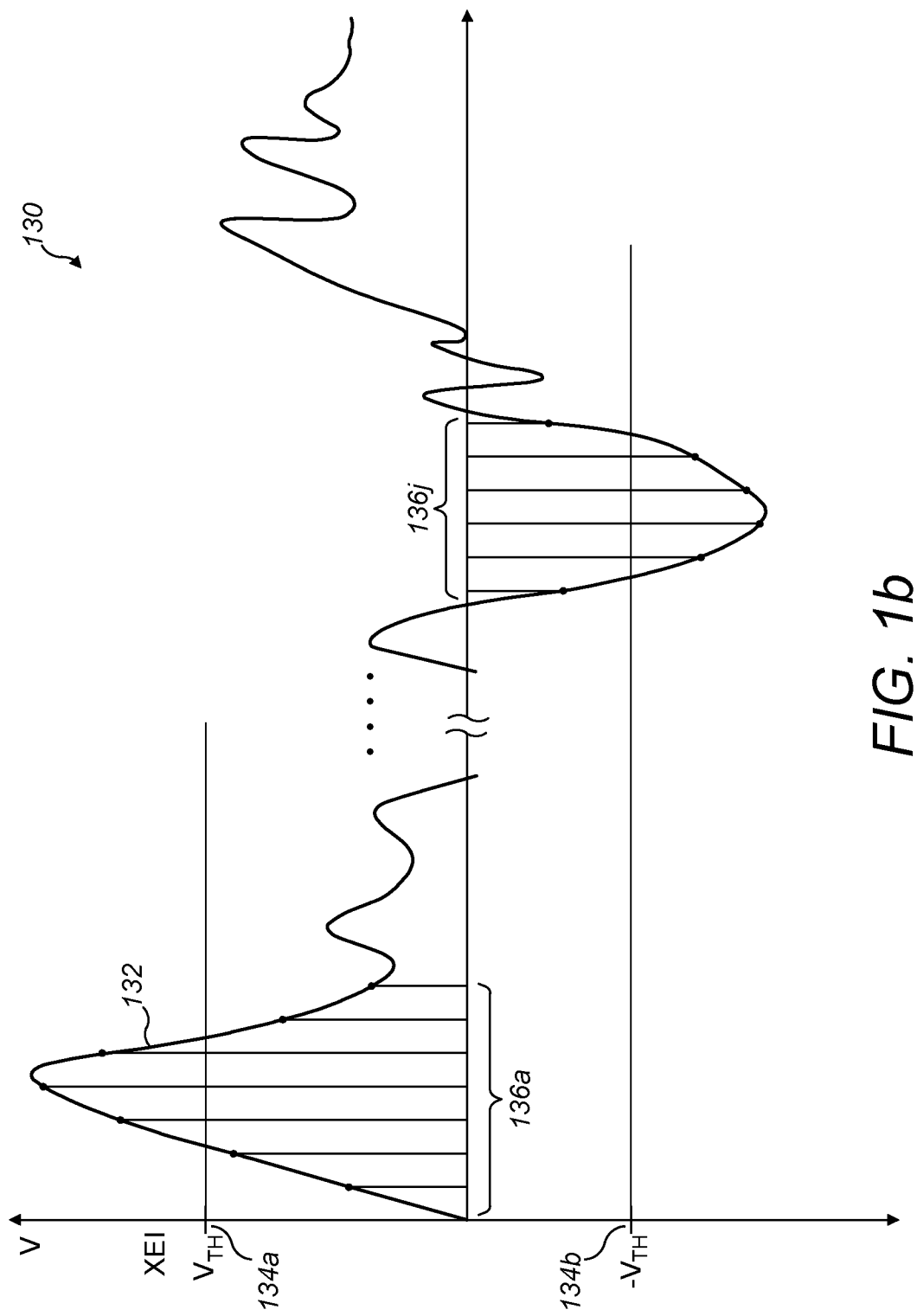
FIG. 1b is a schematic illustration of an example neurological signal for use by a neural interface according to the invention.

FIG. 1b is a schematic diagram illustrating a voltage waveform of an example neurological signal waveform x(t) 130 that may be received at communication interface 112 from any one of the plurality of neural receivers 116i or 116j. Communication interface 112 may be configured to sample the received neurological signal x(t) 130. The communication interface 112 may be configured to capture samples of neural activity, which may be, by way of example only but not limited to, in the form of an electrochemical impulse or "spike", and represented by a neurological signal waveform x(t) 130. For example, neurological signal waveform x(t) 130 may be sampled a number of L times to capture a set of neurological data samples or a neurological sample sequence $(x_i)$ for $1 \leq i \leq L$ that is associated with neural data 136a or 136j, where L is the length of the sample sequence or number of samples.

For example, the neural activity containing neural data 136a or 136j and received as a neurological signal waveform x(t) 130 may be represented as, by of example only but not limited to, a positive or negative voltage spike above a certain threshold voltage, $|V_{TH}|$. This may be used to trigger the capture of samples in and around the neurological signal waveform x(t) 130. For example, the neurological signal waveform x(t) 130 may be continuously sampled and when there is an indication of the presence of neural activity (and hence neural data) in the received neurological signal waveform x(t) 130, then those samples in and around the indication may be captured to generate a neurological sample sequence $(x_i)$ for $1 \leq i \leq L$ associated with the neural data of the neural activity for storage and/or processing. The neural interface 106 may be configured to process each neurological sample sequence $(x_i)$ using trained ML techniques to estimate, identify, classify and/or label the neural data that may be present in the neurological sample sequence $(x_i)$. The neural interface 106 may then send data representative of the estimated neural data to one or more device(s) 108a-108p that may operate on the estimated neural data to assist or provide care to the body of the subject 102. The neurological sample sequence $(x_i)$ for $1 \leq i \leq L$ may be sampled at a predetermined sampling rate, such as by way of example only but not limited to, a typical range of 5 kHz to 50 kHz.

For example, in this example the sampling rate may be 30 kHz. Although a range of 5 kHz o 50 kHz is described herein, this is by way of example only, it is to be appreciated by the person skilled in the art that any other sampling rate (e.g. another sampling rate in the range of 5 kHz to 50 kHz, a sampling rate higher than or equal to 50 kHz, or a sampling rate lower than or equal to 5 kHz) may be selected depending on, by way of example only but not limited to, the fidelity or quality required for the neurological sample sequence $(x_i)$; the computational and storage resources of the neural interface 106; the componentry of its communication interface and other hardware; the bandwidth available for communicating with one or more external computing system(s) 128 for further storing and/or processing of the neurological sample sequence $(x_i)$; and/or other factors that may limit, raise or lower, and/or enhance the selection of the sampling rate.

In real-time operation, the neurological signal waveform x(t) 130 may be continuously sampled, buffered and/or processed at a particular sample rate and when neural activity (and hence neural data) is evident, a neurological sample sequence $(x_i)$ for $1 \leq i \leq L$ associated with this neural activity may be captured from the buffer and/or from further sampling of the neurological signal waveform x(t) 130. The number of samples L may chosen to be large enough to sufficiently capture the necessary portion of the neurological signal waveform x(t) 130 that sufficiently contains the neural activity comprising the neural data. The neural interface 106 may then process the neurological sample sequence ($x_i$) for $1 \le i \le L$ associated with the neural activity using one or more ML techniques that have been trained to estimate, recognise, identify, classify and/or label the neural data in the neural activity and output data representative of the estimated neural data that is suitable for processing by one or more devices 108a-108p.

Although the neurological signal waveform x(t) 130 may be continuously sampled and/or buffered and all the samples stored for post-processing such as to for generating a training dataset of neural data, and/or processed, this may result in large and onerous storage and/or processing requirements. Thus, it is preferred that only those neurological data samples representing neural data are either stored for post-processing and/or processed. That is, the neurological data samples of the neurological signal waveform x(t) 130 at certain time instances that indicate that neural data that may be present may be stored for later processing such as, by way of example only but not limited to, generating bodily variable training datasets and/or processed by the trained ML technique(s) of the neural interface 106 for detecting, estimating and classifying neural data as an information-rich data representation for processing by one or more device(s) 108a-108p.

In FIG. 1b, the number of samples L may be set to capture a sufficient number of samples of neural data 132 carried by neurological signal waveform x(t) 130, which may be represented by a spike. The spike may be detected, by way of example only but not limited to, when the neurological signal waveform x(t) 130 exceeds a voltage spike above a threshold voltage, $|V_{TH}|$, in which neurological data samples associated with the voltage spike are captured to form a neurological sample sequence ($x_i$) 136a for $1 \le i \le L$ associated with the neural data 132, where L is the length of the sample sequence or number of samples. For example, communication interface 112 may be configured to sample and buffer data at 30 kHz, and whenever a spike is detected for up to 50 time steps then a number L of samples in and/or around this spike (e.g. L may be 50 or 300 etc.) may be read out of the buffer and/or further captured to form a neurological sample sequence ($x_i$) 136a for $1 \le i \le L$ associated with the neural data 132. Similarly, another spike associated with other neural data and neural activity may detected at a later time and a further portion of the neurological signal waveform x(t) 130 that exceeds $|V_{TH}|$ may be sampled and captured to form neurological sample sequence ($x_i$) 136j $1 \le i \le L$. A neurological signal waveform x(t) 130 may, at different times, represent neural activity with different neural data or different combinations of neural data. The k-th neural activity with neural data may be detected, sampled and captured from neurological signal waveform x(t) 130 to form a k-th neurological sample sequence $(x_i)^k$ for $1 \le i \le L$ and $k \ge 1$.

Although sampling of the neurological signal waveform x(t) 130 of FIG. 1b, has been described with reference to detecting a spike and using thresholds to capture samples of neural activity including neural data, this method of sampling is described by way of example only, and it is to be appreciated by the skilled person that sampling a neurological signal waveform is not limited to the method of sampling as described herein, rather, the skilled person would understand that other method(s) of sampling a neurological signal waveform exist such as, by way of example only but not limited to, sampling methods based on spike count, spike density, population activity: latency code and phase code, interspike interval and its coefficient of variation or any other suitable method and apparatus for sampling a neurological signal waveform x(t).

Referring to FIG. 1a, a multi-channel neurological signal based on neurological signals $x_1(t), \ldots, x_i(t), x_j(t), \ldots, x_n(t)$ may be received in parallel from different neuronal populations. For example, neurological signal $x_i(t)$ may be received from neuronal population 118i and neurological signal $x_j(t)$ may be received from neuronal population 118j. Each of the neuronal populations associated with the neurological signals $x_1(t), \ldots, x_i(t), x_j(t), \ldots, x_n(t)$ may be associated with the same k-th neural activity that includes neural data or a set of neural data. Given that the multi-channel neurological signal $x_1(t), \ldots, x_i(t), x_j(t), \ldots, x_n(t)$ has a number of n neurological signals, the j-th received neurological signal $x_j(t)$ associated with the k-th neural activity with neural data may be sampled a number of $L_j$ times to generate the j-th neurological sample sequence $(x_i)_j^k$ for $1 \le i \le L_j$, $1 \le j \le n$, and $k \ge 1$, where $L_j$ is the length of the sample sequence for the j-th neurological sample sequence. Thus, a single data point associated with the k-th neural activity with neural data for the j-th neurological signal $x_j(t)$ may consist of $L_j$ sample variables. Should the k-th neural activity with neural data be carried on all n multi-channel neurological signal $x_1(t), \ldots, x_i(t), x_j(t), \ldots, x_n(t)$ simultaneously, and $L_j = L$ for all $1 \le j \le n$, then the single data point associated with the k-th neural activity with neural data may consist of L×n sample variables.

However, the neural activity with neural data detected on each of the neurological signals $x_1(t), \ldots, x_i(t), x_j(t), \ldots, x_n(t)$ may not necessarily be simultaneously received at communication interface 112. There may be a delay in each neuronal population or the neural activity with neural data may comprise one or more neurological signal spikes that arrive at each neuronal population at different times during a period associated with the neural activity including neural data. In order to capture the k-th neural activity including neural data associated with the multi-channel neurological signals $x_1(t), \ldots, x_i(t), x_1(t), \ldots, x_n(t)$, each of the neurological signals $x_1(t), \ldots, x_i(t), x_j(t), \ldots, x_n(t)$ may be sampled a number of $L_k$ times where $L_k$ is the number of samples that are sufficient to capture the k-th neural activity encoding one or more bodily variable(s). In other words, $L_k$ may be a sampling window of sufficient size that can be used to capture the first indication of the k-th neural activity including neural data from one of the neurological signals $x_1(t), \ldots, x_i(t), x_j(t), \ldots, x_n(t)$ and to capture the last indication of the k-th neural activity including neural data from another of the neurological signals $x_1(t), \ldots, x_i(t), x_j(t), \ldots, x_n(t)$.

In another example, the communication interface 112 may be configured to receive each neurological signal $x_1(t)$ to $x_n(t)$ as a multi-channel neurological signal of, say n=M>1 channels. Whenever an indication of the k-th neural activity including neural data (e.g. a voltage spike) is detected on any of the M channels the neurological signal waveforms $x_1(t)$ to $x_n(t)$ for all channels is sampled for up to $L_k$ time steps (e.g. 50, 300 or 500 time steps). Thus, the k-th neural activity including neural data may be represented by a k-th neurological sample vector sequence $(x_i)^k$ for $1 \le i \le L_k$ and $k \ge 1$, where $x_i$ is the i-th sample vector of an M-dimensional vector space in which each element of $x_i$ represents a sample from the corresponding channel and $L_k$ is the length of the sample sequence or number of samples sufficient to capture the k-th neural activity including neural data. Thus a data point for a neural activity including neural data may consist of $L_j \times M$ samples or variables.

The k-th neurological sample vector sequence $(x_i)^k$ may be processed using one or more ML technique(s) by the processor unit 110, which may be configured to perform feature analysis/classification on the received k-th neurological sample vector sequence $(x_i)^k$ to determine an information-rich data representation of an estimate and/or classification of the neural activity including neural data. The information-rich data representation may be in the form, by way of example only but is not limited to, an N-dimensional neural data vector and may be classified/labelled. This information-rich data representation of the k-th neural activity including neural data may be sent via communication interface 112 to one or more devices 108 for performing processing, control, monitoring and/or operations associated with the k-th neural activity including neural data.

Figure 1C:
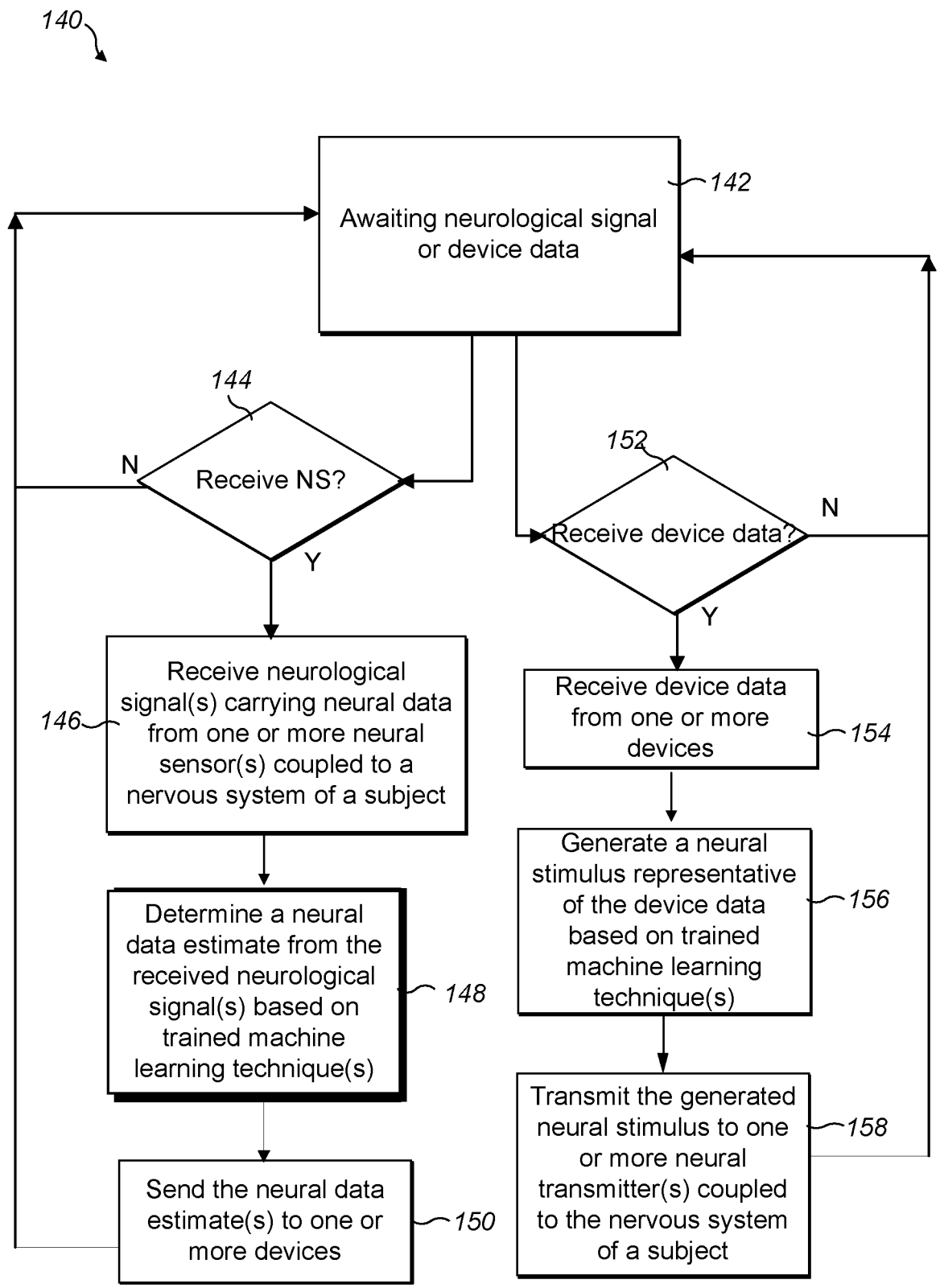
FIG. 1c is a flow diagram illustrating an example process for operating a neural interface according to the invention.

FIG. 1c is a flow diagram illustrating an example process or method 140 for interfacing with the nervous system of a subject 102. This process or method 140 may be implemented to operate the neural interface 106 as illustrated in FIG. 1a. In this example, it is assumed that a first set of one or more ML technique(s) have been trained to estimate/recognise and/or interpret/decipher neural activity from received neurological signals that have been captured and sampled. This enables seamless neural operation of devices 108a-108p associated with body parts/portions and the like of a subject 102. The neural interface 106 is coupled via a communication interface 112 to a plurality of neural receivers 116i or 116j positioned at corresponding neuronal populations 118i or 118j and is configured to receive multi-channel neurological signals $x_1(t), \ldots, x_i(t), x_j(t), \ldots, x_n(t)$. When a k-th neural activity is detected, the neural interface 106 captures neural data samples of the received multi-channel neurological signals $x_1(t), \ldots, x_i(t), x_j(t), \ldots, x_n(t)$ in the form of a k-th neurological sample vector sequence $(x_i)^k$ for $1 \leq i \leq L_k$ and $k \geq 1$, where $x_i$ is the i-th sample vector of an n-dimensional vector space in which each element of $x_i$ represents a sample from the corresponding channel and $L_k$ is the length of the sample sequence or number of samples sufficient to capture the k-th neural activity.

Similarly, it is assumed that a second set of one or more ML technique(s) have been trained to receive device data from one or more devices 108a-108p and estimate or transform the device data into a neural stimulus signal for transmission to one or more neural transmitters in the vicinity of one or more neuronal populations 118j or 118k. The neural stimulus signal is applied or converted by the neural transmitter(s) as a neural stimulus to the one or more neuronal populations 118j or 118k in accordance with the device data. The applied neural stimulus may be in the form of a neural stimulus representative of neural activity associated with the device data. The neural stimulus signal may be a multi-channel neural stimulus signal comprising a plurality of neural stimulus signals $z_1(t), z_2(t), \ldots, z_j(t), \ldots, z_{n-1}(t), z_m(t)$ associated with a plurality of neuronal populations. The process or method 140 includes, by way of example only but not limited to, the following steps of:

In step 142, the method or process 140 awaits for reception of neurological signals and/or device data. For example, the neural interface 106 may be in idle mode and is awaiting reception a plurality of neurological signal(s) $x_1(t), \ldots, x_i(t), x_j(t), \ldots, x_n(t)$ associated with neural activity from the nervous system of the subject 102. The neural interface 106 may be awaiting reception of device data from one or more device(s) 108a-108p. In the meantime, the neural interface 106 may be performing other operations such as training or retraining the first and/or second one or more ML technique(s). At least one of the first one or more ML technique(s) may correspond with at least one of the second one or more ML technique(s). Alternatively or additionally, the first one or more ML technique(s) may correspond to the second one or more ML technique(s).

In step 144, an indication of a plurality of neurological signal(s) $x_1(t), \ldots, x_i(t), x_j(t), \ldots, x_n(t)$ carrying neural data associated with a k-th neural activity may be received from a first portion of the nervous system of the subject 102. If the indication indicates neurological signal(s) $x_1(t), \ldots, x_i(t), x_j(t), \ldots, x_n(t)$ are received (e.g. Y), then the method proceeds to step 146, otherwise (e.g. N) the method 140 returns to step 142 to await an indication that one or more neurological signals and/or one or more device data from one or more device(s) are received. In step 146, the method 140 receives the indicated a plurality of neurological signal(s) $x_1(t), \ldots, x_i(t), x_j(t), \ldots, x_n(t)$ carrying neural data associated with the k-th neural activity. For example, the neural interface 106 may receive, via communication interface 112, an indication of one or more neurological signal(s) $x_1(t), \ldots, x_i(t), x_j(t), \ldots, x_n(t)$ carrying neural data associated with a k-th neural activity from one or more neural receivers (e.g. neural sensors) 116i or 116j coupled to one or more neuronal populations 118i or 118j of the first portion of the nervous system of a subject 102. Additionally, the neural interface 106 may be configured to capture samples of the k-th neural activity including the neural data to be estimated from the one or more neurological signal(s) $x_1(t), \ldots, x_i(t), x_j(t), \ldots, x_n(t)$ to generate neural sample data in the form of, by way of example only but not limited to, a k-th neurological sample vector sequence $(x_i)^k$ for $1 \leq i \leq L_k$ and $k \geq 1$, where $x_i$ is the i-th sample vector of an n-dimensional vector space in which each element of $x_i$ represents a sample from the corresponding channel and $L_k$ is the length of the sample sequence or number of samples sufficient to capture the neural data associated with the k-th neural activity.

In step 148, in response to receiving a plurality of neurological signals $x_1(t), \ldots, x_i(t), x_j(t), \ldots, x_n(t)$ associated with the neural activity of the first portion of nervous system of the subject 102, one or more neural data estimate(s) are determined from the received neurological signal(s) or neural sample data representative of the received plurality of neurological signals $x_1(t), \ldots, x_i(t), x_j(t), \ldots, x_n(t)$. This may include processing neural sample data representative of the received plurality of neurological signals $x_1(t), \ldots, x_i(t), x_j(t), \ldots, x_n(t)$ using the first one or more machine learning (ML) technique(s) trained for generating estimates of neural data representative of the neural activity of the first portion of nervous system of the subject 102. For example, the processing unit 110 of the neural interface 106 may select and apply a first one or more ML technique(s) that have been suitably trained as described herein to the k-th neurological sample vector sequence $(x_i)^k$. The first one or more ML technique(s) may determines a k-th neural data estimate(s) and/or classifies the k-th neural data estimate(s) based on the k-th neural activity detected from the neural sample data represented by the k-th neurological sample vector sequence $(x_i)^k$. The ML technique(s) may output a data representation of the k-th neural data estimate(s) in the form of an N-dimensional neural data vector. In step 150, data representative of the neural data estimate(s) may be transmitted to a first device associated with the first portion of nervous system of the subject. For example, the data representative of the k-th neural data estimate(s) and/or classified k-th neural data estimate(s) is transmitted from the neural interface 106 via the communication interface 112 to one or more devices 108a-108p that are operable on the neural data estimate(s) to manage, control, deliver care and/or assist the subject 102 and/or assist in the operation of a biological site/body part(s)/body portions/organ(s)/ tissue(s) or sub-systems of the body of the subject 102.

In step 152 an indication of device data received from one or more device(s) 108a-108p (e.g. from a second device) is received in which the device data may be associated with a second portion of the nervous system of the subject 102. For example, the device data may be associated with providing neural stimulus (e.g. excitatory or inhibitory neural stimulus) of a second portion of the nervous system of the subject 102 such as, by way of example only but not limited to, neuronal populations 118j or 118k located near neural transmitters 120j and 120k, respectively. If the indication indicates device data is to be or are being received (e.g. Y), then the method proceeds to step 154, otherwise (e.g. N) the method 140 returns to step 142 to await an indication that one or more neurological signals and/or one or more device data from one or more device(s) are received. In step 154, the method 140 receives the indicated device data from one or more devices 108a-108p (e.g. a second device). For example, the neural interface 106 may receive, via the communication interface 112, device data from a device 108a that is managing, delivering care or assisting in and/or controlling the operation of a biological site, body part/ portion, organ/tissue or sub-system of the body of a subject 102. The device data may be data representative of the device 108a providing, by way of example only but not limited to, neural stimulus (e.g. neural stimulus associated with an excitatory signal associated with the device data) and/or neural blocking/inhibition (e.g. neural stimulus associated with an inhibitory signal based on the device data) to one or more neuronal populations 118j or 118k associated with a biological site, body part/portion, organ/tissue or sub-system of the body of a subject 102.

In step 156, in response to receiving device data from a device 108a associated with a second portion of the nervous system of the subject, the method 140 may include generating one or more neurological stimulus signal(s) by inputting the received device data to a second one or more ML technique(s) trained for estimating one or more neurological stimulus signal(s) associated with the device data for input to the second portion of nervous system of the subject 102. For example, the second one or more ML technique(s) of the neural interface 106 may be used to transform or operate on the device data received from the device 108a into one or more neural stimulus signal estimates representative of the required neural stimulus or blocking (e.g. excitatory or inhibitory signal(s)) that corresponds to the device data. The ML technique(s) may generate a multi-channel neurological stimulus signal in the form of one or more neural stimulus signals $z_1(t), z_2(t), \ldots, z_j(t), \ldots, z_{n-1}(t), z_m(t)$ representative of, by way of example only but not limited to, an excitatory signal capable of exciting neural activity of a neuronal population local to a neural transmitter 120j or 120k, and/or an inhibitory signal capable of inhibiting neural activity of a neuronal population local to a neural transmitter 120j or 120k. The estimated neural stimulus signal may be configured for application by one or more neural transmitter(s) 120j and/or 120k to corresponding neuronal populations 118j and/or 118k. In step 158, the one or more estimated neurological stimulus signal(s) may be transmit towards the second portion of nervous system of the subject 102. For example, the neural interface 106 may transmit, via the communication interface 112, multi-channel neural stimulus signal(s) $z_1(t), z_2(t), \ldots, z_j(t), \ldots, z_{n-1}(t), z_m(t)$ to multiple neural transmitters 120j and 120k each of which may apply a neural stimulus signal $z_j(t)$ and $z_k(t)$ to the corresponding neuronal population 118j and 118k, respectively and/or transform the neural stimulus signal $z_j(t)$ and $z_k(t)$ into a suitable neural activity that represents the intended stimulus associated with the device data towards the corresponding neuronal population(s) 118j and/or 118k.

The method 140 may further include one or more of: receiving, from an external computing system, one or more data representative of corresponding one or more trained ML technique(s); storing the received data representative of a trained ML technique; selecting and retrieving data representative of a trained ML technique for generating estimates of neural activity or combinations thereof associated with the neural activity of the portion of nervous system. Alternatively or additionally, the method 140 may also include one or more of: receiving, from an external computing system, one or more data representative of corresponding one or more trained ML technique(s); storing the received data representative of a trained ML technique; selecting and retrieving data representative of a trained ML technique for estimating one or more neurological stimulus signal(s) for input to the nervous system.

FIGS. 1a-1d described and illustrated the neural interface system 100 and neural interface 106 in which neural activity including neural data or contained neural data therein and/or device data was used for generating a stimulus signal for stimulating the nervous system of a subject 102. The neural interface system 100 and neural interface 106 of FIGS. 1a and 1b will now be described using an information theoretic definition of neural activity in which the neural activity is considered to encode one or more variables of information associated with the body or bodily functions or organs/ tissues/cells of the subject 102, also described herein as one or more bodily variable(s) or combinations thereof. Furthermore, the device data may be considered to include data representative of one or more bodily variable(s) that may be encoded on neural activity for providing a neural stimulus to the nervous system of the subject 102. In the following example, the device data may be considered and described herein to relate to signal(s) associated with the body or bodily functions or organs/tissues/cells of the subject 102, also described herein as bodily variable signal(s). It is to be appreciated by the skilled person that the phrase "neural data" and "one or more bodily variable(s)" may be interchanged and/or used interchangeably without loss of understanding throughout the description. It is to be appreciated by the skilled person that the phrase "device data" and "bodily variable signal(s)" may be interchanged and/or used interchangeably without loss of understanding throughout the description.

In FIG. 1a, the communication interface 112 is coupled to, by way of example only but is not limited to, a plurality of neural receivers 116i or 116j and a plurality of neural transmitters 120j or 120k. It is to be appreciated that the communication interface 112 may be coupled to one or more neural receivers 116a or 116j, one or more neural transmitters 120j or 120k, or both one or more neural receivers 116a or 116j and one or more neural transmitters 120j or 120k. The communication interface 112 may include communication circuitry and the like for: a) receiving a plurality of neurological signal(s) $x_1(t), \ldots, x_i(t), x_j(t), \ldots, x_n(t)$ from one or more neural receiver(s) 116i or 116j; b) transmitting one or more neural stimulus signal(s) $z_1(t), \ldots, z_j(t), z_k(t), \ldots, z_m(t)$ to one or more neural transmitters 120j or 120k; c) transmitting data representative of an estimate of bodily variable(s) to one or more device(s) 108; d) receiving data representative of a neurological stimulus signal from one or more device(s) 108; and/or e) receiving further sensor data from one or more sensor(s) 124a-124q.

The communication interface 112 may be further configured to process and transmit the received one or more neurological signal(s) $x_1(t), \ldots, x_i(t), x_j(t), \ldots, x_n(t)$ as neurological signal samples or neural data samples and the sensor data to storage unit 114 and/or one or more external computing system(s) 128 that may provide additional one or more storage/processing unit(s) and/or neural interface system(s)/platform(s) (e.g. one or more server(s) and/or cloud storage/processing facilities). Given that the neural interface 106 may be a wearable device fitted to a subject 102, it may have limited computational and storage resources, and may be configured to allow one or more steps of the method(s) and/or process(es) as herein described to make use of additional computational and storage resources of the one or more external computing system(s) 128. For example, the one or more external computing system(s) 128 may be used to, by way of example only but not limited to, generate and store training dataset(s) based on the neurological signal samples and/or corresponding sensor data for training one or more ML technique(s); train one or more ML technique(s) based on the training dataset(s) to estimate bodily variable(s) from neurological signal samples and transmit data representative of the trained ML technique(s) to neural interface 106 for configuring the ML technique(s) of neural interface 106 accordingly; and/or assist neural interface 106 on further storage and/or processing of neurological signal samples and/or sensor data for, by way of example only but not limited to, calibration and/or retraining of the ML technique(s) of neural interface 106, and/or in estimating bodily variable(s) from neural activity in real-time for neural interface 106. For example, external computing system(s) 128 may train one or more ML technique(s) and transmit data representative of the trained one or more ML technique(s) to the neural interface 106 via the communication interface 112, which may be stored in storage 114 and used to configure the neural interface 106 to operate based on the trained one or more ML technique(s). The communication interface 112 may be configured for wireless and/or wired connection to device(s) 108a-108p, sensors 124a-124q, and/or external computing system(s) 128, wireless and/or wired connection to one or more other components of the neural interface 106, wireless and/or wired transmission and/or wired and/or wireless reception of data and/or signal(s) as described herein.

In this example the neurological signals $x_1(t), \ldots, x_i(t), x_j(t), \ldots, x_n(t)$ are received in parallel by the communication interface 112 as a multi-channel neurological signal. That is, the i-th channel of the multi-channel neurological signal corresponds to the i-th neurological signal $x_i(t)$ received from the i-th neural receiver 116i for $1 \leq i \leq n$. Although a multi-channel signal is described by way of example only, it is to be appreciated by the skilled person that other methods of communicating the neurological signals $x_1(t), \ldots, x_i(t), x_j(t), \ldots, x_n(t)$ from the corresponding neural receivers may be used, by way of example only but not limited to, multiplexing one or more of the neurological signals $x_1(t), \ldots, x_i(t), x_j(t), \ldots, x_n(t)$ onto a single channel or one or more channels at the communication interface 112.

Similarly, the neurological stimulus signals $z_1(t), \ldots, z_j(t), z_k(t), \ldots, z_m(t)$ are transmitted in parallel by the communication interface 112 as a multi-channel neurological stimulus signal. That is, the j-th channel of the multi-channel neurological stimulus signal corresponds to the j-th neurological stimulus signal $z_j(t)$ transmitted to the j-th neural transmitter 116j for $1 \leq j \leq n$. Although a multi-channel neurological stimulus signal is described herein this is by way of example only, and it is to be appreciated by the skilled person that other methods of communicating the neurological stimulus signals $z_1(t), \ldots, z_j(t), z_k(t), \ldots, z_m(t)$ to the corresponding neural transmitters may be used, by way of example only but not limited to, multiplexing one or more of the neurological stimulus $z_1(t), \ldots, z_j(t), z_k(t), \ldots z_m(t)$ onto a single channel or one or more channels at the communication interface 112.

The neural interface 106 may be configured to use one or more ML technique(s) for estimating an informationally rich or dense data representation of the bodily variable information encoded as neural activity and received as neurological signal(s) $x_1(t), \ldots, x_i(t), x_j(t), \ldots, x_n(t)$. The informationally rich of dense data representation of the bodily variable(s) may be determined/estimated and represented by a ML technique as a bodily variable vector of an N-dimensional vector space that can be sent to a device 108a-108p and operated on by the device 108a-108p. In some examples, the ML technique(s) may be applied to transform the bodily variable(s) encoded as neural activity and received as neurological signal(s) into an N-dimensional vector in a latent space. The ML technique, once trained, may further classify the resulting N-dimensional vector as corresponding to a particular one or more bodily variable(s) and/or a combination of bodily variable(s) that were encoded as neural activity. Essentially, the neural interface 106 transforms the bodily variable(s) encoded as neural activity and received as neurological signal(s) $x_1(t), \ldots, x_i(t), x_j(t), \ldots, x_n(t)$ into a suitable information rich data representation (e.g. an N-dimensional vector) that can be used and/or operated on by one or more devices 108a-108p for controlling, monitoring or operating mechanisms associated with the one or more body portions/organs/tissues of the subject 102.

FIG. 1b is a schematic diagram illustrating a voltage waveform of an example neurological signal waveform x(t) 130 that may be received at communication interface 112 from any one of the plurality of neural receivers 116i or 116j. Communication interface 112 may be configured to sample the received neurological signal x(t) 130. The communication interface 112 may be configured to capture samples of neural activity encoding one or more bodily variable(s), which may be in the form of an electrochemical impulse or "spike", and represented by a neurological signal waveform x(t) 130. For example, neurological signal waveform x(t) 130 may be sampled a number of L times to capture a set of neurological data samples or a neurological sample sequence $(x_i)$ for $1 \leq i \leq L$ that is associated with one or more bodily variable(s) 136a or 136j, where L is the length of the sample sequence or number of samples.

For example, the neural activity encoding one or more bodily variable(s) 136a or 136j and received as a neurological signal waveform x(t) 130 may be represented as, by of example only but not limited to, a positive or negative voltage spike above a certain threshold voltage, $|V_{TH}|$. This may be used to trigger the capture of samples in and around the neurological signal waveform x(t) 130. For example, the neurological signal waveform x(t) 130 may be continuously sampled and when there is an indication of the presence of neural activity encoding one or more bodily variable(s) in the received neurological signal waveform x(t) 130, then those samples in and around the indication may be captured to generate a neurological sample sequence $(x_i)$ for $1 \leq i \leq L$ associated with the bodily variable(s) for storage and/or processing. The neural interface 106 may be configured to process each neurological sample sequence ($x_i$) using trained ML techniques to estimate, identify, classify and/or label the bodily variable(s) that may be present in the neurological sample sequence ($x_i$). The neural interface 106 may then send data representative of the estimated bodily variable(s) to one or more device(s) 108a-108p that may operate on the estimated bodily variable(s) to assist or provide care to the body of the subject 102. The neurological sample sequence ($x_i$) for $1 \leq i \leq L$ may be sampled at a predetermined sampling rate, such as by way of example only but not limited to, a typical range of 5 kHz to 50 kHz.

For example, in this example the sampling rate may be 30 kHz. Although a range of 5 kHz o 50 kHz is described herein, this is by way of example only, it is to be appreciated by the person skilled in the art that any other sampling rate (e.g. another sampling rate in the range of 5 kHz to 50 kHz, a sampling rate higher than or equal to 50 kHz, or a sampling rate lower than or equal to 5 kHz) may be selected depending on, by way of example only but not limited to, the fidelity or quality required for the neurological sample sequence ($x_i$); the computational and storage resources of the neural interface 106; the componentry of its communication interface and other hardware; the bandwidth available for communicating with one or more external computing system(s) 128 for further storing and/or processing of the neurological sample sequence ($x_i$); and/or other factors that may limit, raise or lower, and/or enhance the selection of the sampling rate.

In real-time operation, the neurological signal waveform x(t) 130 may be continuously sampled, buffered and/or processed at a particular sample rate and when neural activity encoding one or more bodily variable(s) is evident, a neurological sample sequence ($x_i$) for $1 \leq i \leq L$ associated with this neural activity may be captured from the buffer and/or from further sampling of the neurological signal waveform x(t) 130. The number of samples L may chosen to be large enough to sufficiently capture the necessary portion of the neurological signal waveform x(t) 130 that sufficiently contains the neural activity encoding one or more bodily variable(s). The neural interface 106 may then process the neurological sample sequence ($x_i$) for $1 \leq i \leq L$ associated with the neural activity encoding bodily variable(s) using one or more ML techniques that have been trained to estimate, recognise, identify, classify and/or label the one or more bodily variable(s) or a combination of bodily variable(s) and output data representative of the bodily variable(s) estimated that is suitable for processing by one or more devices 108a-108p.

Although the neurological signal waveform x(t) 130 may be continuously sampled and/or buffered and all the samples stored for post-processing such as to for generating a bodily variable training dataset, and/or processed, this may result in large and onerous storage and/or processing requirements. Thus, it is preferred that only those neurological data samples representing one or more bodily variable(s) and/or a combination of bodily variable(s) are either stored for post-processing and/or processed. That is, the neurological data samples of the neurological signal waveform x(t) 130 at certain time instances that indicate that a bodily variable may be present may be stored for later processing such as, by way of example only but not limited to, generating bodily variable training datasets and/or processed by the trained ML technique(s) of the neural interface 106 for detecting, estimating and classifying one or more bodily variables or combinations thereof an information rich data representation for processing by one or more device(s) 108a-108p.

In FIG. 1b, the number of samples L may be set to capture a sufficient number of samples of one or more bodily variables 132 carried by neurological signal waveform x(t) 130, which may be represented by a spike. The spike may be detected when the neurological signal waveform x(t) 130 exceeds a voltage spike above a threshold voltage, $|V_{TH}|$, in which neurological data samples associated with the voltage spike are captured to form a neurological sample sequence ($x_i$) 136a for $1 \leq i \leq L$ associated with the bodily variable(s) 132, where L is the length of the sample sequence or number of samples. For example, communication interface 112 may be configured to sample and buffer data at 30 kHz, and whenever a spike is detected for up to 50 time steps then a number L of samples in and/or around this spike (e.g. L may be 50 or 300 etc.) may be read out of the buffer and/or further captured to form a neurological sample sequence ($x_i$) 136a for $1 \leq i \leq L$ associated with the bodily variable(s) 132. Similarly, another spike associated with another one or more bodily variables or combination thereof may detected at a later time and a further portion of the neurological signal waveform x(t) 130 that exceeds $|V_{TH}|$ may be sampled and captured to form neurological sample sequence ($x_i$) 136j $1 \leq i \leq L$. A neurological signal waveform x(t) 130 may, at different times, represent neural activity encoding different bodily variable(s) or different combinations of bodily variables. The k-th neural activity encoding a set of one or more bodily variable(s) may be detected, sampled and captured from neurological signal waveform x(t) 130 to form a k-th neurological sample sequence $(x_i)^k$ for $1 \leq i \leq L$ and $k \geq 1$.

Referring to FIG. 1a, a multi-channel neurological signal based on neurological signals $x_1(t), \ldots, x_i(t), x_j(t), \ldots, x_n(t)$ may be received in parallel from different neuronal populations. For example, neurological signal $x_i(t)$ may be received from neuronal population 118i and neurological signal $x_j(t)$ may be received from neuronal population 118j. Each of the neuronal populations associated with the neurological signals $x_1(t), \ldots, x_i(t), x_1(t), \ldots, x_n(t)$ may be associated with the same k-th neural activity that encodes a set of one or more bodily variable(s). Given that the multi-channel neurological signal $x_1(t), \ldots, x_i(t), x_1(t), \ldots, x_n(t)$ has a number of n neurological signals, the j-th received neurological signal $x_j(t)$ associated with the k-th neural activity encoding one or more bodily variable(s) may be sampled a number of $L_j$ times to generate the j-th neurological sample sequence $(x_{i,j})^k$ for $1 \leq i \leq L_1$, $1 \leq j \leq n$, and $k \geq 1$, where $L_j$ is the length of the sample sequence for the j-th neurological sample sequence. Thus, a single data point associated with the k-th neural activity encoding one or more bodily variable(s) for the j-th neurological signal $x_j(t)$ may consist of $L_j$ sample variables. Should the k-th neural activity encoding one or more bodily variable(s) be carried on all n multi-channel neurological signal $x_1(t), \ldots, x_i(t), x_1(t), \ldots, x_n(t)$ simultaneously, and $L_j = L$ for all $1 \leq j \leq n$, then the single datapoint associated with the k-th neural activity encoding one or more bodily variable(s) may consist of L×n sample variables.

However, the neural activity encoding one or more bodily variable(s) detected on each of the neurological signals $x_1(t), \ldots, x_i(t), x_1(t), \ldots, x_n(t)$ may not necessarily be simultaneously received at communication interface 112. There may be a delay in each neuronal population or the neural activity encoding one or more bodily variable(s) may comprise one or more neurological signal spikes that arrive at each neuronal population at different times during a period associated with the neural activity encoding one or more bodily variable(s). In order to capture the k-th neural activity encoding one or more bodily variable(s) associated with the multi-channel neurological signals $x_1(t), \ldots, x_i(t), x_1(t), \ldots, x_n(t)$, each of the neurological signals $x_1(t), \ldots, x_i(t), x_j(t), \ldots, x_n(t)$ may be sampled a number of $L_k$ times where $L_k$ is the number of samples that are sufficient to capture the k-th neural activity encoding one or more bodily variable(s). In other words, $L_k$ may be a sampling window of sufficient size that can be used to capture the first indication of the k-th neural activity encoding one or more bodily variable(s) from one of the neurological signals $x_1(t), \ldots, x_i(t), x_j(t), \ldots, x_n(t)$ and to capture the last indication of the k-th neural activity encoding one or more bodily variable(s) from another of the neurological signals $x_1(t), \ldots, x_i(t), x_1(t), \ldots, x_n(t)$.

In another example, the communication interface 112 may be configured to receive each neurological signal $x_1(t)$ to $x_n(t)$ as a multi-channel neurological signal of, say n=M>1 channels. Whenever an indication of the k-th neural activity encoding one or more bodily variable(s) (e.g. a voltage spike) is detected on any of the M channels the neurological signal waveforms $x_1(t)$ to $x_n(t)$ for all channels is sampled for up to $L_k$ time steps (e.g. 50, 300 or 500 time steps). Thus, the k-th neural activity encoding one or more bodily variable(s) may be represented by a k-th neurological sample vector sequence $(x_i)^k$ for $1 \leq i \leq L_k$ and $k \geq 1$, where $x_i$ is the i-th sample vector of an M-dimensional vector space in which each element of $x_i$ represents a sample from the corresponding channel and $L_k$ is the length of the sample sequence or number of samples sufficient to capture the k-th neural activity encoding one or more bodily variable(s). Thus a data point for a neural activity encoding one or more bodily variable(s) may consist of $L_j \times M$ samples or variables.

The k-th neurological sample vector sequence $(x_i)^k$ may be processed using one or more ML technique(s) by the processor unit 110, which may be configured to perform feature analysis/classification on the received k-th neurological sample vector sequence $(x_i)^k$ to determine an information rich data representation of an estimate and/or classification of the neural activity encoding one or more bodily variable(s). The information rich data representation may be in the form, by way of example only but is not limited to, an N-dimensional bodily variable vector and may be classified/labelled. This information rich data representation of the k-th neural activity encoding one or more bodily variable(s) may be sent via communication interface 112 to one or more devices 108 for performing processing, control, monitoring and/or operations associated with the k-th neural activity encoding one or more bodily variable(s).

Figure 1D:
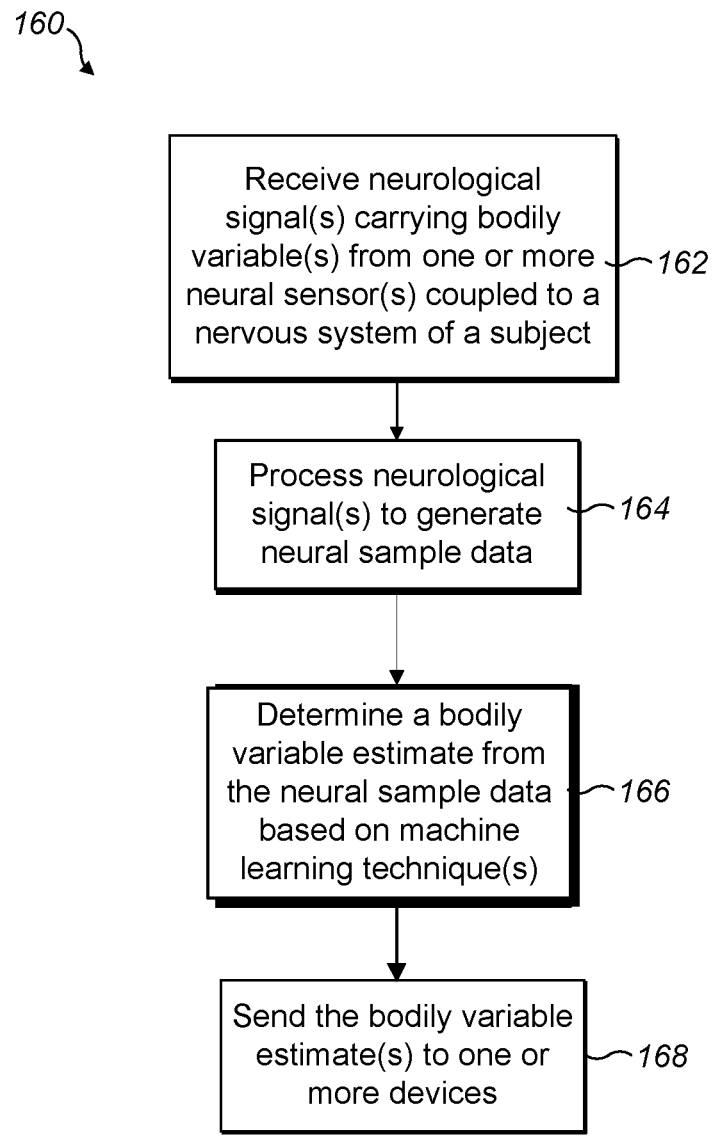
FIG. 1d is another flow diagram illustrating another example process of operating a neural interface according to the invention.

FIG. 1d is a flow diagram illustrating an example process or method 160 for operating a neural interface 106 as illustrated in FIG. 1a. In this example, it is assumed that one or more ML technique(s) have been trained to estimate/recognise and/or interpret/decipher neural activity encoding one or more bodily variable(s) from received neurological signals that have been captured and sampled. This enables seamless neural operation of devices 108a-108p associated with body parts/portions and the like of a subject 102. The neural interface 106 is coupled via a communication interface 112 to a plurality of neural receivers 116i or 116j positioned at corresponding neuronal populations 118i or 118j and is configured to receive multi-channel neurological signals $x_1(t), \ldots, x_i(t), x_j(t), \ldots, x_n(t)$. When a k-th neural activity encoding one or more bodily variable(s) is detected, the neural interface 106 captures neural data samples of the received multi-channel neurological signals $x_1(t), \ldots, x_i(t), x_j(t), \ldots, x_n(t)$ in the form of a k-th neurological sample vector sequence $(x_i)^k$ for $1 \leq i \leq L_k$ and $k \geq 1$, where $x_i$ is the i-th sample vector of an n-dimensional vector space in which each element of $x_i$ represents a sample from the corresponding channel and $L_k$ is the length of the sample sequence or number of samples sufficient to capture the k-th neural activity encoding one or more bodily variable(s). The process or method 160 includes, by way of example only but is not limited to, the following steps of:

In step 162, the neural interface 106 receives, via a communication interface 112, an indication of one or more neurological signal(s) $x_1(t), \ldots, x_i(t), x_j(t), \ldots, x_n(t)$ carrying information associated with a k-th neural activity encoding one or more bodily variable(s) from one or more neural receivers (e.g. neural sensors) coupled to one or more neuronal populations 118i or 118j of the nervous system of a subject 102. In step 164, the neural interface 106 captures samples of the k-th neural activity encoding one or more bodily variable(s) from the one or more neurological signal(s) $x_1(t), \ldots, x_i(t), x_j(t), \ldots, x_n(t)$ to generate neural sample data in the form of, by way of example only but not limited to, a k-th neurological sample vector sequence $(x_i)^k$ for $1 \leq i \leq L_k$ and $k \geq 1$, where $x_i$ is the i-th sample vector of an n-dimensional vector space in which each element of $x_i$ represents a sample from the corresponding channel and $L_k$ is the length of the sample sequence or number of samples sufficient to capture the k-th neural activity encoding one or more bodily variable(s). In step 166, the processing unit 110 of the neural interface 106 applies one or more ML technique(s) that have been suitably trained as described, by way of example only but not limited to, herein to the k-th neurological sample vector sequence $(x_i)^k$. The one or more ML technique(s) determines a k-th bodily variable estimate(s) and/or classifies the k-th bodily variable estimate(s) based on the k-th neural activity encoding one or more bodily variable(s) detected from the neural sample data represented by the k-th neurological sample vector sequence $(x_i)^k$. The ML technique(s) may output a data representation of the k-th bodily variable estimate(s) in the form of an N-dimensional bodily variable vector. In step 168, data representative of the k-th bodily variable estimate(s) and/or classified k-th bodily variable estimate(s) is transmitted from the neural interface 106 via the communication interface 112 to one or more devices 108a-108p that are operable to assist the subject 102 and/or assist in the operation of a biological site/body part(s)/body portions/organ(s)/tissue(s) or sub-systems of the body of the subject 102.

Figure 1E:
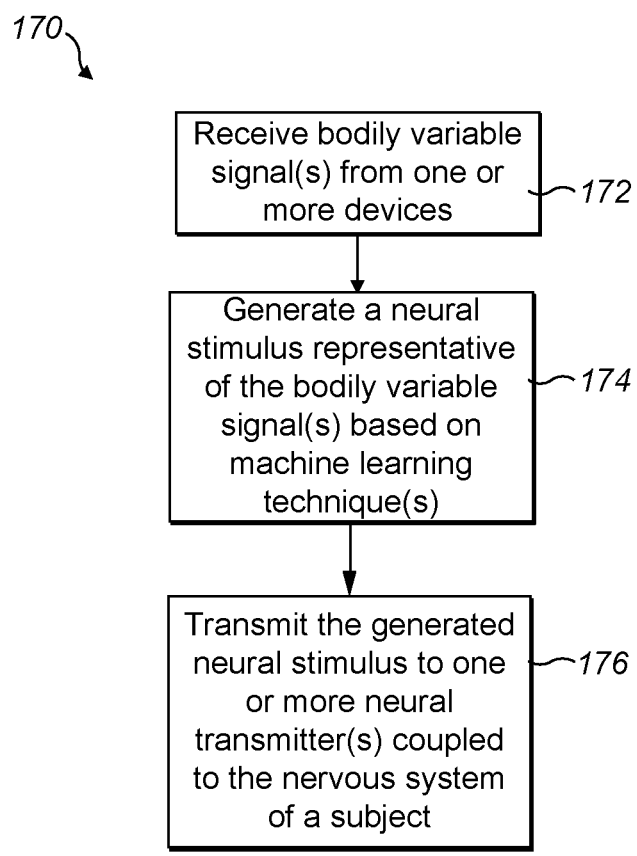
FIG. 1e is another flow diagram illustrating a further example process of operating a neural interface according to the invention.

FIG. 1e is a flow diagram illustrating an example process or method 170 for operating a neural interface 106 as illustrated in FIG. 1a. In this example, it is assumed that one or more ML technique(s) have been trained to receive bodily variable signal(s) from a device 108a and estimate or transform the bodily variable signal(s) into a neural stimulus signal for transmission to one or more neural transmitters in the vicinity of one or more neuronal populations 118j or 118k. The neural stimulus signal is applied or converted by the neural transmitter(s) as a neural stimulus to the one or more neuronal populations 118j or 118k in accordance with the bodily variable signal(s). The applied neural stimulus may be in the form of a neural stimulus representative of neural activity encoding the bodily variable signal(s). The neural stimulus signal may be a multi-channel neural stimulus signal comprising one or more neural stimulus signals $z_1(t), z_2(t), \ldots, z_j(t), \ldots, z_{n-1}(t), z_m(t)$ associated with the one or more neuronal populations. The method or process 170 is based, by way of example only but not limited to, the following steps of:

In step 172 the neural interface 106 receives, via the communication interface 112, one or more bodily variable signal(s) from a device 108a that is assisting in and/or controlling the operation of a biological site, body part/portion, organ/tissue or sub-system of the body of a subject 102. The bodily variable signal(s) may be data representative of the device 108a providing neural stimulus and/or neural blocking to one or more neuronal populations 118j or 118k associated with a biological site, body part/portion, organ/tissue or sub-system of the body of a subject 102. In step 174, the one or more ML technique(s) of the neural interface 106 may be used to transform or operate on the bodily variable signal(s) received from the device 108a into one or more neural stimulus signal estimates representative of the required neural stimulus or blocking that corresponds to the bodily variable signal(s). The ML technique(s) may generate a multi-channel neurological stimulus signal in the form of one or more neural stimulus signals $z_1(t)$, $z_2(t), \ldots, z_j(t), \ldots, z_{n-1}(t), z_m(t)$ representative of the estimated neural stimulus/blocking for application by one or more neural transmitter(s) to corresponding neuronal populations 118j or 118k. In step 178, the neural interface 106 transmits, via the communication interface 112, multi-channel neural stimulus signal(s) $z_1(t), z_2(t), \ldots, z_j(t), \ldots z_{n-1}(t)$, $z_m(t)$ to one or more neural transmitters 120j or 120k each of which may apply a neural stimulus signal $z_j(t)$ to the corresponding neuronal population and/or transform the neural stimulus signal $z_j(t)$ into a suitable neural activity that represents an encoding of the bodily variable signal(s) for stimulating the corresponding neuronal population.

As described above and herein, the neural interface 106 generates neural sample data or neurological data by capturing samples of neural activity encoding one or more bodily variable(s) from the one or more neurological signal(s) $x_1(t), \ldots, x_i(t), x_j(t), \ldots, x_n(t)$ output by a plurality of neural receivers 116i, 116j. The neural sample data (also referred to as neurological data) may include a plurality of sets of neural sample data, each set of neural sample data corresponding to the output from one of the plurality of neural receivers 116a, 116j. An ML technique may be trained to generate an ML model capable of predicting a bodily variable when receiving neural sample data derived from one or more neurological signals $x_1(t), \ldots, x_i(t)$, $x_j(t), \ldots, x_n(t)$. There are various supervised, semi-supervised or unsupervised methods for training an ML technique to generate an ML model for predicting a bodily variable. For simplicity, the following describes, by way of example only but is not limited to, a supervised method for training a ML technique to generate an ML model for predicting a bodily variable. Although are supervised ML technique training methods is described, this is by way of example only and the description is not so limited, it is to be appreciated by the skilled person that one or more steps of the following supervised training techniques may be applied or modified for use in training any suitable ML technique in a supervised, semi-supervised and/or unsupervised fashion, modifications thereof, and/or combinations thereof, and/or as the application demands. Supervised training techniques typically require the a labelled training neural sample dataset associated with a bodily variable for training a ML technique to generate a ML model for predicting or estimating data representative of the bodily variable when, after training, the ML model is presented with neural sample data or neurological data as input.

Figure 1F:
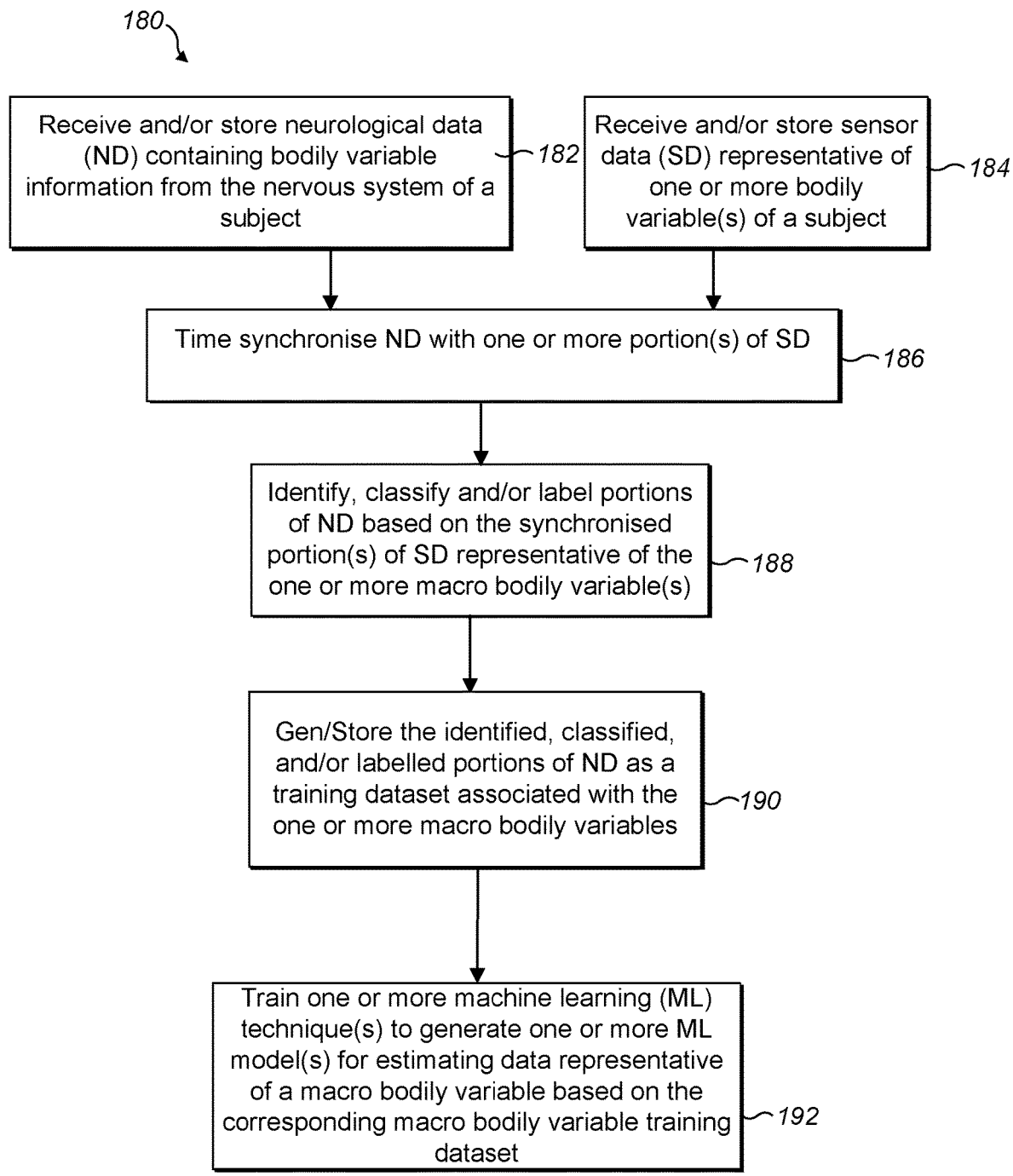
FIG. 1f is a flow diagram illustrating another example process for generating a labelled training dataset from neurological data for training a machine learning (ML) model of the neural interface according to the invention.

FIG. 1f is a flow diagram illustrating another example process 180 for generating a labelled training neural sample dataset from neurological data and sensor data for performing supervised training of a ML technique to generate an ML model for use by the neural interface 106 in predicting one or more bodily variable(s) according to the invention. The method 180 is based on, by way of example only but is not limited to, one or more of the following steps of: In step 182, neurological data (e.g. neural sample data) containing bodily variable information from the nervous system of a subject 102 is received from one or more neural receivers 116i, 116j and recorded or stored (e.g. in external system 128 or neural interface 106 and the like). The neurological data may be a plurality of sets of neural data samples, each set of neural data samples generated from a neurological signal of a corresponding neural receiver. At the same time that the neurological data is recorded or stored, in step 184 one or more sensor(s) associated with sensing data representative of one or more bodily variable(s) of the subject 102 may be generating raw sensor data may also be recorded or stored (e.g. in external system 128 or neural interface 202a or 202b). The sensor data from the one or more sensors is continuously recorded throughout the recording of each set of neural data samples of the neurological data. This means that fully supervised training may be used because the sensor data may be time synchronised with the neurological data. In step 186, the recorded or stored neurological data may be time synchronised with the recorded or stored sensor data from the one or more sensor(s). Each sensor may generate sensor data associated with a bodily variable.

Each set of neural data samples generated from each neural receiver may include a plurality of portions of neural data samples in which each portion of neural data samples corresponds to neural activity encoding one or more bodily variables. The portions of neural data samples from each neural receiver may be spaced apart in time and/or contiguous in time. The portions of neural data samples from each neural receiver may occur in the vicinity of when neural activity encoding one or more bodily variables is detected. The portions of neural data samples from each neural receiver may be recorded and stored. At the same time, the sensor data may be continuously generated from a sensor and recorded and stored at the same time neurological signals are received and processed. The sensor data may also be processed or partitioned into a set of sensor data samples that includes a plurality of portions of sensor data samples corresponding to the portions of neural data samples. That is each portion of sensor data samples coincides in time or is within the same time interval as a corresponding portion of neural data samples is generated, recorded and/or stored.

For example, as described previously, the neurological signals $x_1(t), \ldots, x_i(t), x_j(t), \ldots, x_n(t)$ may be received in parallel by the communication interface 112 as a multi-channel neurological signal. That is, the i-th channel of the multi-channel neurological signal corresponds to the i-th neurological signal $x_i(t)$ received from the i-th neural receiver 116i for $1 \leq i \leq n$, where n is the number of neural receivers. From the i-th neural receiver 116i, the neural interface 106 may capture a set of neural data samples comprising a plurality of portions of neural data samples, in which each portion of neural data samples corresponds to neural activity encoding one or more bodily variables. That is, a k-th portion of neural data samples may correspond to the k-th neural activity encoding one or more bodily variable(s) from the one or more neurological signal(s) $x_1(t), \ldots, x_i(t), x_j(t), \ldots, x_n(t)$. This may be used to generate the k-th portion of multi-channel neural sample data in the form of, by way of example only but not limited to, a k-th neurological sample vector sequence $(x_i)^k$ for $1 \leq i \leq L_k$ and $k \geq 1$, where $x_i$ is the i-th sample vector of an n-dimensional vector space in which each element of $x_i$ represents a sample from the corresponding channel (e.g. corresponding neural receiver) and $L_k$ is the length of the sample sequence or number of samples sufficient to capture the k-th neural activity encoding one or more bodily variable(s). Thus, the k-th neurological sample vector sequence $(x_i)^k$ corresponds to the k-th portion of multi-channel neurological data from the multi-channel neurological signal. At the same time, sensor data may be continuously generated from a sensor and recorded and stored at the same time the multi-channel neurological signals are received and processed. The sensor data may also be processed or partitioned into a set of sensor data samples that includes a plurality of portions of sensor data samples corresponding to the plurality of portions of the multi-channel neurological data samples. Each k-th portion of sensor data samples corresponds to the k-th portion of multichannel neurological data. There may be a number of $S_k \geq 1$ sensor data samples in each k-th portion of sensor data samples, where $S_k \leq L_k$. That is the k-th portion of sensor data samples typically coincides in time or are generated within the same time interval as the corresponding k-th portion of multi-channel neurological data.

In step 188, the sensor data associated with a bodily variable may be analysed, identified, classified, labelled and/or characterised in which each portion of the sensor data may be labelled with a particular label from a set of Y labels $\{ \ell_1, \ell_2, \ell_3, \ldots, \ell_i, \ldots \ell_Y \}$, where $Y \geq 1$, characterising the bodily variable. As described above, the sensor data may be processed and partitioned or divided into a plurality of time intervals or portions corresponding to the portions of neurological data. Each k-th time interval or portion of the sensor data is analysed and assigned a label from the set of Y labels $\{ \ell_1, \ell_2, \ell_3, \ldots, \ell_i, \ldots \ell_Y \}$ for characterising the variation of the bodily variable described by the sensor data. The time intervals or portions may be, by way of example only but is not limited to, equal time intervals or portions, unequal time intervals or portions, or combinations of equal and unequal time intervals or portions and the like depending on the application. For example, if the sensor data is associated with bodily variable(s) describing heart rate (e.g. an ECG sensor or heart rate sensor), then a heart rate label set may include a set of several heart rate labels $\{ \ell_{HR1}, \ell_{HR2}, \ell_{HR3} \}$ representing low (e.g. $\ell_{HR3}$), medium (e.g. $\ell_{HR2}$), and high heart rate (e.g. $\ell_{HR1}$). Each portion of sensor data is analysed to determine whether that portion of sensor data corresponds to a low, medium or high heart rate after which that portion of sensor data is assigned the corresponding heart rate label $\ell_i$, for $1 \leq i \leq 3$, from the set of HR labels $\{ \ell_{HR1}, \ell_{HR2}, \ell_{HR3} \}$.

Once each of the portions of sensor data have been labelled, then the corresponding portions of the neurological data are labelled. That is, the k-th portion of sensor data may be labelled with a particular label, so the corresponding k-th portion of neurological data is also labelled with this particular label. Given a k-th portion of the sensor data is assigned a label from a set of labels $\{ \ell_1, \ell_2, \ell_3, \ldots, \ell_i, \ldots \ell_Y \}$ characterising a bodily variable, then the corresponding k-th portion neurological data is assigned the same label from the set of labels $\{ \ell_1, \ell_2, \ell_3, \ldots, \ell_i, \ldots \ell_Y \}$. The k-th portion of neurological data includes the k-th portion of a plurality of sets neural sample data, each k-th portion of the set of neural sample data being generated or received from one of the neural receivers.

For a multi-channel neurological signal, there are a plurality of portions of multi-channel neurological data, each portion forming a neurological sample vector sequence. The k-th neurological sample vector sequence $(x_i)^k$ corresponds to the k-th portion of multi-channel neurological data from the multi-channel neurological signal. Once each k-th portion of sensor data samples has been assigned a label from a set of labels $\{ \ell_1, \ell_2, \ell_3, \ldots, \ell_i, \ldots \ell_Y \}$ characterising a bodily variable represented by that portion of sensor data samples, then the corresponding k-th portion of multichannel neurological data is assigned the same label. This then forms a labelled set of multichannel neurological data that includes a plurality of portions of labelled multichannel neurological data.

In step 190, the labelled portions of the neurological data, which has been labelled with a set of labels $\{ \ell_1, \ell_2, \ell_3, \ldots, \ell_i, \ldots \ell_Y \}$ characterising a bodily variable, may be generated and/or stored as a training neural sample dataset associated with a bodily variable (e.g. or bodily variable training dataset), where the sensor data was used to characterise the bodily variable. In the case of the multi-channel neurological signal, the labelled set of multichannel neurological data forms a training set of neurological sample vector sequences that may be denoted $\{(x_i)^k\}_{k=1}^{T}$, where $1 \leq i \leq L_k$ and $1 \leq k \leq T$, in which $L_k$ is the length of the k-th neurological sample vector sequence and T is the number of training neurological sample vector sequences. Each of the neurological sample vector sequences in the training set $\{(x_i)^k\}_{k=1}^{T}$ has been assigned a label that corresponds to the labels derived from the corresponding portions of sensor data.

In step 192, one or more ML technique(s) may be trained using the bodily variable training dataset to generate one or more ML models for predicting the bodily variable when given, after training, neural sample data. The ML technique(s) may be trained to generate ML models that are capable of determining or estimating data representative of bodily variable(s). For example, in response to neural sample data input to the ML model, the ML model may classify the neural sample data and output a label from the set of labels characterising the bodily variable.

Figure 1G:
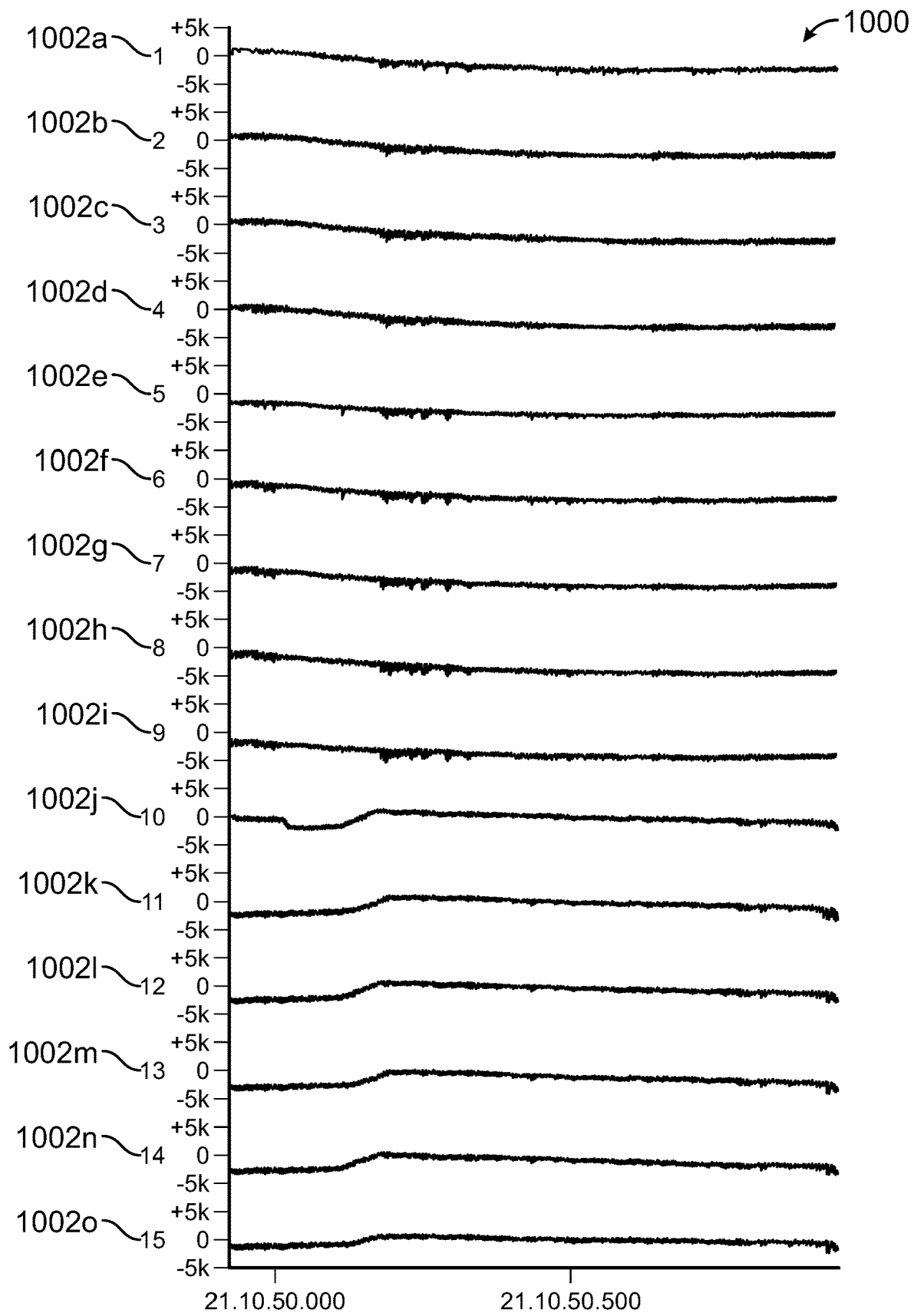
FIG. 1g is a schematic diagram illustrating neurological data of a subject received from a plurality of neural receivers for use in training a ML model of the neural interface according to the invention.

FIG. 1g is a schematic diagram illustrating neurological data 1000 of a subject received from a plurality of neural receivers for training and/or input to a ML model of the neural interface 106 according to the invention. The neural interface 106 may receive a plurality of neurological signal(s) $x_1(t), \ldots, x_i(t), x_j(t), \ldots, x_n(t)$ output from a corresponding plurality of neural receivers 116i, 116j. The neural interface 106 may sample the plurality of neurological signal(s) $x_1(t), \ldots, x_i(t), x_j(t), \ldots, x_n(t)$ into neurological data (or neural sample data), the neurological data comprising a plurality of sets of neural sample data 1002a-1002o. In this case, a set of 15 neural receivers generates 15 sets of neural sample data 1002a-1002o.

FIG. 1g illustrates each set of neural sample data corresponding to the output from one of the plurality of neural receivers 116a, 116j over a time period of approximately 1 second, which in this example is from 21:10:50:000 (hr:min:sec:msec) to approximately 21:10:51:000. Each set of neural sample data 1002a-1002o may be divided into a plurality of portions or a plurality of time intervals (e.g. time intervals of X msec) in which each portion spans a different time interval in which neural activity encoding one or more bodily variable(s) is detected. For example, each portion of each of the sets of neural data samples 1002a-1002o may cover a time interval of, by way of example only but is not limited to, between 30 to 500 msec. In essence, the plurality of portions of the neurological data and sensor data may be determined based on the granularity of the sensor data. This is because the neurological data 1000 may be sampled at a much higher sampling rate than the sensor data (e.g. $L_k >> S_k$). For example, if the bodily variable associated with the sensor data only changes once per X msec (e.g. 500 msec), then the time interval for each portion of neurological and sensor data may be set to X msec (e.g. 500 msec).

The plurality of portions of the labelled neurological sample data, which comprises a plurality of portions of a plurality of labelled sets of neural sample data, forms a training set of neurological sample data (also referred to herein as a training neural sample dataset associated with a bodily variable, or bodily variable training dataset). The training set of neurological sample data may be formed into a set of labelled neurological sample sequences $\{(x_i)^k\}_{k=1}^T$, where $1 \leq i \leq L_k$ and $1 \leq k \leq T$, in which $L_k$ is the length of the k-th neurological sample vector sequence and T is the number of training neurological sample vector sequences. The set of labelled neurological sample sequences $\{(x_i)^k\}_{k=1}^T$ may be used to assist vector based ML techniques to be trained to generate a ML model that classifies and/or estimates the neural activity encoding one or more bodily variable(s) from the neurological sample data. In order to use the neurological data 1000 for training a ML technique to generate an ML model for predicting a bodily variable, the portions of the neurological data 1000 (e.g. each of the portions of each of the plurality of sets of neural sample data 1002a-1002o) should be labelled with a set of labels that characterise a bodily variable of interest.

As described with reference to FIG. 1f, sensor data associated with a bodily variable of interest may be output at the same time that the plurality of neurological signal(s) $x_1(t), \ldots, x_i(t), x_j(t), \ldots, x_n(t)$ are output from a corresponding plurality of neural receivers 116i, 116j. Given that the neurological data 1000 and the sensor data can be generated at the same time, the sensor data may be used to label the neurological data 1000. This may be achieved by partitioning the sensor data into a plurality of portions that correspond (e.g. correspond to the same time interval or portion) with the plurality of portions of the neurological data 1000 that is captured or generated etc. The plurality of portions of the sensor data are then analysed and labelled with a set of labels characterising the bodily variable of interest (or to be modelled). For each labelled portion of sensor data a corresponding portion of the neurological data is then assigned the same label from the set of labels characterising the bodily variable of interest (or to be modelled). The labelling of the neurological data is performed on each of the plurality of sets of neural sample data 1002a-1002o.

As described above, there are a plurality of bodily variables at different levels of granularity from the neurological level to the macro level. A bodily variable may comprise or represent any parameter, metric, value, or information that describes something about the information, state, motion or output of the body of a subject, or part or subpart of the body of a subject and the like. There are a lot of different levels of bodily variables that may describe the state of any part of the body of a subject whether it is in physical motion, chemical, electrical or any other states. For example, a bodily variable may include at least one from the group of, by way of example only but not limited to: any data representative of vital sign(s) of the subject including data representative of at least one from the group of: heart rate of the subject; activity of the subject; temperature of the subject; blood pressure of the subject; blood glucose of the subject; respiratory rate; any other vital sign of the subject; any physiological measurement of the whole of the subject, a body part of the subject, or a sub-part of the subject; any data representative of a state of the whole of a subject, a body part of the subject, or a sub-part of the subject; any data representative of information, values, parameters of the subject associated one or more genomic fields including at least one from the group of: epigenetics; phenotype; genotype; transcriptomics; proteomics; metabolomics; microbiomics; and any other term describing a number, state, metric, variable or information associated with the whole body of a subject, any part and/or subpart of the body of the subject and the like; equivalents thereof, modifications thereof, combinations thereof, as the application demands, any information associated with the body of a subject as the application demands; and/or as herein described.

Figures 1H, 1I:
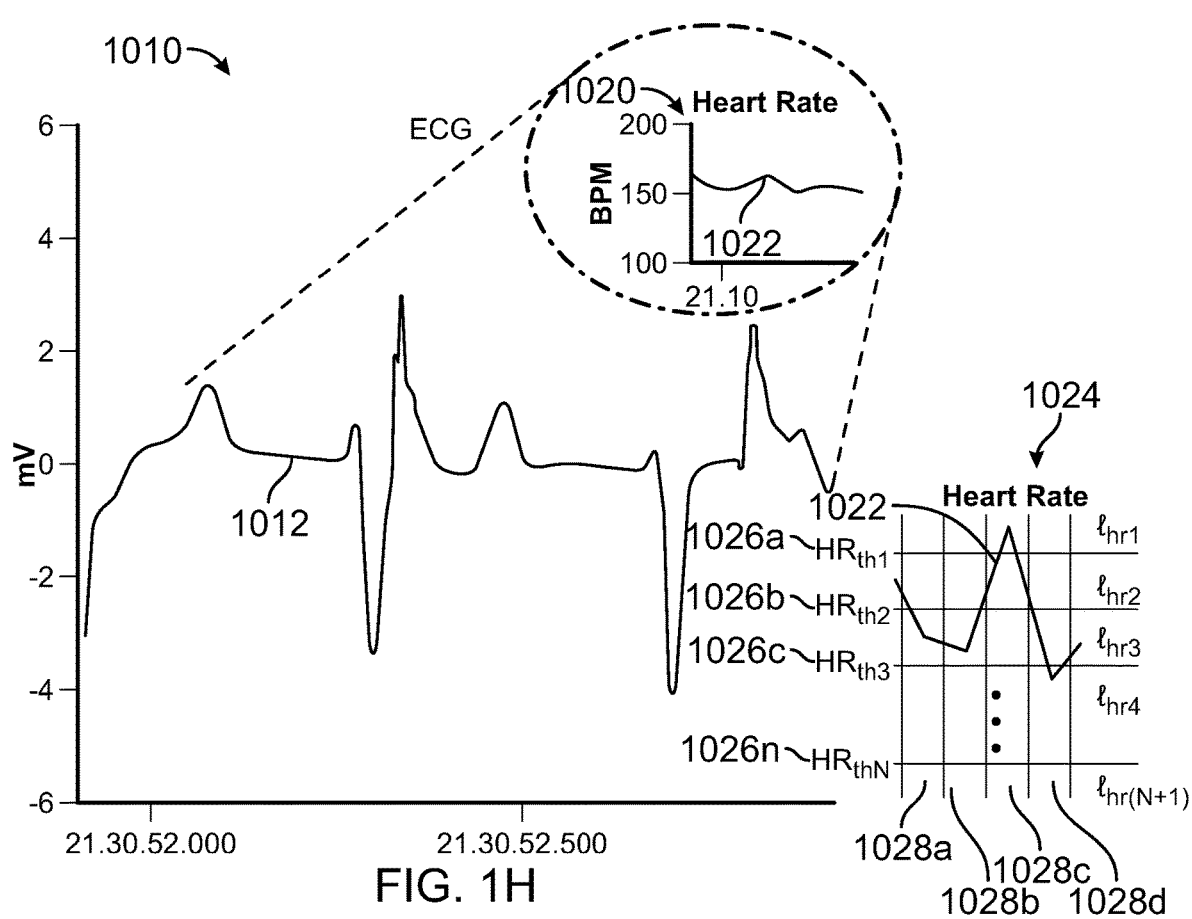
FIG. 1h is a graph diagram illustrating ECG physiological data of a subject from which heart rate of the subject can be extracted, both of which are examples of bodily variables, for use in labelling neurological data of FIG. 1g according to the invention.
FIG. 1i is a graph diagram illustrating blood pressure physiological data of a subject from which average blood pressure cam be extracted, both of which are examples of bodily variables, for use in labelling neurological data of FIG. 1g according to the invention.

Sensor data may provide meta-data derived bodily variables, that is higher level bodily variables that are derived from low level granularity bodily variables detected by a sensor and output as sensor data. FIGS. 1h to 1n illustrate different types of sensor data that may be used for describing one or more bodily variables at a higher level (or macro level/scale). Such sensor data may include, by way of example only but is not limited to, the vital signs of a subject, ECG trace and/or heart rate of the subject, temperature of the subject, activity of the subject, blood glucose variations of a subject, joint angle of a finger of the subject or movement of the whole body of the subject, a body part or subpart of the subject in some manner. Sensor data may also describe bodily variables that may be derived from one or more other bodily variables that also describes a state, motion or output of the subject. For example, activity is a higher level bodily variable of a subject that may be derived from a combination bodily variables associated with the acceleration and/or gyroscopic motion of the whole body of a subject, a part or sub-part of the body of a subject, etc. In another example, the ECG trace of FIG. 1h may be considered lower level bodily variable of the subject, but the ECG trace may be analysed to calculate other bodily variables such as, by way of example only but not limited to, a heart rate of the subject as illustrated in FIG. 1h. Thus, heart rate of the subject is a higher level bodily variable of the subject.

FIG. 1h is an ECG graph diagram 1010 illustrating ECG physiological sensor data 1012 of a subject for use in labelling neurological data 1000 of FIG. 1g with labels characterising bodily variables associated with, by way of example only but not limited to, heart rate of the subject. The ECG sensor data 1012 as illustrated in ECG graph 1010 by a time varying ECG trace signal in which the y-axis represents the amplitude of the ECG trace signal in millivolts (e.g. mV) and the x-axis represents time in milliseconds (msec). The ECG sensor data 1012 is illustrated for the same time period as the neurological data 1000 of FIG. 1g. ECG sensor data 1012 may convey a multitude of bodily variable information such as, by way of example only but not limited to, bodily variables associated with the structure of the heart of a subject and the function of its electrical conduction system. For example, ECG sensor data 1012 may be used to derive various bodily variables including, by way of example only but not limited to, heart rate, heart rate variability, heart rhythm, or any other bodily variable associated with the ECG sensor data 1012 and the like.

In this example, the ECG sensor data 1012 is used to compute heart rate or heart rate data, which is a bodily variable, in heartbeats per minute (or bpm). This may be based on various methods using the R wave-to-R wave (RR) interval of the ECG sensor data 1012 and, depending on the calculation method, multiplying/dividing by a factor or parameter in order to derive heart rate in heartbeats/min. FIG. 1h illustrates a heart rate graph 1020 of the heart rate data 1022 in bpm on the y-axis vs time (msec) on the x-axis. The heart rate data may be labelled by dividing the heart rate data into a plurality of portions or time intervals, corresponding to the portions or time intervals of neurological data that is captured. Each portion of the heart rate data is analysed to determine a suitable label from a set of labels that characterise the heart rate bodily variable (e.g. variations in the heart rate bodily variable) associated with the heart rate (HR) data.

An example analysis and labelling of the HR data 1022 is shown in HR graph 1024 of FIG. 1h, where the y-axis is heart rate in bpm and the x-axis is time in msec. The HR amplitude of the HR data may be divided into R>=1 heart rate thresholds 1026a-1026n (e.g. $HR_{th1}>HR_{th2}>HR_{th3}> \ldots >HR_{thR}$) to form R+1 HR zones or regions. Each of the R+1 HR regions is assigned a different label $\ell_{hri}$ from a set of R+1 HR labels { $\ell_{hr1}$, $\ell_{hr2}$, $\ell_{hr3}$, . . . , $\ell_{hri}$, . . . $\ell_{hr(R+1)}$}. For simplicity, the HR data 1022 is partitioned into a plurality of time intervals or portions 1028a-1028d of HR data, which should correspond to the plurality of time intervals or portions of the neurological data 1000 that is captured by the neural interface from the plurality of neural receivers. The portions of HR data 1022 may then be labelled based on which HR region each portion of HR data 1022 may be characterised to be in.

For example, each portion of HR data may be analysed and characterised into one of the HR regions and labelled accordingly. In another example, each portion of the HR data may be analysed using a characterising ruleset to ensure consistent labelling and/or characterisation of the HR data. For example, a ruleset may be defined to, by way of example only but not limited to, label each portion of the HR data based on the maximum HR in that portion of HR data; label each portion of the HR data based on what region the HR falls within at the time interval mid-point of that portion of HR data; label each portion of the HR data based on the (max HR-min HR)/2 over that portion of HR data; label each portion of the HR data based on the average HR in that portion of HR data; label each portion of the HR data based on the minimum HR in each portion of HR data; or any other suitable method/ruleset that is used to characterise each portions of HR data to be in a particular HR region and label accordingly.

For example, labelling each of the portions of the HR data 1028a-1028d based on the maximum HR in said each portion of HR data would give the following set of label mappings of: {( $\ell_{hr2}$; HR data portion 1028a), ( $\ell_{hr2}$; HR data portion 1028b), ( $\ell_{hr1}$; HR data portion 1028c), ( $\ell_{hr2}$; HR data portion 1028d), and so on . . . }, where (<label>; <HR data portion>) means that <HR data portion> is assigned <label>. For example, labelling each of the portions of the HR data 1028a-1028d based on the minimum HR in said each portion of HR data would give the following set of label mappings of: {( $\ell_{hr3}$; HR data portion 1028a), ( $\ell_{hr3}$; HR data portion 1028b), ( $\ell_{hr2}$; HR data portion 1028c), ( $\ell_{hr4}$; HR data portion 1028d), and so on . . . }. For example, labelling each of the portions of the HR data 1028a-1028d based on the minimum HR in said each portion of HR data would give the following set of label mappings of: {( $\ell_{hr3}$; HR data portion 1028a), ( $\ell_{hr3}$; HR data portion 1028b), ( $\ell_{hr2}$; HR data portion 1028c), ( $\ell_{hr4}$; HR data portion 1028d), and so on . . . }. For example, labelling each of the portions of the HR data 1028a-1028d based on what region the HR falls within at the time interval mid-point of that portion of HR data would give the following set of label mappings of: {( $\ell_{hr3}$; HR data portion 1028a), ( $\ell_{hr3}$; HR data portion 1028b), ( $\ell_{hri}$; HR data portion 1028c), $\ell_{hr4}$ HR data portion 1028d), and so on . . . }.

The portions of the neurological data 1000 may be labelled based on the labelling of the corresponding portions of the HR data 1028a-1028d and so on. The neurological data 1000 includes a plurality of sets of neural sample data 1002a-1002o, in which each of the plurality of sets of neural sample data 1002a-1002o includes portions of neural sample data that correspond to the portions or time intervals of the HR data. Thus, the portions of each set of neural sample data 1002a-1002o are assigned the HR label that was assigned to corresponding portions of the HR data. The labelled neurological data 1000, which includes the labelled sets of neural sample data 1002a-1002o, forms a labelled training neural dataset associated with a HR bodily variable. An ML technique may be trained based on this labelled training dataset to generate a heart rate ML model that predicts the heart rate bodily variable given neural sample data. That is, the ML heart rate model may then receive any time series neurological data as input (e.g. recorded or in real-time) and classify it based on the HR labels { $\ell_{hr1}$, $\ell_{hr2}$, $\ell_{hr3}$, . . . , $\ell_{hri}$, . . . $\ell_{hr(N+1)}$}.

FIG. 1i is a blood pressure (BP) graph 1030 diagram illustrating BP physiological sensor data 1032 of a subject that is representative of bodily variable(s) associated with BP of the subject for use in labelling neurological data 1000 of FIG. 1g according to the invention. The BP sensor data 1032 is illustrated in BP graph 1030 by a time varying BP signal in which the y-axis represents the BP amplitude in millimetres of mercury (e.g. mmHg) and the x-axis represents time in milliseconds (msec). The BP sensor data 1032 is illustrated for the same time period as the neurological data 1000 of FIG. 1g. BP sensor data 1032 may convey a measure of the bodily variables associated with blood pressure (e.g. BP bodily variable) of a subject. Portions of BP sensor data that correspond with portions of the neurological data 1000 that is captured may be analysed and labelled with a set of BP labels characterising a BP-related bodily variable based on the BP sensor data. From this, the portions of the neurological data 1000 may be assigned BP labels used to label corresponding portions of the BP sensor data. The labelled portions of neurological data 1000 form a training neural dataset associated with the BP-related bodily variable characterised by the BP labels.

For example, the BP sensor data provides a measure of BP in terms of mmHg, so the BP sensor data 1032 may be analysed in a similar manner as the HR data 1022 illustrated by HR graph 1024 of FIG. 1h. In this case, the y-axis is BP measured in mmHg and the x-axis is time in msec. The BP amplitude of the BP sensor data 1032 may be divided into multiple BP thresholds (e.g. $BP_{th1}>BP_{th2}>BP_{th3}> \ldots >BP_{thR}$) to form R+1 BP zones or regions. Each of the R+1 BP regions is assigned a different label $\ell_{bp}$, from a set of R+1 BP labels { $\ell_{bp1}$, $\ell_{bp2}$, $\ell_{bp3}$, . . . , $\ell_{bpi}$, . . . $\ell_{bp(R+1)}$}. For simplicity, the BP data 1032 is partitioned into a plurality of time intervals or portions, which should correspond to the plurality of time intervals or portions of the neurological data 1000 that is captured by the neural interface from the plurality of neural receivers. The portions of BP data 1032 may then be labelled based on which BP region each portion of BP data 1032 may be characterised to be in. The corresponding portions of the neurological data 1000 are then assigned the labels { $\ell_{bp1}$, $\ell_{bp2}$, $\ell_{bp3}$, . . . , $\ell_{bpi}$, . . . $\ell_{bp(R+1)}$} used to label the corresponding portions of BP data 1032.

Alternatively or additionally, the portions of BP sensor data 1032 may be analysed using any other analysis technique for characterising a particular BP bodily variable. For example, a BP bodily variable related to increasing BP or decreasing BP may be derived based on the gradient of the BP sensor data 1032 in each portion of BP sensor data 1032. For example, two labels may be defined with a first label representing BP increasing and a second label representing BP decreasing. Thus, each portion of BP sensor data 1032 may be analysed based on the gradient, if the gradient is positive then that portion of BP sensor data 1032 may be labelled with the first label, if the gradient is negative then that portion of BP sensor data 1032 may be labelled with the second label. The corresponding portions of the neurological data 1000 are then assigned the labels used to label the corresponding portions of BP data 1032.

Figure 1J:
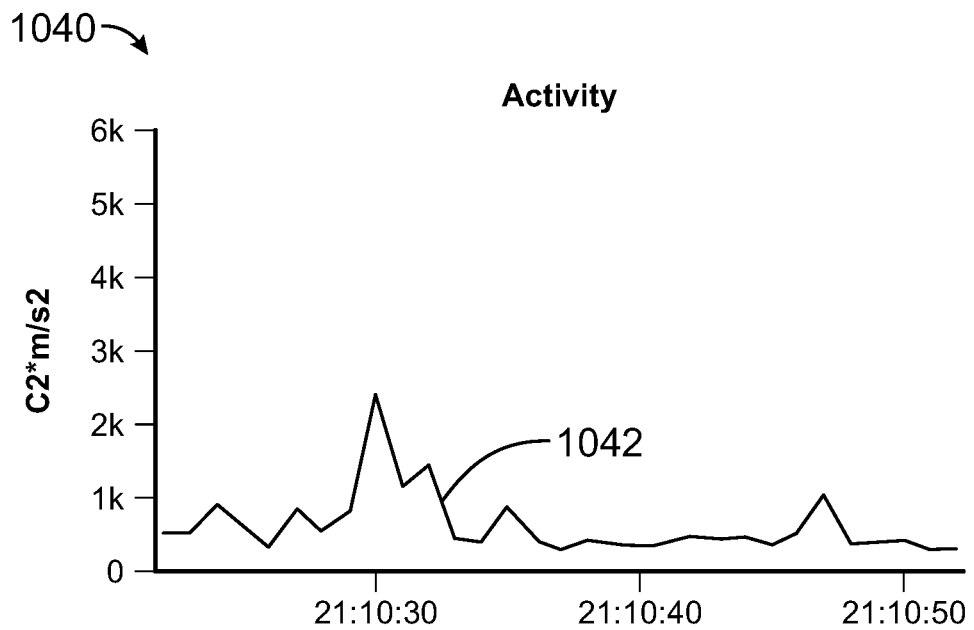
FIG. 1j is a graph diagram illustrating activity data of a subject that is a bodily variable(s) for use in labelling neurological data of FIG. 1g according to the invention.

FIG. 1j is an activity graph 1040 diagram illustrating activity physiological data 1042 derived from inertial motion unit (IMU) sensor(s) associated with a subject that is representative of bodily variable(s) related to the activity of the subject for use in labelling neurological data 1000 of FIG. 1g according to the invention. The activity data 1042 is illustrated in activity graph 1040 by a time varying activity signal in which the y-axis represents the activity in degrees meters per second squared (e.g. deg m/s$^2$) and the x-axis represents time in milliseconds (msec). The activity data 1042 is illustrated for the same time period as the neurological data 1000 of FIG. 1g. Activity is another bodily variable that is representative of the activity of a subject, body parts of a subject and/or subparts of a subject. The activity data 1042 may be measured based on the standard deviation of one or more accelerometer signal(s) and/or one or more gyroscopic signal(s) from one or more IMU(s) attached or associated with the subject (e.g. see accelerometer graph 1070 and/or gyroscopic graph 1080). The activity data 1042 can give a measure of how much, by way of example only but is not limited to, a subject is moving. For example, if the subject is stationary all IMUs may have an output reading of zero, and so the activity data has a zero value (e.g. IMUs read no motion). However, if subject moves around, then one or more IMUs will have a non-zero reading and the activity data will have a non-zero value, as represented when the standard deviation of the IMU output is non-zero. The greater the standard deviation the more the subject is moving or the more the subject is active.

Portions of the activity data 1042 that correspond with portions of the neurological data 1000 that is captured may be analysed and labelled with a set of activity labels characterising a activity-related bodily variable associated with the activity data 1042. From this, the portions of the neurological data 1000 may be assigned activity labels used to label corresponding portions of the activity data 1042. The labelled portions of neurological data 1000 form a training neural dataset associated with the activity-related bodily variable characterised by the activity labels. The portions of activity data corresponding to relevant portions of the neurological data 1000 may be analysed and labelled using, by way of example only but is not limited to, thresholding and/or gradient analysis in a similar manner as described with reference to FIG. 1h or 1i, where the activity labels characterise an activity-related bodily variable of interest. It is to be appreciated that any other type of analysis may be applied on the activity data 1042 for defining activity labels for characterising one or more activity-related bodily variables and the like.

Figure 1K:
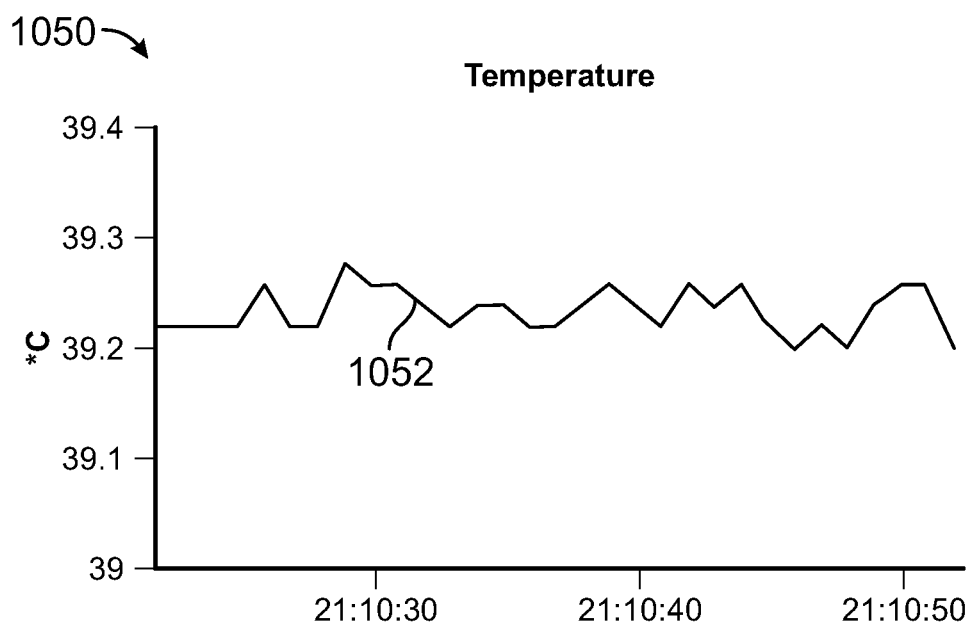
FIG. 1k is a graph diagram illustrating temperature physiological data of a subject that is a bodily variable(s) for use in labelling neurological data of FIG. 1g according to the invention.

FIG. 1k is a temperature graph 1050 diagram illustrating temperature physiological sensor data 1052 of a subject that is representative of bodily variable(s) associated with the temperature of the subject for use in labelling neurological data 1000 of FIG. 1g according to the invention. The temperature data 1052 is illustrated in temperature graph 1050 by a time varying temperature signal in which the y-axis represents the temperature in degrees Celsius (e.g. deg. Cel or ° C.) and the x-axis represents time in milliseconds (msec). Temperature may be read as a voltage on a temperature sensor, which can be calibrated to, by way of example but is not limited to, degrees Celsius and the like. The temperature data 1052 is illustrated for the same time period as the neurological data 1000 of FIG. 1g.

Portions of the temperature data 1052 that correspond with portions of the neurological data 1000 that is captured may be analysed and labelled with a set of temperature labels characterising a temperature-related bodily variable associated with the temperature data 1052. From this, the portions of the neurological data 1000 may be assigned temperature labels used to label corresponding portions of the temperature data 1052. The labelled portions of neurological data 1000 form a training neural dataset associated with the temperature-related bodily variable characterised by the temperature labels. The portions of temperature data 1052 corresponding to relevant portions of the neurological data 1000 may be analysed and labelled using, by way of example only but is not limited to, thresholding and/or gradient analysis in a similar manner as described with reference to FIG. 1h or 1i, where the temperature labels characterise changes in an temperature-related bodily variable of interest. It is to be appreciated that any other type of analysis may be applied on the temperature data 1052 for defining temperature labels for characterising one or more temperature-related bodily variables and the like.

Figure 1L:
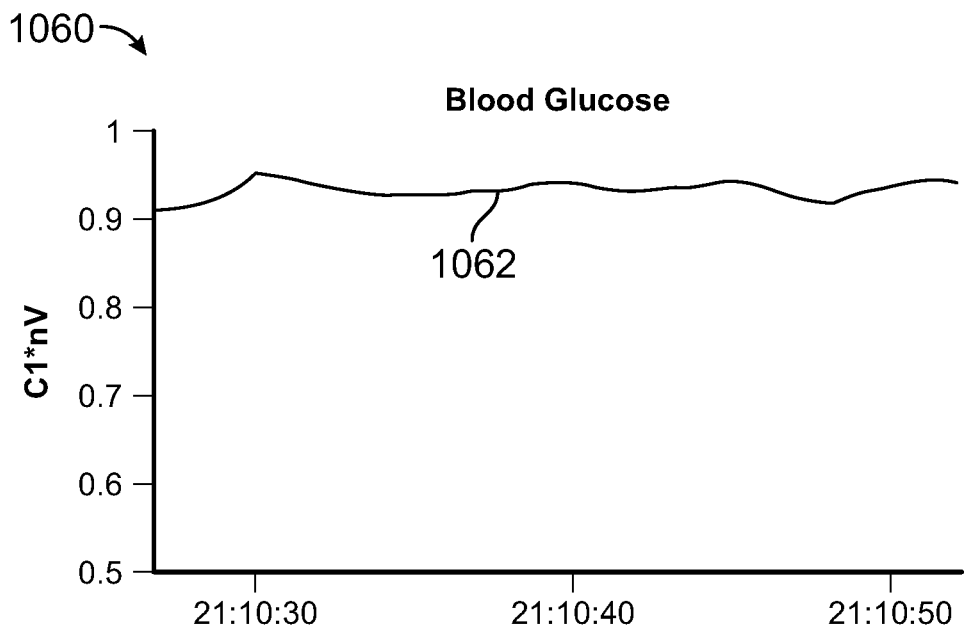
FIG. 1l is a graph diagram illustrating blood glucose physiological data of a subject that is a bodily variable(s for use in labelling neurological data of FIG. 1g according to the invention.

FIG. 1l is a blood glucose graph 1060 diagram illustrating blood glucose (BG) physiological sensor data 1062 of a subject that is representative of bodily variable(s) associated with blood glucose of the subject for use in labelling neurological data 1000 of FIG. 1g according to the invention. The BG data 1062 is illustrated in BG graph 1060 by a time varying BG signal in which the y-axis represents the BG in nanovolts (e.g. nV) and the x-axis represents time in milliseconds (msec). BG may be read as a voltage on a BG sensor, which can be calibrated to, by way of example but is not limited to, glucose per decilitre amount and the like. The BG data 1062 is illustrated for the same time period as the neurological data 1000 of FIG. 1g.

Portions of the BG data 1062 that correspond with portions of the neurological data 1000 that is captured may be analysed and labelled with a set of BG labels characterising a BG-related bodily variable associated with the BG data 1062. From this, the portions of the neurological data 1000 may be assigned BG labels used to label corresponding portions of the BG data 1062. The labelled portions of neurological data 1000 form a training neural dataset associated with the BG-related bodily variable characterised by the BG labels. The portions of BG data corresponding to relevant portions of the neurological data 1000 may be analysed and labelled using, by way of example only but is not limited to, thresholding and/or gradient analysis in a similar manner as described with reference to FIG. 1h or 1i, where the BG labels characterise changes in an BG-related bodily variable of interest. It is to be appreciated that any other type of analysis may be applied on the BG data 1062 for defining BG labels for characterising one or more BG-related bodily variables and the like.

Figure 1M:
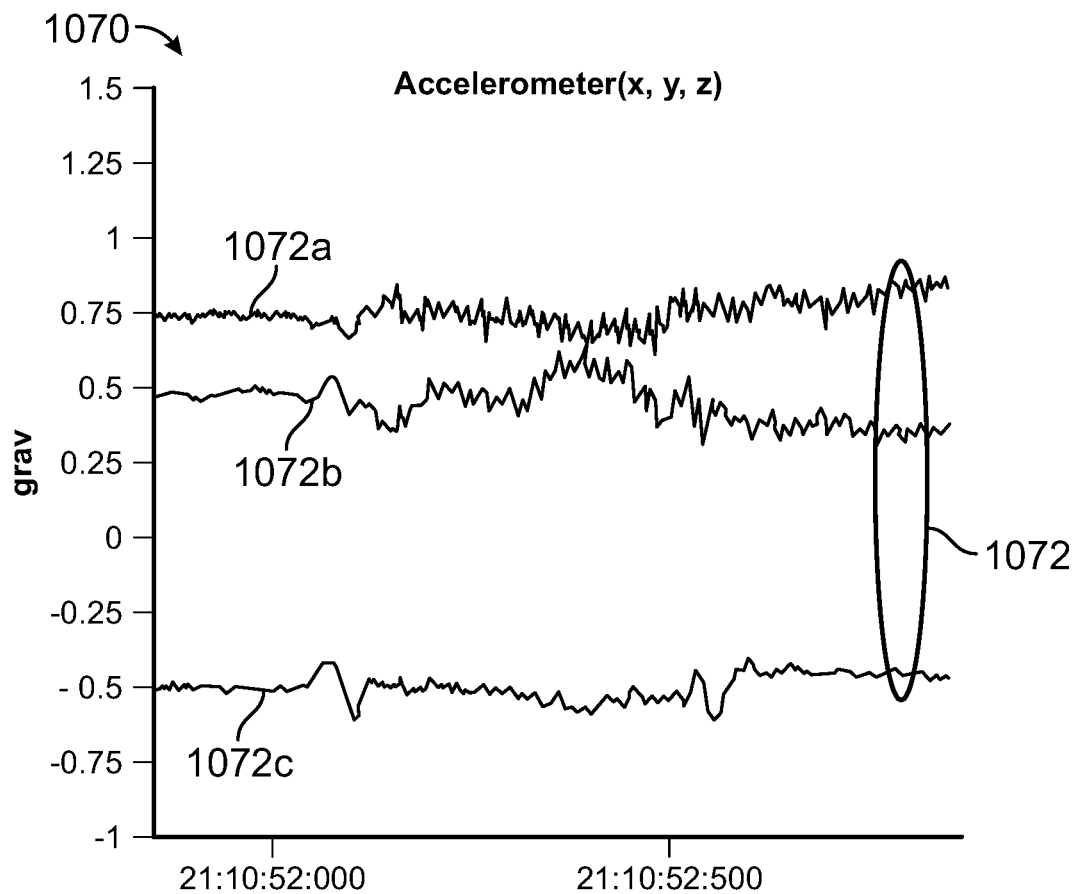
FIG. 1m is a graph diagram illustrating accelerometer physiological data of a subject from which gross Activity of the subject can be extracted, both of which are examples of bodily variables, for use in labelling neurological data of FIG. 1g according to the invention.
Figure 1N:
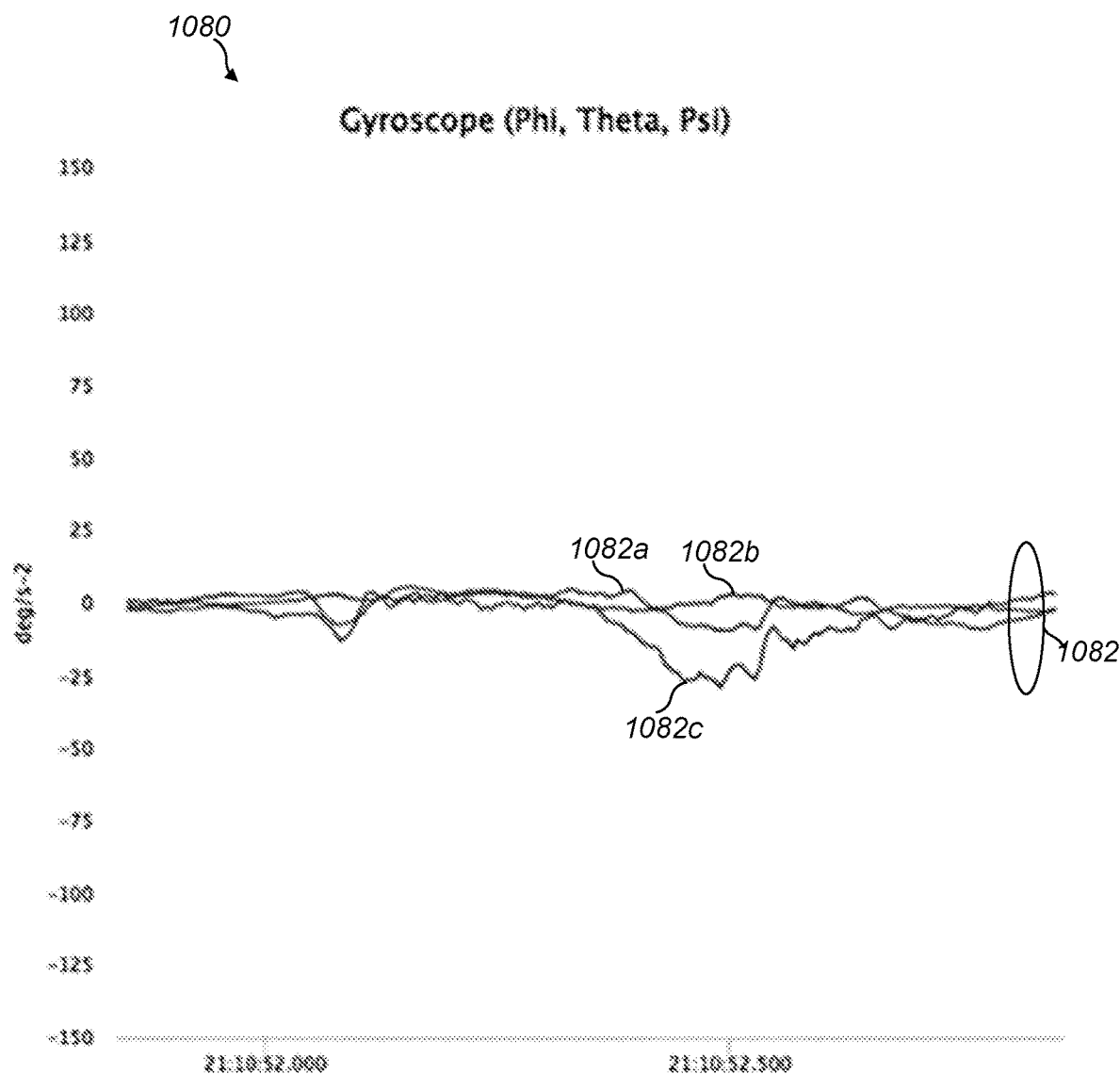
FIG. 1n is a graph diagram illustrating gyroscope physiological data of a subject from which gross Activity of the subject can be extracted, both of which are examples of bodily variables, for use in labelling neurological data of FIG. 1g according to the invention.

FIG. 1m is a accelerometer graph 1070 diagram illustrating accelerometer physiological data 1072 from inertial motion unit (IMU) sensors associated with a subject that is representative of bodily variable(s) associated with movement of the subject for use in labelling neurological data 1000 of FIG. 1g according to the invention. In this case, the accelerometer data 1072 is illustrated in accelerometer graph 1070 by a three time varying accelerometer signals in an x, y and z co-ordinate system 1072a, 1072b, 1072c, respectively, in which the y-axis represents the acceleration in grays (e.g. m/s$^2$) and the x-axis of acceleration graph 1070 represents time in milliseconds (msec). The accelerometer data 1072 is illustrated for the same time period as the neurological data 1000 of FIG. 1g. FIG. 1n is a gyroscope graph diagram 1080 illustrating gyroscope physiological data 1082 from IMU sensors associated with a subject that is representative of bodily variable(s) associated with gyroscopic movement of the subject for use in labelling neurological data 1000 of FIG. 1g according to the invention. In this case, the gyroscope data 1082 is illustrated in gyroscope graph 1080 by a three time varying gyroscopic signals of an x, y and z co-ordinate system 1082a, 1082b, 1082c, respectively, based on the IMU(s) sensors. The y-axis of the gyroscope graph 1080 represents the gyrosopic motion in degrees per second squared (e.g. deg/s$^2$) and the x-axis of acceleration graph 1070 represents time in milliseconds (msec). The gyroscope data 1082 is illustrated for the same time period as the neurological data 1000 of FIG. 1g.

The accelerometer sensor data 1072 and/or gyroscope sensor data 1082 from IMUs may be combined to generate activity data 1042 that describes activity-related bodily variable(s) as illustrated in activity graph 1040. Additionally or alternatively, the accelerometer sensor data 1072 and/or gyroscopic sensor data 1082 may be analysed separately to describe one or more motion-related bodily variables that may not be apparent from the activity data 1042. For example, varying levels of gross motor activity of the whole body, or motor activity of one or more body parts or subparts of a subject may be described using x, y, z, accelerometer data 1072a, 1072b, 1072c and/or x, y, z gyroscope sensor data 1082a, 1082b, 1082c of FIG. 1n or 1o, respectively. These may be analysed and used to define labels for characterising motion-related bodily variables associated with the whole body, one or more body parts or subparts of the subject.

For example, the movement of a body part of a subject, such as an arm or the individual sub-parts of the arm, may be represented by motion sensor data 1072 and/or 1082 such as, by way of example only but not limited to, accelerometer data 1072 and/or gyroscope sensor data 1082. This motion sensor data may be analysed to determine the fine or gross motor activity of the arm as it moves, which may include, by way of example only but not limited to, arm movement left, right, up and/or down. Although this example describes the arm as a body part of the subject, this is by way of example only as the invention is not so limited, it is to be appreciated by the skilled person that any other body part of a subject may be analysed such as, by way of example only but not limited to, the whole of the subject, one or more arms of the subject (if any), one or more legs of the subject, one or more sub-parts of the arms and/or legs of the subject, the neck or any other moveable body part or sub-part of the subject, and the like. Thus, varying levels of detail of the motion of the whole of a subject, a body part of the subject and/or a subpart of the subject may be analysed from such motion sensor data 1072 and/or 1082. The motion sensor data may be analysed and used to generate labels characterising one or more motion-related bodily variables associated with the subject, body parts of the subject, and/or sub-parts of the subject and the like. The labelled motion sensor data 1072 and/or 1082 may be used to label corresponding portions of the neurological data 1000.

Although several techniques (e.g. thresholding techniques and/or gradient techniques) have been described herein for analysing sensor data and generating labels characterising a bodily variable associated with the sensor data, it is to be appreciated by the skilled person that any other analysis technique may be applied as the application demands to the sensor data to derive labels that characterise one or more bodily variables associated with the sensor data.

Figure 1O:
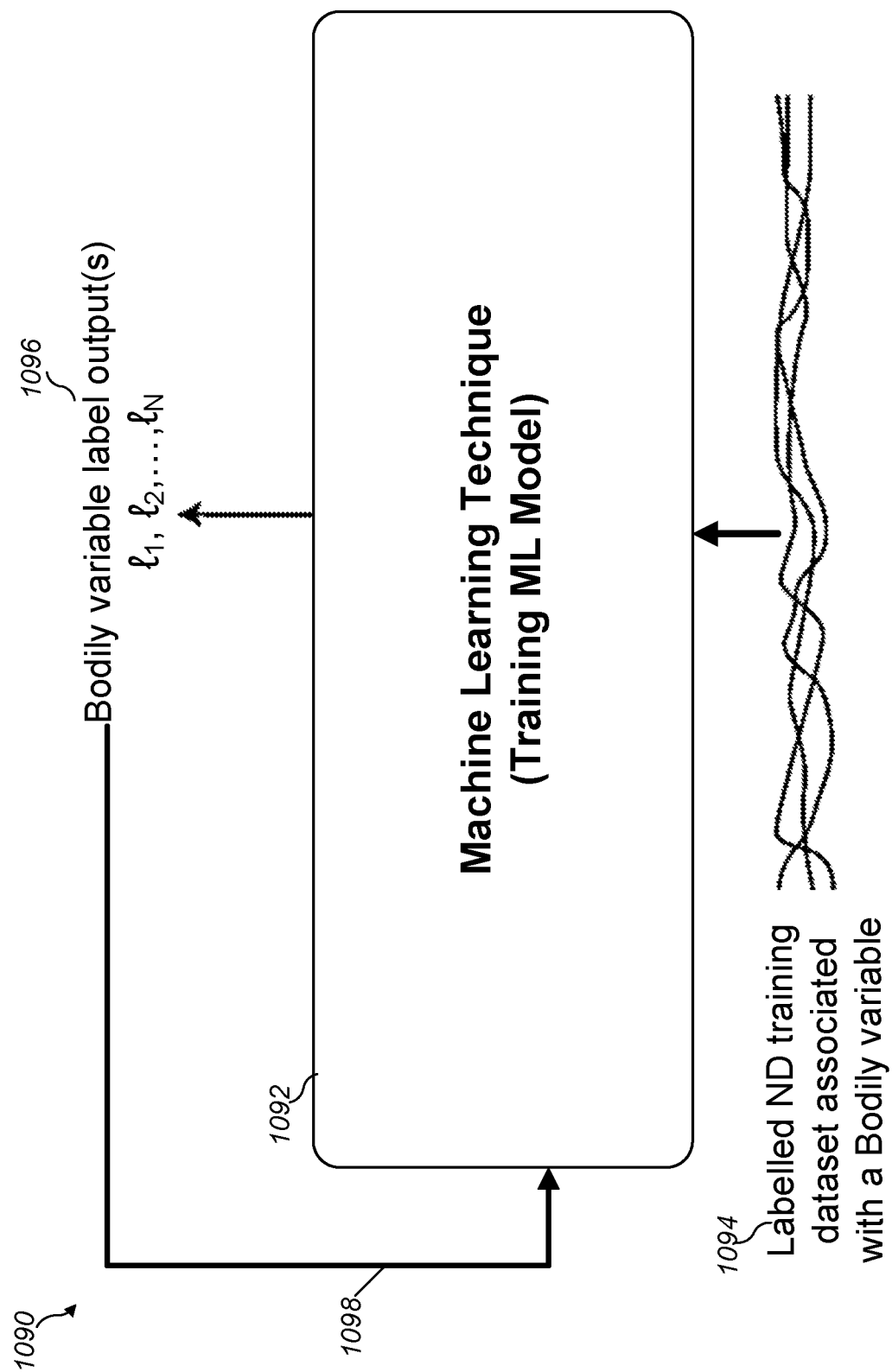
FIG. 1o is a schematic diagram illustrating an example of training a ML technique to generate a ML model for predicting bodily variables from input neurological data according to the invention.
Figure 1P:
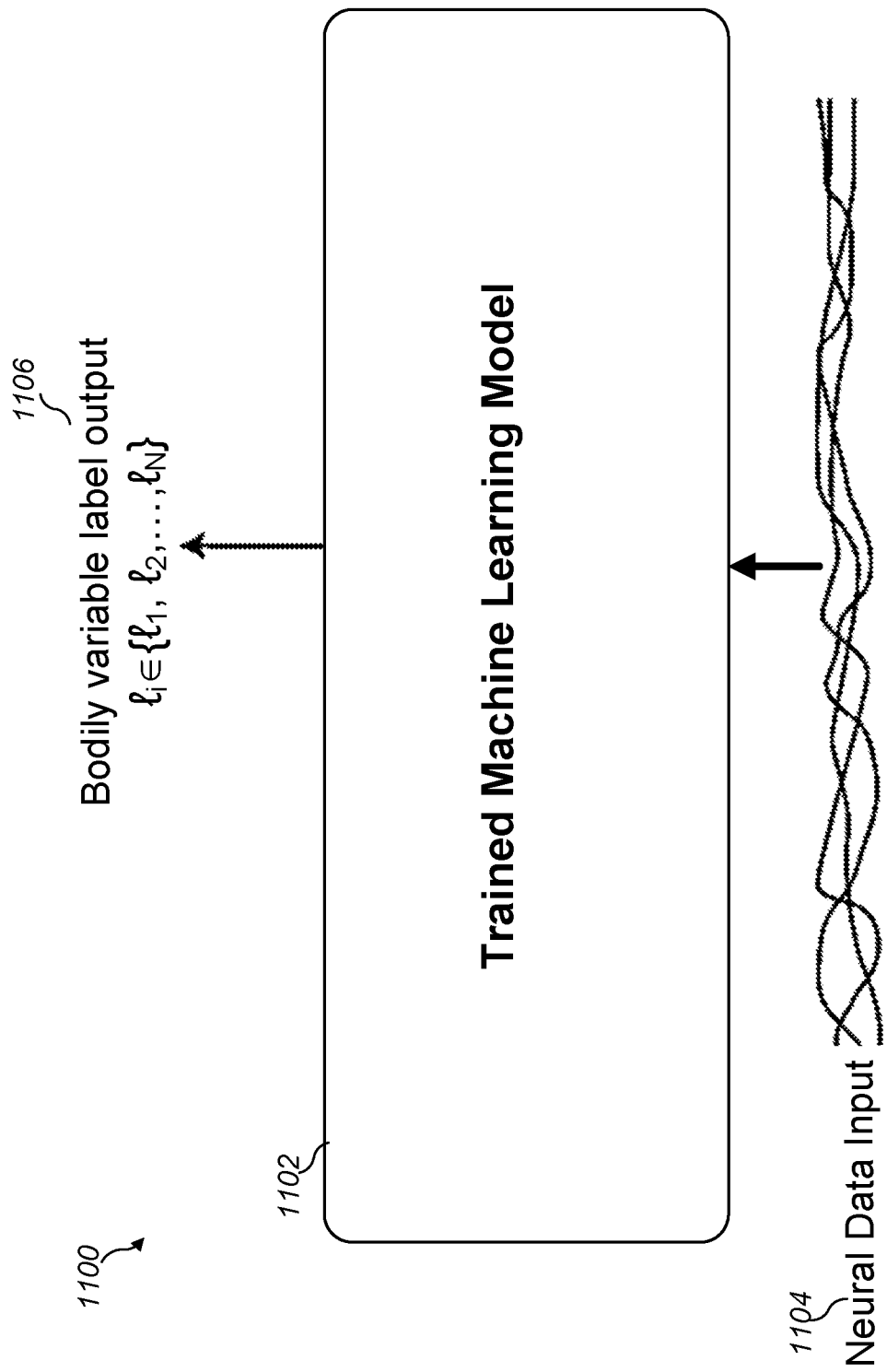
FIG. 1p is a schematic diagram illustrating an example of a trained ML model for predicting bodily variables from input neurological data according to the invention.

FIG. 1o is a schematic diagram illustrating an example training module 1090 for training an ML technique 1092 to generate a ML model 1100 of FIG. 1p for predicting a bodily variable or changes in a bodily variable of interest when given input neurological data according to the invention. For example, the bodily variable of interest may relate to, by way of example only but not limited to, bodily variables associated with heart rate, blood pressure, activity, temperature, blood glucose, acceleration motion, gyroscopic motion, as described with reference to any one of FIGS. 1h-1n, respectively, or any other state or measurable state of the subject, body part of the subject, or subpart of the subject and the like as herein described.

Firstly, a ML technique 1092 may be selected and trained using a labelled training neurological dataset 1094 associated with a bodily variable of interest. The ML technique 1092 may be selected from a plurality of ML techniques suitable for operating on time series and/or time series multi-channel data. ML techniques that may be selected may include, by way of example only but is not limited to, any one or more ML techniques from the group of: neural networks; recursive neural networks; convolutional neural networks; WaveNet structured neural networks; long-short term memory neural networks; any other suitable ML technique for operating on time-series datasets; any other ML technique as herein described; modifications thereto; and/or combinations thereof; and/or any other neural network structure as herein described or as the application demands. The labelled training neurological dataset 1094 is labelled with bodily variable labels characterising changes in the bodily variable. The bodily variable labels and changes in the bodily variable may be derived from sensor data associated with the bodily variable.

The labelled training neurological dataset 1094 includes a plurality of portions of neurological data in which each portion of neurological data has been labelled with a particular bodily variable label from a set of bodily variable labels that characterise changes in the bodily variable. As described with reference to FIGS. 1f to 1n, each portion of neurological data has been labelled based on analysing and labelling corresponding portions of sensor data associated with the bodily variable. Each portion of labelled neurological data further includes a plurality of sets of neural data samples 1002a-1002o, each set of neural data samples generated or received from a different neurological signal from a neural receiver.

The ML technique 1092 may be iteratively trained based on the labelled training neurological dataset 1094. Each of the portions of the labelled neurological data is input to the ML technique 1092. Initially, in the first iteration the ML technique generates an initial ML model by performing various processing operations associated with the ML technique on each of the portions of the labelled neurological data. The generated ML model of the ML technique 1092 outputs a bodily variable label estimate 1096 for each portion of the labelled neurological data that is input. For each portion of labelled neurological data that is input, a corresponding bodily variable label estimate 1096 is output from the ML technique 1092. These bodily variable label estimates 1096 are fed back via feed back loop 1098 into the ML technique 1092, which compares the bodily variable label estimates 1096 with the labels of the corresponding portions of the labelled neurological data and adapts or updates the generated ML model accordingly. In subsequent iterations, the ML technique uses the updated ML model from the previous iteration to process each of the portions of the labelled neurological data to generate corresponding bodily variable label estimates 1096. These bodily variable label estimates 1096 are fed back via feed back loop 1098 into the ML technique 1092, which again updates the ML model accordingly. The iterative procedure may be repeated until it is determined the ML model has been adequately trained and the bodily variable label estimates 1096 substantially agree with the bodily variable labels assigned to the corresponding portions of labelled neurological data. Once this occurs, the ML technique 1092 may output a trained ML model 1100 associated with the bodily variable of interest. The trained ML model 1100 may be used on unseen neurological data (e.g. previously stored neurological data or real-time neurological data) for predicting bodily variable labels characterising changes in the bodily variable of interest that may be encoded within the neurological data.

FIG. 1p is a schematic diagram illustrating an example of a trained ML model system 1100 including a trained ML model 1102 for predicting bodily variables from input neurological data 1104 according to the invention. The trained ML model 1102 may be trained using ML technique 1092 of FIG. 1o, which has been trained on labelled neurological data in which the labels characterise changes of the bodily variable of interest, which may be derived from sensor data related to the bodily variable of interest. The trained ML model 1102, once trained, may be used on neurological data 1104 (e.g. previously stored neurological data or real-time neurological data) for predicting bodily variable labels 1106 characterising changes in the bodily variable of interest, which may be encoded within the neurological data 1104.

The labelled neurological data generated by the method 180 of FIG. 1f synchronises labelled sensor data with corresponding portions of neurological data samples, which may be used for supervised/semi-supervised ML training and/or learning cases when generating ML models as described above and/or as described herein and/or as the application demands. This approach relies on generating or determining bodily variable labels from sensor data. Alternative or additional methods/method steps may be used to modify and/or enhance the method 180 of FIG. 1f by using semi/unsupervised ML techniques to determine the presence of bodily variables and/or bodily variable labels characterising bodily variables within portions of neurological data samples and using these to further synchronise/enhance the labelling of the neurological data samples and/or the sensor data when generating labelled training neural datasets. The unsupervised ML approaches may be advantageous when there is a limited set of bodily variables that might be currently available, e.g. from sensor data or other means. The unsupervised ML approach may generate a ML model that is capable of finding additional bodily variable labels within the one or more neurological signals or neurological data samples.

In essence, one or more ML technique(s) may be trained in an unsupervised manner to generate an ML model capable of generating or finding one or more intermediary low dimensional representative states (also referred to herein as label-like representations and/or latent representations) from the neurological data samples of the received neurological signals. Each of the intermediary low dimensional representative states may correspond to a particular portion (e.g. time interval) of the neurological data samples. The neurological data samples may be input to the ML model, which outputs the one or more intermediary low dimensional states (e.g. one or more vectors in a latent vector space). The one or more intermediary low dimensional states may then be analysed to determine whether they correspond to a current set of bodily variables and/or further sets of one or more bodily variables. The intermediary low dimensional states may be associated and/or labelled by a set of bodily variable labels. This set of bodily variable labels may include any currently known bodily variables (prior to passing the neurological data samples through the ML model) and/or one or more further bodily variables or variations thereof that have been found by the ML model based on analysing the intermediary low dimensional representative states output. Additionally or alternatively, the one or more intermediary low dimensional states may be synchronised with corresponding portions of sensor data, which may be used to label the intermediary low dimensional representative states. Additionally or alternatively, the one or more intermediary low dimensional states may be used to labelled the corresponding portions of sensor data. This may then be used to further label and/or confirm the labelling of the corresponding portions of neurological signals/sample data.

For example, the ML technique may be based on one or more neural network (NN) structures to generate a NN model for use for use determining one or more bodily variables of subject from neurological signals received by one or more neural receiver(s) situated to a corresponding one or more neuronal population(s) in part of the nervous system of the subject. The ML technique may use the NN structure to generate latent representations of the neurological signals. The neurological signals may be received by the neural receiver(s) from one or more neuronal populations of, by way of example only but not limited to, an efferent nerve or other nerves and the like. The NN model may be configured to constrain the latent representations to be label-like, which may be in the form of data representative of one or more intermediary low dimensional states. An intermediary low dimensional state may be represented by a vector of a low dimensional vector space capable of representing one or more bodily variables that are detected by the ML model. The label-like latent representation or intermediary low dimensional state allows classification/labelling of the label-like latent representations in relation to neural activity encoding one or more bodily variables or combinations thereof. For example, the labelling of the neuralogical data samples may be achieved by matching portions of the received neurological data samples of the neurological signal(s) associated with bodily variable(s) with sensor data associated with the subject when the bodily variable was detected or output in the form of the label-like latent representation or low dimensional intermediary state; this allows the bodily variable(s) to be identified based on the matched sensor data and bodily variable labels to be assigned to allow labelling of the latent representations that classify the associated neural activity encoding the bodily variable(s). Such ML models may be used to, by way of example only but are not limited to, generate intermediary low dimensional representative states or label-like latent vectors may be used, by way of example only but is not limited to, in the following processes 1110 and/or 1130 of FIG. 1q or 1r.

FIGS. 2e to 2h describe and illustrate, by way of example only but are not limited to, one or more example ML technique(s) for training ML models 260 and 290 in an unsupervised or semi-supervised manner that are capable of detecting and/or outputting label-like latent representations or low dimensional intermediary states (e.g. vector y) representative of one or more bodily variables encoded as neural activity in neurological signals. Although FIGS. 2e to 2h describe some particular examples of using NN structures for training ML models 260 and 290, this is by way of example only and the invention is not so limited, it is to be appreciated by the skilled person that other neural network structures and/or any other one or more ML technique(s) that are capable of training an ML model to output label-like representations or intermediary low dimensional states representative of one or more bodily variables or representative of bodily variable labels associated with one or more bodily variables may be used as the application demands. Such ML models may be used to, by way of example only but are not limited to, generate intermediary low dimensional representative states or label-like latent vectors may be used, by way of example only but is not limited to, in the following processes 1110 and/or 1130 of FIG. 1q or 1r.

For example, an ML technique may be used to generate a machine learning (ML) model for predicting bodily variable label estimates associated with a bodily variable of interest. This may include one or more steps of: receiving neural sample data representative of neurological signals encoding neural activity associated with one or more bodily variables; training the ML technique to generate an ML model for determining a low dimensional latent space representative of the neurological signals, where the ML technique may be trained in an unsupervised or semi-supervised manner (e.g. based on the received neural sample data); and generating one or more intermediary low dimensional representative states (or label-like latent vectors and the like) based on associating the dimensions of the determined low dimensional latent space with one or more bodily variable labels. The neural sample data may be representative of samples of neurological signals, the neurological signals including neural activity encoding one or more bodily variable(s) of the portion of a nervous system of a subject. The intermediary low dimensional representative states may be used in generating or detecting possible bodily variables encoded in portions of neurological sample data, and synchronising with corresponding portions of sensor data for analysis to generate a set of bodily variable labels, and labelling the corresponding portions of neurological sample data to generate labelled training neural datasets for use in one or more ML techniques for generate a machine learning (ML) model for predicting bodily variable label estimates associated with a bodily variable of interest. The ML model may be used to generate intermediary low dimensional representative states or label-like latent vectors may be used, by way of example only but is not limited to, in the following processes 1110 and/or 1130 of FIG. 1q or 1r.

Figure 1Q:
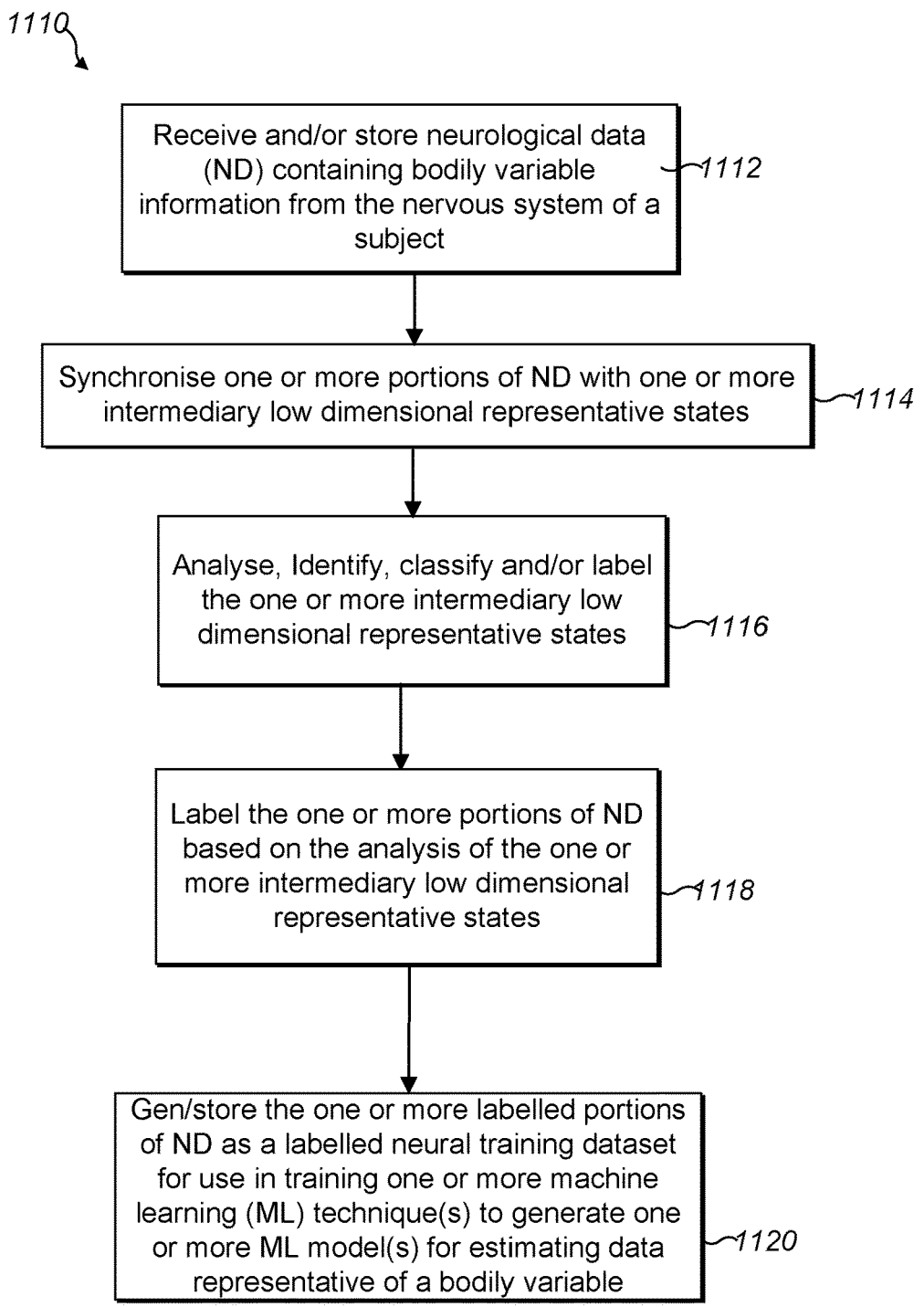
FIG. 1q is a flow diagram illustrating another example process for generating a labelled training dataset from neurological data for training a machine learning (ML) model of the neural interface according to the invention.

FIG. 1q is another flow diagram illustrating another example process 1110 for generating a labelled training neural sample dataset from neurological data and/or sensor data for performing training of an ML technique to generate an ML model for use by the neural interface 106 in predicting one or more bodily variable(s) according to the invention. The method/process 1110 may be used to modify method 180 of FIG. 1f. The method/process 1110 is based on, by way of example only but is not limited to, one or more of the following steps of:

In step 1112, neurological data (e.g. neural sample data) containing bodily variable information from the nervous system of a subject 102 is received from one or more neural receivers 116i, 116j and recorded or stored (e.g. in external system 128 or neural interface 106 and the like). The neurological data may be a plurality of sets of neural data samples, each set of neural data samples generated from a neurological signal of a corresponding neural receiver.

In step 1114, one or more portions of the neural data samples may be synchronised with corresponding one or more intermediary low dimensional states. For example, this may be achieved by inputting the neurological data samples into a ML model that is capable of determining one or more intermediary low dimensional states (e.g. a low dimensional latent space) representative of the neurological signals.

For example, the ML model may be trained by a ML technique based on a labelled training neural dataset associated with one or more bodily variable labels representative of one or more bodily variables. The labelled training neural dataset may be associated with a set of bodily variable labels, which may be a subset of the bodily variable labels that may be determined from the one or more intermediary low dimensional states. In another example, an ML technique may be trained in an unsupervised or semi-supervised manner to generate the ML model for determining a low dimensional latent space representative of the neurological signals. The ML model may generate one or more intermediary low dimensional representative states based on associating the dimensions of the determined low dimensional latent space with one or more bodily variable labels.

Although the ML technique may be trained to generate an ML model for determining a low dimensional latent space representative of the neurological signals based on, by way of example only but is not limited to, unsupervised and/or semi-supervised techniques, it is to be appreciated by the skilled person that the ML technique may be modified and/or combined with one or more semi-supervised or supervised techniques for determining the low dimensional latent space representative of the neurological signals, which may include, by way of example only but is not limited to, semi-supervised and/or supervised techniques that use one or more labelled training dataset(s) associated with one or more bodily variable labels representative of one or more bodily variables.

As a further example, the ML techniques and ML models 260 and 290 of FIGS. 2e to 2h may be used, by way of example only but are not limited to, for generating, detecting and/or outputting label-like latent representations or low dimensional intermediary states (e.g. vector y) representative of one or more bodily variables encoded as neural activity in neurological signals. Although FIGS. 2e to 2h describe some particular examples of using NN structures for training ML models 260 and 290, this is by way of example only and the invention is not so limited, it is to be appreciated by the skilled person that other neural network structures and/or any other one or more ML technique(s) that are capable of training an ML model to output label-like representations or intermediary low dimensional states representative of one or more bodily variables or representative of bodily variable labels associated with one or more bodily variables may be used as the application demands.

In step 1116, the intermediary low dimensional state(s) may be analysed, identified and/or labelled based on a set of bodily variable labels, which may characterise changes in a bodily variable of interest. This may be based on sensor data captured during recording of the neurological data samples. For example, sensor data representative of, by way of example only but not limited to, one or more bodily variables as illustrated from FIGS. 1g to 1n and/or other bodily variables as described and/or defined herein, and/or as the application demands. The portions of the sensor data may be synchronised with the one or more intermediary low dimensional states, which may be used to label the corresponding portions of the sensor data.

In step 1118, the portions of the neural sample data may be labelled based on the labelled portions of the sensor data and/or the one or more intermediary low dimensional state(s). In step 1120 a labelled training set of neural sample data associated with the bodily variable of interest may be generated based on the labelled portions of neural sample data. The generated labelled training set of neural sample data may be stored as a labelled training set of neural sample data associated with the bodily variable of interest.

The labelled training set of neural sample data associated with the bodily variable of interest of step 1118 may be used for training a ML technique to generate a trained ML model for predicting bodily variable label estimates associated with the bodily variable of interest when neural sample data is input.

Figure 1R:
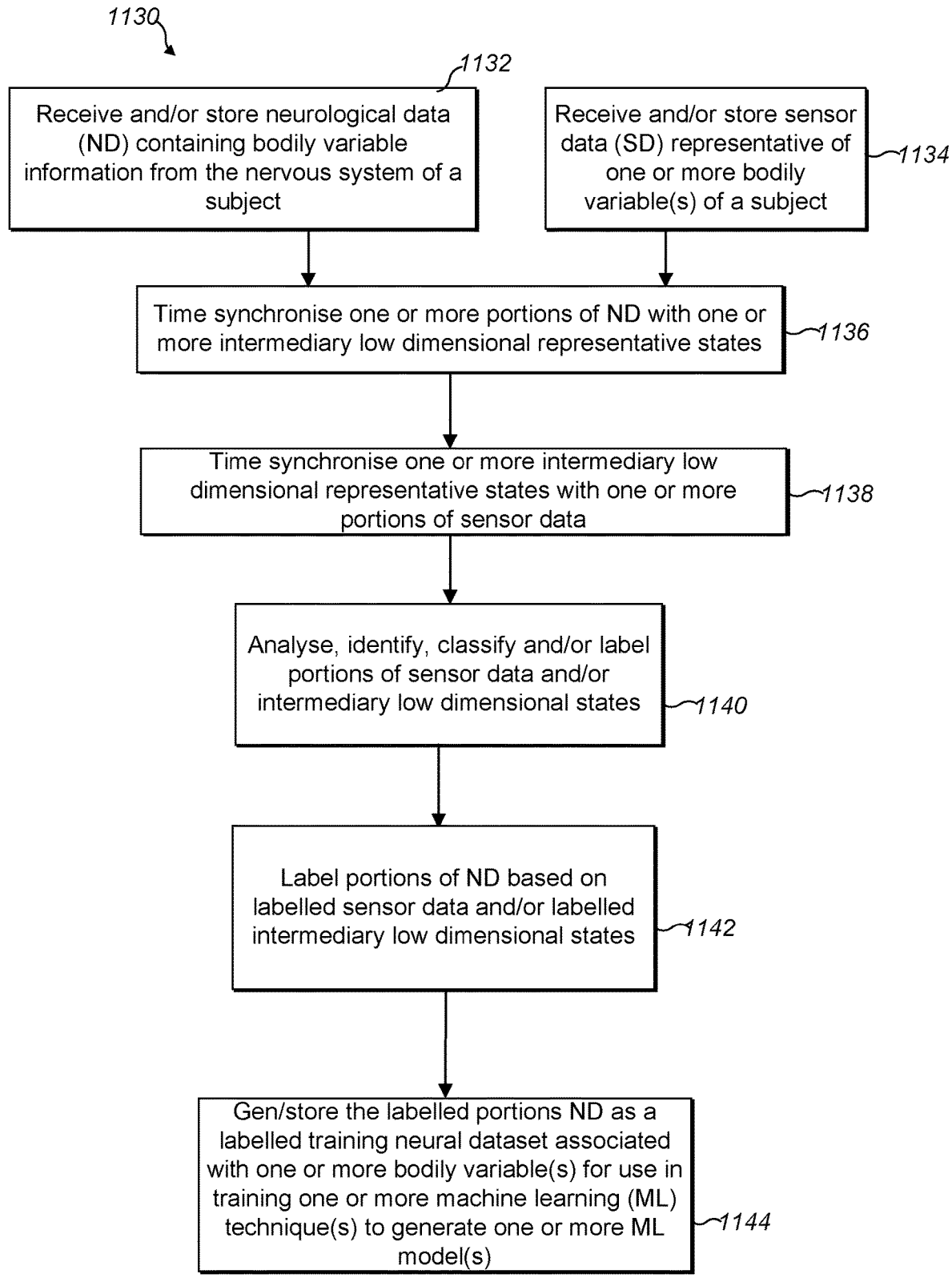
FIG. 1r is a flow diagram illustrating another example process for generating a labelled training dataset from neurological data for training a machine learning (ML) model of the neural interface according to the invention.

FIG. 1r is another flow diagram illustrating another example process 1130 for generating a labelled training neural sample dataset from neurological data and/or sensor data for performing training of an ML technique to generate an ML model for use by the neural interface 106 in predicting one or more bodily variable(s) according to the invention. The process 1130 may be used to modify or combined with the process 180 and/or 1110 of FIG. 1f or 1q. This process 1130 may be a modification of the process 1110 and/or 180 of FIG. 1f or 1q. The process/method 1130 is based on, by way of example only but is not limited to, one or more of the following steps of:

In step 1132, neurological data (e.g. neural sample data) containing bodily variable information from the nervous system of a subject 102 is received from one or more neural receivers 116i, 116j and recorded or stored (e.g. in external system 128 or neural interface 106 and the like). The neurological data may be a plurality of sets of neural data samples, each set of neural data samples generated from a neurological signal of a corresponding neural receiver.

At the same time that the neurological data is recorded or stored, in step 1134 one or more sensor(s) associated with sensing data representative of one or more bodily variable(s) of the subject 102 may be generating raw sensor data may also be recorded or stored (e.g. in external system 128 or neural interface 202a or 202b). The sensor data from the one or more sensors is continuously recorded throughout the recording of each set of neural data samples of the neurological data. The sensor data may be time synchronised with the neurological data as described with reference to FIG. 1f.

In step 1136, the recorded or stored neurological data may be time synchronised with one or more intermediary low dimensional representative states. For example, this may be achieved by inputting portions (or time intervals) of the neurological data samples into an ML model that is capable of determining one or more intermediary low dimensional states (e.g. a low dimensional latent space) representative of the corresponding portions of neurological signals. The output intermediary low dimensional representative state(s) is thus synchronised with the corresponding portion of neurological sample data that was input to the ML model that generate the output intermediary low dimensional representative state(s).

For example, the ML model may be trained by a ML technique based on a labelled training neural dataset associated with one or more bodily variable labels representative of one or more bodily variables. The labelled training neural dataset may be associated with a set of bodily variable labels, which may be a subset of the bodily variable labels that may be determined from the one or more intermediary low dimensional states. In another example, an ML technique may be trained in an unsupervised or semi-supervised manner to generate the ML model for determining a low dimensional latent space representative of the neurological signals. The ML model may generate one or more intermediary low dimensional representative states based on associating the dimensions of the determined low dimensional latent space with one or more bodily variable labels.

In another example, the ML techniques and ML models 260 and 290 of FIGS. 2e to 2h may be used, by way of example only but are not limited to, for generating, detecting and/or outputting label-like latent representations or low dimensional intermediary states (e.g. vector y) representative of one or more bodily variables encoded as neural activity in neurological signals. Although FIGS. 2e to 2h describe some particular examples of using NN structures for training ML models 260 and 290, this is by way of example only and the invention is not so limited, it is to be appreciated by the skilled person that other neural network structures and/or any other one or more ML technique(s) that are capable of training an ML model to output label-like representations or intermediary low dimensional states representative of one or more bodily variables or representative of bodily variable labels associated with one or more bodily variables may be used as the application demands.

Although the ML technique may be trained to generate an ML model for determining a low dimensional latent space representative of the neurological signals based on, by way of example only but is not limited to, unsupervised and/or semi-supervised techniques, it is to be appreciated by the skilled person that the ML technique may be modified and/or combined with one or more semi-supervised or supervised techniques for determining the low dimensional latent space representative of the neurological signals, which may include, by way of example only but is not limited to, semi-supervised and/or supervised techniques that use one or more labelled training dataset(s) associated with one or more bodily variable labels representative of one or more bodily variables.

In step 1138, the intermediary low dimensional state(s) may be synchronised with corresponding portions of the sensor data. These portions (or time intervals) of sensor data correspond to the portions of neurological data that were synchronised with the one or more intermediary low dimensional state(s). That is, the portions of sensor data may by synchronised with the portions of neurological sample data (e.g. as described with reference to FIG. 1f in step 186) that output the one or more intermediary low dimensional representative states and thus may be synchronised with the corresponding one or more intermediary low dimensional representative state(s).

In step 1140, the synchronised portions of sensor data may be analysed, identified and/or labelled based the one or more intermediary low dimensional representative states, which may characterise changes in a bodily variable of interest. Alternatively or additionally, the one or more intermediary low dimensional representative states may be labelled based on the corresponding synchronised portions of sensor data. Alternatively or additionally, the synchronised portions of sensor data may be analysed and labelled based on a set of bodily variable labels characterising changes in a bodily variable of interest. The sensor data may be based on or representative of, by way of example only but not limited to, sensor data representative of one or more bodily variables as illustrated from FIGS. 1g to 1n and/or other bodily variables as described and/or defined herein, and/or as the application demands.

In step 1142, the portions of the neurological sample data that were synchronised with the intermediary low dimensional representative state(s) may be labelled based on the corresponding portions of the labelled sensor data. In step 1144 a labelled training set of neural sample data associated with the bodily variable of interest may be generated based on the labelled portions of neural sample data. The labelled training set of neural sample data may be stored as a labelled training set of neural sample data associated with one or more bodily variables of interest.

The labelled training set of neural sample data associated with the bodily variable(s) of interest of step 1144 may be used for training a ML technique to generate a trained ML model for predicting bodily variable label estimates associated with the bodily variable of interest when neural sample data is input. Additionally or alternatively, another ML technique may be trained based on the labelled training set of neural sample data associated with the bodily variable of interest, where the ML technique generates another ML model for predicting bodily variable label estimates associated with the bodily variable of interest when neural sample data is input.

Further, the ML model for detecting, determining, or generating the intermediary low-dimensional representative state(s) characterising bodily variables (or label-like vectors characterising bodily variables), may be updated based on the labelled training set of neural sample data, which may further improve the latent space and/or the corresponding intermediary low-dimensional representative state(s). Retraining or updating the ML model may be achieved by retraining the ML technique based on the labelled training set of neural sample data associated with the bodily variable of interest, where the ML technique generates an updated ML model for further determining the low dimensional latent space representative of one or more bodily variables and generating the one or more intermediary low-dimensional representative state(s) (or label-like vectors associated with the low dimensional latent space). This may be used to further enhance the labelled training neural dataset associated with one or more bodily variables as described with reference to, by way of example but not limited to, FIGS. 1q and/or 1r and methods/processes 1110 and/or 1130. The labelled training dataset may then be used by one or more ML techniques for training ML models for predicting bodily variable label estimates associated with the bodily variable of interest when neural sample data is input.

As described with reference to FIGS. 1g to 1r, the one or more ML technique(s) for training one or more ML models may include at least one or more ML technique(s) from the group of: neural networks; Hidden Markov Models; Gaussian process dynamics models; autoencoder/decoder networks; adversarial/discriminator networks; convolutional neural networks; long short term memory neural networks; any one or more combinations thereof; any other ML technique for generating an ML model based on a time-series labelled training set of neural sample data; any other ML or classifier/classification technique or combinations thereof suitable for operating on said received neurological signal(s); and/or any other ML technique for generating or training an ML model for operating on neurological sample data, modifications thereof, one or more combinations thereof, and/or as described herein, and/or as the application demands.

As described with reference to FIGS. 1g to 1r, the neurological sample data may include neural activity that encodes one or more bodily variables or combinations thereof. The method(s)/process(es) may be associated with labelling portions of neurological sample data for generating labelled training neural datasets associated with one or more bodily variables of interest. As described, a bodily variable may include data representative or encoded by neural activity representing a state of the whole of a subject, a body part of the subject, or a sub-part of the subject. For example, a bodily variable may include, be derived from, and/or based on, by way of example only but is not limited to, at least one from the group of: heart rate of the subject; activity of the subject; temperature of the subject; blood glucose of the subject; any vital sign of the subject; any physiological measurement of the whole of the subject, a body part of the subject, or a sub-part of the subject; and any data representative of a state of the whole of a subject, a body part of the subject, or a sub-part of the subject; and/or any other bodily variable or equivalent term representing a state of used in whole of a subject, a body part of the subject, or a sub-part of the subject and/or as described herein. Sensor data for deriving or determining one or more bodily variables may be generated from one or more sensors trained on the subject, and/or fitted to or on the subject. For example, one or more sensors that may be used may include or be derived from, or based on, by way of example only but is not limited to, at least one sensor from the group of: ECG or heart rate sensor; Activity sensor; Temperature sensor; Blood Glucose sensor; Blood Pressure sensor; any sensor for outputting sensor data associated with one or more vital signs of the subject; any sensor for outputting sensor data associated with physiological measurement of the whole of the subject, a body part of the subject, or a sub-part of the subject; and any sensor for outputting sensor data associated with data representative of a state of the whole of a subject, a body part of the subject, or a sub-part of the subject; and/or any sensor capable of outputting sensor data associated with data representative of one or more bodily variables, and/or a state of the whole of a subject, a body part of the subject, or a sub-part of the subject and the like.

The following description and figures may use the terms "bodily variable(s)" and "bodily variable signal(s)". It is to be appreciated by the skilled person that the phrases "neural data" and "bodily variable(s)" may be interchanged where applicable and that the phrases "device data" and "bodily variable signal(s)" may be interchanged where applicable.

Figure 2A:
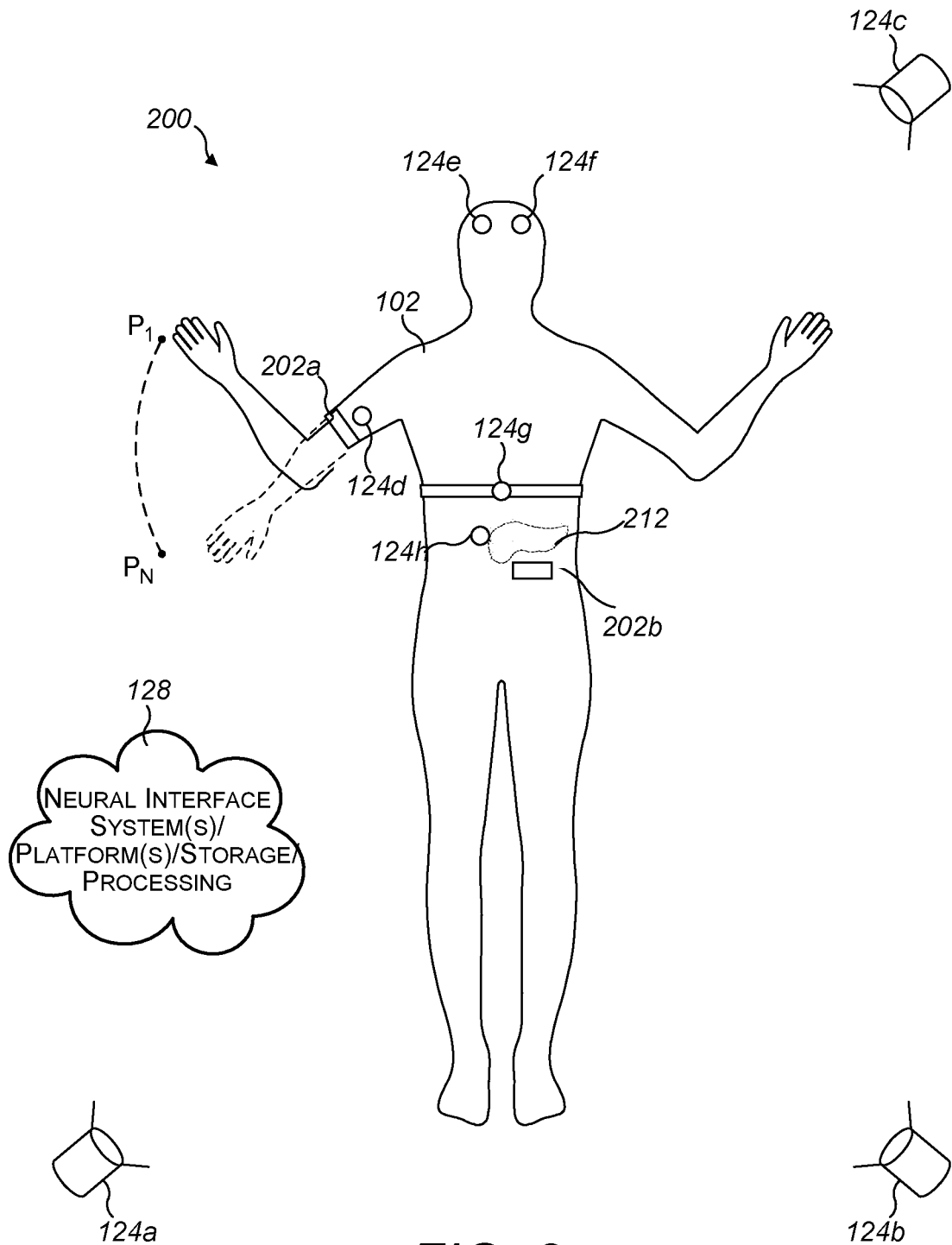
FIG. 2a is a schematic illustration of an example neural interface system for training one or more machine learning technique(s) for use in a neural interface for determining data representative of bodily variables according to the invention.

FIG. 2a is a schematic diagram illustrating an example neural interface 202a or 202b that may be based on neural interface 106 for recording neurological sample sequences and corresponding sensor data for use in generating a training set of neurological sample sequences of neural activity encoding bodily variable(s) associated with subject 102. In order for a ML technique to be trained to classify and/or estimate the neural activity encoding one or more bodily variable(s) from one or more neurological sample sequences, a suitable training set of neurological sample sequences (or a bodily variable training dataset) should be generated. The training set of neurological sample vector sequences may be denoted $\{(x_i)^k\}_{k=1}^{T}$, where $1 \le i \le L_k$ and $1 \le k \le T$, in which $L_k$ is the length of the k-th neurological sample vector sequence and T is the number of training neurological sample vector sequences. Each of the neurological sample vector sequences in the training set $\{(x_i)^k\}_{k=1}^{T}$ may be associated with a label that corresponds to one or more bodily variables or combinations of bodily variables represented within that neurological sample vector sequence. For example, as described previously in relation to FIGS. 1a-1d, each of the neurological sample vector sequences of the training set $\{(x_i)^k\}_{k=1}^{T}$ may correspond to one or more bodily variables that have been identified and labelled by analysing the neurological sample vector sequence with a corresponding portion of sensor data of the subject 102.

The bodily variable training dataset (or training set of neurological sample sequences) $\{(x_i)^k\}_{k=1}^{T}$ may be used to train a ML technique to classify and/or estimate the neural activity encoding one or more bodily variable(s) that may be present in one or more received neurological sample sequences. For example, once a training set of neurological sample vector sequences $\{(x_i)^k\}_{k=1}^{T}$ has been labelled/classified and generated, each one or more ML technique may be trained to estimate bodily variable(s) from the training set of neurological sample vector sequences $\{(x_i)^k\}_{k=1}^{T}$, and/or classify and map bodily variable estimate(s) onto a set of categories or labels associated with the corresponding bodily variables labelled in the training set of neurological sample vector sequences $\{(x_i)^k\}_{k=1}^{T}$.

In FIG. 2a, the subject 102 may have a neural interface 202a or 202b coupled to the nervous system (not shown) of the subject 102 that may be configured for identifying and receiving neurological sample vector sequences associated with neural activity encoding one or more bodily variable(s). As an example, the neural interface 202a may be configured to record and/or process neurological sample vector sequences with the movement of a body part of the subject 202 (e.g. an arm of the subject) from, by way of example only but not limited to, a position $P_1$ to one or more positions $P_N$. As another example, the neural interface 202b may be configured to record and/or process neurological sample vector sequences associated with the operation of a body part or organ 212 of the subject 202 (e.g. the pancreas of the subject 202). External or internal sensors 124a-124h may also be placed on, in and/or around the subject 102 for sensing one or more biological, pathological, physical and/or emotional aspects of the subject 102, which may include sensors such as, by way of example only but not limited to, a video camera 124a, inertial measurement unit 124d, motion detection sensors 124b-124c, heart rate sensors 124g, brain sensors 124e or 124f associated with EEG, EOG and/or EMG signals or any other form of heart or brain activity, or sensor(s) 124h associated with monitoring one or more parameters and/or function(s) of the body and/or bodily organ(s)/tissues. In addition, the communication interface of neural interface(s) 202a or 202b may be coupled to one or more external systems 128 for providing further storage and processing resources due to, by way of example only but is not limited to, the limited storage and processing resources of the neural interface(s) 202a or 202b.

The one or more external computing system(s) 128 may include, by way of example only but not limited to, neural interface system(s) and/or platform(s) configured to operate on the neurological sample sequences and/or sensor data using one or more server(s) or cloud computing system(s) and the like. The one or more external computing system(s) 128 may include one or more storage unit(s), one or more processor(s), one or more computing device(s), and/or server(s) for providing additional storage and computing resources to neural interfaces 202a and 202b. For example, the one or more external computing system(s) 128 may be used to, by way of example only but not limited to, generate and store training dataset(s) based on the neurological signal samples and/or corresponding sensor data for training one or more ML technique(s); train one or more ML technique(s) based on the training dataset(s) to estimate bodily variable(s) from neurological signal samples and transmit data representative of the trained ML technique(s) to neural interface(s) 202a and 202b for configuring the ML technique(s) of neural interface 202a and 202b accordingly; and/or assist neural interface 202a and 202b on further storage and/or processing of neurological signal samples and/or sensor data for, by way of example only but not limited to, calibration and/or retraining of the ML technique(s) of neural interface 202a and 202b, and/or in estimating bodily variable(s) from neural activity in real-time for neural interface 202a and 202b. For example, external computing system(s) 128 may train one or more ML technique(s) and transmit data representative of the trained one or more ML technique(s) to the neural interface 202a and 202b via the communication interface 112, which may be stored in storage 114 and used to configure the neural interface 202a and 202b to operate based on the trained one or more ML technique(s).

For example, the external computing system(s) 128 may process and generate training dataset(s) based on the neurological signal samples (or neurological sample vector sequences) and/or corresponding sensor data for training one or more ML technique(s). This may include processing neurological sample vector sequences to form a set of pre-recorded neurological sample vector sequences that have been analysed to identify the presence of one or more bodily variable(s) and labelled and/or classified according to one or more bodily variable(s) identified to be present in the neurological sample vector sequences. These can be used in training the one or more ML technique(s) to estimate one or more bodily variables from received neurological signal samples. The trained ML technique(s) may be used to configure a neural interface 202a or 202b to classify and/or estimate one or more bodily variables from received neurological signal samples.

As an example, the neurological sample vector sequences that are stored may be labelled based on sensor data of the subject 102 received from sensors 124a-124h and recorded or stored and processed by external computing system(s) 128 during recording and storage of one or more neurological sample vector sequences from the subject 102. The neurological sample vector sequences may then be correlated with the sensor data to assist in identifying those neurological sample vector sequences that correspond to a particular one or more bodily variable(s). The sensor data and the neurological sample vectors may be timestamped when they are stored to assist in identification of which portions of the sensor data and the corresponding portions of the neurological sample vector sequences are associated with one or more bodily variable(s). The sensor data and the corresponding neurological sample vector sequence may be automatically analysed to identify one or more bodily variable(s) or combinations thereof and given a bodily variable label associated with that bodily variable, that one or more bodily variable(s) or combinations thereof. All the neurological sample vector sequences that have been identified and labelled with an associated bodily variable label may be stored as a training set of neurological sample vector sequences $\{(x_i)^k\}_{k=1}^{T}$. Of course the corresponding bodily variable labels associated with each vector sequence may also be stored as part of the training set of neurological sample vector sequences $\{(x_i)^k\}_{k=1}^{T}$ also referred to herein as a bodily variable training dataset.

For example, sensor 124a may be a video camera that may be used to record images of the subject 102 at the time the neurological signals from the subject 102 are captured, sampled, stored and recorded by neural interface 202a and/or external computing system 128. Both the video footage and the corresponding neurological sample vector sequences may be timestamped to allow synchronisation of the recorded video footage with the neurological sample vector sequence. The subject 102 may be instructed to perform specific movements during recording of the video footage. The subject 102 may be instructed to move their limbs from position $P_1$ through one or more positions to a position $P_N$. The timestamps of the neurological sample vector sequences and the video footage that is recorded as the subject 102 moves their limbs allows identification of which neurological sample vector sequences correspond with which portions of video footage that is recorded. This can be used to identify one or more bodily variable(s) or combinations thereof in the neurological sample vector sequences associate with the limbs moving from position $P_1$ through one or more positions to position $P_N$. That is, each of the neurological sample vector sequences may be labelled or classified by bodily variable labels/categories that are associated with the identified bodily variables from the corresponding video footage. From this, a training set of neurological sample vector sequences or a bodily variable training dataset $\{(x_i)^k\}_{k=1}^T$ that has been labelled with bodily variable labels may be used to train one or more ML technique(s) associated with movement of a limb and for use by a neural interface 202a or 106. The analysis of the sensor data with the neurological sample vector sequences may be performed partially or fully in an automatic fashion.

In another example, sensor(s) 124g and 124h may be a heart rate sensor and/or a insulin monitoring sensor, respectively, that may be used to heart rate sensor data and insulin level sensor data of the subject 102 at the time the neurological signals associated with the pancreas 212 of the subject 102 are captured, sampled, stored and recorded by neural interface 202b and/or external computing system 128. The heart rate sensor data, insulin sensor data and the corresponding neurological sample vector sequences may be timestamped to allow synchronisation of the sensor data with the neurological sample vector sequence. The subject 102 may be instructed to eat certain foods that may raise or lower their insulin levels and so observe the functioning of the pancreas 212. The timestamps of the neurological sample vector sequences and the heart rate and/or insulin sensor data that is recorded as the subject 102 eats and/or digests the food allows identification of which neurological sample vector sequences correspond with which portions of the heart rate and/or insulin sensor data that is recorded. This can be used to identify one or more bodily variable(s) or combinations thereof associated with the functioning of the pancreas in the neurological sample vector sequences. That is, each of the neurological sample vector sequences may be labelled or classified by bodily variable labels/categories that are associated with the identified bodily variables corresponding to the functioning of the pancreas and from the corresponding sensor data. From this, a training set of neurological sample vector sequences or a bodily variable training dataset $\{(x_i)^k\}_{k=1}^T$ that has been labelled with bodily variable labels may be used to train one or more ML technique(s) associated with the functioning of the pancreas and for use by a neural interface 202a or 106. The analysis of the sensor data with the neurological sample vector sequences may be performed partially or fully in an automatic fashion.

Figure 2B:
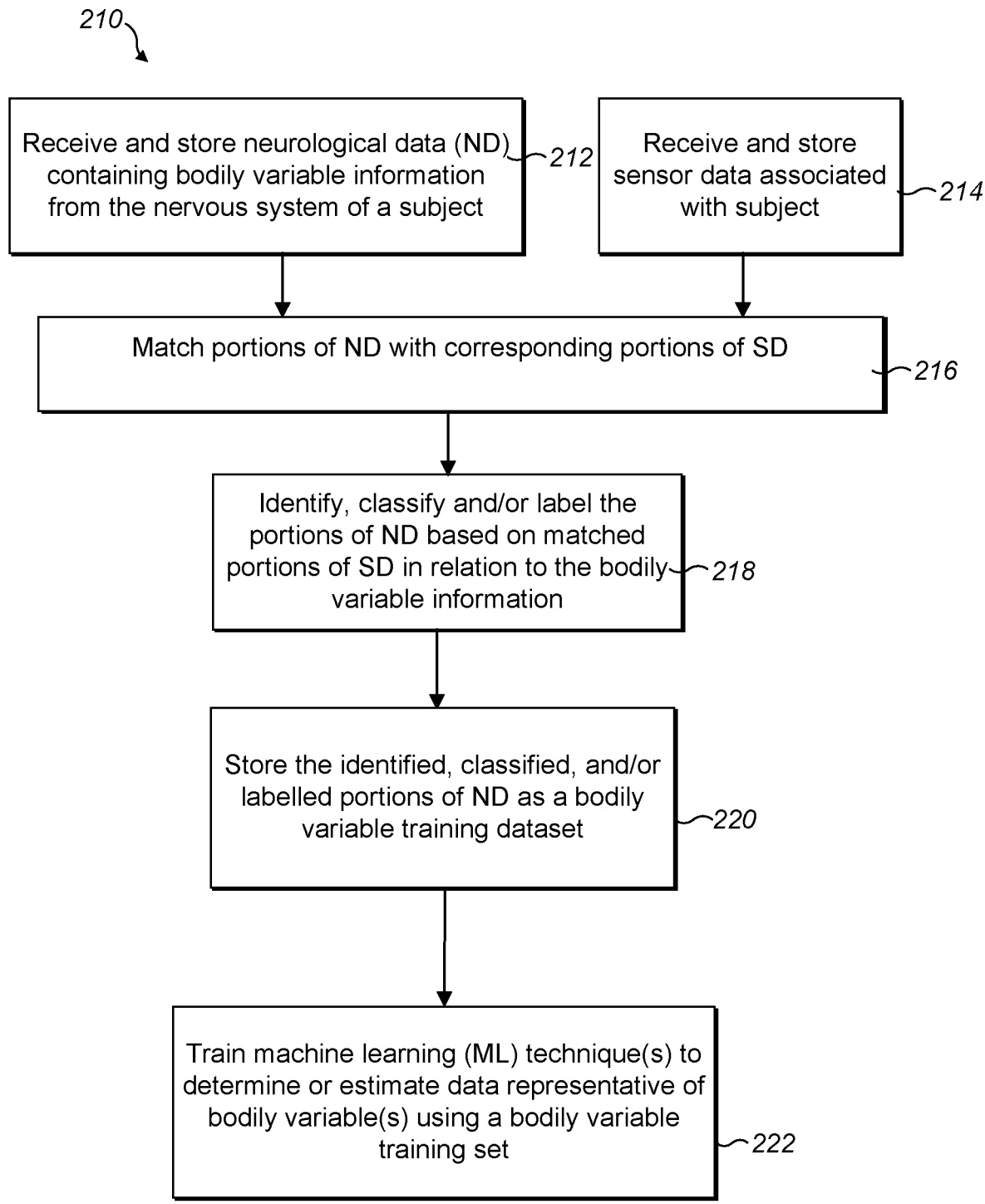
FIG. 2b is a flow diagram illustrating another example process for generating a training dataset and training one or more machine learning technique(s) for use by a neural interface according to the invention.

FIG. 2b is a flow diagram illustrating a process or method 210 for generating a training set of neurological sample vectors $\{(x_i)^k\}_{k=1}^T$ based on a system 200 as described with reference to FIG. 2a. The method 210 is based on, by way of example only but is not limited to, one or more of the following steps of: In step 212, neurological data containing bodily variable information from the nervous system of a subject 102 is received from one or more neural receivers and stored (e.g. in external system 128 or neural interface 202a or 202b). The neurological data may be neurological sample vector sequences as described herein. At the same time, in step 214 one or more sensor(s) may be observing the subject 102 and sensor data associated with the subject 102 may also be received and stored (e.g. in external system 128 or neural interface 202a or 202b). Both the neurological data and the sensor data may be timestamped to allow correlation and/or allow identification and classification of bodily variables that may be present in the neurological data.

In step 216, portions of neurological data are matched or correlated with portions of sensor data. If the neurological data and sensor data is timestamped, then portions of the neurological data and sensor data may be synchronised and analysed together. In step 218, the neurological data and the sensor data may be analysed to identify, classify and/or label the portions of neurological data based on the matched portions of the sensor data in relation to the bodily variable information. This may include analysing the neurological data to determine when neural activity that encodes one or more bodily variable(s) is present. The portions of the neurological data in which bodily variable(s) are identified to be present may be further analysed or passed through one or more ML technique(s) capable of classifying the portions of neurological data. The portions of neurological data or classified portions of neurological data may be matched with corresponding portions of sensor data to identify the one or more bodily variable(s) or combinations thereof. The bodily variable(s) may be identified by analysing the corresponding portions of sensor data and using this to directly or indirectly identify the one or more bodily variables or combinations thereof that may be present. These identified bodily variable(s) may be given bodily variable labels that can be associated with the corresponding portions of the neurological data. Thus a mapping of bodily variable labels to portions of neurological data is generated.

In step 220, the identified, classified and/or labelled portions of the neurological data may be stored as a bodily variable training dataset. In step 222, one or more ML technique(s) may be trained using the bodily variable training dataset. The ML technique(s) may be trained to determine or estimate data representative of bodily variable(s) based on the bodily variable training dataset. For each portion of the bodily variable training data set (e.g. for each neurological sample vector sequence associated with a bodily variable label in the bodily variable training dataset), the ML technique(s) may be trained to output an information dense bodily variable vector or estimate for the subject 102.

Figure 2C:
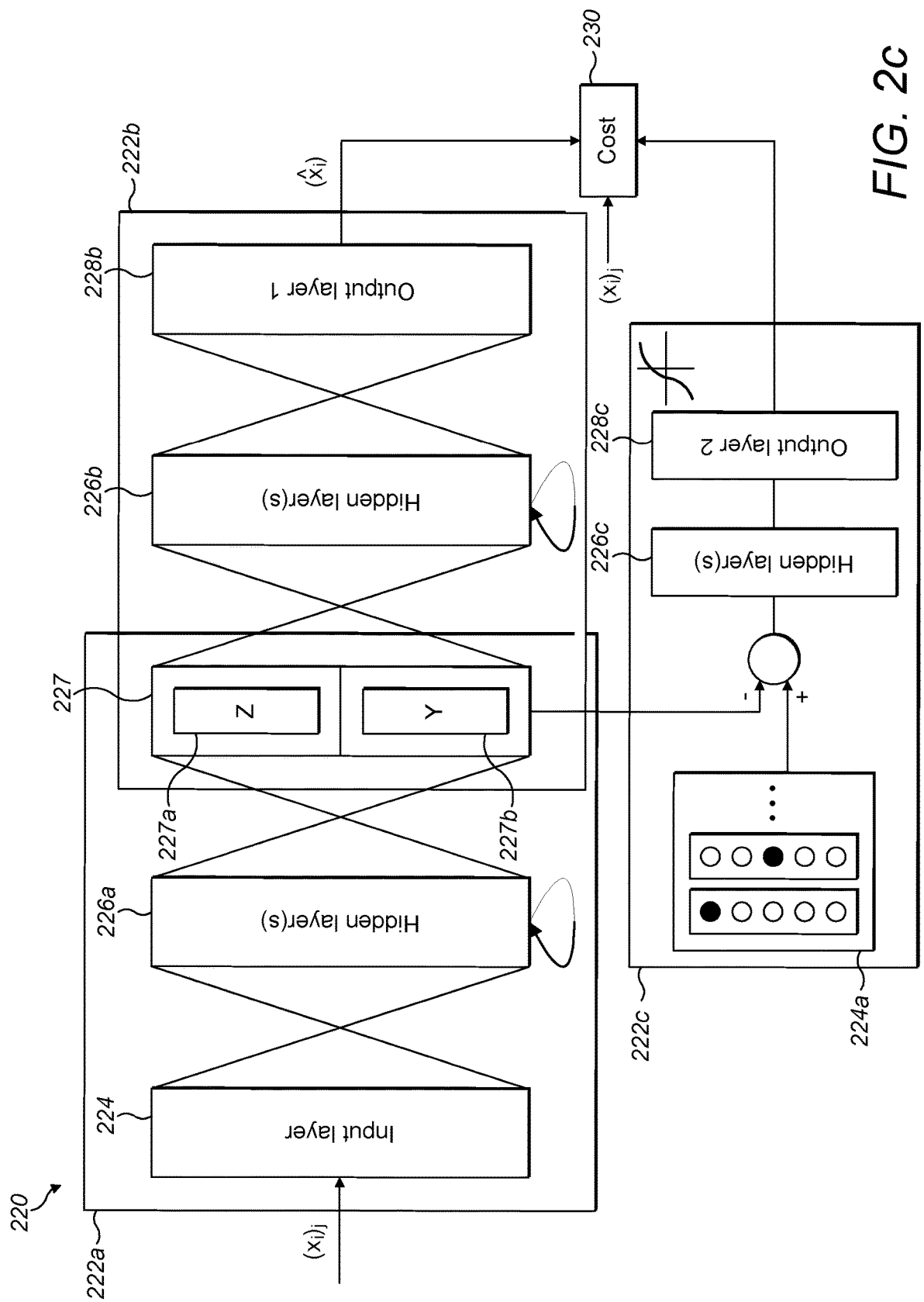
FIG. 2c is a schematic illustration of an example machine learning technique for use with a neural interface according to the invention.

FIG. 2c is a schematic diagram illustrating an example ML technique in the form of a neural network (NN) classifier 220 for use by a neural interface 106 or 202a/202b to classify multi-channel neurological signals $x_1(t), \ldots, x_i(t), x_j(t), \ldots, x_M(t)$ containing neural activity encoding one or more bodily variable(s). The NN classifier 220 may be trained on a bodily variable dataset comprising a set of neurological sample vector sequences in which each sequence may already be associated with a bodily variable label. Alternatively, the NN classifier 220 may be trained on a bodily variable dataset comprising only a set of neurological sample vector sequences that have been identified to contain neural activity encoding one or more bodily variables. That is, the NN classifier 220 may be used to determine bodily variable labels from a stored set of neurological sample vector sequences and corresponding sensor data.

The NN classifier 220 is trained, for each neurological sample vector sequence associated with bodily variable(s) that is input, to output a unique bodily variable vector estimate (e.g. a one hot vector) that can be mapped to a bodily variable label. If the bodily variable training dataset is not labelled, the portion of sensor data corresponding to the neurological sample vector sequence that is input to the NN classifier 220, and which outputs a corresponding unique bodily variable vector estimate, may be analysed to identify a bodily variable label corresponding to the bodily variable(s) present in that neurological sample vector sequence. The unique bodily variable vector estimate may then be mapped to the bodily variable label.

In real-time operation, or when trained, the NN classifier 220 may receive neurological sample vector sequences based on multi-channel neurological signals $x_1(t), \ldots, x_i(t), x_j(t), \ldots, x_M(t)$ containing neural activity encoding one or more bodily variable(s) and output data representative of a corresponding bodily variable vector estimate and/or bodily variable labels. This allows an information dense representation of the raw neurological sample vector sequences to be transmitted (e.g. in the form of a bodily variable vector estimate and/or bodily variable label) to one or more device(s) for performing various actions or operations on the bodily variable vector estimate.

In this example, the NN classifier 220 comprises an encoding NN structure 222a and a decoding NN structure 222b. The encoding NN structure 222a (or encoder 222a) includes an input layer 224 connected to one or more hidden layers 226a that are connected to an latent space representation layer 227. The input layer 224 is configured to receive the multichannel neurological signals as data representative of the k-th neural activity encoding one or more bodily variable(s) in the form of a k-th neurological sample vector sequence $(x_i)^k$ for $1 \leq i \leq L_k$ and $k \geq 1$, where $x_i$ is the i-th sample vector of the multi-channel neurological signal $x_1(t), \ldots, x_i(t), x_j(t), \ldots, x_M(t)$, which is an M-dimensional vector in which each element of $x_i = [x_1(t_i), \ldots, x_m(t_i), \ldots, x_M(t_i)]^T$ represents a sample from the corresponding m-th channel for $1 \leq m \leq M$ taken at sampling time step i for $1 \leq i \leq L_k$, M is the number of channels and $L_k$ is the length of the sample sequence or number of samples sufficient to capture the k-th neural activity encoding one or more bodily variable(s). Thus, data representative of the k-th neural activity encoding one or more bodily variable(s) may consist of $L_k \times M$ samples.

The decoding NN structure 222b (or decoder 222b) includes latent space representation layer 227 connected to one or more further hidden layers 226b that are connected to an decoding output layer 228b. The decoder 222b outputs in the decoding output layer 228b an estimate of the k-th neurological sample vector sequence $(\hat{x}_i)^k$ $1 \leq i \leq L_k$ and $k \geq 1$, which is a reconstruction of the input k-th neurological sample vector sequence $(x_i)^k$ $1 \leq i \leq L_k$ and $k \geq 1$. As illustrated in FIG. 2c the latent space representation layer 227 of the encoder 222a is configured to form a latent vector comprising a label vector, $y_k$, 227b and continuous latent variable vector, $z_k$, 227a corresponding to the k-th neurological sample vector sequence. The number of elements of $y_k$ may correspond to the number of unique bodily variable labels associated with the bodily variable training dataset, assuming the bodily variable training dataset has been previously labelled with bodily variable labels. Alternatively, the number of elements of $y_k$ may also correspond to the expected number of bodily variable labels that may be found when using an unlabelled bodily variable training dataset. Alternatively, the number of elements of $y_k$ may correspond to the number of uncorrelated or unique neurological sample vector sequences that are in an unlabelled bodily variable training dataset. The number of elements of $y_k$ may alternatively be determined through trial and error by observing how the number of unique bodily variable vector estimates changes as the NN classifier 220 is trained on the same unlabelled bodily variable training dataset.

The NN classifier 220 is augmented with an adversarial discriminator 222c that is trained to distinguish between label vectors, $y_k$, generated by the latent space representation layer 227 and samples from a categorical distribution of a set of one hot vectors 224a, which are input to the further hidden layer(s) 226c of the adversarial discriminator in which output layer 228c outputs a binary result to a cost module 230. The binary output is used to improve the estimate of label vector, $y_k$, by rating how close it is to a one hot vector. The cost module 230 uses this binary result to further improve the latent space representation layer 227 and ensure label vector, $y_k$, is estimated to be closer to a one-hot vector. The adversarial neural network 222c is trained to distinguish between label vectors, $y_k$, generated by the latent space representation layer 227 and samples from the categorical distribution of a set of one hot vectors 224a. Thus, the encoder 222a generates two fixed size latent vector representations latent vector z 227a and also label vector $y_k$ 227b of an arbitrary length sequence $p(z_k; Y_k|(x_i)^k)$.

During training, a training set of neurological sample vector sequences $\{(x_i)^k\}_{k=1}^T$ (which may be unlabelled) can be used to train the NN classifier 220 to label vectors, $y_k$, that map to a set of categories or bodily variable labels, where $1 \leq i \leq L_k$ and $1 \leq k \leq T$, in which $L_k$ is the length of the k-th neurological sample vector sequence and T is the number of training neurological sample vector sequences. For each k-th neurological sample vector sequence, the cost module 230 receives the result from the adversarial discriminator 222c, the estimate of the k-th neurological sample vector sequence is represented as $(\hat{x}_1)^k$, the original k-th neurological sample vector sequence $(x_i)^k$, and the latent space representation layer 227 to generate a cost or loss function that is used to update the weights of the hidden layers 226a, 226b and 226c using, by way of example only but not limited to, back-propagation through time techniques or other statistical techniques. Once trained, the weights of the NN classifier 220 can be fixed for use in classifying received neurological sample vector sequences from storage or in real-time.

The neural network structure of the hidden layers 226a and 226b of the NN classifier 220 may include, by way of example only but is not limited to, a Long Short Term Memory (LSTM) recurrent NN for encoding data representing the k-th neurological sample vector sequence received at the input layer 224 into a fixed-size continuous representation. In this example, the NN classifier 220 comprises a single hidden layer 226a in the encoder 222a that is a LSTM recurrent neural network. The decoder 222b also includes single hidden layer 226b that is a LSTM recurrent neural network. Although a single hidden layer 226a and 226b are illustrated, it is to be appreciated that more than one hidden layer 226a and 226b or multiple hidden layers may be used.

The decoder 222b uses both the latent variable $z_k$ and label vector $y_k$ representations to generate an estimate of the original input neurological signal sample vector sequence, denoted $(\hat{x}_i)^k$. At each step the decoder 222b generates a vector with the same length as $z_k$. After the initial decoder step, the input becomes the concatenation of the output from the previous step and the original $y_k$ representation. This places more importance on generating an informative $y_k$ representation for the decoder 222b to use at each step. Methods to make learning stable may include, by way of example only but is not limited to, alternating the input feed for each time step between true inputs and the output of the decoder.

The latent space representation layer 227 generates two fixed size latent representations, latent vector z and label vector $y_k$ for an arbitrary length neurological vector sample sequence $(x_i)^k$, denoted as $p(z_k; y_k|(x_i)^k)$. The decoder 222b then uses both the latent vector z and label vector $y_k$ representations to reconstruct the original input neurological sample vector sequences $(x_i)^k$. At each step in the decoder 222b, the $y_k$-section of the class vector is forced to be the original $y_k$, where the rest of the vector is allowed to change over time. This places more importance on generating an informative $y_k$ representation for the decoder 222b to use at each step and could be regarded similar to a residual connection. To simultaneously make learning stable and the model robust, alternate feeding the decoder the true inputs for each time step instead of feeding the decoder output as input.

Further modifications to the NN classifier 220 may include using a Wasserstein generative adversarial network and mini batch discrimination to prevent mode collapse and stabilise training. The NN classifier 220 may be trained in three separate stages. In the first stage, the autoencoder structure 222a and 222b is trained against the reconstruction error. Thus, for the k-th neurological sample vector sequence comprising N data points ($1 \le n \le N$), with input denoted as $(x_n)^k$ and the reconstructed input as $(\hat{x}_n)^k$, a first loss function may be defined as:

$$L_{AE} = -\frac{1}{N}\sum_n^N (x_n - \hat{x}_n)^2$$

where $x_n = (x_n)^k$ and $\hat{x}_n = (\hat{x}_n)^k$. In some embodiments, the number of data points N may equal $L_k$.

Then at the second stage, the encoder 222a is trained to output labels $y_k$ that are "one-hot-like" by applying a discriminator function f(.) to the generated $y_k$ representation output from the latent space representation layer 228a. Low values of the linear output $f(y_k)$ are penalized with:

$$L_G = -\frac{1}{N}\sum_n^N f(y_n)$$

where $L_G$ is calculated for each n-th data point and $y_n = y_k$ at the n-th data point.

At the third stage, the discriminator 222c is trained to know the difference between generated labels $y_k$ and categorical samples 224a, denoted $y_k'$, and so the discriminator network 222c is penalised for low values of $f(y_k')$ and high values of $f(y_k)$ by the loss function $$L_D = \frac{1}{N}\sum_n^N (-f(y'_n) + f(y_n))$$

where $L_D$ is calculated for each n-th data point and $y_n = y_k$ and $y'_n = y'_k$ at the n-th data point. Note, each $y'_n$ is sampled at random from the categorical distribution 224a.

Figure 2D:
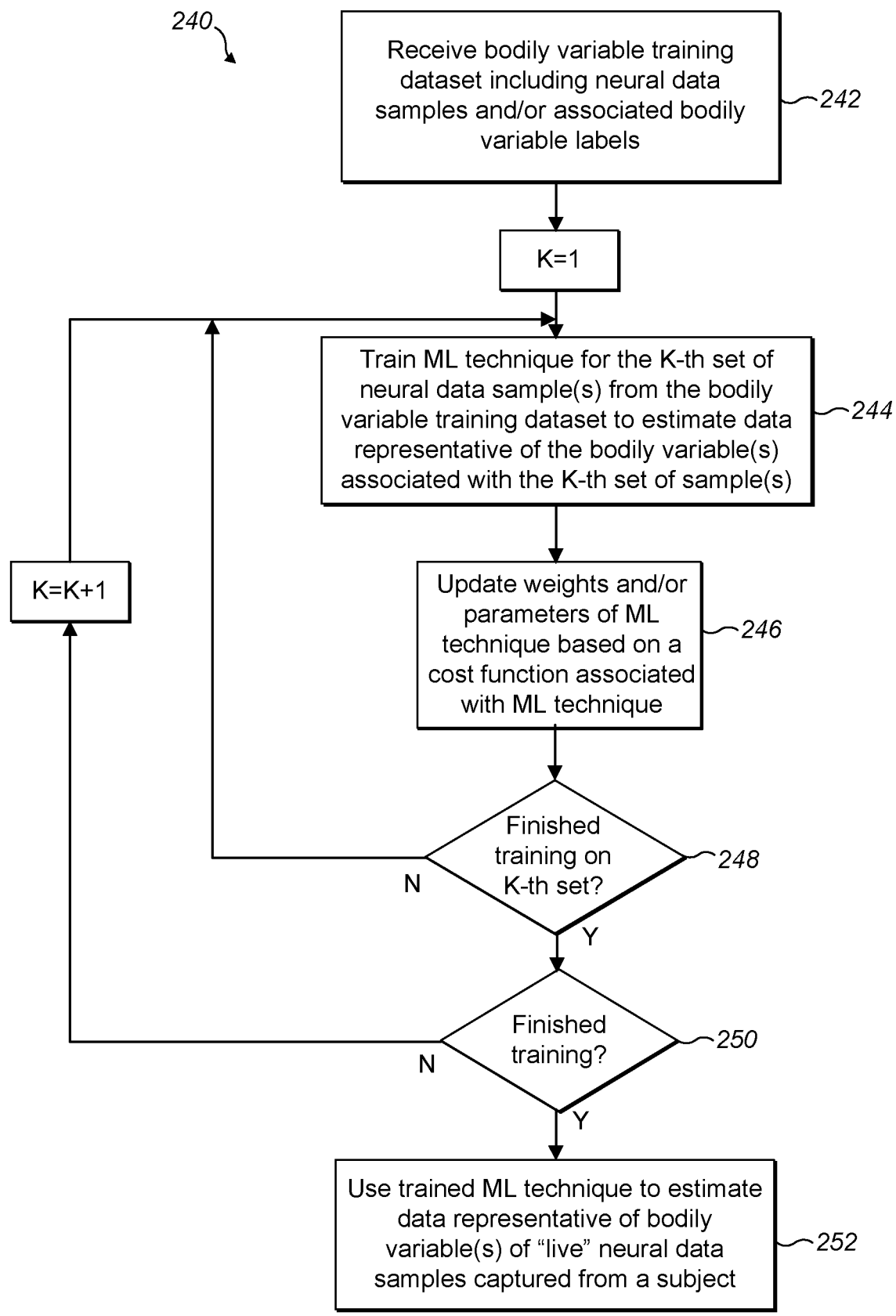
FIG. 2d is flow diagram illustrating an example process for training the machine learning technique of FIG. 2c for use with a neural interface according to the invention.

FIG. 2d is a flow diagram illustrating a training process for method 240 for a ML technique implemented by a neural interface 106. The training process or method is based, by way of example only but is not limited to, the following steps of: In step 242, a training set of neurological sample vector sequences or bodily variable training dataset, $\{(x_i)^k\}_{k=1}^T$ is retrieved. The training set of neurological sample vector sequences $\{(x_i)^k\}_{k=1}^T$ is assumed to have been classified and/or labelled based on sensor data taken at the same time as when each of the neurological sample vector sequences in the training set of neurological sample vector sequences $\{(x_i)^k\}_{k=1}^T$ was received/measured. Thus, the training set of neurological sample vector sequences includes neural data samples or neurological vector data sequences and/or associated bodily variable labels. The training counter, k, is set to the first neurological sample vector sequence (e.g. k=1) that is to be used to train the ML technique. In step 244, the ML technique is trained by applying the k-th neurological sample vector sequence $(x_i)^k$ of $\{(x_i)^k\}_{k=1}^T$, where $1 \le i \le L_k$ and $1 \le k \le T$, as an input to the ML technique. The ML technique may produce some output data representative of a classification and/or a bodily variable estimate representative of one or more bodily variables present in the k-th neurological sample vector sequence $(x_i)^k$. For example, if the ML technique is based on an autoencoder, the output data representative of a classification and/or a bodily variable estimate representative of one or more bodily variables may be output from the encoder portion of the autoencoder. In step 246, the weights and/or parameters of the ML technique are updated based on calculating a cost function associated with the ML technique, the input k-th neurological sample vector sequence $(x_i)^k$, and the output data representation of the k-th classification and/or bodily variable estimate. For example, this may be achieved by comparing the output data representative of the classification and/or bodily variable estimate with the original classification or bodily variable label/vector of the k-th neurological sample vector sequence $(x_i)^k$, which has been classified and/or labelled based on sensor data taken at the time the k-th neurological sample vector sequence $(x_i)^k$ was received/measured and stored. Alternatively, the ML technique may reconstruct the input k-th neurological sample vector sequence $(x_i)^k$ based on the estimated k-th classification, where the reconstructed k-th neurological sample vector sequence may be compared with the original input k-th neurological sample vector sequence. It is to be appreciated by the person skilled in the art that there are many method(s) and combinations thereof for generating a cost function associated with a ML technique. The comparison may produce an error estimate or be used in a cost function that is used to update the weights and/or parameters of the ML technique. The weights and/or parameters of the ML technique may be updated based on the cost function or the error estimate that the ML technique uses.

In step 248, it may be determined whether the ML technique has sufficiently been trained on the k-th neurological sample vector sequence $(x_i)^k$. For example, the cost function may produce an error estimate that is below a certain error threshold. Alternatively or additionally, the ML technique may be considered trained in respect of the k-th neurological sample vector sequence $(x_i)^k$ if it reliably outputs data representative of a bodily variable estimate that corresponds and/or maps to the bodily variable label associated with the k-th neurological sample vector sequence $(x_i)^k$. If training is considered not to have finished (e.g. N) for the k-th neurological sample vector sequence $(x_i)^k$ in the training set, then the steps 244 and 246 may be repeated one or more or multiple times until the error estimate or cost function associated with the k-th neurological sample vector sequence $(x_i)^k$ as reached a certain error or cost function threshold. If the error estimate or the cost function of the ML technique is small enough, or below a certain error or cost function threshold, then the ML technique may be considered to be trained for the k-th neurological sample vector sequence $(x_i)^k$ (e.g. Y) and the method proceeds to step 250.

In step 250, it is determined whether all of the training set of neurological samples or the neurological sample vector sequences of $\{(x_i)^k\}_{k=1}^T$ have been used to train the ML technique. If there are still some neurological samples vector sequences left in the training set (e.g. N), then the training counter, k, is incremented (e.g. k=k+1) and the process proceeds to step 244 with the (k+1)-th neurological sample vector sequence $(x_i)^{k+1}$, otherwise, if all of the neurological sample vector sequences of the training data set has been used or it has been determined that enough neurological sample vector sequences of the training data set have been used (e.g. Y), then the process proceeds to step 252. In step 252, the ML technique is considered to be trained and may now be used to classify neural activity encoding bodily variable(s) and/or output estimates of bodily variable(s) that may be present in further neurological sample vector sequences that may be received from one or more neural receiver(s) connected to the neural interface 106, 202a or 202b.

Figure 2E:
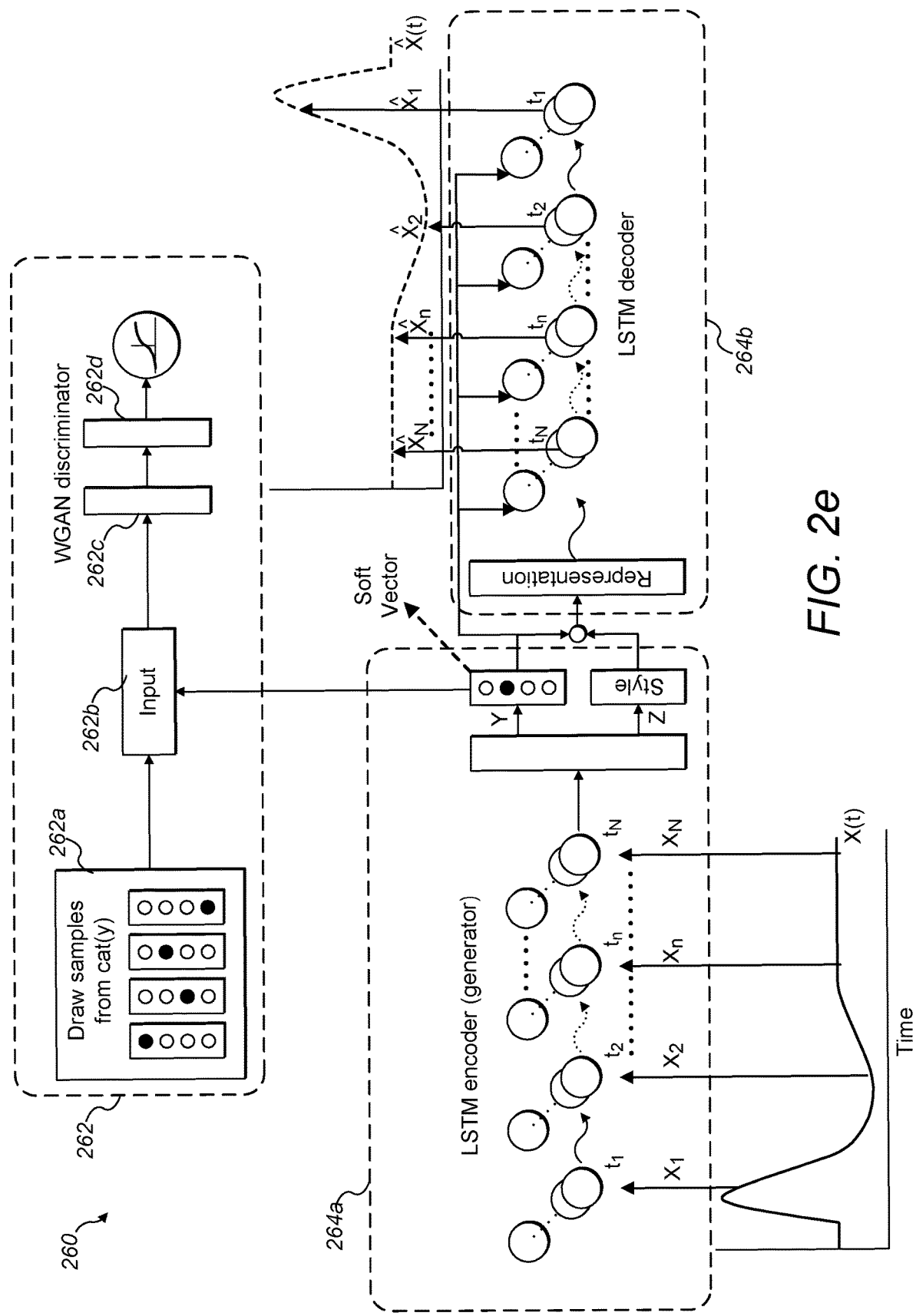
FIG. 2e is a schematic illustration of another example machine learning technique for use with a neural interface according to the invention.

FIG. 2e is a schematic illustration of another example ML technique based on a sequence-to-sequence recurrent neural network model 260 for use with a neural interface 106 and/or 202a/202b according to the invention. The NN model 260 is augmented by a Wasserstein Generative Adversarial Network (WGAN) 262 for use in inferring the actions of a subject (not shown) from neurological signals received by one or more neural receiver(s) situated to a corresponding one or more neuronal population(s) in part of the nervous system of the subject. For example, the neurological signals may be received by the neural receiver(s) from one or more neuronal populations of, by way of example only but not limited to, an efferent nerve. The WGAN 262 is used to constrain the latent representations of the sequence-to-sequence network 260 to be label-like, which allows classification/labelling of the latent representations in relation to neural activity encoding one or more bodily variables or combinations thereof. The label-like representations, also referred to herein as intermediary low dimensional states, may be data representative of one or more bodily variables or representative of bodily variable labels associated with one or more bodily variables. For example, the labelling may be achieved by matching portions of the received neurological signal(s) associated with bodily variable(s) with sensor data associated with the subject when the bodily variable was detected; this allows the bodily variable(s) to be identified based on the matched sensor data and bodily variable labels to be assigned to allow labelling of the latent representations that classify the associated neural activity encoding the bodily variable(s).

As previously described, the neural interface 106 or 202a/202b receives, samples and collects multi-channel neurological signals $x_1(t), \ldots, x_i(t), x_j(t), \ldots, x_M(t)$ received from a number of M neural receivers to form multi-channel neurological signal samples $(x_i)$ for $i \geq 1$, where $x_i$ is the i-th sample vector of an M-dimensional vector space of the multi-channel neurological signal in which each element of $x_i$ represents the i-th sample from the corresponding m-th channel for $1 \leq m \leq M$. Each k-th section of the multi-channel neurological signal $x_1(t), \ldots, x_i(t), x_j(t), \ldots, x_M(t)$ that indicates neural activity (e.g. a set of neural impulse(s)) may be sampled and stored as a sample vector sequence $(x_i)^k$ for $1 \leq i \leq L_k$ and $k \geq 1$, where $L_k$ is the length of the k-th sample sequence or number of samples taken from the k-th section that captures the k-th neural activity encoding one or more bodily variable(s) or combinations thereof. Data representative of the k-th neural activity encoding one or more bodily variables or combinations thereof may consist of $L_k \times M$ samples. Thus, a set of neurological sample vector sequences may be collected and represented as $\{(x_i)^k\}$.

A training set of neurological sample vector sequences may be generated from the collected set of neurological sample vector sequences $\{(x_i)^k\}$ and represented as $\{(x_i)^k\}_{k=1}^T$, where T is the number of neurological sample vector sequences in the training set. The training set $\{(x_i)^k\}_{k=1}^T$ may be generated from previously recorded or stored multichannel neurological signals that identifies T neural activities, in which each neural activity encodes one or more bodily variable(s) or combinations thereof. This training set $\{(x_i)^k\}_{k=1}^T$ may be generated from $\{(x_i)^k\}$ by analysing and comparing each of T neural activities (e.g. automatically analysed as described previously) with corresponding sensor data (e.g. video, audio, motion tracking, blood, heart rate etc.) recorded/stored/collected at the same time the multichannel neurological signals were recorded/stored/sampled and collected. This comparison may be used to identify the action(s) of the subject and so identify each k-th neural activity $1 \leq k \leq T$, which may be used to label the latent representations output from the neural network model 260 in relation to the neural activity.

Alternatively, the training set $\{(x_i)^k\}_{k=1}^T$ may be generated from a collected set of neurological sample vector sequences $\{(x_i)^k\}$ using NN model 260 as a classifier that outputs, from encoder network 264a, a labelling vector (e.g. this may be a soft vector) for each of the neurological sample vector sequences $\{(x_i)^k\}$. After which each labelling vector may be labelled with a bodily variable label that may be identified by comparing each of the neural activities of $\{(x_i)^k\}$ (e.g. automatically analysed as described previously) with corresponding sensor data (e.g. video, audio, motion tracking, blood, heart rate etc.) recorded/stored/collected at the same time the multichannel neurological signal sample vector sequences $\{(x_i)^k\}$ were recorded/stored/sampled and collected. A set of T unique bodily variable labels and their associated neurological signal sample vector sequences $\{(x_i)^k\}$ may be stored as a bodily variable training dataset $\{(x_i)^k\}_{k=1}^T$ that has been labelled. This may be used to further train one or more ML technique(s).

Given the collected set of neurological sample vector sequences $\{(x_i)^k\}$ can be very large and contain features too nuanced for manual human analysis, ML techniques such as NN model 260 can assist in analysing, learning and labelling representations of the neurological sample vector sequences $\{(x_i)^k\}$ suitable for outputting to one or more device(s) for managing bodily functions of the subject. In this example, the NN model 260 is based on a semi-supervised sequence-to-sequence model. The NN model 260 is a sequence-to-sequence model that encodes a given neurological sample vector sequence $(x_i)^k$ for $1 \leq i \leq L_k$ and $k \geq 1$ into a fixed-size continuous vector representation or latent vector representation. The NN model 260 includes an encoder 264a and decoder 264b, both of which are long short-term memory (LSTM) recurrent neural networks (RNNs). As described, the NN model 260 is augmented with an adversarial discriminator 262 that is trained to distinguish between labels y generated by the encoder 264a and samples (e.g. one-hot vector samples) from a categorical distribution 262a. This augmentation enables the NN model 260 to be trained to learn an informative label-like latent vector y from unlabelled collected multichannel neurological signal sample vector sequences $\{(x_i)^k\}$ that may be labelled to identify the corresponding neural activity encoding one or more bodily variable(s). Data representative of the label-like latent vector y may be sent to one or more device(s) that require a representation of the neural activity encoding one or more bodily variable(s) for their operation and/or management of bodily parts and/or functions of the subject.

In this example, the NN model 260 makes use of, by way of example only but is not limited to, a single layer LSTM as an encoder network 264a and decoder network 264b in an autoencoder fashion. More than one layer may be used in the LSTM, but a single layer LSTM is described for simplicity. The encoder network 264a generates two fixed size latent representations z and y of an arbitrary length neurological vector sample sequence $x_i=(x_i)^k$ for $1 \leq i \leq L_k$ and $k \geq 1$, denoted as $q(z, y|x_i)$. The decoder network 264b then uses both the z and y representations to reconstruct the original input neurological vector sample sequence $(x_i)^k$ for $1 \leq i \leq L_k$ and $k \geq 1$. At each time step i or t, in the decoder network 264b, the y-section of the state memory is replaced by the original y, where the rest of the vector is left to change over time. This places more importance on generating an informative y representation for the decoder network 264b to use at each time step. Alternating the input to the decoder network 264b at each training iteration between the true input $x_i=(x_i)^k$ or the output from the previous time step in the LSTM stabilised the training and made the neural network model 260 more robust. In addition, reversing the output when decoding made training easier and faster by allowing the neural network model 260 to start off with low-range correlations.

Alternatively, the k-th sequence of $L_k$ multichannel neurological sample vectors $(x_i)^k$ $1 \leq i \leq L_k$ may be grouped into $N < L_k$ data points or subgroups/subsequences of multichannel neurological sample vectors for $1 \leq n \leq N$, where $L_k/N$ is an integer and each data point or subgroup, may be denoted $X_n$ as an N×M matrix of N multichannel neurological sample vectors (e.g. each multichannel neurological sample vector is an M-dimensional vector) made up from N multichannel neurological sample vectors contiguously selected from the k-th set or k-th sequence of $L_k$ multichannel neurological sample vectors $(x_i)^k$, $1 \leq i \leq L_k$. Thus, there may be a total of N time steps for $1 \leq n \leq N$ that may be used to encode each k-th sequence of $L_k$ multichannel neurological sample vectors $(x_i)^k$ $1 \leq i \leq L_k$; and N time steps for $1 \leq n \leq N$ that may be used to decode or reconstruct the input k-th sequence of $L_k$ multichannel neurological sample vectors $(x_i)^k$ $1 \leq i \leq L_k$. As illustrated in FIG. 2e, at each time step n or t for $1 \leq n \leq N$, a data point or subgroup $X_n$ of multichannel neurological sample vectors is input to the encoder network 264a for use in generating, by time step N, the two fixed size latent representations z and y of an arbitrary length neurological vector sample sequence $x_i=(x_i)^k$ for $1 \leq i \leq L_k$ and may be denoted as $q(z, y|x_i)$. Thus, after N time steps the encoder has generated the two fixed size latent representations z and y. In the decoder network 264b, the reverse essentially occurs where the y-section of the state memory is replaced by the original y, where the rest of the vector is left to change over time. This places more importance on generating an informative y representation for the decoder network 264b to use at each time step n. Alternating the input to the decoder network 264b at each training iteration between the true input $x=(x_i)^k$ or the output from the previous time step in the LSTM stabilised the training and made the neural network model 260 more robust. In addition, reversing the output when decoding made training easier and faster by allowing the neural network model 260 to start off with low-range correlations.

In order to ensure that the y representation is label-like, a discriminator network 262 was used as an additional loss term in the cost function. The adversarial component 262 of the neural network model allows clustering of data in an unsupervised fashion. The discriminator network 262 follows a generative adversarial network approach in which the generator is the encoder recurrent neural network 264a and the discriminator network 262 learns to distinguish between samples from a categorical distribution 262a (e.g. random one-hot vectors) and the y representation generated by the encoder network 264a. This encourages the y representation to converge towards a degenerate distribution from which actions associated with the input neurological vector sample sequence $(x_i)^k$ can be inferred, whilst keeping the distribution over a continuous space. To prevent mode collapse in y and to stabilize training the discriminator network 262 was based on the Wasserstein generative adversarial network in which batch normalization and minibatch discrimination were used.

In this example, the first hidden layer 262c of the discriminator network 262 had a larger number of hidden units (e.g. 50 units) than the second hidden layer 262d (e.g. 20 units). This was followed by minibatch discrimination before being linearly transformed into a scalar value and input to the cost function associated with training the encoder network 264a and decoder network 264b. Batch normalization may be applied to the input and the first activated hidden layers of the discriminator.

In a similar fashion as for FIG. 2d, the NN model 260 may be trained in three separate stages. First the autoencoder comprising the encoder network 264a and the decoder network 264b is trained against the reconstruction error. For example, for $N < L_k$ in which $L_k/N$ is an integer and each data point or subgroup, may be denoted $X_n$ as an N×M matrix of N multichannel neurological sample vectors (e.g. each multichannel neurological sample vector is an M-dimensional vector) made up from N multichannel neurological sample vectors contiguously selected from the k-th set or k-th sequence of $L_k$ multichannel neurological sample vectors $(x_i)^k$, $1 \leq i \leq L_k$ samples the data points for the k-th multichannel neurological sample vector sequence may be represented as $(X_n)^k$ in which the N×M samples of $X_n$ is denoted as the input at the n-th time step and the reconstructed input is denoted as $\hat{X}_n$ at the n-th time step and the loss cost function of the autoencoder, $L_{AE}$, may be defined as:

$$L_{AE} = -\frac{1}{N}\sum_{n}^{N}(x_n - \hat{x}_n)^2$$

In the second stage, the discriminator function f learns the difference between labels y generated from the generator function $g(X_n)$ and categorical samples y' by means of the following loss function $L_D$:

$$L_D = \frac{1}{N}\sum_{n}^{N}(-f(y'_n) + f(g(x_n)))$$

where each $y'_n$ is sampled at random from a categorical distribution 262a. Effectively, the discriminator network 262 is trained to produce negative values when the input is generated and positive values when the input is sampled from a categorical distribution 262a.

In the third stage, the encoder network 264a (e.g. generator) is trained to generate a y representation that is one-hot-like by 'fooling' the discriminator network 262. The following loss function, $L_G$, encourages or trains/adapts the encoder network 264a to generate a y such that the now fixed discriminator function f yields positive values, $$L_G = -\frac{1}{N}\sum_n^N f(g(x_n))$$

The discriminator network 262 may be updated several times (e.g. 3 times) for every update of the encoder network 264a (e.g. the generator). This ensures that the discriminator network 262 directs or points the encoder network 264a (e.g. the generator) in the correct direction at each of the encoder network's 264a update steps.

As an example trial of the NN model 260, 4 hours of a 15 channel neurological signal sample data (e.g. M=15) was collected from the left front leg of a subject. The neurological signal sample data was sampled at, by way of example only but not limited to, 30 kHz and spikes representing neural activity encoding bodily variable(s) in the neurological signal sample data were detected using a voltage threshold of, by way of example only but not limited to, 26 mV. It is to be appreciated by the skilled person that other voltage threshold levels may be used depending on the sensitivity required. Two datasets were used in order to determine how well the NN model 260 performed. The first dataset consisted of the raw neurological signals from all of the 15 channels for, by way of example only but not limited to, 50 time steps after a spike (e.g. neural activity) was detected on any of the channels. In this case, a total of 250,911 spikes of neural activity were detected in the recorded period. The second dataset consisted of the number of spikes on each channel within, by way of example only but not limited to, a 0.01 s bin. Both sets are normalised to range from 0 to 1 and are then sliced into segments of 50 consecutive counts resulting in a total of 6,840 data points. This variation of the data reduces some of the noise present in the raw data, and takes into account for the longer periods that actions of the subject may take to execute. In this example, for both datasets, a single data point has 50 time steps and 15 variables.

Sensor data was also collected whilst the 15 channel neurological signal sample data was collected. In this trial, the sensor data was video footage of the subject that was collected for a period of 24 minutes. The video footage of the subject was analysed and 5 distinct actions performed by the subject were identified, hence 5 distinct neural activities, each of which represented an encoding of a different set of one or more bodily variable(s) or combinations thereof. These actions were: walking forwards, standing, shuffling, reversing, and turning. When the video footage was synchronized to the recorded neurological signal sample data, and neurological signal sample vector sequences or segments of the time series were labelled according to the identified actions with a granularity of 0.1 s. Of the total number of data points in the raw spike data and the count data, 3003 and 74 were labelled respectively. These labelled data points allowed the determination of how good the generated y representations are by using the accuracy in classifying these data points as a proxy. The labelled data were removed from the datasets and not used during training.

In order to establish whether the NN model 260 operated as expected, it was evaluated on 2 other datasets. The first is a synthetic dataset with 4 classes (sinus-, cosine-, sawtooth-, and square-waves). Here 1,000,000 samples were generated with unit amplitudes and random periods between 4 and 30 time steps. All the waveforms had a length of 50 time steps. 200,000 data points were held out for testing. The second dataset was a low-resolution versions of images from the Modified National Institute of Standards and Technology database (MNIST). In this case, the MNIST images were resized from a size of 28×28 pixels to 7×7. The images were processed in scanline order and the shorter sequences made learning easier for the model.

For each dataset a validation set was constructed by randomly splitting the training data with a 80:20 (training: validation) ratio. The best model was selected based on the lowest reconstruction error achieved over the course of training. To prevent overfitting on the smaller count and synthetic datasets, the size of the vector y was set to 20 and the size of z was set to 44. For the raw spike and MNIST data, the size of the vector y was set to 30 and the size of z was set to 98. Larger y-representations were chosen and resulted in more accurate classifications.

In order to establish the classification accuracy that the NN model 260 achieves for each dataset, the following evaluation protocol was applied: For each dimension i in y we find the probabilities of the set of data points in x that have maximum probabilities in this dimension $q(y_i|x)$. The true class labels are then weighted by these probabilities and the class with the maximum average over the selected set of samples is assigned to $y_i$ by means of a hashmap. The accuracy is then computed based on the labels assigned to each data point.

The classification accuracies obtained for the 4 datasets are shown in Table 1 below.

TABLE 1

Experiment Accuracies

| Dataset | Accuracy | Reconstruction squared error |
| --- | --- | --- |
| Synthetic | 0.90 | 0.00131593 |
| MNIST | 0.781 | 111.1957773 |
| Neural-raw | 0.64 | 0.0015137 |
| Neural-count | 0.833 | 4.231e-5 |

The accuracies reported are the averages over 10 independent runs. The squared loss achieved on the test sets were calculated to show the efficacy of the data reconstruction achieved by the NN model 260. High accuracies were achieved for both the synthetic and MNIST datasets, which confirms that the NN model 260 operates as expected. For the MNIST data, the accuracies were lower than usual because a low resolution version of the MNIST images were used, which makes some digits hard to distinguish. A higher classification accuracy was achieved on the count dataset compared to the raw spike dataset. This is most likely due to the count dataset observing actions over longer periods, which provides more informative information and possibly noise robustness. The NN model 260 has shown that having a continuous vector space y to represent the actions of the subject provides a substantial benefit from a modelling perspective compared to discrete approaches. In addition, the continuous vector space y representing estimates of bodily variable(s) or combinations thereof is a data friendly representation that may be used by one or more device(s) for managing or operating bodily functions or one or more body parts of a subject.

Modifications to the NN model 260 may include stitching together datasets collected from different subjects in order to make a large part of the NN model 260 agnostic to the specific subject. The NN model 260 may be further modified to be based on convolutional neural networks instead of LSTMs and/or based on a WaveNet generative model. The WaveNet generative model includes a fully convolutional neural network, where the convolutional layers have various dilation factors that allow its receptive field to grow exponentially with depth and cover thousands of time steps, which may improve analysis of neurological time series.

Figure 2F:
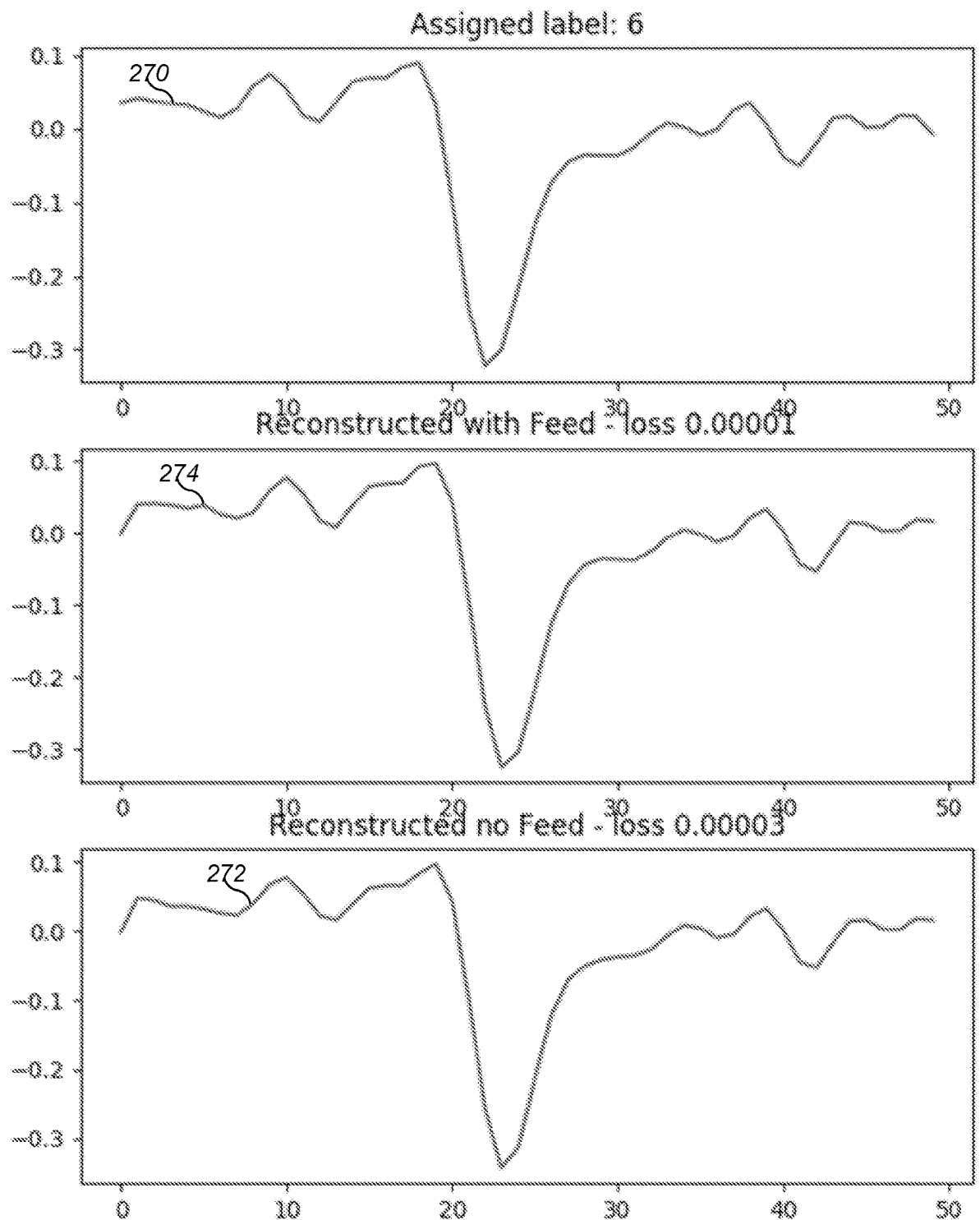
FIGS. 2f and 2g are graphical diagrams illustrating, in relation to the machine learning technique of FIG. 2e, an input neurological signal that is encoded into a latent representation and the reconstructed neurological signal decoded from its latent representation according to the invention.

FIG. 2f are graphical diagrams illustrating an input neurological signal 270 to the encoder network 264a and several corresponding reconstructed neurological signals 272 and 274 output from the decoder network 264b of the NN model 260 of FIG. 2e. For these diagrams, the x-axis represents the number of samples (e.g. in this example it is 50) and the y-axis represents the amplitude of the neurological signal (e.g. voltage). The original input neurological signal 270 that was collected has been assigned a bodily variable label: "6". The reconstructed neurological signal 274 is based on the label vector y and latent space vector z that the encoder 264a generates after training. The label vector y may be assigned the bodily variable label "6". The decoder network 264b uses the label vector y and latent space vector z to generate after N time steps without a feedback loop the reconstructed neurological signal 274. It can be seen that the NN model 260 encodes the input neurological signal 270 in a sufficiently informationally dense data representation of the label vector y and latent space vector z because the reconstructed neurological signal 274 has a very low loss of 0.00003.

The reconstructed neurological signal 272 is based on a feedback loop from the decoder to the input y so that the next stage of the LSTM has knowledge of the previous signal. It can be seen that this modification to decoder network 264b of the NN model 260 encodes the input neurological signal 270 in an improved informationally dense data representation of the label vector y and latent space vector z compared with the no feedback case (e.g. reconstructed neurological signal 274) because the reconstructed neurological signal 272 has a low loss of 0.00001.

Figure 2G:
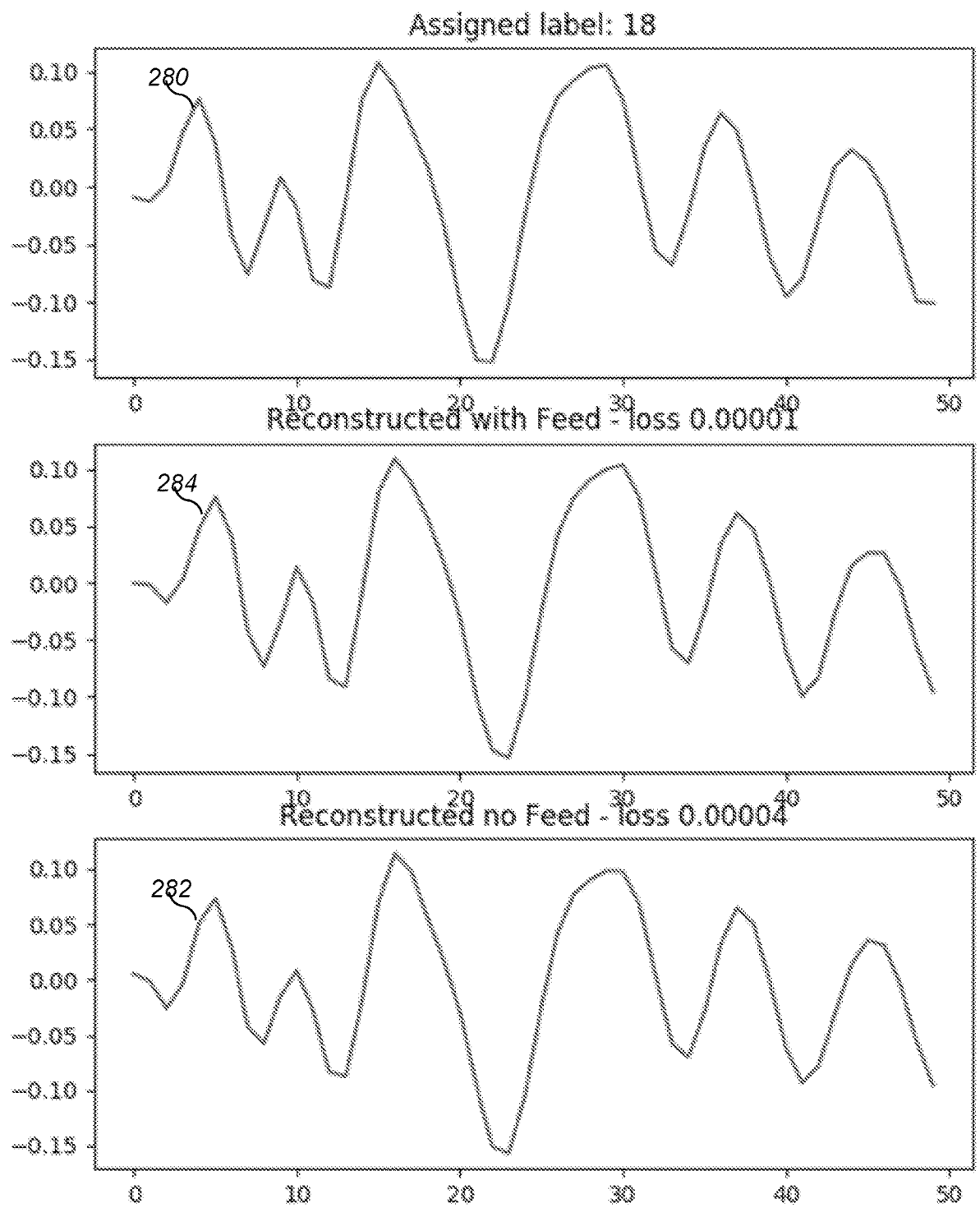

FIG. 2g are further graphical diagrams illustrating an input neurological signal 280 to the encoder network 264a and several corresponding reconstructed neurological signals 282 and 284 output from the decoder network 264b of the NN model 260 of FIG. 2e. For these diagrams, the x-axis represents the number of samples (e.g. in this example it is 50) and the y-axis represents the amplitude of the neurological signal (e.g. voltage). The original input neurological signal 280 that was collected has been assigned a bodily variable label: "18". The reconstructed neurological signal 284 is based on the label vector y and latent space vector z that the encoder 264a generates after training. The label vector y may be assigned the bodily variable label "18". The decoder network 264b uses the label vector y and latent space vector z to generate after N time steps without a feedback loop the reconstructed neurological signal 284. It can be seen that the NN model 260 encodes the input neurological signal 280 in a sufficiently informationally dense data representation of the label vector y and latent space vector z because the reconstructed neurological signal 284 has a very low loss of 0.00004.

The reconstructed neurological signal 282 is based on a feedback loop from the decoder to the input y so that the next stage of the LSTM has knowledge of the previous signal. It can be seen that this modification to decoder network 264b of the NN model 260 encodes the input neurological signal 280 in an improved informationally dense data representation of the label vector y and latent space vector z compared with the no feedback case (e.g. reconstructed neurological signal 284) because the reconstructed neurological signal 282 has a low loss of 0.00001.

Figure 2H:
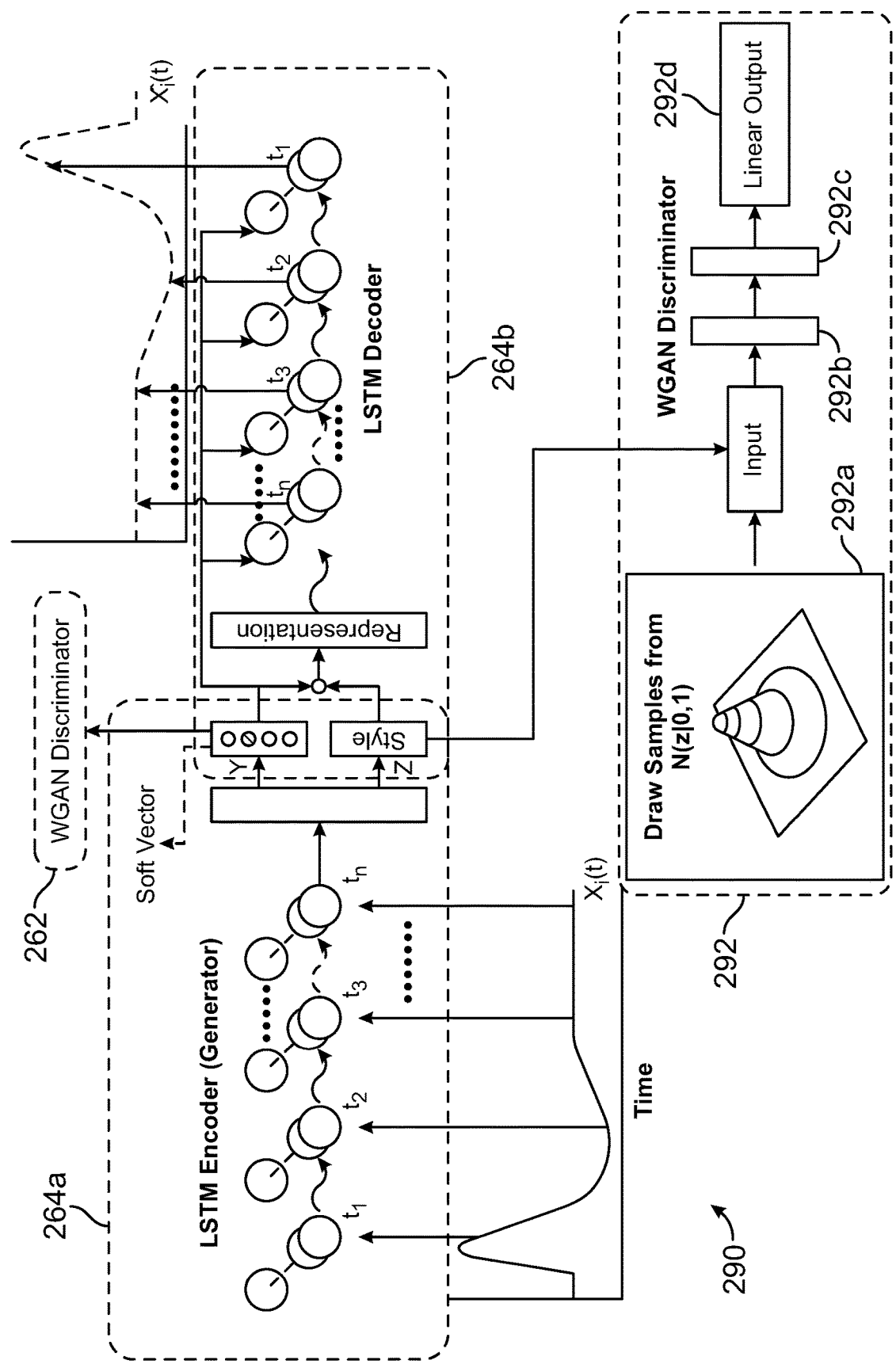
FIG. 2h is a schematic illustration of another example machine learning technique for use with a neural interface according to the invention.

FIG. 2h is a schematic diagram illustrating of a further example ML technique based on a modified NN model 290 that is based on the sequence-to-sequence recurrent NN model 260 of FIG. 2e. The modified NN model 290 may be used in a neural interface 106 and/or 202a/202b according to the invention. The modified NN model 290 includes an encoder network 264a, a decoder network 264b and a first WGAN discriminator network 262 and a second WGAN discriminator network 292. The second WGAN discriminator network 292 is employed to encourage the z representation to be more Gaussian distributed. Although a Gaussian distribution or a normal distribution is described, this is by way of example only and the invention is not so limited, and it is to be appreciated that the skilled person may use, by way of example only but is not limited to, any other probability distribution and the like, or any other probability distribution that further improves the convergence of the networks 264a, 264b, improves the latent space or representation of the latent vector, and/or improves the labelling/classifying and any other aspects of the invention.

The second adversarial discriminator network 292 is trained to distinguish between latent vector, z, generated by the encoder network 264a and samples from a Gaussian distribution $N(z|0, I)$ 292a. The latent vector, z, generated by the encoder network 264 and a Gaussian sample are input to hidden layer(s) 292b and 292c of the second adversarial discriminator 292. The output layer 292d outputs a linear Gaussian result that is used to improve the estimate of latent vector, z, to be more Gaussian by rating how close it is to the Gaussian sample/distribution. For example, a cost module (now shown) may use this Gaussian result to further improve the latent space representation of latent vector z is estimated to be closer to a Gaussian distributed vector. The second adversarial neural network 292 is trained in a similar manner as that described for the first adversarial neural network 262. This enables generation of signals for arbitrary categories by selecting a specific y representation, ỹ, sampling ž from a Gaussian distribution and using the concatenation of z=ž and y=ỹ as the input to the decoder network 264b. Additionally, this allows generation of mixed categories in y. Thus, the encoder network 264a generates two fixed size latent vector representations latent vector ž and also label vector ỹ, which is used as the bodily variable estimate and may be labelled as described with reference to FIGS. 2a to 2g.

Although a Gaussian distributed variables or the Gaussian distribution and/or normal distribution are described, this is by way of example only and the invention is not so limited, and it is to be appreciated that the skilled person may use, by way of example only but is not limited to, any other probability distribution and the like, or any other probability distribution that further improves the convergence of the networks 264a, 264b, improves the latent space or representation of the latent vector, and/or improves the labelling/classifying and any other aspects of the invention.

Although FIGS. 2a to 2h describe examples of the invention, this is by way of example only and for simplicity but these examples of the invention are not so limited, it is to be appreciated by the skilled person that the examples of the invention described in FIGS. 2a to 2h may be applied in relation to any one or more bodily variables and/or any one or more sets of bodily variable labels, and may further include any of the one or more process(es), one or more method(s), labelled training datasets, one or more features and/or one or more functionalities of the different aspects of the invention, modifications thereof or thereto, combinations thereof or thereto, with reference to FIGS. 1a-4j and 5a-6b and/or as described herein.

Figure 3A:
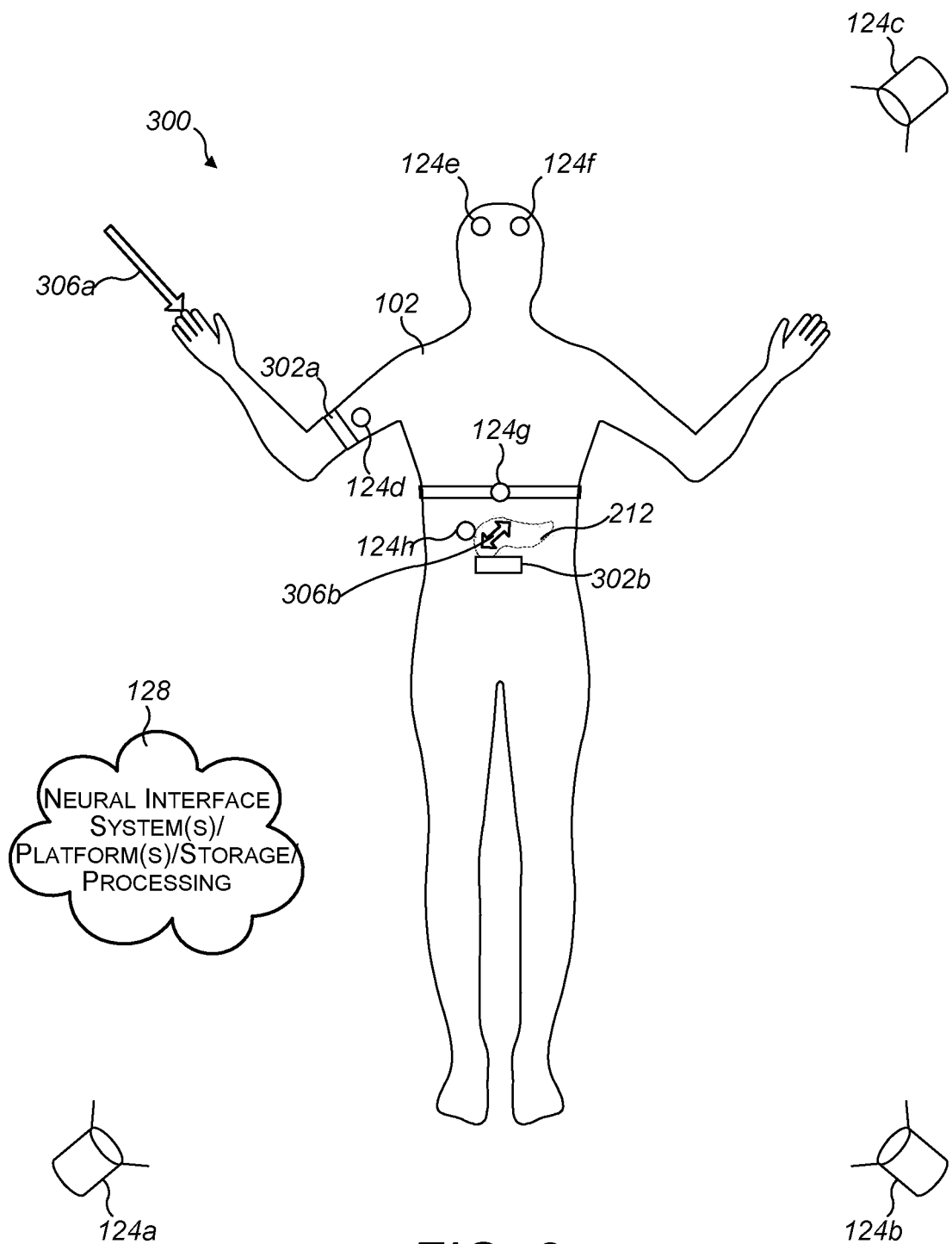
FIG. 3a is a schematic illustration of an example neural interface system for use in training one or more machine learning technique(s) of a neural interface for neural stimulus according to the invention.

FIG. 3a is a schematic illustration of an example neural interface system 300 for use in training one or more ML technique(s) for a neural interface 302a or 302b to output a neural stimulus to one or more neurons or neuronal populations in part of the nervous system of a subject 102 according to the invention. The neural interfaces 302a and 302b may include similar components and be configured in a similar manner as neural interface 106 as described with reference to FIG. 1a. The subject 102 may be observed by a plurality of sensors 124a-124h. External or internal sensors 124a-124h may also be placed on, in and/or around the subject 102 for sensing one or more biological, pathological, physical and/or emotional aspects of the subject 102, which may include sensors such as, by way of example only but not limited to, a video camera 124a, inertial measurement unit 124d, motion detection sensors 124b-124c, heart rate sensors 124g, brain sensors 124e or 124f associated with EEG, EOG and/or EMG signals or any other form of heart or brain activity, or sensor(s) 124h associated with monitoring one or more parameters and/or function(s) of the body and/or bodily organ(s)/tissues.

A neural interface 302a or 302b may be positioned on the subject 102 and in communication with one or more neural receiver(s) and/or neural transmitter(s) coupled to part of the nervous system of the subject 102. Each of the neural receiver(s) and/or neural transmitter(s) are located near one or more neurons or one or more neuronal populations on nerve(s) of the nervous system that are associated with a target neuronal population (e.g. sensory neurons), which generate neural activity encoding one or more bodily variable(s) in response to, by way of example only but not limited to, an external stimulus 306a to the target neuronal population (e.g. a touch stimulus) or an internal stimulus 306b to the target neuronal population (e.g. a stimulus to/from an organ such as the pancreas 212).

The neural interface(s) 302a or 302b may be configured to capture data representative neurological stimulus signals containing neural activity encoding one or more bodily variable(s) or combinations thereof associated with a stimulus to a body part or organ of the subject 102. The neurological stimulus signals may, in fact, be captured by one or more neural receiver(s) that may be located near a target neuronal population that receives the neural stimulus. As an example, the neural interface 302a may be configured to record and/or process neurological stimulus sample vector sequences in response to one or more touch stimuli 306a to a body part of the subject 202 (e.g. a hand of the subject). As another example, the neural interface 302b may be configured to capture neurological stimulus sample vector sequences associated with the internal stimuli 306b associated with the operation of a body part or organ 212 of the subject 202 (e.g. the pancreas of the subject 102). At substantially the same time, sensor data from one or more sensors 124a-124h observing the subject 102 may also be captured. In addition, the communication interface of neural interface(s) 302a or 302b may be coupled to one or more external systems 128 for providing further storage and processing resources due to, by way of example only but is not limited to, the limited storage and processing resources of the neural interface(s) 302a or 302b.

The one or more external computing system(s) 128 may include, by way of example only but not limited to, neural interface system(s) and/or platform(s) configured to operate on the neurological stimulus sample sequences and/or sensor data using one or more server(s) or cloud computing system(s) and the like. The one or more external computing system(s) 128 may include one or more storage unit(s), one or more processor(s), one or more computing device(s), and/or server(s) for providing additional storage and computing resources to neural interfaces 302a and 302b. For example, the one or more external computing system(s) 128 may be used to, by way of example only but not limited to, generate and store neural stimulus training dataset(s) based on the neurological stimulus signal samples and/or corresponding sensor data for training one or more ML technique(s); train one or more ML technique(s) based on the neural stimulus training dataset(s) to estimate bodily variable(s) associated with neural stimulus from the neurological stimulus signal samples and transmit data representative of the trained ML technique(s) to neural interface(s) 302a and 302b for configuring the ML technique(s) of neural interface 302a and 302b accordingly; and/or assist neural interface 302a and 302b on further storage and/or processing of neurological stimulus signal samples and/or sensor data for, by way of example only but not limited to, calibration and/or retraining of the ML technique(s) of neural interface 302a and 302b, and/or in estimating bodily variable(s) from neural activity associated with neural stimulus in real-time for neural interface 302a and 302b. For example, external computing system(s) 128 may train one or more ML technique(s) and transmit data representative of the trained one or more ML technique(s) to the neural interface 302a and 302b via the communication interface 112, which may be stored in storage 114 and used to configure the neural interface 302a and 302b to operate based on the trained one or more ML technique(s).

In operation, the captured neurological stimulus signal data and corresponding sensor data may be processed to generate a neural stimulus training dataset for training one or more ML technique(s) to determine estimates of bodily variable(s) associated with the neural stimulus based on the training dataset. The one or more ML techniques may also be trained and/or configured to determine a neurological stimulus signal corresponding to the bodily variable estimates associated with the neural stimulus for use by one or more neural transmitter(s) in applying an appropriate stimulus signal to one or more target neuronal population(s). Once the one or more ML technique(s) are trained, they may be used by neural interface 302a or 302b for interfacing with one or more device(s) that are configured to manage or target one or more neuronal population(s) of the nervous system of the subject 102 with a stimulus or neural activity associated with bodily variable signals or data generated by said device(s). The bodily variable signals may be generated by one or more device(s) to enable the one or more device(s) to input a neural stimulus to the nervous system of the subject 102. This may be achieved by mapping the bodily variable signal(s) generated by a device to one or more categorised or labelled neurological stimulus signal estimates, as determined by the ML technique(s) during training, that correspond to the bodily variable signal(s). The ML technique(s)

may transmit the neurological stimulus signal estimates to one or more neural transmitter(s) associated with the target neuronal population(s). The one or more neural transmitter(s) may apply a stimulus that causes neural activity associated with the bodily variable signal(s) to be applied to the targeted one or more neuronal population(s).

For example, a neural stimulus may be generated by one or more target neurons and/or target neuronal populations, such as sensory neurons, when they are stimulated by one or more stimuli 306a that may correspond, by way of example only but is not limited to, to touch. The neural interface 302a may be coupled to one or more neural receiver(s) and/or one or more neural transmitter(s) sited near one or more target neuronal population(s) of one or more nerves. The neural interface 302a may thus capture a neurological stimulus signal containing neural activity encoding one or more bodily variable(s) associated the neural stimulus, which is generated by the one or more target neurons and/or target neuronal populations (e.g. sensory neurons). When the target neuronal population is stimulated by one or more stimuli 306a, the one or more of the neural receiver(s) may capture corresponding neural activity encoding bodily variables associated with the stimulus/stimuli in the neuronal populations in the form of one or more neurological stimulus signal(s). For example, multiple neural receiver(s) may be used to capture multichannel neurological stimulus signal(s), which may be sampled to form multichannel neurological stimulus sample vector sequences, which may be collected and stored either by neural interface 302a or 302b or external computing system(s) 128.

Figure 3B:
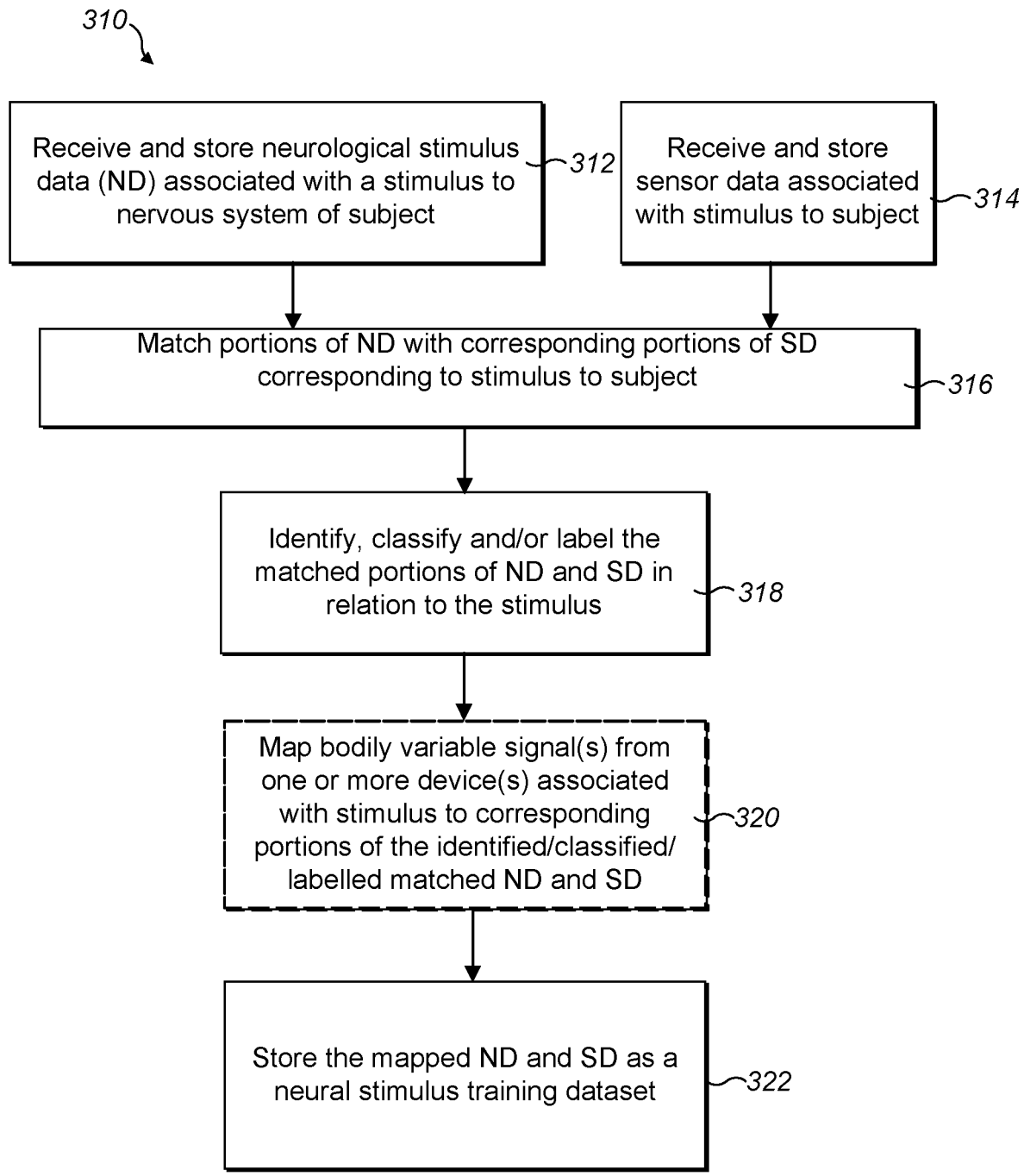
FIG. 3b is a flow diagram illustrating another example process for generating a training dataset for use in training one or more machine learning technique(s) of a neural interface for neural stimulus according to the invention.

FIG. 3b is a flow diagram illustrating another example process 310 for generating a training dataset to use in training one or more ML technique(s) of a neural interface for generating an appropriate neural stimulus when data representative of bodily variable signal(s) or data are received from a device according to the invention. The process 310 may include, by way of example only but not limited to, the following steps of:

In step 312, one or more neurological stimulus signal(s) containing neural activity encoding one or more bodily variable(s) associated with corresponding one or more stimulus to the nervous system of a subject 102 may be received from one or more neural receiver(s) coupled to one or more neuronal populations of the nervous system of the subject 102. There may be a plurality of neural receiver(s) coupled to a corresponding plurality of neuronal populations. Thus a plurality of neurological stimulus signal(s) containing neural activity encoding one or more bodily variables associated with a stimulus may be received in relation to the stimulus. The neurological stimulus signal(s) may be received, sampled and stored as neurological stimulus sample data or multichannel neurological stimulus sample vector sequences associated with each stimulus to the nervous system of the subject 102. The neurological stimulus sample data may be timestamped for use in identifying when neural activity associated with each stimulus may occur. In step 314, one or more sensors 124a-124h may be observing the subject 102 during when a stimulus is applied to or detected in the nervous system of the subject 102 and the corresponding sensor data may be captured and stored. The sensor data may also be timestamped.

In step 316, portions of the neurological stimulus signal data are matched with corresponding portions of sensor data that correspond to stimulus of the subject 102. For example, the captured neurological stimulus signal/sample data and corresponding sensor data may be processed to: a) identify portions of the neurological stimulus signal data in which neural activity encoding one or more bodily variables associated with the stimulus occurs; b) identify portions of the sensor data from one or more sensors 124a-124h that correspond to when the neural activity encoding one or more bodily variables and/or stimulus occurs. Both the neurological stimulus signal data and sensor data may be timestamped to assist in identifying and matching those portions of neurological stimulus signal data with corresponding portions of the sensor data that are related to stimulus to the subject 102.

In step 318, the matched portions of neurological stimulus signal data and sensor data may be identified, classified and/or labelled in relation to the neural activity encoding one or more bodily variables associated with the stimulus to the subject 102. For example, each of the matched portions of the sensor data may be used to identify the neural stimulus associated with one or more bodily variables that correspond to each portion of the neurological stimulus signal data in which neural activity encoding one or more bodily variables associated with the stimulus is present. The portions of the neurological stimulus signal data may then be labelled with a bodily variable label based on the identified neural stimulus associated with the one or more bodily variable(s).

Step 318 may further include analysing the neurological stimulus signal data to determine when neural activity that encodes one or more bodily variable(s) associated with a neural stimulus is present. The portions of the neurological stimulus signal data in which bodily variable(s) are identified to be present may be further analysed or passed through one or more ML technique(s) capable of classifying the portions of neurological stimulus signal data. The portions of neurological stimulus signal data or classified portions of neurological stimulus signal data may be matched with corresponding portions of sensor data to identify the one or more bodily variable(s) or combinations thereof associated with one or more stimuli. The bodily variable(s) or combinations thereof associated with the neural stimulus may be identified by analysing the corresponding portions of sensor data and using this to directly or indirectly identify the one or more bodily variables or combinations thereof that may be present. These identified bodily variable(s) associated with the stimulus may be given bodily variable labels that can be associated with the corresponding portions of the neurological stimulus signal data. Thus a mapping of bodily variable labels to portions of neurological stimulus signal data may be generated.

In step 320, bodily variable signal(s) or data from one or more device(s) that are associated with a stimulus may be mapped to corresponding portions of the identified/classified/labelled portions of the neurological stimulus signal data and/or sensor data. For example, a device that generates bodily variable signal(s) for stimulating one or more neuronal populations with neural activity encoding the bodily variable signal(s) may have these bodily variable signal(s) mapped to a corresponding bodily variable label. In step 322, the labelled and/or mapped portions of neurological stimulus signal data and/or sensor data may be stored as a neural stimulus training dataset.

Figure 3C:
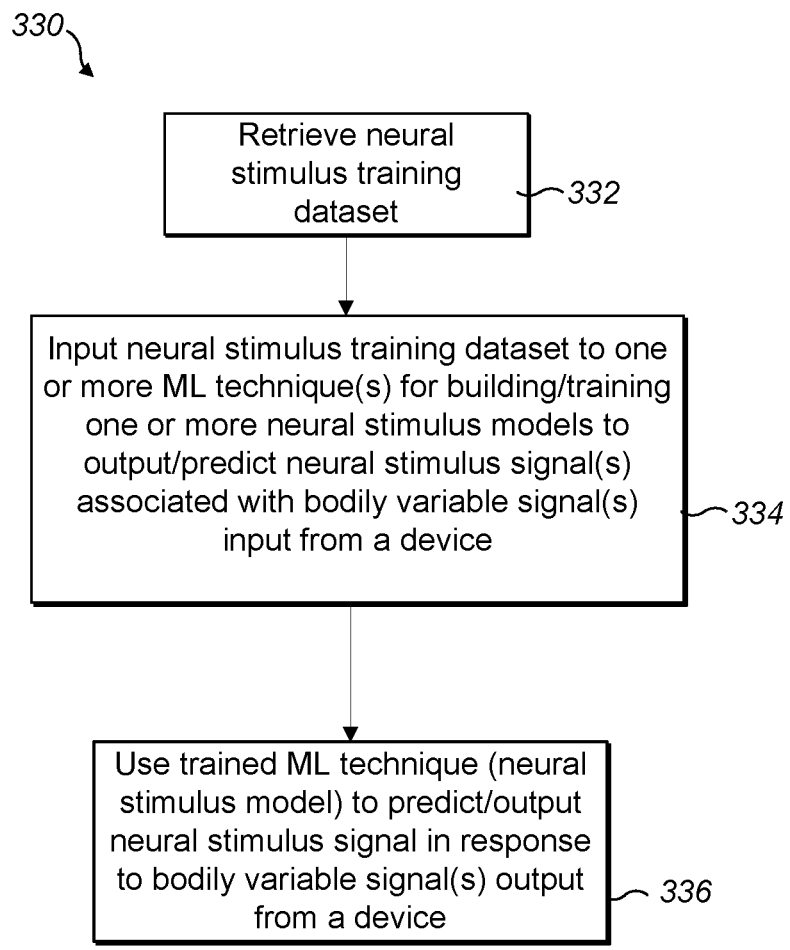
FIG. 3c is a schematic illustration of an example machine learning technique for use with a neural interface according to the invention.

FIG. 3c is a flow diagram illustrating an example training process 330 for training a ML technique for use with a neural interface according to the invention. The process 330 may include, by way of example only but not limited to, the following steps of: In step 332, a neural stimulus training dataset may be retrieved from storage. The neural stimulus training dataset may include portions of neurological stimulus signal data that have been labelled with corresponding bodily variable labels associated one or more identified stimulus/stimuli to the subject 102. In step 334, the training neural stimulus sample data from the neural stimulus training dataset may be input to one or more ML technique(s) for building and/or training one or more neural stimulus model(s) for outputting and/or predicting neural stimulus signal(s) associated with bodily variable signal(s) input or generated by a device. The ML technique(s) may also take the one or more bodily variable signal(s) when building and/or training the one or more neural stimulus model(s) such that data representative of the bodily variable signal(s) may be input to a trained neural stimulus model and an appropriate neural stimulus signal estimate may be output/predicted for use by one or more neural transmitter(s) in applying neural activity encoding data representative of the bodily variable signals to one or more neuronal populations. In step 336, a trained neural stimulus model is used to predict and/or output one or more neural stimulus signal(s) given a bodily variable signal from a device as input.

Figure 3D:
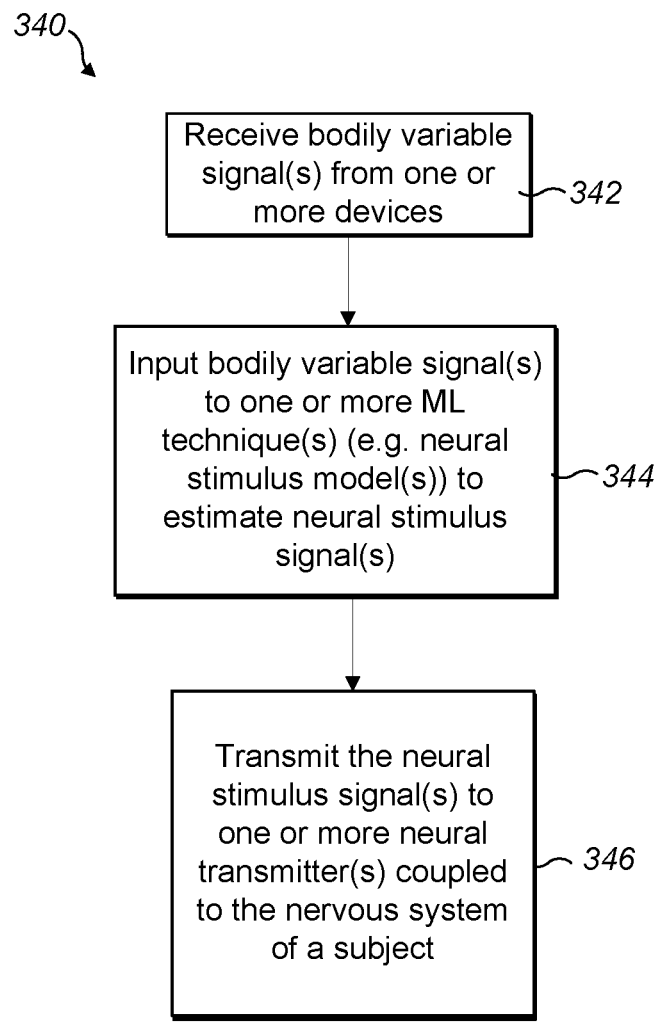
FIG. 3d is flow diagram illustrating an example process for training the machine learning technique of FIG. 3c for use with a neural interface according to the invention.

FIG. 3d is flow diagram illustrating an example process 340 for operating a neural stimulus model generated by training a ML technique of FIG. 3c for use with a neural interface according to the invention. In this example, one or more device(s) may be in communication with a neural interface that has been configured to implement the neural stimulus model. The neural interface may be coupled to one or more neural transmitter(s) associated with neuronal population(s) that the one or more device(s) have targeted for stimulation of the neuronal population or for managing/controlling the neural activity of the neuronal population. The process 340 may include, by way of example only but not limited to, the following steps of:

In step 342, the neural interface receives a bodily variable signal from a device or one or more device(s). The neural interface may receive the bodily variable signal via a communication interface that is coupled either wirelessly or wired to the device. The bodily variable signal may be input to one or more neural stimulus model(s) that have been trained on a neural stimulus training dataset associated with the bodily variable signal. That is, the neural stimulus training dataset may include neural stimulus sample data and corresponding bodily variable labels that have been mapped to corresponding bodily variable signal(s). The neural stimulus model(s) may operate on the bodily variable signal and determine or output a corresponding neural stimulus signal that may be suitable for one or more neural transmitter(s) to generate corresponding neural activity encoding data representative of the one or more bodily variable signal(s) onto the one or more target neuronal populations. In step 346, the neural interface transmits the output neural stimulus signal or data representative of the output neural stimulus signal to one or more neural transmitter(s) coupled to the nervous system of the subject 102 for stimulating or controlling/managing the neural activity of one or more target neuronal population(s).

Figure 3E:
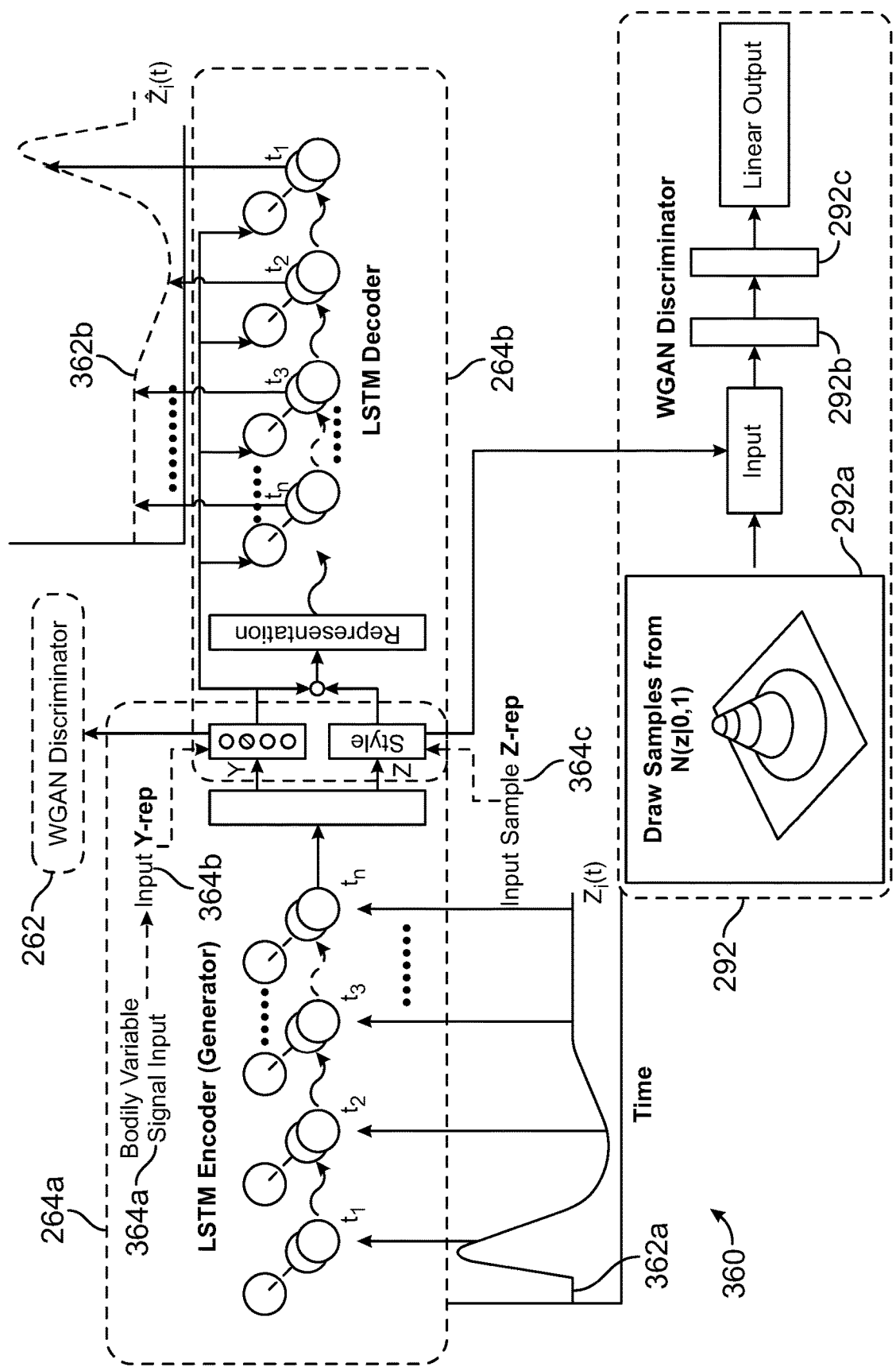
FIG. 3e is a schematic illustration of another example machine learning technique for use with a neural interface according to the invention.

FIG. 3e is schematic diagram illustrating an example ML technique of a neural stimulus network model 360 based on the NN model 260 and modified NN model 290 as described with reference to FIGS. 2e and 2h but which has been configured to generate a neurological stimulus signal or waveform 362b based on inputting a bodily variable signal generated by a device. The neural interface, in response to receiving a bodily variable signal from a device, may provide data representative of a neural stimulus signal or waveform 362b representative of the bodily variable signal to one or more neural transmitter(s) for generating neural activity associated with the bodily variable signal in one or more target neuronal populations of part of the nervous system of a subject 102.

Although FIGS. 2a-2h describe multi-channel neurological signals using the notation $x_1(t), \ldots, x_i(t), x_j(t), \ldots, x_M(t)$, this notation will be reused in relation to multi-channel neurological stimulus signals because these may also be received by one or more neural receiver(s). Thus, the neural interface 106 or 302a/302b may receive, sample and collect a multi-channel neurological stimulus signals $x_1(t), \ldots, x_i(t), x_j(t), \ldots, x_M(t)$ received from a number of M neural receiver(s) in relation to one or more neural stimulus/stimuli. The multi-channel neurological stimulus signals $x_1(t), \ldots, x_i(t), x_j(t), \ldots, x_M(t)$ may be sampled to form multi-channel neurological stimulus signal samples ($x_i$) for $i \geq 1$, where $x_i$ is the i-th sample vector of an M-dimensional vector space of the multi-channel neurological stimulus signal in which each element of $x_i$ represents the i-th sample from the corresponding m-th channel for $1 \leq m \leq M$. Each k-th section of the multi-channel neurological stimulus signal $x_1(t), \ldots, x_i(t), x_j(t), \ldots, x_M(t)$ that indicates neural activity encoding one or more bodily variables associated with a k-th neural stimulus may be sampled and stored as a sample vector sequence $(x_i)^k$ for $1 \leq i \leq L_k$ and $k \geq 1$, where $L_k$ is the length of the k-th sample sequence or number of samples taken from the k-th section that captures the k-th neural activity encoding one or more bodily variable(s) or combinations thereof associated with the k-th neural stimulus. Data representative of the k-th neural activity encoding one or more bodily variables or combinations thereof may consist of $L_k \times M$ samples. Thus, a set of neurological stimulus sample vector sequences may be collected and represented as $\{(x_i)^k\}$.

A training set of neurological stimulus sample vector sequences may be generated from the collected set of neurological stimulus sample vector sequences $\{(x_i)^k\}$ and represented as $\{(x_i)^k\}_{k=1}^T$, where T is the number of neurological stimulus sample vector sequences in the training set. The training set $\{(x_i)^k\}_{k=1}^T$ may be generated from previously recorded or stored multichannel neurological stimulus signals that identifies T neural activities, in which each neural activity encodes one or more bodily variable(s) or combinations thereof associated with the stimulus. This training set $\{(x_i)^k\}_{k=1}^T$ may be generated from $\{(x_i)^k\}$ by analysing and comparing each of T neural activities (e.g. automatically analysed as described previously) with corresponding sensor data (e.g. video, audio, motion tracking, blood, heart rate etc.) recorded/stored/collected at the same time the multichannel neurological stimulus signals associated with stimuli were recorded/stored/sampled and collected. This comparison may be used to identify the action(s) or reaction(s) of the subject and so identify each k-th neural activity associated with a stimulus $1 \leq k \leq T$, which may be used to label the latent representations output from the neural stimulus network model 360 in relation to the neural activity encoding one or more bodily variables associated with a stimulus.

Alternatively, the training set $\{(x_i)^k\}_{k=1}^T$ may be generated from a collected set of neurological stimulus sample vector sequences $\{(x_i)^k\}$ using NN model 360 as a classifier that outputs a bodily variable labelling vector, y, for each of the neurological sample vector sequences $\{(x_i)^k\}$. After which each bodily variable labelling vector, y, may be labelled with a bodily variable label that may be identified by comparing each of the neural activities of $\{(x_i)^k\}$ associated with a stimulus (e.g. automatically analysed as described previously) with corresponding sensor data (e.g.

video, audio, motion tracking, blood, heart rate etc.) recorded/stored/collected at the same time the multichannel neurological stimulus signal sample vector sequences $\{(x_i)^k\}$ were recorded/stored/sampled and collected. A set of T unique bodily variable labels and their associated neurological stimulus signal sample vector sequences $\{(x_i)^k\}$ may be stored as a neural stimulus training dataset $\{(x_i)^k\}_{k=1}^T$ that has been labelled. This may be used to further train one or more ML technique(s).

Given the collected set of neurological sample vector sequences $\{(x_i)^k\}$ can be very large and contain features too nuanced for manual human analysis, ML techniques such as NN model 360 can assist in analysing, learning and labelling representations of the neurological stimulus sample vector sequences $\{(x_i)^k\}$ suitable for outputting to one or more device(s) for managing bodily functions of the subject. In this example, the NN model 260 is based on a semi-supervised sequence-to-sequence model. The NN model 260 is a sequence-to-sequence model that encodes a given neurological sample vector sequence $(x_i)^k$ for $1 \le i \le L_k$ and $k \ge 1$ into a fixed-size continuous vector representation or latent vector representation. The NN model 260 includes an encoder 264a and decoder 264b, both of which are long short-term memory (LSTM) recurrent neural networks (RNNs).

The encoder 264a may receive a k-th neurological stimulus sample vector sequence $X_k=(x_i)^k$ 362a which may be processed by an LSTM RNN over n time steps to generate a fixed size continuous latent vector representation comprising a fixed size latent style vector z and a fixed size label-like vector y of arbitrary length. The decoder 264b may then receive a corresponding latent style vector z and a label-like vector y to reconstruct the k-th neurological stimulus sample vector sequence $X_k=(x_i)^k$ 362a via another LSTM RNN over n time steps to generate a reconstructed k-th neurological stimulus sample vector sequence $\hat{X}_k=(\hat{x}_i)^k$. As previously described with reference to FIG. 2e or 2h, the encoder 264a and decoder 264b may be trained based on a loss function to minimise the reconstruction error between $X_k$ and $\hat{X}_k$. Thus, once trained or when the latent vector representation (e.g. y and z) are well formed the decoder 264b may be configured to generate a neurological stimulus signal based on inputting a particular y and inputting a sample vector z by sampling a Gaussian distribution N(z|0, I).

As described with reference to FIG. 2e or 2h, the NN model 360 may be augmented with a first adversarial discriminator 262 that is trained to distinguish between labels y generated by the encoder 264a and samples (e.g. one-hot vector samples) from a categorical distribution 262a. This augmentation enables the NN model 360 to be trained to learn an informative label-like latent vector y from unlabelled collected multichannel neurological stimulus signal sample vector sequences $\{(x_i)^k\}$ that may be labelled to identify the corresponding neural activity encoding one or more bodily variable(s) associated with a neural stimulus.

Bodily variable signal(s) 364a received from one or more device(s) may be mapped to corresponding bodily variable labels each of which are associated with a unique label-like latent vector y. So, a given bodily variable signal 364a may be mapped to a label-like latent vector y, which may be input to the decoder 264b as an input y-rep 364b along with a sample vector, z-rep 364c, sampled from a Gaussian distribution N(z|0, I). The decoder 264b processes the inputs y-rep 364b and z-rep 364b using its LSTM RNN to reconstruct neurological stimulus signal $\hat{X}$ corresponding to bodily variable signal via the inputs y-rep 364b and z-rep 364b.

As described with reference to FIG. 2h, the NN model 360 may be further augmented with second adversarial discriminator 292 that is employed to encourage the latent style vector, z, representation to be more Gaussian distributed. The second adversarial discriminator network 292 is trained to distinguish between latent vector, z, generated by the encoder network 264a and samples from a Gaussian distribution N(z|0, I) 292a. The latent style vector, z, generated by the encoder network 264 and a Gaussian sample are input to hidden layer(s) 292b and 292c of the second adversarial discriminator 292. The output layer 292d outputs a linear Gaussian result that may be used to improve the estimate of latent vector, z, to be more Gaussian by rating how close it is to the Gaussian sample/distribution. This may improve the latent representation of the latent style vector z. This may also enables generation of neurological stimulus signals for arbitrary categories by selecting a specific y representation, ŷ-rep 364b, sampling a z representation, ž-rep 364c from a Gaussian distribution and using the concatenation of z=ž-rep 364b and y=ŷ-rep 364c as the input to the decoder network 264b, where a neurological stimulus signal or waveform 362b associated with the label vector ŷ-rep can be reconstructed.

Once the encoder 264a and decoder 264b have been trained on a neural stimulus training dataset as describe above and/or with reference to FIGS. 2c, 2e and/or 2h, only the decoder network 264b is retained. The bodily variable signal(s) generated by a device may define one or more actions that may be mapped to one or more bodily variable labels each of which represents a specific y vector. Thus, a bodily variable signal may be mapped to a specific y vector. This specific y vector is selected as a y representation, ŷ-rep 364b, which may be a one-hot encoded vector representing one or more actions associated with the bodily variable signal. As well, a new z representation, ž-rep 364b, is generated by sampling z from a Gaussian distribution N(z|0, I). If the most common signals are required, then the new z representation, ž-rep 364b, is generated by sampling from a distribution with a smaller standard deviation. The selected and/or generated ŷ-rep 364b and ž-rep 364b are input into the decoder network 264b, which outputs data representative of a corresponding reconstructed neurological stimulus signal waveform 362b, which may be a neurological stimulus sample vector sequence. The data representative of the reconstructed neurological stimulus signal waveform 362b may be transmitted to one or more neural transmitter(s) for generating neural activity corresponding to the bodily variables based on the reconstructed neurological stimulus signal waveform 362b.

Although a Gaussian distribution N(z|0, I) or a normal distribution is described, this is by way of example only, it is to be appreciated that the skilled person may use any other probability distribution and the like, or any other probability distribution that further improves the reconstruction of the neurological stimulus signal waveform and/or other labelling/classifying aspects of the invention.

In the above examples, the selected or generated y representation of ŷ-rep 364b may be chosen to be a one-hot vector, or it may be chosen to be a mix of actions or bodily variable signal(s). For example, a first bodily variable may be associated with lying down and a second bodily variable may be associated with standing up. Thus, a mix of actions of 50% lying down and 50% standing may be selected by proportionally combining the ŷ-rep 364b vectors associated with the first and second bodily variable signals (e.g. multiply each ŷ-rep 364b by 0.5 and add together) to possibly generate a neural stimulus signal or waveform for sitting. If each ỹ-rep 364*b* were a different one-hot vector, then 2 of the elements in the combined ỹ-rep 364*b* vector would have values of 0.5, where the rest of the elements would be zero.

Figure 3F:
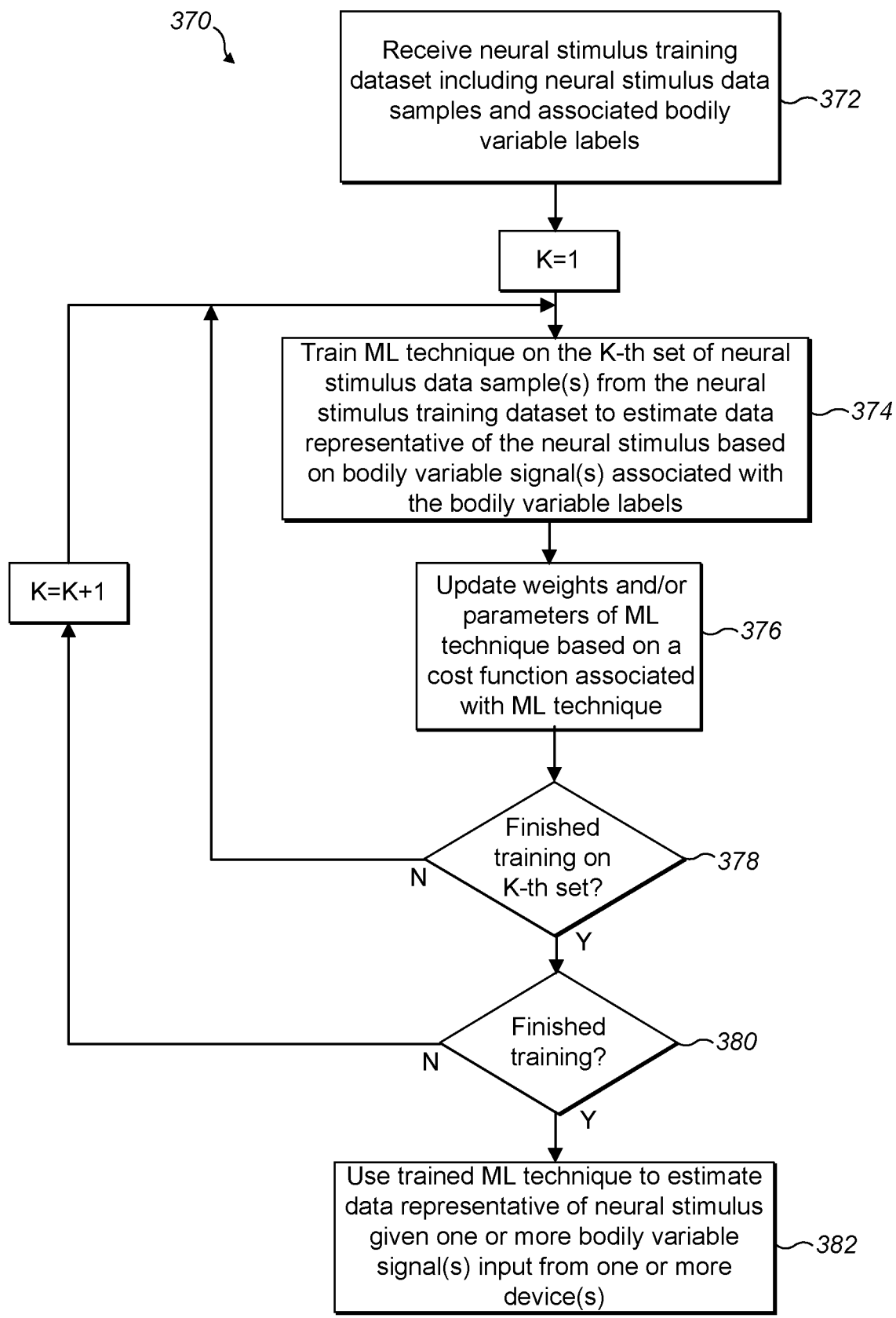
FIG. 3f is flow diagram illustrating an example process for training the machine learning technique of FIG. 3e for use with a neural interface according to the invention.

FIG. 3*f* is a flow diagram illustrating a training process or method 370 for a ML technique implemented by a neural interface 106, 302*a* or 302*b*. The training process or method is based, by way of example only but is not limited to, the following steps of: In step 372, a training set of neurological stimulus sample vector sequences or neural stimulus training dataset, $\{(x_i)^k\}_{k=1}^{T}$, is retrieved. The training set of neurological stimulus sample vector sequences $\{(x_i)^k\}_{k=1}^{T}$ is assumed to have been classified and/or labelled based on sensor data taken at the same time as when each of the neurological stimulus sample vector sequences in the training set of neurological stimulus sample vector sequences $\{(x_i)^k\}_{k=1}^{T}$ was received/measured. Thus, the training set of neurological stimulus sample vector sequences includes neural stimulus data samples or neurological stimulus vector data sequences and/or associated bodily variable labels corresponding to neural stimuli. The training counter, k, is set to the first neurological stimulus sample vector sequence (e.g. k=1) that is to be used to train the ML technique. In step 374, the ML technique may be trained by applying the k-th neurological stimulus sample vector sequence $(x_i)^k$ of $\{(x_i)^k\}_{k=1}^{T}$, where $1 \leq i \leq L_k$ and $1 \leq k \leq T$, as an input to the ML technique. The ML technique may produce an output data representative of the neural stimulus based on bodily variable signal(s) associated with the bodily variable labels. For example, the ML technique may produce a classification and/or a bodily variable estimate representative of one or more bodily variables present in the k-th neurological stimulus sample vector sequence $(x_i)^k$, which may be mapped to one or more bodily variable signal(s). This classification may then be used, based on an input bodily variable signal, to generate a neural stimulus. In step 376, the weights and/or parameters of the ML technique may be updated based on calculating a cost function associated with the ML technique, the input k-th neurological stimulus sample vector sequence $(x_i)^k$, and the output data representation of the neural stimulus, k-th classification and/or bodily variable estimate. For example, this may be achieved by comparing the output data representative of the classification and/or bodily variable estimate with the original classification or bodily variable label/vector of the k-th neurological stimulus sample vector sequence $(x_i)^k$, which has been classified and/or labelled based on sensor data taken at the time the k-th neurological stimulus sample vector sequence $(x_i)^k$ was received/measured and stored. Alternatively, the ML technique may reconstruct the input k-th neurological sample stimulus vector sequence $(x_i)^k$ based on the estimated k-th classification, where the reconstructed k-th neurological stimulus sample vector sequence may be compared with the original input k-th neurological stimulus sample vector sequence. It is to be appreciated by the person skilled in the art that there are many method(s) and combinations thereof for generating a cost function associated with a ML technique that is trained to output a neural stimulus given a bodily variable signal from a device as input. The comparison may produce an error estimate or be used in a cost function that is used to update the weights and/or parameters of the ML technique. The weights and/or parameters of the ML technique may be updated based on the cost function or the error estimate that the ML technique uses.

In step 378, it may be determined whether the ML technique has been sufficiently trained on the k-th neurological stimulus sample vector sequence $(x_i)^k$. For example, the cost function may produce an error estimate that is below a certain error threshold. Alternatively or additionally, the ML technique may be considered trained in respect of the k-th neurological stimulus sample vector sequence $(x_i)^k$ if it reliably outputs data representative of a neural stimulus signal estimate that corresponds and/or maps to the bodily variable label associated with the k-th neurological stimulus sample vector sequence $(x_i)^k$. If training is considered not to have finished (e.g. N) for the k-th neurological stimulus sample vector sequence $(x_i)^k$ in the training set, then the steps 374 and 376 may be repeated one or more or multiple times until the error estimate or cost function associated with the k-th neurological stimulus sample vector sequence $(x_i)^k$ has reached a certain error or cost function threshold. If the error estimate or the cost function of the ML technique is small enough, or below a certain error or cost function threshold, then the ML technique may be considered to be trained for the k-th neurological stimulus sample vector sequence $(x_i)^k$ (e.g. Y) and the method proceeds to step 250.

In step 250, it is determined whether all of the training set of neurological stimulus samples or the neurological stimulus sample vector sequences of $\{(x_i)^k\}_{k=1}^{T}$ have been used to train the ML technique. If there are still some neurological stimulus sample vector sequences left in the training set (e.g. N), then the training counter, k, is incremented (e.g. k=k+1) and the process proceeds to step 374 with the (k+1)-th neurological sample vector sequence $(x_i)^{k+1}$, otherwise, if all of the neurological stimulus sample vector sequences of the training data set have been used or it has been determined that enough neurological stimulus sample vector sequences of the training data set have been used (e.g. Y), then the process proceeds to step 252. In step 252, the ML technique is considered to be trained and may now be used to classify neural activity encoding bodily variable(s) associated with neural stimulus and/or output estimates of neural stimulus signal(s) associated with bodily variable signal(s) that may be received from one or more device(s) connected to the neural interface 106, 302*a* or 302*b*.

Although FIGS. 3*a* to 3*f* describe examples of the invention, this is by way of example only and for simplicity but these examples of the invention are not so limited, it is to be appreciated by the skilled person that the examples of the invention described in FIGS. 3*a* to 3*f* may be applied in relation to any one or more bodily variables and/or any one or more sets of bodily variable labels, and may further include any of the one or more process(es), one or more method(s), labelled training datasets, one or more features and/or one or more functionalities of the different aspects of the invention, modifications thereof or thereto, combinations thereof or thereto, with reference to FIGS. 1*a*-4*j* and 5*a*-6*b* and/or as described herein.

Figure 4A:
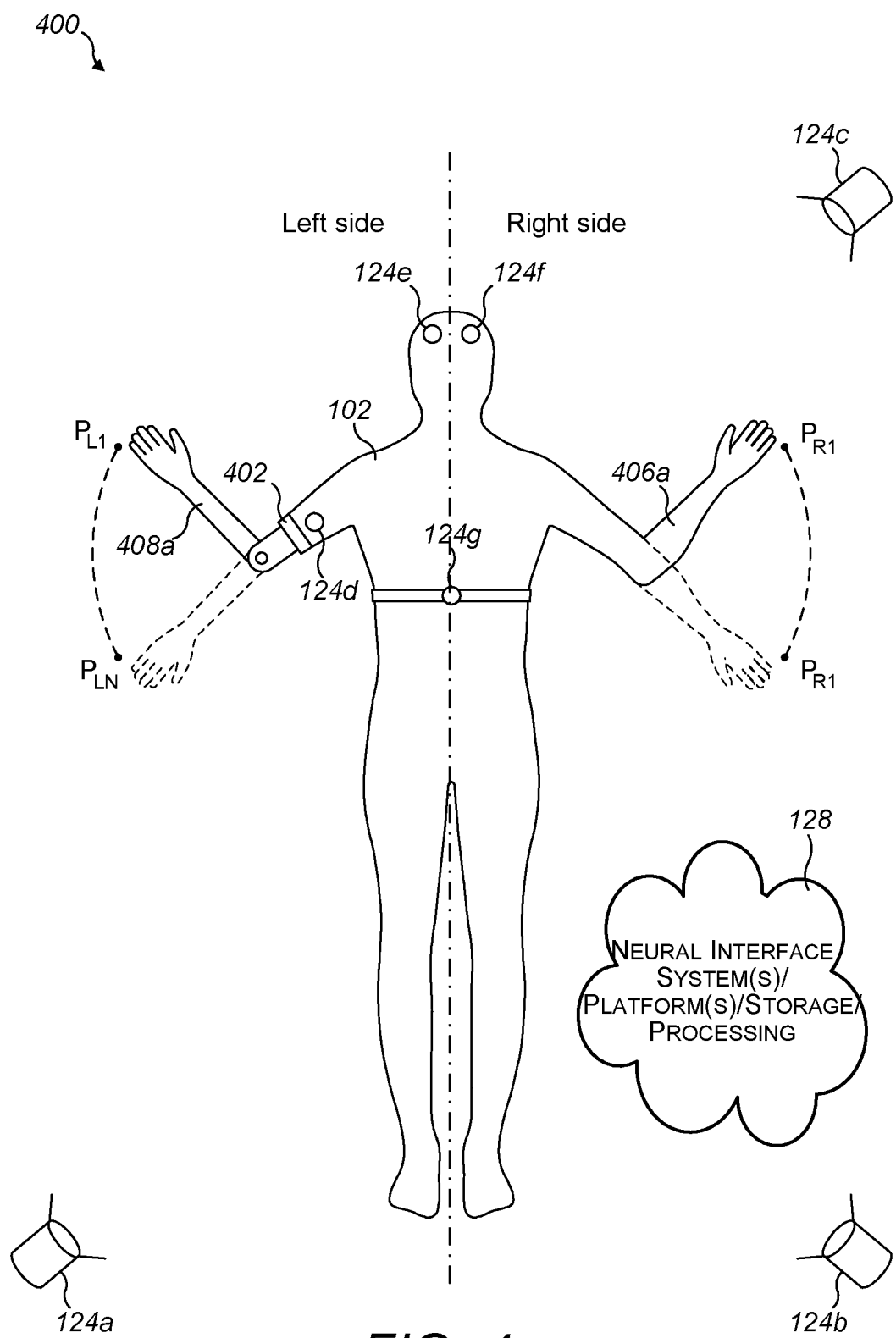
FIG. 4a is a schematic diagram illustrating a prosthetic device use case with an example neural interface according to the invention.

FIG. 4*a* is a schematic diagram illustrating an example neural interface system 400 in which a subject 102 uses a neural interface 402 coupled to a prosthetic device 408*a*, which in this example is a prosthetic arm. The neural interface 402 may be based on one or more of the neural interface(s) 106, 202*a*, 202*b*, 302*a*, 302*b* and configured to operate based on one or more process(es) and method(s) as described with reference to FIGS. 1*a* to 3*f* and FIG. 5*a* or 5*b*. The neural interface 402 can be configured for receiving neurological signal(s) containing neural activity encoding one or more bodily variable(s) or combinations thereof from the somatic nervous system of the subject 102. The neural interface 402 can be configured to use one or more ML technique(s) trained to interpret/decipher or estimate data representative of the bodily variable(s) from the received neurological signal(s) for controlling the prosthetic device 408*a* (e.g. controlling the motion of the prosthetic device).

The neural interface 402 can also be configured for receiving data representative of feedback signal(s) or bodily variable signal(s) from the prosthetic device 408a (e.g. data associated with touch or pressure signal(s) from touch or pressure sensors on the device) and using one or more ML technique(s) trained to assist with applying the received bodily variable signal(s) as neural stimulus/stimuli to the nervous system of the subject 102. Thus, the subject 102 may operate the prosthetic device 408a in a similar manner as the subject 102 may have operated their original limb or body part that the prosthetic device 408a replaced. Alternatively the subject 102 may learn to use different neural activity to operate the prosthetic device 408a.

The neural interface system 400 further includes one or more sensors 124a-124g that may be trained on the subject 102 in which the sensor data may be used along with a set of neurological signal data for training the ML technique(s) used by the neural interface 406. The neural interface 402 may also be coupled to the nervous system of the subject 102 by one or more neural receivers (or neural sensors), which are capable of measuring neural activity of one or more neurons or one or more neuronal population(s) and outputting one or more neurological signal(s) that may be received by the neural interface 406. The neural interface 402 may also be coupled to the nervous system of the subject 102 by one or more neural transmitters (or neural modulators/stimulators/transducers), which are capable of receiving neurological stimulus signal(s) from the neural interface 402 and applying these as neural activity representative of the neurological stimulus signal(s) to one or more neurons or one or more neuronal population(s).

The neural interface system 400 may further include external computing system(s) 128, which may include other neural interface system(s), other neural interface(s), processing unit(s), server(s), storage unit(s), cloud processing and/or storage system(s) and the like for assisting neural interface 402 in managing and operating prosthetic device 408a. The neural interface 402 may be coupled to these external computing system(s) 128 in a wired or wireless fashion. The neural interface 402 may include the capabilities or necessary software, hardware, computational and/or storage resources for performing the method(s) and/or process(es) as described with reference to FIGS. 1a to 3f and 5a to 6b such as, by way of example only but not limited to:

1) receiving and/or sampling neurological signal(s);
2) storing data representative of neurological signal(s);
3) receiving sensor data from sensors 124a-124g;
4) storing data representative of sensor data from sensor(s) 124a-124g;
5) analysing the received neurological signal(s) and/or sensor data and generating one or more bodily variable training datasets;
6) analysing the received neurological signal(s) associated with neural stimuli and/or sensor data and generating one or more neural stimulus training datasets;
7) training/re-training one or more ML technique(s) for outputting data representative of one or more bodily variables in response to receiving neurological signal(s), in which the data representative of the one or more bodily variable(s) are sent to device 408a;
8) training/re-training one or more ML technique(s) for outputting data representative of neural stimulus to one or more neural transmitters in response to bodily variable signal(s) or other feedback data received from device 408a;
9) using trained ML technique(s) for outputting data representative of one or more bodily variables in response to receiving neurological signal(s), in which the data representative of the one or more bodily variable(s) are sent to device 408a;
10) using trained ML technique(s) for outputting data representative of neural stimulus to one or more neural transmitters in response to bodily variable signal(s) or other feedback data received from device 408a; and
11) any other operational steps etc.

However, given that the neural interface 402 is an apparatus that is coupled to the nervous system of the subject 102 and also coupled to prosthetic device 408a it may only have limited capabilities, software, hardware, computational and/or storage resources and be power constrained so may not have the capabilities of performing, by way of example only one or more of items 1) to 7). For example, the neural interface 402 may only be configured to perform a limited number of functions such as items 1), 2), 9) and 10) whilst one or more external computing system(s) 128 are configured to perform one or more other items in order to support the neural interface 402.

In operation, the neural interface 402 may be configured to operate on one or more trained ML technique(s) for estimating bodily variable(s) or neural data received in neurological signals and operate on one or more trained ML technique(s) for estimating neural stimulus associated with device data, bodily variable signal(s) or feedback signal(s) from device 408a. The neural interface 402 is fitted or coupled to the user 102 such that neurological signals may be received by the neural interface 402. The neural interface 402 is also fitted, coupled or at least in communication with prosthetic device 408a. The neural interface 104 may perform a feature analysis and/or classification on the received neurological signals using trained ML technique(s) to determine data representative of neural data or one or more bodily variables contained within the received neurological signals. The determined neural data estimate(s) or bodily variable estimate(s) can be sent to the device 408a, which can use this data for controlling the prosthetic device 408a.

For example, the estimated bodily variable(s) or neural data may be associated with motion and used by the device 408a to control the motion of the prosthetic. The neural interface 402 may be trained for classifying the neurological signals as one or more bodily variable(s) associated with motion. The training of the ML technique(s) of the neural interface 402 may use pre-stored neurological signals and pre-recorded sensor data for identifying the corresponding operations of prosthetic device 408a in respect of the subject 102. The training of the ML technique(s) may be performed by the neural interface 402 or performed by an external computing system 128, which then transmits or uploads data representative of the trained ML technique(s) to the neural interface 402. Additionally or alternatively, the training of the neural interface 402 may be performed in real-time, where a real-time neurological signal is used along with real-time sensor data from the one or more sensors 124a-124g.

The neural interface 402 or an external computing system 128 may be configured to determine a pattern of neurological signals that are associated with one or more movement(s) of the prosthetic device 408a and map each pattern of neurological signals to a corresponding movement. This can be done by determining estimates for one or more bodily variable(s) or neural data. Each calibration movement may correspond to one or more bodily variable estimate(s) or neural data estimate(s) that may be interpreted/processed by the device 408a for controlling or operating the prosthetic device 408a. Once mapped, the neurological interface 402 may be used in real-time in which real-time neurological signals are received, processed, classified and mapped to one or more bodily variable(s), bodily variable label(s), neural data estimate(s) and/or neural data label(s) and sent to the device 408a for processing/interpreting as one or more neural commands for controlling the prosthetic.

In another example, real-time sensor data and neurological signals may be used to calibrate the neural interface 402. Timestamps may be used to further allow identification of which portions of the pre-recorded sensor data correspond to which portions of the neurological signals. Alternatively, training data may be updated based on current sensor data and neurological signals. One of more of the sensors 124a-124g may be, by way of example only but not limited to, a motion detection sensors or depth cameras that are used to track the movements of the subject 102 simultaneously whilst the neurological signals from the subject 102 are received. The motion detection sensors may be coupled to a skeletal tracking system that performs skeletal tracking of the subject 102 and the prosthetic device 408a. The skeletal position may be fed back to the neural interface 402 in real-time for identifying the portions of neurological signals corresponding with portions of the skeletal tracking data. In this way, timestamped portions of the skeletal position may be associated, in real-time, with timestamped portions of the neurological signal.

During calibration, the subject 102 may be instructed to perform a set of calibration movements (e.g. like calibration movement from PL1 to PLN and PR1-PRN), which are tracked by the motion capture system and fed back as timestamped, calibrated skeletal position to the neural interface 402. The timestamps of the neurological signals and the calibrated skeletal tracking data allows identification by the neural interface 402 of which portions of the neurological signals correspond with which portions of the calibrated skeletal tracking. Using the portions of skeletal tracking data and corresponding portions of the neurological signal that correspond with the calibration movements, the neural interface 402 is configured to determine a pattern of neurological signals associated with each of the calibration movements. Each determined pattern of neurological signals is mapped to the corresponding calibration movement. Each calibration movement may correspond to one or more neural data estimate(s) or label(s) and/or bodily variable estimate(s) or label(s) neural for use by prosthetic device 408a in operating or performing movements according to the desires/wishes of the subject 102. Once mapped, the neurological interface 402 may continue to be used to classify and map real-time neurological signals to one or more neural data estimates or one or more bodily variable(s) for interpretation or processing by the prosthetic device 408a.

Recalibration using methods outlined above may be performed partially or fully in an automatic and/or manual fashion on a regular basis as determined by on board algorithms monitoring accuracy.

Figure 4B:
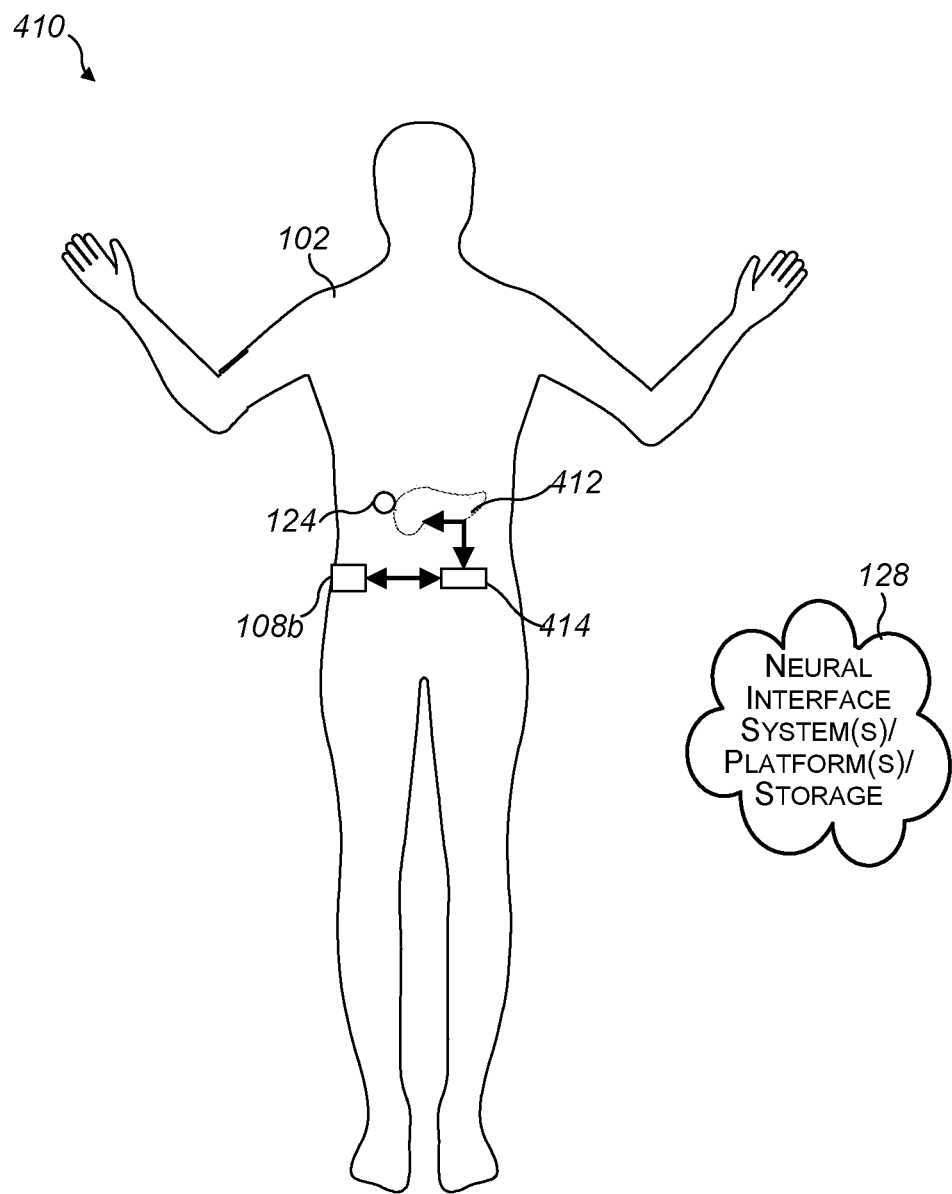
FIG. 4b is a schematic diagram illustrating a biological device use case with an example neural interface according to the invention.

FIG. 4b is a schematic diagram illustrating an example neural interface system 410 including a neural interface 414 configured for use with a pancreatic device 108b for assisting the operation of the pancreas 412 of a subject 102. The neural interface system 410 includes a neural interface 414 coupled to a plurality of neuronal populations of the autonomic nervous system by one or more neural receivers (not shown) and one or more neural transmitter(s) (not shown). The neural interface 414 is also coupled to a pancreatic device 108b configured for intercepting and capturing/receiving neural data and/or one or more bodily variable(s) associated with the function and/or operation of the pancreas 412 and for transmitting bodily variable signal(s) or neural stimulus data or device data from pancreatic device 108b to the neural interface 414 for managing the pancreas 412 in response to the neural data estimate(s). The pancreatic device 108b receives a data representation of the neural data carried by neural activity over the autonomic nervous system (not shown) from neural interface 106, processes the data representation of the neural data estimate to develop an understanding of what the pancreas 412 is supposed to be doing. In response, the pancreatic device 108b may change or stimulate/inhibit the neural activity efferent/afferent to the pancreas 412 depending on the operation of the pancreatic device 108b.

For example, neural activity associated with a rise in insulin may be transmitted over the autonomic nervous system, which means the pancreas 412 may upregulate insulin or glycogen production. The neural activity associated with the rise in insulin is received as one or more neurological signal(s) by the neural interface 414. The ML technique(s) of the neural interface 414 may estimate neural data associated with the neural activity and hence may be associated with the rise in insulin. This may be embodied as one or more bodily variables or bodily variable labels depending on the extent of training the ML technique(s) of the neural interface 414 with pancreatic training neural dataset. In any event, the neural interface 414 sends the neural data estimate associated with the rise in insulin to the pancreatic device 108b. After processing the neural data estimate, the pancreatic device 108b may conclude that the subject 102 should not be raising their insulin levels as they may be diabetic or be insulin sensitive in someway. Thus, the pancreatic device 108b transmits device data associated with lowering insulin to the neural interface 414 which may be communicated on to the nervous system of the subject 102, i.e. onto the pancreatic nerve to the pancreas 412. The neural interface 414 receives the device data from device 108b and the associated ML technique(s) corresponding to stimulus of the pancreas 412 estimate a neural stimulus signal or one or more neural stimulus signal(s) based on the device data. The data representative of the neural stimulus signal estimate(s) may be associated with lowering or keeping insulin at the current level etc. The neural interface 414 sends the data representative of the one or more neural stimulus signal(s) to one or more neural transmitter(s) positioned at one or more neurons or neuronal populations associated with the pancreatic nerve. The neural transmitter(s) operate to apply the neural stimulus signal estimate(s) by generating neural activity associated with the neural stimulus signal estimate(s) on the corresponding neuronal populations. Thus, a neural stimulus signal provides an appropriate stimulus/inhibition to the pancreas 412.

The neural interface 414 may be used in the autonomic nervous system (ANS) to provide the necessary input and output with the bodies natural control system (i.e. the nervous system) in order that a device 108b can be used to modify the control of an organ or bodily system in a continuous closed loop manner. By way of example but not limited to, the pancreas 412, the neural interface 141 may operate as follows: in normal function the ANS innervates and controls pancreatic function, it does this by exciting or inhibiting the sub functions of the pancreas 412 in response to the global bodily conditions in order to maintain homeostasis of the body's microenvironment. For example, the ANS would increase insulin production in response to spikes in blood glucose. In a disease case where the pancreas 414 is being incorrectly signalled by the ANS (as can happen in certain types of diabetes) a device 108b in communication with a neural interface 414 coupled to one or more neuronal populations of the pancreatic nerve could take over control by reading, understanding and modifying neural activity or neurological signals passing to the pancreas 412 such that it returns to correct function. In order to do this the device 108b needs to read and understand the neural data and/or one or more bodily variable(s) that represent the information contained in the neural activity carried along the pancreatic nerve. The device 108b needs to process estimates of this neural data and/or one or more bodily variables and, if necessary, the device 108b may send device data associated with an appropriate neural stimulus to the neural interface 414, which uses ML techniques to provide a suitable stimulus to the pancreatic nerve such that the pancreas 412 function is correct. The neural interface 414 provides the functionality or the interface with which the device 108b may control or manage the function of the pancreas 412.

FIGS. 4a and 4b illustrate two examples of a neural interface 402 or 414 configured for receiving and processing neurological signals comprising neural activity encoding one or more bodily variable(s) and/or combinations thereof. As described herein, a neural interface may be used to train one or more ML technique(s) that generate and/or, once trained, form ML model(s) for predicting one or more bodily variable estimates. Examples have been shown in relation to estimating bodily variable(s) associated with motion of one or more body parts or one or more devices associated with one or more body parts (e.g. FIG. 4a), and/or function or operation of a bodily organ, such as the pancreas in FIG. 4b. The time series nature of labelled training neural sample datasets also means that sensor data and neural sample data may be used for supervised training of ML techniques to generate ML model(s) for predicting bodily variable estimates of one or more bodily variable(s) that may be present in neural sample data when neural activity is detected.

As described with reference to FIGS. 1f to 10, labelled training neural sample data may be generated from analysing sensor data of a bodily variable of interest to generate bodily variable labels characterising changes of the bodily variable of interest. Portions of the sensor data in which changes in the sensor data occur (i.e. changes in the bodily variable of interest occurs) may be synchronised with corresponding portions of the neural sample data, which may be labelled with the same labels as the respective portions of sensor data. The portions of labelled neural sample data form a labelled training neural sample dataset associated with a bodily variable of interest. Thus, one or more ML techniques may trained to generate one or more ML models for predicting bodily variable estimates based on the labelled training neural sample dataset.

Figure 4C:
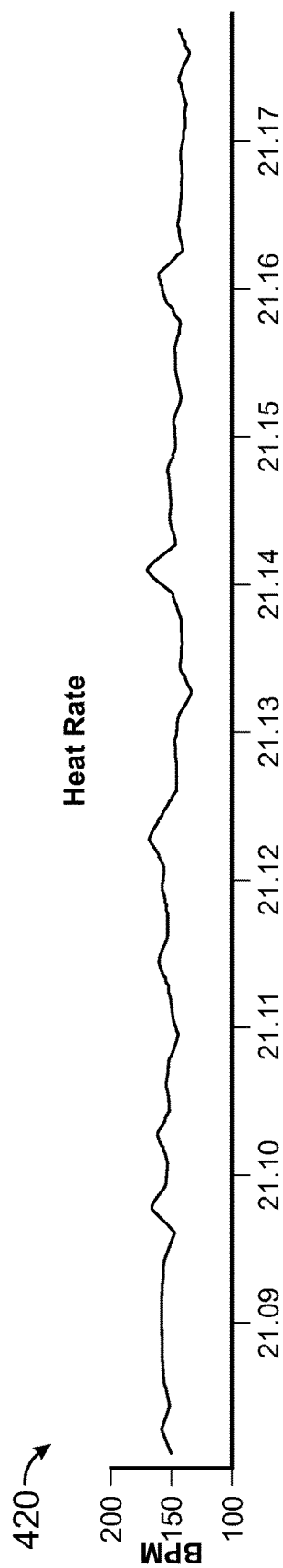
FIG. 4c is a graph diagram illustrating heart rate, a bodily variable for use in labelling neurological data for training a heart rate ML model for use with a neural interface according to the invention.
Figure 4D:
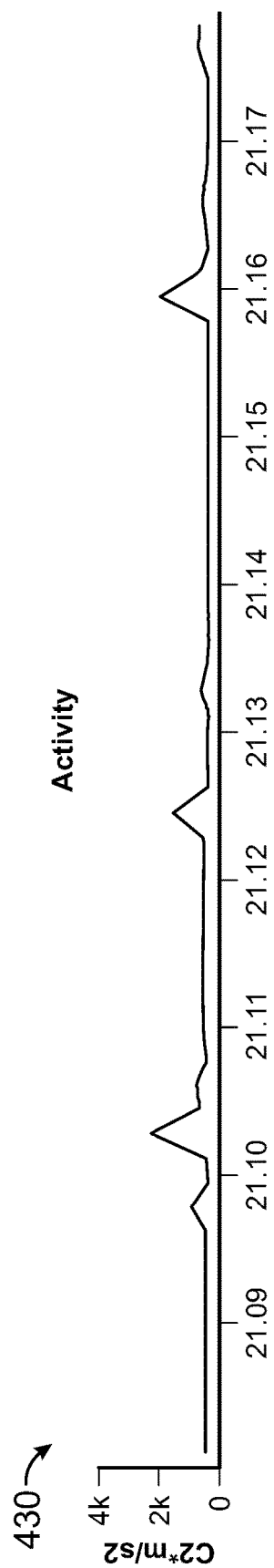
FIG. 4d is a graph diagram illustrating activity, a bodily variable for use in labelling neurological data for training an activity ML model for use with a neural interface according to the invention.
Figure 4E:
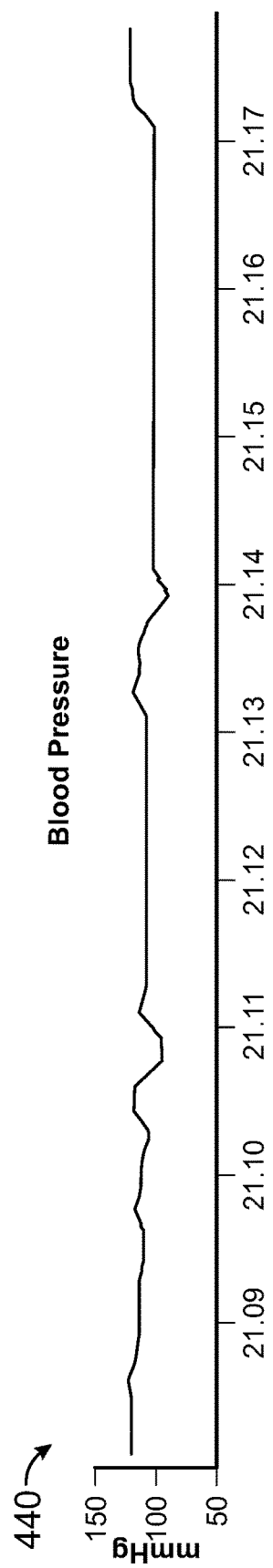
FIG. 4e is a graph diagram illustrating average blood pressure, a bodily variable for use in labelling neurological data for training an blood pressure ML model for use with a neural interface according to the invention.
Figure 4F:
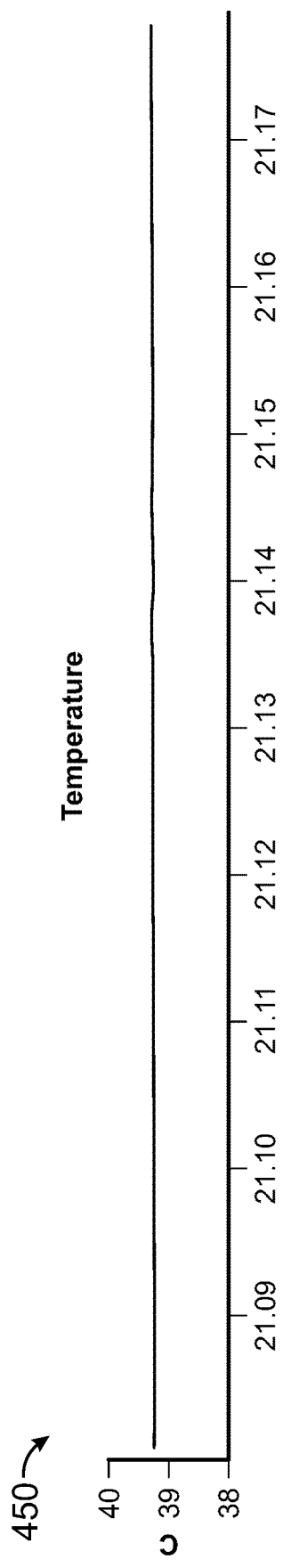
FIG. 4f is a graph diagram illustrating temperature, a bodily variable for use in labelling neurological data for training an temperature ML model for use with a neural interface according to the invention.
Figure 4G:
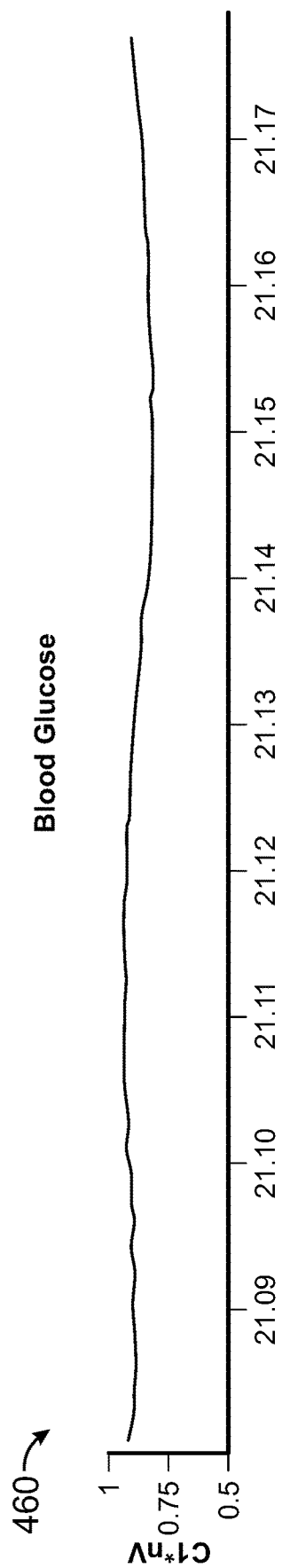
FIG. 4g is a graph diagram illustrating blood glucose concentration, a bodily variable for use in labelling neurological data for training an blood glucose ML model for use with a neural interface according to the invention.

FIGS. 4c to 4g illustrate example graphs of sensor data associated with example bodily variables of a subject. FIG. 4c is a graph diagram 420 illustrating the heart rate associated with the subject, which is a bodily variable (e.g. heart rate bodily variable) that can be used in labelling neurological data for training, by way of example only but is not limited to, a heart rate ML model for use with a neural interface according to the invention. In this example, this type of graph diagram 420 illustrating the heart rate bodily variable may be used for labelling neurological data for training, by way of example only but is not limited to, a heart rate ML model and/or any other ML model as the application demands based at least on the heart rate bodily variable for use with the neural interface. FIG. 4d is a graph diagram 430 illustrating activity of a subject, which is a bodily variable (e.g. activity bodily variable) that may be used in labelling neurological data for training, by way of example only but is not limited to, an activity ML model for use with a neural interface according to the invention. In this example, this type of graph diagram 430 illustrating the activity bodily variable may be used for labelling neurological data for training, by way of example only but not limited to, an activity ML model and/or any other ML model as the application demands based at least on the activity bodily variable for use with the neural interface. FIG. 4e is a graph diagram 440 illustrating average blood pressure associated with the blood pressure of a subject, which is a bodily variable (e.g. blood pressure bodily variable) that may be used in labelling neurological data for training, by way of example only but not limited to, a blood pressure ML model for use with a neural interface according to the invention. In this example, this type of graph diagram 440 illustrating the blood pressure bodily variable may be used for labelling neurological data for training, by way of example only but is not limited to, an blood pressure ML model and/or any other ML model as the application demands based at least on the blood pressure bodily variable for use with the neural interface. FIG. 4f is a graph diagram 450 illustrating temperature associated with a subject, which is a bodily variable (e.g. a temperature bodily variable) that may be used in labelling neurological data for training, by way of example only but not limited to, a temperature ML model for use with a neural interface according to the invention. In this example, this type of graph diagram 450 illustrating the temperature bodily variable may be used for labelling neurological data for training, by way of example only but is not limited to, an temperature ML model and/or any other ML model as the application demands based at least on the temperature bodily variable for use with a neural interface. FIG. 4g is a graph diagram 460 illustrating blood glucose concentration associated with a subject, which is a bodily variable (e.g. a blood glucose bodily variable) that may be used in labelling neurological data for training, by way of example only but is not limited to, an blood glucose ML model for use with a neural interface according to the invention. In this example, this type of graph diagram 460 illustrating the blood glucose bodily variable may be used for labelling neurological data for training, by way of example only but is not limited to, a blood glucose ML model and/or any other ML model as the application demands based at least on the blood glucose bodily variable for use with the neural interface.

As described previously, a bodily variable may comprise or represent data representative of any parameter that describes something about the state, motion or output of the body of a subject or part of the body of a subject. Examples of bodily variable(s) that may be derived or read from sensor data are shown in FIGS. 4c to 4g, which illustrate bodily variables associated with, by way of example only but is not limited to, the vital signs of a subject. As described herein, there are may different bodily variables associated with a subject. For example, bodily variables may be described at different levels from one or more bodily variables at the neurological level, which may then be combined to generate other bodily variables also describing something about the state, motion, or output of the body of a subject. For example, a bodily variable at the macro level may be, by way of example only but is not limited to, the temperature of the subject, activity of the subject, blood glucose changing of the subject, joint angle of a finger of the subject, an ECG trace of the subject, but also anything that may be derived from a bodily variable that also describes a state, motion or output of the subject. For example, the ECG trace is a bodily variable of the subject, but the ECG trace may be analysed to calculate other bodily variables such as, by way of example only but not limited to, a heart rate of the subject. Thus, heart rate of the subject is also a bodily variable of the subject. Although FIGS. 4c to 4g illustrate bodily variables associated with, by way of example only but is not limited to, the vital signs of a subject, this is by way of example only is the invention is not so limited, it is to be appreciated by the skilled person in the art that the neural interface, ML techniques and/or ML models as described herein may process neurological signals with neural activity encoding any number of one or more bodily variables as described and/or defined herein and/or as the application demands.

Figure 4H:
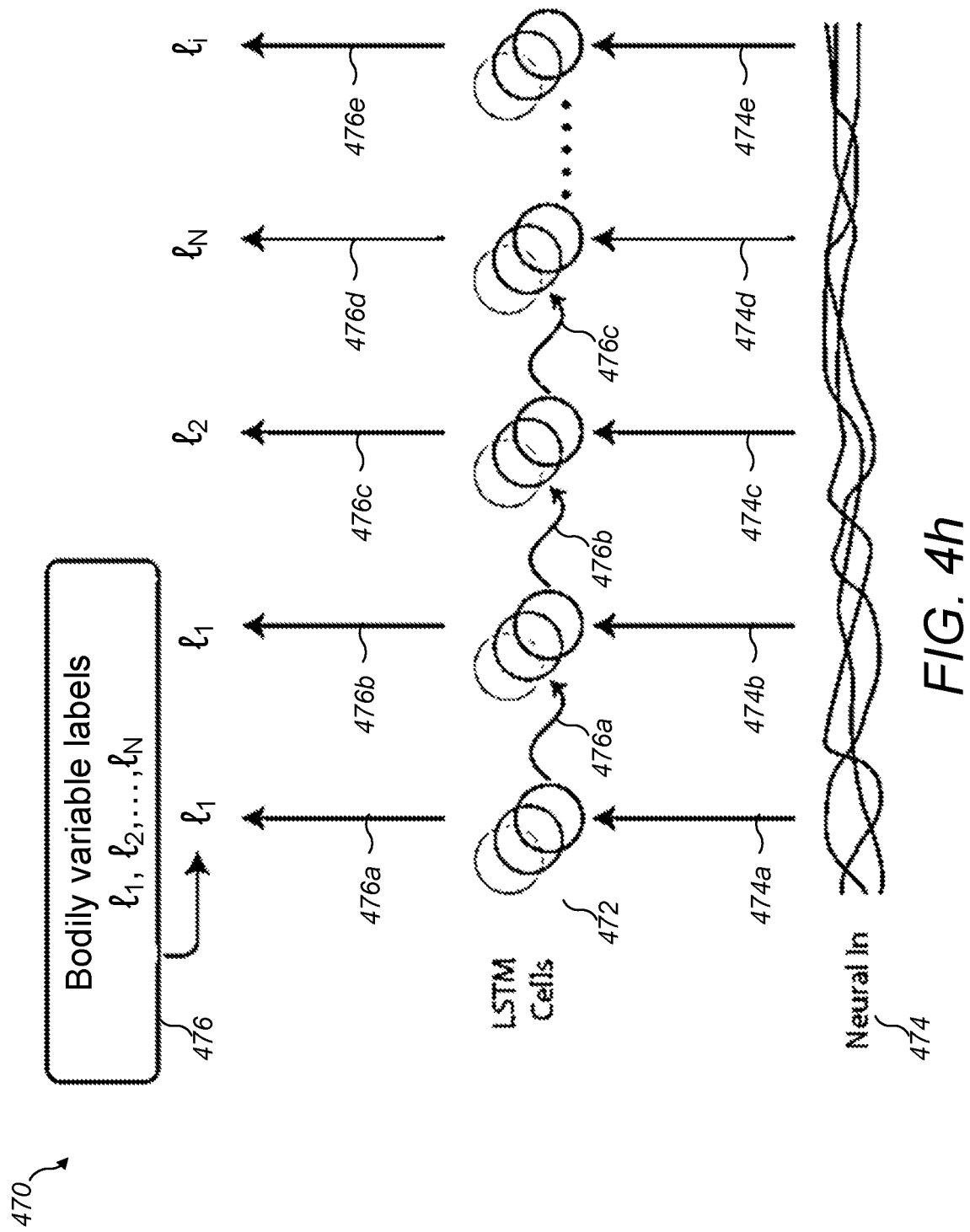
FIG. 4h is a schematic diagram illustrating an example ML model trained for predicting a bodily variable form input neurological data for use with a neural interface according to the invention.

FIG. 4h is a schematic diagram illustrating an example of ML model 470 for predicting a bodily variable estimate in neurological signals 474 for use with a neural interface according to the invention. The neurological signals 474 are time-varying signals received by one or more neural receivers (not shown) and corresponding neural data samples are captured. The neural data samples for a time series dataset, so one or more time-series based ML techniques that may be used such time-series data includes, by way of example only but not limited to, any neural network structure capable of handling time series data; recursive neural networks (RNN); long-short time memory neural network(s); LSTM, any RNN including LSTMs, convolutional neural networks (CNNs); or WaveNet which is an RNN or CNN combination, or any kind of sub-derivation that is suitable or appropriate of any neural network.

The ML model 470 may be trained as described with reference to FIGS. 1f to 10 and/or 4c to 4g in which a labelled training neural sample dataset associated with a bodily variable of interest is generated based on sensor data associated with the bodily variable of interest and neural sample data generated and received at the substantially the same time the sensor data was generated and received. The neural sample data and sensor data may be time stamped to allow synchronisation. Portions of the sensor data associated with the bodily variable of interest are labelled based on a set of bodily variable labels 476 that characterise the bodily variable associated with the sensor data. Corresponding portions of the neural sample data are then labelled to form a labelled training neural sample dataset. This labelled training neural sample dataset is used to train a ML technique and generate a ML model 470 for predicting bodily variable label estimates when neural sample data is input to the ML model 470.

In particular, as described with reference to FIGS. 1f-10 and FIGS. 4c to 4g, neurological sample data may be labelled based on bodily variables detected and/or derived from sensor data associated with a subject. The sensor data may be used to generate a set of bodily variable labels that characterise a bodily variable of interest and/or changes in a bodily variable of interest based on changes in the sensor data and the like. The sensor data and neurological sample data are synchronised in time so that portions of the sensor data and corresponding portions of the neurological sample data coincide within the same or similar time periods. The set of bodily variable labels is used to label portions of the sensor data and subsequently label corresponding portions of the neural sample data to generate a labelled training dataset associated with the bodily variable of interest. Given that neurological signals and corresponding neurological sample data are time series datasets, then the labelled training neural sample datasets are time series datasets. ML techniques that are capable of handling time-series labelled training datasets may be used to generate suitable ML models for predicting bodily variable labels when neural sample data are input.

In this case, the ML model 470 is based on a neural network structure capable of handling time-series datasets such as, by way of example only but is not limited to, a set of long-short term memory (LSTM) cell(s) 472. The set of LSTM cells may include one or more LSTM cells or a plurality of LSTM cells. The LSTM cells have been trained by an LSTM ML technique based on the labelled training neural sample data; the trained LSTM cells form the ML model 470. Once trained, the ML model 470 may receive consecutive portions of neural sample data 474a-474e over a period of time. Each of the portions of neural sample data 474a-474e may include neural activity encoding one or more bodily variables, which may include the bodily variable of interest that the ML model 470 has been trained to estimate/detect. Thus, in a first time period, a first portion of neural sample data 474a is received by the ML model 470, which is processed by the trained LSTM cells 472 and which output a bodily variable label estimate 476a. In a second time period, a second portion of neural sample data 474b is received by the ML model 470, in addition, the bodily variable label estimate 476a from the previous time period may be fed-back to the LSTM cells 472, which are processed and which outputs a second bodily variable estimate 476b. Similarly, in the third time period, a third portion of neural sample data 474c is received by the ML model 470, in addition, the bodily variable label estimate 476b from the previous time period may be fed-back to the LSTM cells 472, which are processed and which outputs a second bodily variable estimate 476c. This proceeds for subsequent time periods in which the ML model 470 outputs a prediction of a bodily variable label estimate associated with a bodily variable of interest for as long as portions of neural sample data 474 are received for processing.

Figure 4I:
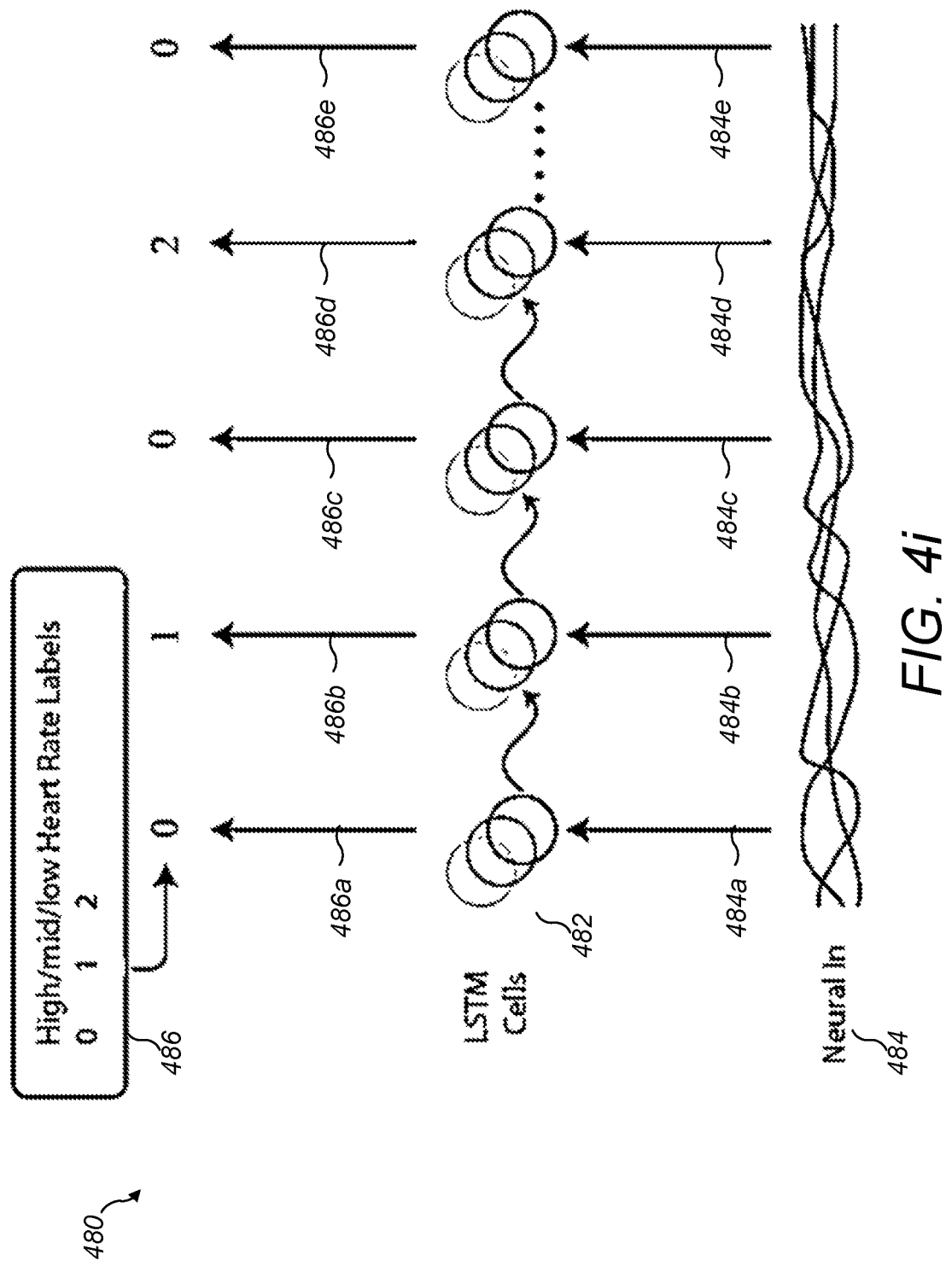
FIG. 4i is a schematic diagram illustrating an example heart rate ML model trained for predicting heart rate from input neurological data for use with a neural interface according to the invention.
Figure 4J:
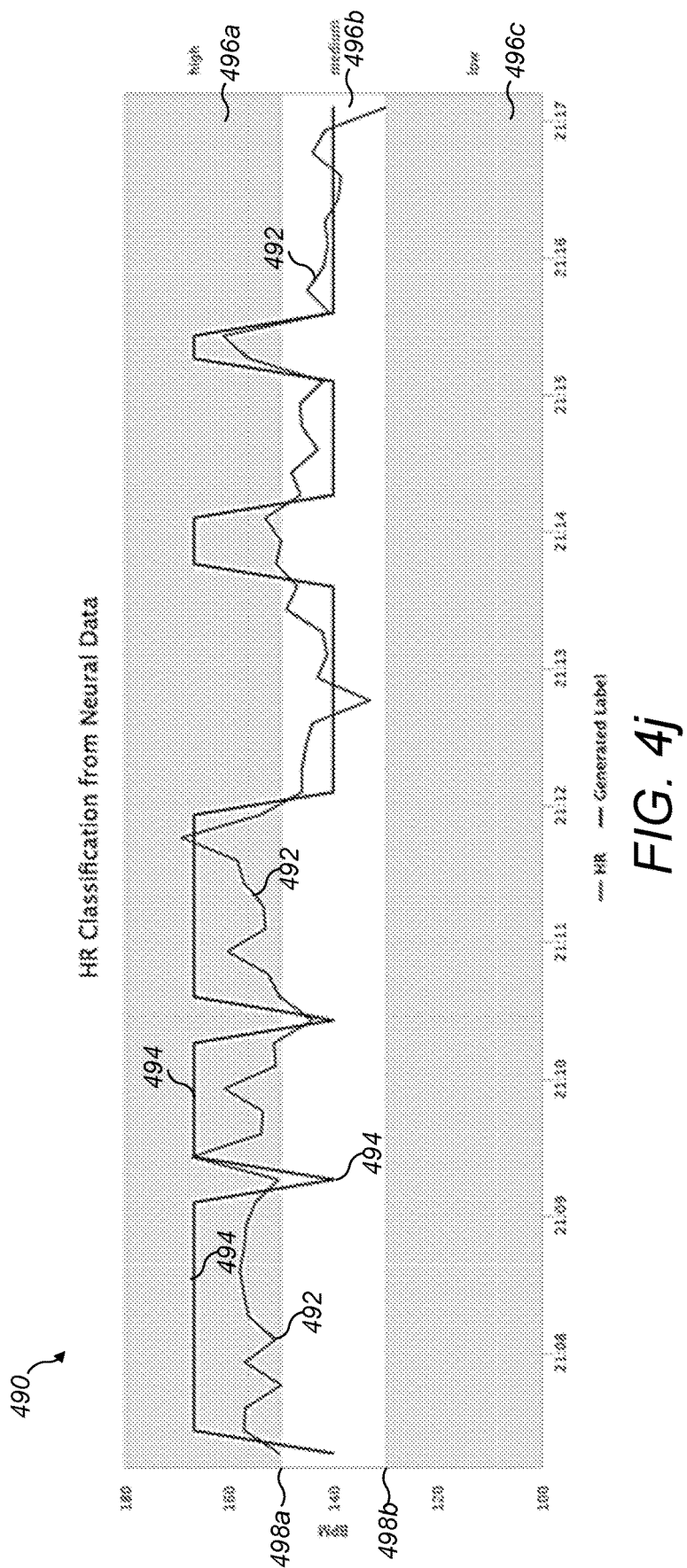
FIG. 4j is a graph diagram illustrating the performance of an ML model for predicting HR zones from input neurological data compared with the raw heart rate data of a subject, for use with a neural interface according to the invention.

FIG. 4i is a schematic diagram illustrating an example heart rate ML model 480 for predicting heart rate from input neurological data 484 for use with a neural interface according to the invention. FIG. 4j is a graph diagram 490 illustrating the performance of the heart rate ML model 470 predicted bodily variable label estimates 494 when compared with the raw heart rate sensor data 492 of a subject. Referring to FIGS. 4i and 4j, in this example, the ML model 480 is generated by training an ML technique based on an LSTM neural network comprising a set of LSTM cell(s) 482. The set of LSTM cells 482 may include one or more LSTM cells or a plurality of LSTM cells. The LSTM cells 482 have been trained by an LSTM ML technique based on the labelled training neural sample data associated with a heart rate bodily variable; the trained LSTM cells form the ML model 470.

The labelled training neural sample dataset associated with the heart rate bodily variable may be based on heart rate sensor data (e.g. ECG trace and/or heart rate sensor) that has been recorded/stored continuously throughout a recording/storing of the corresponding raw neurological sample data 484. For example, HR sensor data 492 as shown in FIG. 4c in relation to graph diagram 420 illustrating heart rate associated with the subject may be used for labelling neurological sample data. This means that fully supervised training can be used because the HR data 492 can be time synchronised with the raw neurological data 484. The HR data 492 can be analysed, characterised in which each portion of the HR data 484 may be labelled with a particular HR label from a set of HR labels 496a-496c accordingly, where portions of neurological data are labelled with the same HR labels as the corresponding portions of the labelled HR data. The labelled neurological data forms a labelled training dataset corresponding to the HR bodily variable that can be used to train an ML technique (e.g. LSTM cells 482) to generate the ML model 480.

Referring to FIG. 4j, the graph diagram 490 illustrates HR sensor data 492 (y-axis) vs time (x-axis) and heart rate regions/zones 496a-496c that are used to label the HR sensor data 492. In this example, the HR amplitude of the HR sensor data 492 is divided into three zones or regions 496a-496c of heart rate. Each of the HR regions 496a-496c is characterised and/or given a label that classifies that region (e.g. low, medium and high). In this case, the HR data 492 is characterised into, by way of example only but is not limited to, high, medium and low regions 496a-496c and may be labelled accordingly. That is, the high region 496a may be labelled "High", or '0' or any other suitable label; the medium region 496b may be labelled "Med", or '1' or any other suitable label; the low region 496c may be labelled "Low", or '2' or any other suitable label. As shown in FIG. 4i, the high HR region 496a is given the label '0', the medium HR region 496b is assigned the label '1', and the low HR region 496c is given the label '2'.

In this example, the three HR zones (or regions) 496a-496c are divided by two HR thresholds 498a and 498b. A first HR threshold 498a corresponds to a high HR threshold (e.g. 150 bpm) and a second HR threshold 498b corresponds to a low HR threshold (e.g. 130 bpm). For example, when the amplitude of the HR data 492 is greater than 150 bpm, then the HR is said to be in the high region 496a, when the HR data 492 is less then 130 bpm, then the HR is said to be in the low region 496c, and when the HR data 492 is between 150 bpm and 130 bpm, then the HR is said to be in the medium region 496b. Thus, when one or more portion(s) of the HR data 492 is above the high HR threshold 498a, then those portion(s) of HR data 492 are given a high HR label (e.g. '0') to classify them as High heart rate and the corresponding portion(s) of neurological data are also given the high HR label. If one or more portion(s) of the HR is below a low HR threshold 498b, then those portion(s) of HR data 492 are given a low HR label (e.g. '2') to classify them as Low Heart rate and the corresponding portion(s) of neurological data may also be given the low HR label. If one or more portions of the HR data 492 is between the high and low HR thresholds 498a and 498b, respectively, then these portion(s) of the HR data 492 are given a medium HR label (e.g. '1') to classify them as medium HR and those corresponding portion(s) of neurological data may also be given the medium HR label. The neurological data may be labelled based on the analysis and labelling of the HR data 492, where the labelled neurological data forms a labelled training dataset for bodily variable(s) representative of the HR. A ML technique (in this case an LSTM) may be trained based on the labelled training dataset for heart rate to generate ML heart rate model 480. The ML heart rate model 480 may then receive any time series neurological data 484 as input (e.g. recorded or in real-time) and classify or predict a bodily variable label estimate based on the HR labels (e.g. high='0', medium='1' or low HR='2').

FIG. 4j illustrates the performance of the ML model 480 when trained and inputting to the heart rate ML model 480 portions neurological sample data 484a-484e based on raw neurological data that the ML model has not seen yet (e.g. test data the ML model 480 has not seen or real-time data etc.,). In this example, the ML model 480 receives raw neurological data 484 from the vagus nerve, which is a nerve in the neck that is a trunk nerve for heart, liver lungs etc. Portions of the neurological samples 484a-484e are captured from the raw neurological data, each portion representing a different time period, and input to the ML model 480, which outputs prediction of the heart rate bodily variable label 486a-486e from the heart rate bodily variable label set 486 (e.g. high='0', medium='1' or low HR='2'). At each timestep (or time period), the HR has been labelled by the ML model 480 as high ('0'), medium ('1') or low ('2'). As can be seen, the supervised learning approach using the set of LSTM cells 482 indicates that the ML technique learns from the labelled training neurological dataset and the resulting ML model 480 can predict whether each section of neural data 484a-484e that is input corresponds to high, medium, or low HR. As is shown in FIG. 4j, the HR ML model 480 outputs predictions of bodily variable class/labels 486a-486e associated with heart rate (e.g. high, medium or low) that closely follows the HR sensor data 492.

Similar devices and/or neural interfaces to device 108b and neural interface 414 with the appropriate ML technique(s) may be applied to a wide variety of bodily functions/organs/tissues to combat diseases and/or various sub-optimal/incorrect functioning of such bodily functions/organs/tissues and the like of the subject 102. For example, devices such as, by way of example only but not limited to, implant or implant devices, sensors, and/or controllers and the like associated with non-prosthetics neural applications for managing or assisting with the operation or function of any one or more of a number of different organs, tissues, biological sites and/or sub-systems in the body of a subject 102, by way of example only but not limited to (e.g. biological site/targeted disease), bladder nerve/urinary incontinence, abdominal vagus nerve/gastric motility, ovarian plexus/birth control, cardiac innervation/blood pressure, upper vagus/inflammation, spinal cord/chronic pain, abdominal vagus/diabetes, adipose innervation/weight loss, pancreatic nerve/diabetes, subcutaneous cardiac nerve/heart arrhythmia, vagus nerve/chronic migraine; and any other device, apparatus, mechanism or system capable of assisting in the operation of any other biological site/organ or sub-system in the body of a subject based on receiving data representative of a bodily variable from a neuronal population associated with a biological site/organ/tissue or sub-system and/or for providing device data (e.g. bodily variable signal(s)) associated with neural stimulus to a neuronal population associated with the biological site/organ/tissue or sub-system. It is to be appreciated by the skilled person that, based on the teachings described herein, the skilled person would be able to implement a neural interface, neural interface platform or system according to the invention with any other device as the application demands.

For example, a device may be operable to manage a biological site affected by a targeted disease, in which the device receives neural data from a neural interface based on neurological signals associated with the biological site (e.g. one or more neurons/neuronal populations located at biological site) and in response to receiving neural data associated with the biological site, the device may manage the targeted disease by providing device data to neural interface, which provides an appropriate neural stimulus (based on ML technique(s)/model(s) etc.) to the biological site, thus managing the targeted disease.

During operation of the neural interface according to the invention, trained ML technique(s) may need to be updated periodically due to, by way of example only but not limited to, a tendency for one or more trained ML technique(s) (e.g. those that use neural networks or LSTM networks/memory units) to prioritise the neural data samples or device data that have most recently been presented to the trained ML technique or received by the neural interface. Such behaviour is known as catastrophic forgetting and can affect the performance of the neural interface leading to erroneous neural data estimates and/or neural stimulus signal estimate(s). Techniques to minimise these issues and other linked phenomenon are known as continuous learning in which a ML technique or model may be encouraged to "generalise" across all the data presented to it, but retain the ability to learn a specificity in recent experiences.

Although FIGS. 4a to 4j describe several examples of the invention, this is by way of example only but these examples of the invention are not so limited, it is to be appreciated by the skilled person that the examples of the invention described in FIGS. 4a-4j may be applied in relation to any one or more bodily variables and/or any one or more sets of bodily variable labels, and may further include any of the one or more process(es), one or more method(s), labelled training datasets, one or more features and/or one or more functionalities of the different aspects of the invention, modifications thereof or thereto, combinations thereof or thereto, with reference to FIGS. 1a-4j and 5a-6b and/or as described herein.

Figure 5A:
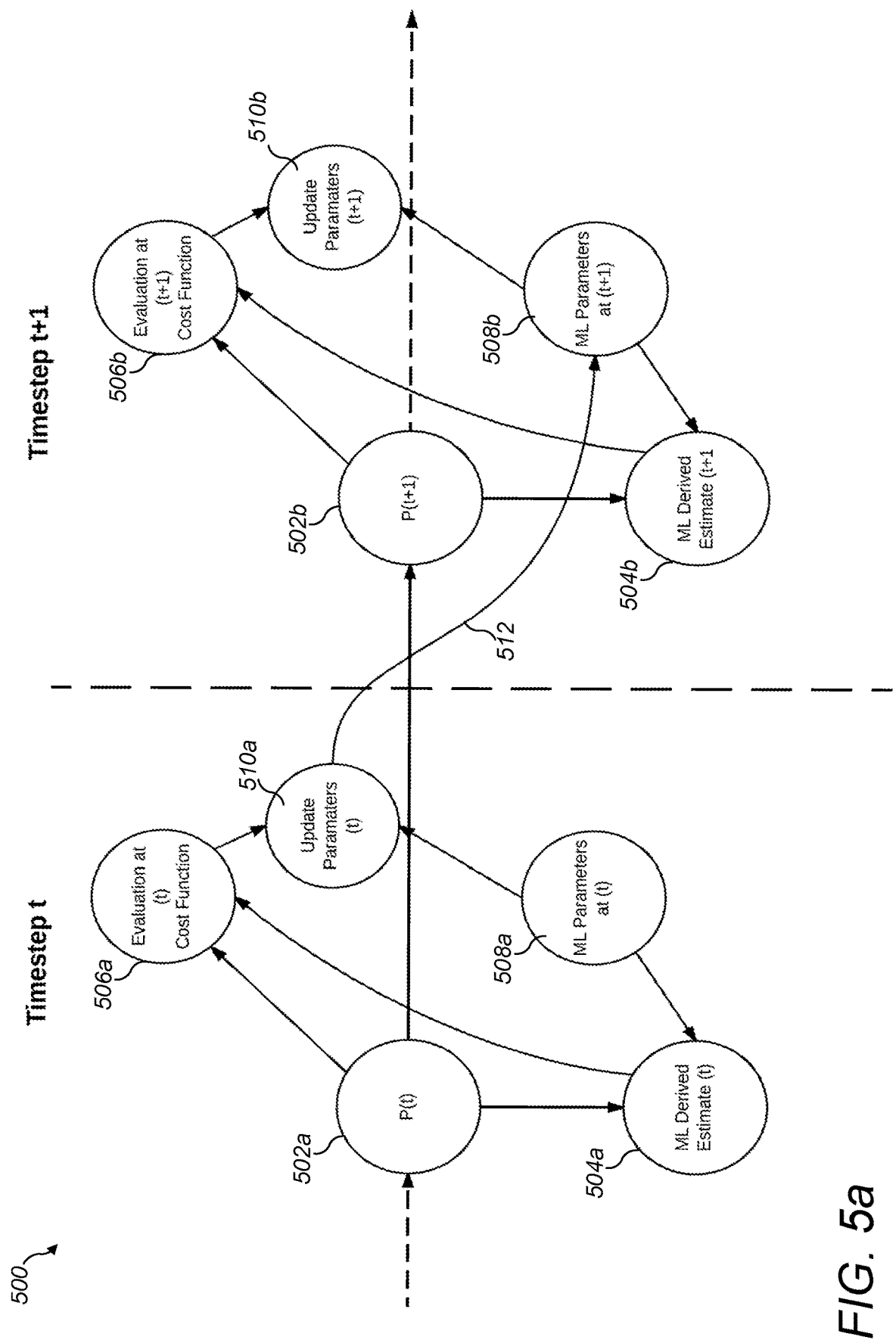
FIG. 5a is a schematic diagram illustrating an example continuous learning model according to the invention.

FIG. 5a is a schematic diagram illustrating an example continuous learning model 500 based on a Markov process illustrating the performance state(s) 502a (e.g. P(t)) and 502b (e.g. P(t+1)) for monitoring or evaluating the performance of one or more trained ML technique(s) that may be used in a neural interface according to the invention. The weights/parameters pf the one or more trained ML technique(s) may be re-trained or updated in response to the evaluation of the performance of the one or more trained ML technique(s) when operating on, by way of example only, neural sample data or device data. The neural interface may be based on, by way of example only but not limited to, one or more neural interface(s) 106, 202a, 202b, 302a, 302b, 402, 414, 600, 620 as described herein with reference to FIGS. 1a-4b and 6a-6b. The continuous learning model 500 model may allow changes in the training methodology for one or more trained ML technique(s) to allow these techniques to adapt to a changing environment. For example, varying the learning rate proportionally to how recently a batch of training data was collected or the correlation of some random samples of training data are to current neural activity may be used to retrain the ML technique(s).

The continuous learning model 500 may be performed for multiple time steps and FIG. 5a illustrates the performance state 502a for a first time step (e.g. Timestep t) and a performance state 502b for a second time step (e.g. Timestep t+1). The time steps between performance states may be periodic, aperiodic, or based on a trigger or event, or based on a predetermined schedule and the like. In this example, the first time step and second time step may be arbitrary time steps. The continuous learning model 500 may be implemented to operate at different time scales to take into account the changing biological environment around the neural receiver(s) and/or transmitter(s) (e.g. implanted electrodes) coupled to the nervous system of the subject. Thus, it is important to be able to re-train the one or more ML technique(s) to adapt or have specificity to changes in the placement or coupling of neural transmitter(s)/receiver(s) in and around the one or more neurons or neuronal populations (e.g. specificity to the 'current' nerve/electrode configuration), whilst benefitting from a knowledge of prior neural activity.

The performance state (e.g. P(t)) 502a for the first time step t represents all the data that has been received and operated on by the neural interface by or at the first time step t. This can be used to evaluate one or more trained ML technique(s) that may be used by the neural interface. This data may include all data collected and estimated for the first time step t by the neural interface, by way of example only but not limited to, all data collected and estimated by the neural interface, performance measurements, metrics, any neural data samples collected at the first time step t, any neural sample data collected at the first time step t, any neural data and/or one or more biological/bodily variable values at the first time step t, any neural stimulus samples collected at the first time step t.

The performance state 502a may depend on the type of trained ML technique(s) that are being used by the neural interface. For example, for an trained ML technique that estimates or classifies neural data or one or more bodily variable(s), the performance state 502a may represent received neural data samples of a received neurological signal, one or more estimated bodily variables/neural data estimates and other related performance metrics/data or status of the neural interface and the like relevant to this trained ML technique. In another example, for a trained ML technique that estimates neural stimulus signal(s) based on receiving device data or bodily variable signal(s), the performance state 502a may represent the estimated neural stimulus signals, the received device data, and other related performance metrics/data or status of the neural interface and the like relevant to this ML technique. Other data included in the performance state 502a at the first time step t may include, by way of example only but not limited to, previous estimate(s) from the one or more trained ML techniques, neural interface and/or device operation & status information, externally provided information such as measures of error in the estimate(s) output from the trained ML technique(s), one or more task(s)/contextual cue(s) or label(s), and additional information about bodily variable(s)/biological variable(s) such as sensor data from one or more sensors trained on the subject.

The performance state 502b (e.g. P(t+1)) is influenced by one or more actions such as, by way of example only but not limited to, ML derived estimate action 504a at the first time step t, cost function evaluation action 506a at the first time step t, ML parameters action 508a at the first time step t, and update parameters action 510a at first time step t. Each of these actions may be performed at or during the first time step t. In the first time step, a trained ML technique may have been selected for use by the neural interface. Thus, ML derive estimate action 504a may perform the selected trained ML technique in which the performance state 502a inputs the necessary data of the neural interface received at the first time step t. As well, the ML parameters action 508a inputs the set of trained ML parameter data that defines the selected trained ML technique to allow it to operate on the data from the performance state 502a at the first time step t.

Each trained ML technique may have a set of trained ML parameter data representative of the weights and/or parameters calculated by training the ML technique on a corresponding neural training data. For example, a trained ML technique may be associated with estimating neural data or one or more bodily variable(s), hence may be trained on a neural data sample training dataset as described herein, by way of example only but not limited to, with reference to FIGS. 2a-2g. In another example, a trained ML technique may be associated with estimating a neural stimulus signal in response to device data and/or one or more bodily variable signal(s) generated by a device for stimulating the nervous system of a subject as described herein, by way of example only but not limited to, with reference to FIGS. 3*a*-3*f*. The weights and parameters of the one or more ML technique(s) are input to the neural interface for implementing at least one of the ML technique(s). The set of trained ML parameter data may be input from ML parameter action 508*a* to ML derived estimate action 504*a*.

Based on the performance state 502*a* at the first time step t and the ML parameter(s) action 508*a*, the selected trained ML technique outputs, from ML derived estimates action 504*a*, ML estimate(s) (e.g. estimated neural data or bodily variable(s); estimated neural stimulus signal(s)) that are output to the cost function action 506*a*. The cost function action 506*a* evaluates a set of performance data comprising all necessary data from the performance state 502*a* at first time step t and also the ML estimate(s) of the selected trained ML technique at the first time step t output from the ML derived estimate(s) action 504*a*. The cost function is evaluated (e.g. using threshold and/or distance estimates) to determine whether the set of trained ML parameter data should be updated (e.g. the selected one or more ML technique(s) should be retrained) or not. If cost function action 506*a* determines that the set of trained ML parameters should be updated, it inputs an indication to Update parameter(s) action 510*a*. The update parameter(s) action 510*a* then directs or causes the set of trained ML parameters associated with the selected ML technique to be updated. This may include retraining the ML technique based on one or more training datasets. The update parameter(s) action 510*a* of the first time step t then updates the ML parameters action 508*b* for the second time step t+1.

In the second time step t+1, the performance state 502*b* (e.g. P(t+1)) is influenced by one or more actions at the second time step t+1 such as, by way of example only but not limited to, ML derived estimate action 504*b* at the second time step t+1, cost function evaluation action 508*a* at the second time step t+1, ML parameters action 508*b* at the second time step t+1, and update parameters action 510*b* at second time step t+1. Each of these actions may be performed at or during the second time step t+1 to determine whether the selected ML technique at the second time step t+1 needs to be updated/retrained.

Figure 5B:
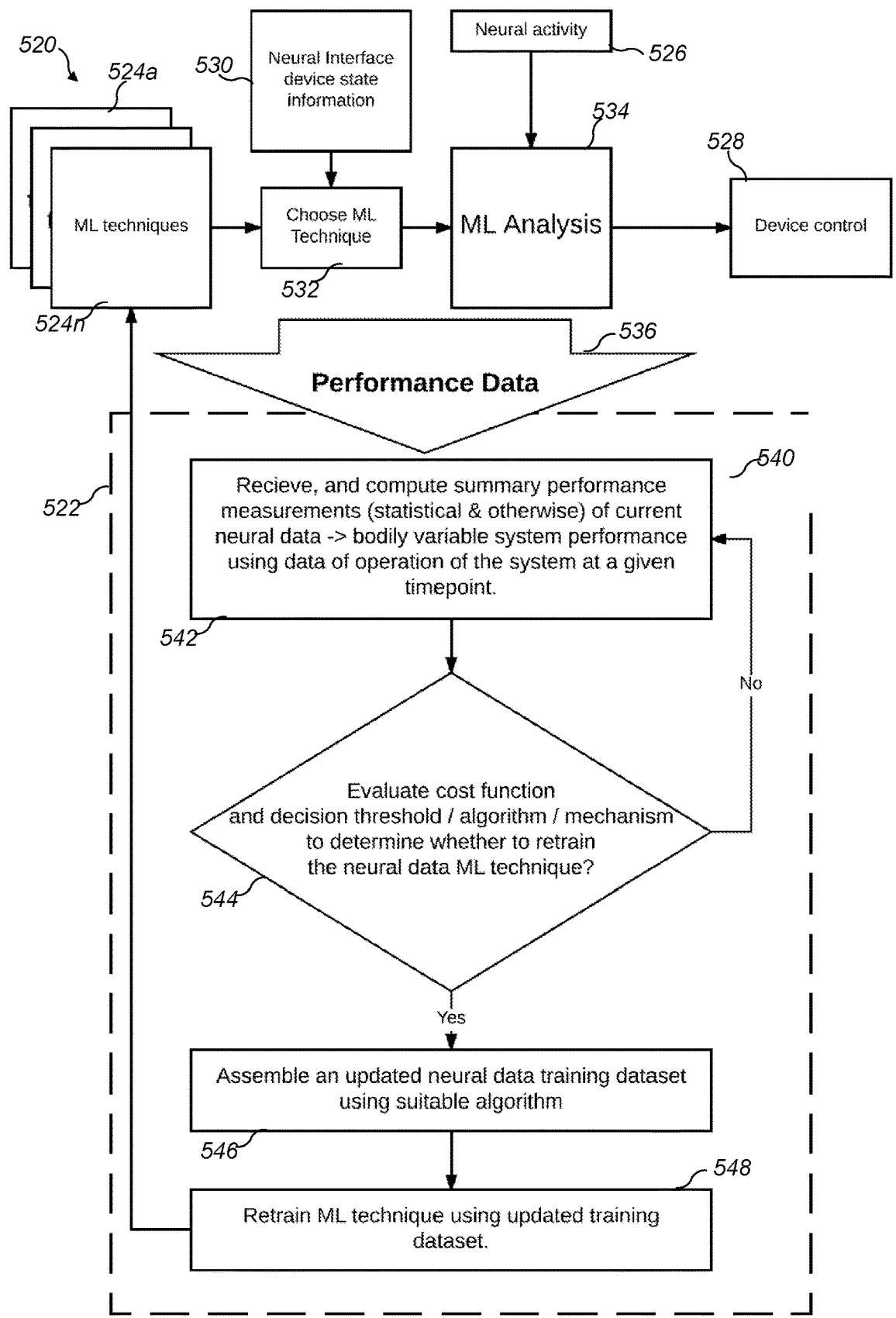
FIG. 5b is a schematic diagram illustrating an example continuous learning system, apparatus and process for updating ML technique(s) estimating neural data according to the invention.

FIG. 5*b* is a schematic illustration and flow diagram illustrating an example continuous learning system 520, apparatus 522 and method or process 540 for interfacing with a nervous system of a subject 102. In this case, the continuous learning system 520 is configured for evaluating the performance of one or more ML technique(s) 524*a*-524*n* configured to operate on neural activity 526 or received neural sample data associated with received neurological signals corresponding to the neural activity 526 from one or more neural receiver(s) coupled to one or more neurons or neuronal populations of the nervous system. In this case, the one or more ML technique(s) may be configured to output neural data estimates and/or data representative of estimates of one or more bodily variable(s) or combinations thereof, which is transmitted to a device 528 or the control of a device 528. In this example, the neural data estimates may be used by device control 528 to manage or assist one or more body parts/organs/tissue(s)/cell(s) of the body of a subject. The continuous learning system 500, apparatus 502 or process 504 may be included, by way of example only but not limited to, as a continuous learning component of a neural interface according to the invention.

The continuous learning system 520 includes a neural interface device state information module 530, which sends a control signal to select or choose a first one or more ML technique(s) 532 for operating on the received neural activity 526. Having selected a first one or more ML technique(s) 532, the corresponding set of trained ML parameter data may be retrieved and used in ML analysis module 534 for implementing or performing the selected first one or more ML technique(s) 532 on data representative of the neural activity 526. Performance data 536 may be collected at each time step or at a given time point by the continuous learning system 520. The performance data 536 comprises or represents any data collected by the continuous learning system for evaluating, using a cost function, the performance of the selected ML technique 532. The performance data 536 may include the most recent performance data defining the performance of the neural interface or system during operation of the neural interface or system at the current time step or given time point. The performance data 536 may further include summary measurements of any data (statistical & otherwise) received by the neural interface that can assist in the performance evaluation of the selected ML technique 532 may be collected and/or computed.

For example, performance data 536 may include, by way of example only but not limited to, neural sample data associated with one or more neurological signal(s) associated with neural activity of a portion of the nervous system of a subject; at least one or more of bodily variable value(s), biological variable value(s), device data, and/or neural data; neural stimulus samples associated with one or more neurological signal(s) associated with a neural stimulus; estimates from the first one or more ML technique(s) such as, by way of example only but not limited to, reconstructed neural data samples output from a ML technique (e.g. decoding network of an autoencoder structure), neural data labels or bodily variable labels at each time step of the ML technique (e.g. each time step of an LSTM network); neural interface device operation and status information (e.g. computing and/or storage resources), one or more connected device(s) operation and status information (e.g. computing and/or storage resources); externally provided information such as, by way of example only but not limited to, measures of error (task level, device operation level, transmission), task/contextual cues or labels, additional information about neural data or bodily variables.

Once all the performance data 536 has been collected by the continuous learning system 520, the continuous learning apparatus 522 performs the following one or more steps of a computer implemented method 540. In step 542, at least one set of performance data 536 associated with the first one or more ML technique(s) is received.

In step 544, a cost function is evaluated on the set of performance data to determine whether to retrain the first one or more ML technique(s). The cost function may be evaluated in addition to one or more decision thresholds, algorithms or mechanism to determine whether to retrain the first one or more ML technique(s) associated with estimating neural data. A cost function may be calculated and a decision threshold used (or decision algorithm or decision mechanism) to determine whether to retrain the ML method. For example, this can be achieved by a simple method such as a using one or more thresholds of allowable errors within the set of performance data. As another example, a more complex implementation may be, by way of example only but not limited to, using another ML technique to estimate the performance of the set of performance data. The ML technique that estimates the performance from the set of performance data may be based on a reinforcement learning (RL) algorithm in which the cost function is represented by a reward signal or a score. The cost function may comprise of represent any function that quantifies and/or takes into account either directly or indirectly the suitability of the selected ML technique 532 to perform well.

In step 546, a training neural dataset is assembled and/or updated using an update/retraining algorithm. For example, a training set of neural sample data may be assembled/ created and/or generated/updated by retrieving by synchronising stored neural sample data with stored sensor data. The stored neural sample data may be updated neural sample data from recent sets of neural data samples. The stored sensor may have been similarly updated. Portions of the neural sample data associated with neural activity may be identified and neural data labels may be determined for each identified portion of neural sample data by analysing portions of sensor data corresponding to the identified portion of neural sample data. The identified portions of neural sample data may be labelled based on neural data labels. The resulting labelled neural sample data may then be stored as an generated/updated set of training neural sample data.

In another example, a training neural sample dataset may be created, recomposed, or selected using various training algorithms/method(s) such as, by way of example only but not limited to, a training algorithm/method that that combines newly collected neural data samples with old training datasets in which the summary measurements of this combined training dataset more closely matches the measures of the currently encountered neural data samples or the current set of performance data in which the cost function is likely to be better satisfied by a retraining on this updated/combined training dataset.

In step 548, the selected trained ML technique 532 may then be updated/retrained using the generated/updated training dataset. For example, the selected ML technique 532 may be retrained using a newly created or updated training neural dataset from step 546. Retraining the selected ML technique 532 may be performed in a similar fashion as the initial or first training of the selected ML technique 532. However, in this case, the set of parameter data (e.g. the set of weights and/or parameters) may converge quick to a new set of parameter data because the selected ML technique 532 is a trained ML technique. Thus, less training may be necessary, which means the selected ML technique 532 may be trained locally by the neural interface or continuous training system 520 and/or apparatus 522.

Retraining the selected trained ML technique 532 may be further possible by performing an the neural interface (e.g. local to the device implementing the neural interface). Alternatively or additionally, retraining of the selected trained ML technique 532 may be performed using an external computing system or a remote computing resource, cloud computing resource, and/or data resource. Some adaptions of retraining may be used to preserve possible utility/performance of the trained ML technique on past and future time points or time steps, which may reduce or lower the learning rate for new training datasets.

The updated trained ML technique may be used to replace the existing selected trained ML technique 532 of the first one or more ML technique(s) 524a-524n. Alternatively, the updated trained ML technique may be stored and added to the first one or more ML technique(s) as an alternative option for analysing the neural sample data. Selection of this particular updated trained ML technique may be based on updated performance data/metrics or other elements of software etc. Neural interface device state information module 530 may perform selection of a ML technique from the first one or more ML technique(s) based on historical model/ML technique prediction uncertainty, and/or based on predicted model/ML technique prediction uncertainty. Alternatively, each of the first one or more trained ML techniques may be given a performance score based on the cost function, and the trained ML technique that has the lowest or best performance score may be selected.

Figure 5C:
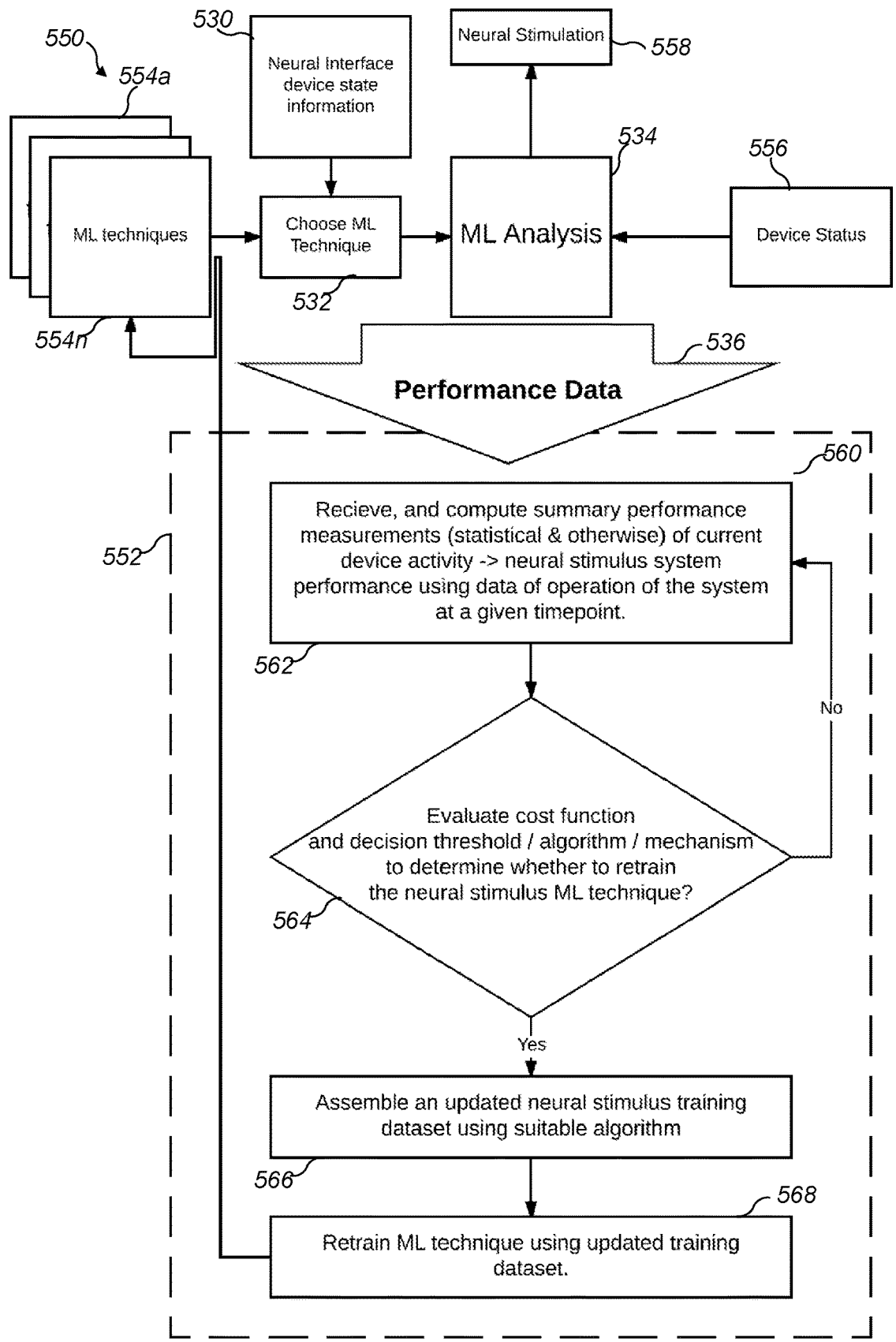
FIG. 5c is a schematic diagram illustrating another example continuous learning system, apparatus and process for updating ML technique(s) estimating neural stimulus according to the invention.

FIG. 5c is a schematic illustration and flow diagram illustrating a continuous learning for when the neural interface inputs neural sample data associated with received neurological signals from one or more neural receiver(s) to one or more ML technique(s) for outputting neural data and/or data representative of one or more bodily variable(s) or combinations thereof.

FIG. 5c is a schematic illustration and flow diagram illustrating another example continuous learning system 550, apparatus 552 and method or process 560 for interfacing with a nervous system of a subject 102. In this case, the continuous learning system 550 is configured for evaluating the performance of a second set of one or more trained ML technique(s) 554a-554n configured to operate on device data from a device or device status 556 connected to the neural interface to estimate one or more neural stimulus signal estimate(s) for neural stimulation 558. Neural stimulation 558 sends the one or more estimated neural stimulus signal estimate(s) to one or more neural transmitter(s) coupled to one or more neurons or neuronal populations of the nervous system. In this case, the second set of one or more trained ML technique(s) 554a-554n may be configured to output neural stimulus signal estimates and/or data representative of estimates of neural stimulus, which is transmitted to one or more neural transmitters coupled to a second portion of the nervous system of the subject.

In this example, the neural stimulus signal estimates may be used by the neural transmitter(s) to stimulate (e.g. using an excitatory signal or an inhibitory signal) the one or more neurons or neuronal populations associated with the device or device status 556. This is for the device 556 managing or assisting in the function or operation of one or more body parts/organs/tissue(s)/cell(s) of the body of the subject. The continuous learning system 550, apparatus 552 or process 560 may be included, by way of example only but not limited to, as a continuous learning component of a neural interface according to the invention.

The continuous learning system 550 includes a neural interface device state information module 530, which sends a control signal to select or choose a trained ML technique 532 from the second set of one or more ML technique(s) 554a to 554n for operating on the received device data or bodily variable signal(s) from device status 556. Having selected a trained ML technique 532 from the second set of trained ML technique(s) 554a-554n, the corresponding set of trained ML parameter data may be retrieved and used in ML analysis module 534 for implementing or performing the selected ML technique 532 on data representative of the device data or bodily variable signal(s) from device status 556.

Performance data 536 may be collected at each time step or at a given time point by the continuous learning system 550. The performance data 536 comprises or represents any data collected by the continuous learning system for evaluating, using a cost function, the performance of the selected ML technique 532. The performance data may be a set of performance data 536 associated with the selected ML technique, where the set of performance data includes the received device data and/or received bodily variable signal(s), and the estimated one or more neurological stimulus signal(s). The performance data 536 may further include the most recent performance data 536 defining the performance of the neural interface or system during operation of the neural interface or system at the current time step or given time point. The performance data 536 may further include summary measurements of any data (statistical & otherwise) received by the neural interface that can assist in the performance evaluation of the selected ML technique 532 that may be collected and/or computed.

For example, performance data 536 may include, by way of example only but not limited to, neural stimulus data associated with one or more neurological signal(s) associated with neural stimulus of a second portion of the nervous system of a subject; neural sample data associated with one or more neurological signal(s) associated with neural stimulus of a second portion of the nervous system of a subject; at least one or more device data and/or bodily variable signal(s); at least one or more of bodily variable value(s), biological variable value(s), and/or neural data; neural stimulus samples associated with one or more neurological signal(s) associated with a neural stimulus; estimates from the second set of one or more ML technique(s) such as, by way of example only but not limited to, reconstructed neural data samples or reconstructed neural stimulus data samples output from a ML technique (e.g. decoding network of an autoencoder structure), neural stimulus data labels, neural data labels or bodily variable labels at each time step of the ML technique (e.g. each time step of an LSTM network); neural interface device operation and status information (e.g. computing and/or storage resources), one or more connected device(s) operation and status information (e.g. computing and/or storage resources); externally provided information such as, by way of example only but not limited to, measures of error (task level, device operation level, transmission), task/contextual cues or labels, additional information about neural data or bodily variables.

Once all the performance data 536 has been collected by the continuous learning system 550, the continuous learning apparatus 552 performs the following one or more steps of a computer implemented method 560. In step 562, at least one set of performance data 536 associated with the selected ML technique 532 from the second set of one or more ML technique(s) 554a-554n is received.

In step 564, a cost function is evaluated on the set of performance data to determine whether to retrain the selected ML technique 532. The cost function may be evaluated in addition to one or more decision thresholds, algorithms or mechanism to determine whether to retrain the selected ML technique associated with estimating neural data. A cost function may be calculated and a decision threshold used (or decision algorithm or decision mechanism) to determine whether to retrain the selected ML method. For example, this can be achieved by a simple method such as a using one or more thresholds of allowable errors within the set of performance data. As another example, a more complex implementation may be, by way of example only but not limited to, using another ML technique to estimate the performance of the set of performance data. The ML technique that estimates the performance from the set of performance data may be based on a reinforcement learning (RL) neural network or algorithm in which case the cost function may be represented by a reward signal or a performance score. The cost function may comprise of represent any function that quantifies and/or takes into account either directly or indirectly the suitability of the selected ML technique 532 to perform well.

In step 566, a training neural dataset is assembled and/or updated using an update/retraining algorithm. For example, a training set of neural sample data may be assembled/created and/or generated/updated by retrieving by synchronising stored neural stimulus sample data with stored sensor data. The stored neural stimulus data may be updated neural stimulus data from recent sets of neural stimulus data samples. The stored sensor may have been similarly updated. Portions of the neural stimulus sample data associated with neural activity may be identified and neural stimulus data labels may be determined for each identified portion of neural stimulus sample data by analysing portions of sensor data corresponding to the identified portion of neural stimulus sample data. The identified portions of neural stimulus sample data may be labelled based on neural stimulus data labels. The resulting labelled neural stimulus sample data may then be stored as an generated/updated set of training neural stimulus sample data.

In another example, a training neural stimulus sample dataset may be created, recomposed, or selected using various training algorithms/method(s) such as, by way of example only but not limited to, a training algorithm/method that that combines newly collected neural stimulus data samples with old training stimulus datasets in which the summary measurements of this combined training stimulus dataset more closely matches the measures of the currently encountered neural stimulus data samples or the current set of performance data in which the cost function is likely to be better satisfied by a retraining on this updated/combined training stimulus dataset.

In step 568, the selected trained ML technique 532 may then be updated/retrained using the generated/updated training neural stimulus dataset. For example, the selected ML technique 532 may be retrained using a newly created or updated training neural stimulus dataset from step 546. Retraining the selected ML technique 532 may be performed in a similar fashion as the initial or first training of the selected ML technique 532. However, in this case, the set of parameter data (e.g. the set of weights and/or parameters) may converge quickly compared to the initial training to a new set of parameter data (e.g. weights/parameters of the selected ML technique) because the selected ML technique 532 is a trained ML technique in relation to neural stimulus. Thus, less training may be necessary, which means the selected ML technique 532 may be trained locally by the neural interface or continuous training system 520 and/or apparatus 522.

Retraining the selected trained ML technique 532 may be further possible by performing training on the neural interface (e.g. local to the device implementing the neural interface). Alternatively or additionally, retraining of the selected trained ML technique 532 may be performed using an external computing system or a remote computing resource, cloud computing resource, and/or data resource. Some adaptions of retraining may be used to preserve possible utility/performance of the trained ML technique on past and future time points or time steps, which may reduce or lower the learning rate for new training neural stimulus datasets.

The updated trained ML technique may be used to replace the existing selected trained ML technique 532 of the second set of one or more ML technique(s) 554a-554n. Alternatively, the updated trained ML technique may be stored and added to the first one or more ML technique(s) as an alternative option for analysing the neural stimulus sample data. Selection of this particular updated trained ML technique may be based on updated performance data/metrics or other elements of software etc. Neural interface device state information module 530 may perform selection of a ML technique from the second set of one or more ML technique(s) based on historical model/ML technique prediction uncertainty, and/or based on predicted model/ML technique prediction uncertainty. Alternatively, each of the second set of one or more trained ML techniques may be given a performance score based on the cost function, and the trained ML technique that has the lowest or best performance score may be selected.

Figure 6A:
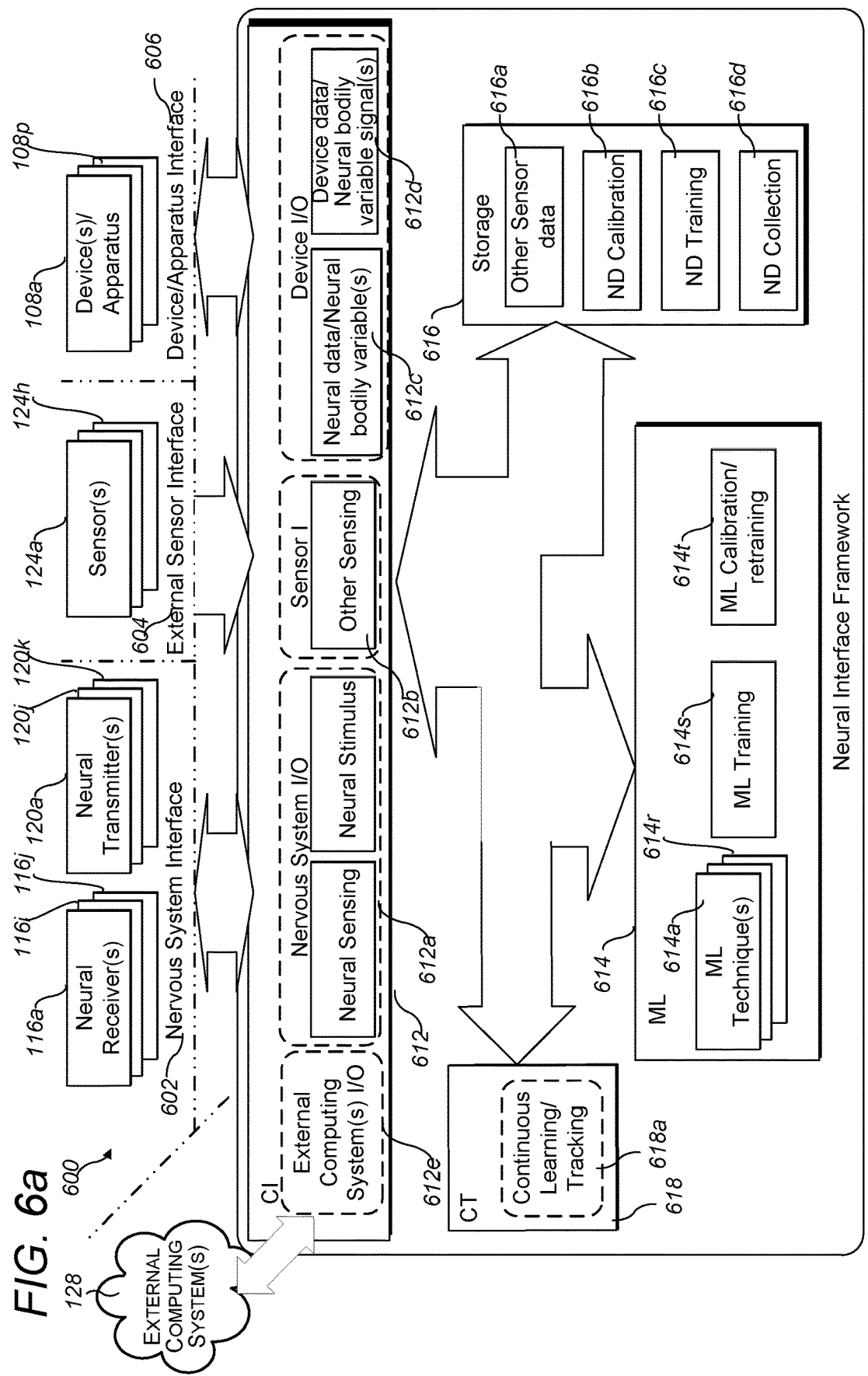
FIG. 6a is a schematic diagram illustrating an example neural network framework (or platform) for use with a neural interface system and/or a neural interface according to the invention.

FIG. 6a is a schematic diagram illustrating a neural interface framework or application programming interface (API) 600 showing one or more components or modules and their interconnections, where a selection of one or more of these components or modules may be used for implementing a neural interface 106 as described herein, and/or a neural interface 106 that implements one or more of the methods and/or processes as described with reference to FIGS. 1a to 5f. The components and/or modules may include instructions or computer code, which when executed on a processor or one or more processors, implements the functionality associated with that component or module. Alternatively or additionally, the components and/or modules may be implemented in hardware, such as by way of example only but not limited to, embedded electronics, field programming gate array(s) (FPGAs), Very-Large-Scale-Integrated (VLSI) chips and the like and/or any other hardware and/or software, and/or combinations thereof.

The neural interface framework 600 may be used to implement a neural interface 106 that includes a nervous system interface 602 for connecting and communicating, via a communication interface (CI) component 612, with one or more neural receiver(s) 116a, ..., 116i and/or 116j, one or more neural transmitters 120a, ..., 120j and/or 120k, and/or both. The neural interface framework 600 may further be used to implement a neural interface 106 that has an external sensor interface 604 for connecting or coupling to one or more sensor(s) 124a-124h and receiving, via the communication interface component 612, sensor data from the one or more sensor(s) 124a-124h. The neural interface framework 600 may also be used to implement a neural interface 106 that has a device/apparatus interface 606 for communicating data representative of neural bodily variable estimates and/or neural bodily variable signal(s) between one or more device(s) 108a-108p and a neural interface 106.

The neural interface framework 600 further includes a communication interface component 612 for providing the necessary input/output with one or more of the neural receivers 116a, ..., 116i and/or 116j, neural transmitters 120a, ..., 120j and/or 120k, one or more sensor(s) 124a-124g, and one or more device(s)/apparatus 108a-108p. The communication interface component 612 further includes functionality for providing a nervous system input/output component(s) 612a, which may include a neural sensing/receiving component(s) for sampling one or more neurological signals from one or more neural receivers 116a, ..., 116i and/or 116j as described herein. The nervous system I/O component 612a may further include a neural stimulus component for transmitting neural stimulus signals based on neural bodily variable signal(s) from one or more device(s)/apparatus 108a-108p to one or more neural transmitters 120a, ..., 120j and/or 120k.

The communication interface component 612 may further include a sensor input component 612b for receiving sensor data from sensors 124a-124h. The sensor input component 612b may include a sensing component that may include functionality for directing and/or processing sensor data, such as by way of example only but not limited to, time stamping sensor data and sending sensor data to storage component 616 for storing the sensor data and/or identifying which neural samples correspond to which sensor data etc.

The communication interface component 612 may further include device input/output component 612b that may include functionality such as, by way of example only but not limited to, a neural bodily variable(s) component for communicating data representative of one or more bodily variable(s) or combinations thereof or result output from machine learning component 614 with one or more device(s)/apparatus 108a-108p. The device I/O component 612c may further include, by way of example only but is not limited to, a neural bodily variable signal(s) component that receives neural bodily variable signal(s) from one or more device(s)/apparatus 108a-108p for input to the ML component 614 or storage component 616. The communication interface component 612 may further include external computing system input/output component 612e that may include functionality such as, by way of example only but not limited to, sending or receiving, wirelessly or wired, neurological data, neurological stimulus data, neural sample data, sensor data and/or neural bodily variable signal(s) to one or more external computing system(s) for storage, generation of training data sets, and/or further processing and/or receiving data representative of trained ML techniques, one or more bodily variable estimates, one or more neural stimulus signals.

The neural interface framework 600 may further include a storage component 616 that is configured to include, by way of example only but not limited to: a sensor storage component 616a for storing and/or retrieving sensor data recorded/stored from one or more sensor(s) 124a-124g and/or data associated with the sensor data such as timestamp data etc.; a neural calibration data component 616b for storing and/or retrieving any necessary calibration/retraining data and/or network parameters that may be required by machine learning component 618 and/or device(s)/apparatus 108a-108p in relation to calibrating/retraining or performing continuous learning/tracking of one or more of said device(s) 108a-108p with a neural interface; a neural training dataset component 616c for storing and/or retrieving one or more training sets of neurological signal samples corresponding to different neural activity encoding one or more bodily variables and/or one or more training sets of neural stimulus signals/signal samples corresponding to different neural activity encoding bodily variable(s) associated with neural stimulus for stimulating one or more neurons or neuronal populations; and/or an neural collection data component 616d for receiving neurological signal signals and/or samples collected/received by communication interface component 612 and for storing, arranging to store said collected/received neurological signals or neurological signal samples, which may include raw neurological signal samples etc. The neural collection data component 616d may be further configured to store timestamped neurological signal sample data for comparing with corresponding timestamped sensor data for labelling portions of the neurological signal sample data with a corresponding neural intent. The neural collection data component 616d may be further configured to store neurological stimulus signal sample data for comparing with corresponding timestamped sensor data, and/or neural bodily variable signal(s) from one or more device(s)/apparatus, for use in labelling portions of the neurological stimulus signal sample data with a corresponding bodily variable(s) and/or mapping said labelled data to bodily variable signal(s) accordingly.

The neural interface framework 600 includes a machine learning (ML) component 614 that communicates with the communication interface component 612 and storage component 616. The ML component 614 comprises one or more ML technique components 614a-614r for implementing one or more ML technique(s) or a combination of multiple ML technique(s), classifying and/or labelling technique(s) and the like, a ML training component 614s configured for arranging training of the one or more ML techniques 614a-614r based on training data sets retrieved from neural training component 616c, and/or a ML Calibration component or retraining component 614t configured for retrain one or more ML technique(s) or calibrating one or more ML technique(s) for use with one or more device(s) 108a-108p and/or tracking long term changes in one or more neuronal population(s). The one or more ML technique(s) component 614a-614r, ML training component 614s and ML calibration/retraining component 614c may include the functionality as described herein in relation to the ML technique(s), training, retraining, tracking and/or calibration process(es)/method(s) or apparatus/mechanism(s) as described and/or illustrated herein with reference to FIGS. 1a to 5c.

The neural interface framework 600 further includes a Continuous Training component 618 that communicates with communication interface component 612, storage component 616 and ML component 614. The CT component 618 includes a continuous learning/tracking component 618a for performing one or more instances of continuous learning/tracking for updating and/or calibrating data representative of the one or more ML technique(s) 614a-614r, which may be defined by their corresponding set of parameters such as weights/parameters used by each ML technique. The continuous learning/tracking component 618a can ensure the one or more ML technique(s) 614a-614r perform optimally and/or track the variations in the environment associated with receiving neural sensing data or neurological signal(s) and/or transmitting neural stimulus data via nervous system I/O component 612a. For example, variations in the locations of the neural transmitter(s) 120a-120k and/or neural receiver(s) 116a-116j with respect to the local one or more neurons and/or neuronal populations may occur, which changes the received neural sensing/sample data or neurological signal(s) and/or the transmitted neural stimulus data via nervous system I/O component 612a. The continuous learning/tracking component 618a may include the functionality as described herein in relation to the training, retraining, continuous learning/tracking and/or calibration process(es)/method(s) as described and/or illustrated herein with reference to FIGS. 1a to 5c.

Figure 6B:
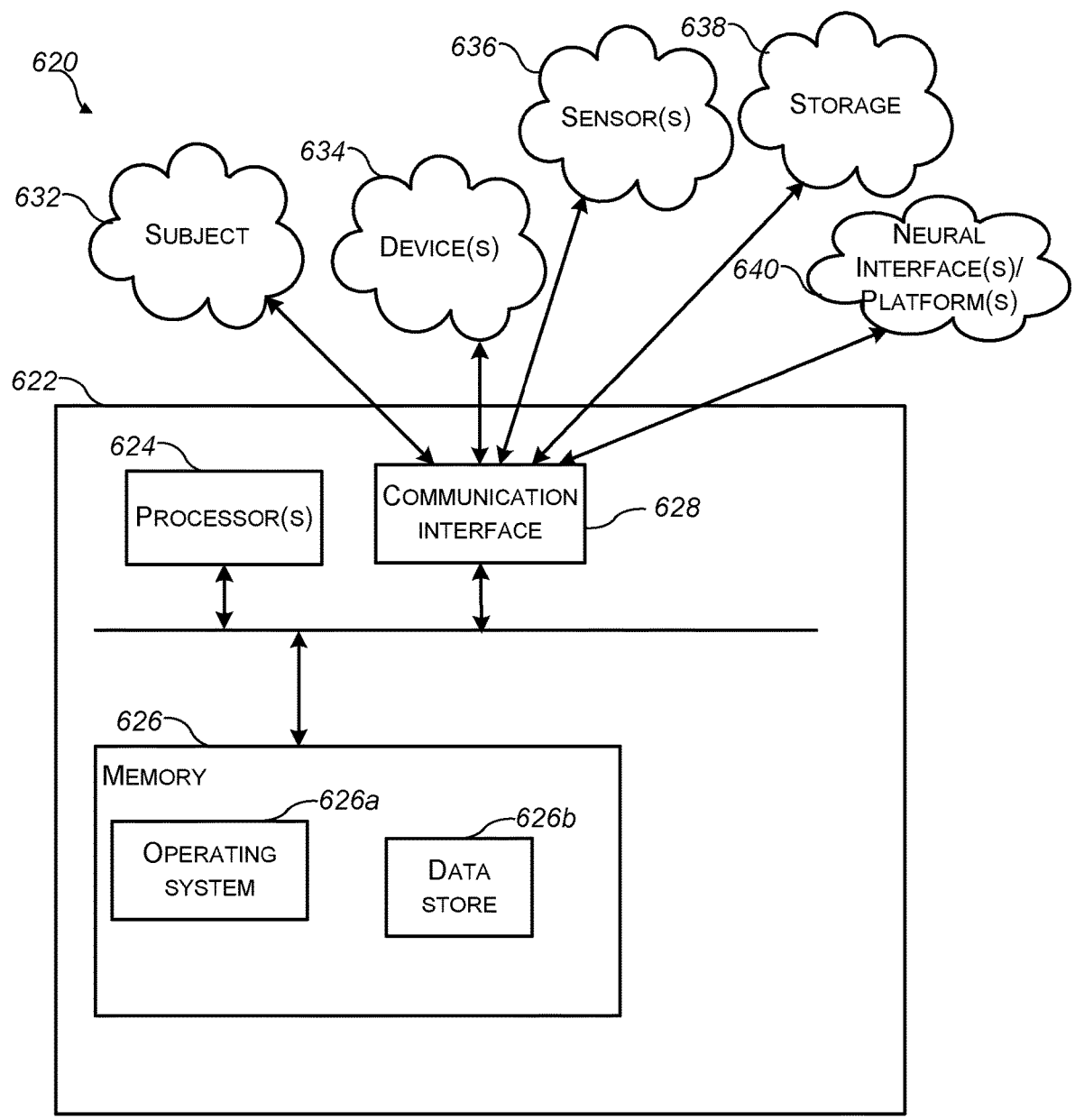
FIG. 6b is a schematic diagram of an example computing device for use with a neural interface system and/or a neural interface according to the invention.

FIG. 6b is a schematic diagram of an example computing system 620 that may be used to implement one or more aspects of the neural interface system 100 or neural interface 106 and/or includes one or more components of the neural interface platform or API 500 as described with reference to FIGS. 1a-6a. Computing system 620 includes a computing device 622 with one or more processor unit(s) 624, memory unit 626 and communication interface 628 in which the one or more processor unit(s) 624 are connected to the memory unit 626 and the communication interface 628. The communications interface 628 may connect the computing device 622 with a subject 632, one or more device(s) 634, one or more sensor(s) 636, external or cloud storage 638, and/or one or more other neural interface(s)/platform(s) 640. The memory unit 626 may store one or more program instructions, code or components such as, by way of example only but not limited to, an operating system 626a for operating computing device 622 and a data store 626b for storing additional data and/or further program instructions, code and/or components associated with implementing the functionality and/or one or more function(s) or functionality associated with one or more neural interface(s), neural interface system(s) and/or platforms, one or more of the method(s) and/or process(es) of neural interface(s), neural interface system(s) and/or platforms, neural interface platform/framework or API component(s) as described with reference to at least one of FIGS. 1a to 6a.

Although several embodiments, examples, and/or teachings of the neural interface and/or neural system have been described for interfacing with one or more device(s), it is to be appreciated that, based on the embodiments, examples, and/or teachings of this description as described herein, a skilled person would be able to implement a neural interface and/or neural interface system for operation with any other device(s) or any type of device as the application demands.

In the embodiments described above the external computing system(s) and/or computing device may be implemented as a server, which may comprise a single server or network of servers. In some examples the functionality of the server may be provided by a network of servers distributed across a geographical area, such as a worldwide distributed network of servers or cloud computing/storage platform, and a subject or user may be connected to an appropriate one of the network of server(s) based upon a subject or user location.

The above description discusses embodiments of the invention with reference to a single user for clarity. It will be understood that in practice the system may be shared by a plurality of users, and possibly by a very large number of users or subjects simultaneously. For example, training the machine learning technique(s) used by the neural interface 106 may make the models associated with the machine learning technique(s) more robust in which a setup for each new subject (e.g. a patient) becomes more of a calibration exercise rather than an entire re-training of the machine learning technique(s) for each new subject.

The embodiments described above may be fully automatic and/or partially automatic with a user or operator of the system manually instructing some step(s) of the method(s) and/or process(es) to be carried out as appropriate.

In the described embodiments of the invention the neural interface system, neural interface or neural interface platform may be implemented as any form of a computing and/or electronic device. Such a device may comprise one or more processors which may be microprocessors, controllers or any other suitable type of processors for processing computer executable instructions to control the operation of the device in order to gather and record routing information. In some examples, for example where a system on a chip architecture is used, the processors may include one or more fixed function blocks (also referred to as accelerators) which implement a part of the method in hardware (rather than software or firmware). Platform software comprising an operating system or any other suitable platform software may be provided at the computing-based device to enable application software to be executed on the device.

Various functions described herein can be implemented in hardware, software, or any combination thereof. If implemented in software, the functions can be stored on or transmitted over as one or more instructions or code on a computer-readable medium. Computer-readable media may include, for example, computer-readable storage media. Computer-readable storage media may include volatile or non-volatile, removable or non-removable media implemented in any method or technology for storage of information such as computer readable instructions, data structures, program modules or other data. A computer-readable storage media can be any available storage media that may be accessed by a computer. By way of example, and not limitation, such computer-readable storage media may comprise RAM, ROM, EEPROM, flash memory or other memory devices, CD-ROM or other optical disc storage, magnetic disc storage or other magnetic storage devices, or any other medium that can be used to carry or store desired program code in the form of instructions or data structures and that can be accessed by a computer. Disc and disk, as used herein, include compact disc (CD), laser disc, optical disc, digital versatile disc (DVD), floppy disk, and blu-ray disc (BD). Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, DSL, or wireless technologies such as infrared, radio, and microwave are included in the definition of communication medium. Combinations of the above should also be included within the scope of computer-readable media.

Alternatively, or in addition, the functionality described herein can be performed, at least in part, by one or more hardware logic components. For example, and without limitation, hardware logic components that can be used may include Field-programmable Gate Arrays (FPGAs), Program-specific Integrated Circuits (ASICs), Program-specific Standard Products (ASSPs), System-on-a-chip systems (SOCs). Complex Programmable Logic Devices (CPLDs), etc.

Although illustrated as a single system, it is to be understood that the neural interface system, neural interface(s), neural interface platform(s) and/or computing device(s) according to the invention may be implemented as part of a distributed system. Thus, for instance, several devices may be in communication by way of a network connection and may collectively perform tasks described as being performed by the neural interface system, neural interface(s), neural interface platform(s) and/or computing device according to the invention.

Although illustrated as a local device it will be appreciated that the computing device may be located remotely and accessed via a network or other communication link (for example using a communication interface).

The term 'computer' is used herein to refer to any device with processing capability such that it can execute instructions. Those skilled in the art will realise that such processing capabilities are incorporated into many different devices and therefore the term 'computer' includes PCs, servers, mobile telephones, personal digital assistants, hardware processors and many other devices.

Those skilled in the art will realise that storage devices utilised to store program instructions can be distributed across a network. For example, a remote computer may store an example of the process described as software. A local or terminal computer may access the remote computer and download a part or all of the software to run the program. Alternatively, the local computer may download pieces of the software as needed, or execute some software instructions at the local terminal and some at the remote computer (or computer network). Those skilled in the art will also realise that by utilising conventional techniques known to those skilled in the art that all, or a portion of the software instructions may be carried out by a dedicated circuit, such as a Digital Signal Processor, programmable logic array, or the like.

It will be understood that the benefits and advantages described above may relate to one embodiment or may relate to several embodiments. The embodiments are not limited to those that solve any or all of the stated problems or those that have any or all of the stated benefits and advantages.

Any reference to 'an' item refers to one or more of those items. The term 'comprising' is used herein to mean including the method steps or elements identified, but that such steps or elements do not comprise an exclusive list and a method or apparatus may contain additional steps or elements.

As used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices.

Further, as used herein, the term "exemplary" is intended to mean "serving as an illustration or example of something".

Further, to the extent that the term "includes" is used in either the detailed description or the claims, such term is intended to be inclusive in a manner similar to the term "comprising" as "comprising" is interpreted when employed as a transitional word in a claim.

The figures illustrate exemplary methods. While the methods are shown and described as being a series of acts that are performed in a particular sequence, it is to be understood and appreciated that the methods are not limited by the order of the sequence. For example, some acts can occur in a different order than what is described herein. In addition, an act can occur concurrently with another act. Further, in some instances, not all acts may be required to implement a method described herein.

Moreover, the acts described herein may comprise computer-executable instructions that can be implemented by one or more processors and/or stored on a computer-readable medium or media. The computer-executable instructions can include routines, sub-routines, programs, threads of execution, and/or the like. Still further, results of acts of the methods can be stored in a computer-readable medium, displayed on a display device, and/or the like.

The order of the steps of the methods described herein is exemplary, but the steps may be carried out in any suitable order, or simultaneously where appropriate. Additionally, steps may be added or substituted in, or individual steps may be deleted from any of the methods without departing from the scope of the subject matter described herein. Aspects of any of the examples described above may be combined with aspects of any of the other examples described to form further examples without losing the effect sought.

It will be understood that the above description of a preferred embodiment is given by way of example only and that various modifications may be made by those skilled in the art. What has been described above includes examples of one or more embodiments. It is, of course, not possible to describe every conceivable modification and alteration of the above devices or methods for purposes of describing the aforementioned aspects, but one of ordinary skill in the art can recognize that many further modifications and permutations of various aspects are possible. Accordingly, the described aspects are intended to embrace all such alterations, modifications, and variations that fall within the scope of the appended claims.

The invention claimed is:

1. A computer implemented method for interfacing with a nervous system of a subject, the method comprising:
   in response to receiving a plurality of neurological signals associated with the neural activity of the first portion of nervous system, performing the steps of:
   processing neural sample data representative of the received plurality of neurological signals using a first one or more machine learning (ML) technique(s) trained for generating estimates of neural data representative of the neural activity of the first portion of nervous system; and
   transmitting data representative of the neural data estimates to a first device associated with the first portion of nervous system; and
   in response to receiving device data from a second device associated with a second portion of the nervous system, performing the steps of:
   generating one or more neurological stimulus signal(s) by inputting the received device data to a second one or more ML technique(s) trained for estimating one or more neurological stimulus signal(s) associated with the device data for input to the second portion of nervous system; and
   transmitting the one or more estimated neurological stimulus signal(s) towards the second portion of nervous system of the subject.

2. The computer implemented method as claimed in claim 1, wherein the estimates of neural data representative of neural activity as generated or calculated by at least one of the ML techniques are associated with one or more bodily variables.

3. The computer implemented method of claim 1, further comprising:
   receiving at least one set of performance data associated with the first one or more ML technique(s) or the second one or more ML technique(s);
   evaluating the set of performance data to determine whether to retrain the first one or more ML technique(s) or the second one or more ML technique(s); and
   retraining the first one or more ML technique(s) in response to determining to retrain the first one or more ML technique(s) or the second one or more ML.

4. The computer implemented method of claim 1, further comprising:
   receiving one or more neurological signals from the neural receivers associated with the plurality of neurons of the subject; and
   classifying the one or more neurological signals into one or more categories of neural data using at least one of the first one or more ML technique(s)
   wherein the first portion of the nervous system comprises a first plurality of neurons of the subject clustered around multiple neural receivers, each neural receiver configured for outputting neurological signals associated with neural activity on one or more of the plurality of neurons.

5. The computer implemented method of claim 1, further comprising:
   generating neural sample data representative of the neurological signals by capturing samples of the neurological signals when neural activity is detected; and
   processing the neural sample data using at least one of the first one or more ML technique(s) to generate neural data representative of neural information associated with the neural activity.

6. The computer implemented method as claimed in claim 5, further comprising generating a training set of neural sample data by:
   storing captured neural sample data received from the plurality of neurological signals, wherein the neural sample data is timestamped;
   capturing and storing sensor data from one or more sensors trained on the subject, wherein the sensor data is timestamped;
   synchronising the neural sample data with the sensor data; and
   identifying portions of the neural sample data associated with neural activity;
   determining neural data labels for each identified portion of neural sample data by analysing portions of the sensor data corresponding to the identified portion of neural sample data;
   labelling the identified portions of neural sample data based on the determined neural data labels; and
   storing the labelled identified portions of neural sample data as the training set of neural sample data.

7. The computer implemented method of claim 1 further comprising training at least one of the first one or more ML technique(s) based on a training set of neural sample data, wherein each neural sample data in the training set is labelled associated with a neural data label identifying the neural data contained therein.

8. The computer implemented method of claim 1, further comprising:
   wherein at least one of the first one or more ML technique(s) comprise at least one or more ML technique(s) or combinations thereof from the group of:
   a) neural networks;
   b) Hidden Markov Models;
   c) Gaussian process dynamics models;
   d) autoencoder/decoder networks;
   e) adversarial/discriminator networks;
   f) convolutional neural networks; and
   g) long short term memory neural networks.

9. The computer implemented method of claim 1, further comprising:
   inputting neural sample data to the autoencoder for real-time classification of neurological signals,
   wherein at least one of the first one or more ML technique(s) is based on a neural network autoencoder structure, the neural network autoencoder structure comprising an encoding network and a decoding network, the encoding network comprising one or more hidden layer(s) and the decoding network comprising one or more hidden layer(s), wherein the neural network autoencoder is trained to output a neural data label vector that is capable of classifying each portion of neural sample data from a training set of neural sample data into one or more neural data labels.

10. The computer implemented method as claimed in claim 9, the method further comprising:
    training the neural network autoencoder for outputting a neural data label vector that is capable of classifying each portion of neural sample data from a training set of neural sample data into one or more neural data labels; and
    using the trained weights of the hidden layer(s) of the autoencoder for real-time classification of neurological signals.

11. An apparatus for interfacing with a nervous system of a subject, the apparatus comprising:
- a communications interface;
- a memory unit; and
- a processor unit, the processor unit connected to the communications interface and the memory unit, wherein:
- the communications interface is configured to receive a plurality of neurological signals associated with the neural activity of a first portion of nervous system;
- in response to receiving a plurality of neurological signals associated with the neural activity of the first portion of nervous system, the processor and communication interface are configured to:
- process neural sample data representative of the received plurality of neurological signals using a first one or more machine learning (ML) technique(s) trained for generating estimates of neural data representative of the neural activity of the first portion of nervous system; and
- transmit data representative of the neural data estimates to a first device associated with the first portion of nervous system; and
- the communications interface is further configured to receive device data from a second device associated with a second portion of the nervous system; and
- in response to receiving device data from the second device associated with the second portion of the nervous system, the processor and communication interface are further configured to:
- generate one or more neurological stimulus signal(s) by inputting the received device data to a second one or more ML technique(s) trained for estimating one or more neurological stimulus signal(s) associated with the device data for input to the second portion of nervous system; and
- transmit the one or more estimated neurological stimulus signal(s) towards the second portion of nervous system of the subject.

* * * * *